(12) United States Patent
Bradley et al.

(10) Patent No.: US 12,384,855 B2
(45) Date of Patent: Aug. 12, 2025

(54) PCSK9 ANTAGONISTS

(71) Applicant: KYMAB LIMITED, Cambridge (GB)

(72) Inventors: Allan Bradley, Cambridge (GB); Qi Liang, Cambridge (GB); E-Chiang Lee, Cambridge (GB); Li-Ying Liou, Xinyi District Taipei (TW); Yu-Hui Huang, Xinyi District Taipei (TW); Yen-Ju Chen, Xinyi District Taipei (TW); Li-Tzu Chen, Xinyi District Taipei (TW)

(73) Assignee: KYMAB LIMITED, Cambridge (GB)

( * ) Notice: Subject to any disclaimer, the term of this patent is extended or adjusted under 35 U.S.C. 154(b) by 975 days.

(21) Appl. No.: 17/299,147

(22) PCT Filed: Dec. 18, 2019

(86) PCT No.: PCT/GB2019/053607
§ 371 (c)(1),
(2) Date: Jun. 2, 2021

(87) PCT Pub. No.: WO2020/128467
PCT Pub. Date: Jun. 25, 2020

(65) Prior Publication Data
US 2022/0049017 A1    Feb. 17, 2022

(30) Foreign Application Priority Data
Dec. 19, 2018 (GB) .................................. 1820687

(51) Int. Cl.
| | | |
|---|---|---|
| *C07K 16/40* | (2006.01) | |
| *A61K 39/00* | (2006.01) | |
| *A61K 45/06* | (2006.01) | |
| *A61P 3/06* | (2006.01) | |

(52) U.S. Cl.
CPC ............ *C07K 16/40* (2013.01); *A61K 45/06* (2013.01); *A61P 3/06* (2018.01); *A61K 2039/505* (2013.01); *C07K 2317/56* (2013.01); *C07K 2317/565* (2013.01)

(58) Field of Classification Search
CPC .... C07K 16/40; C07K 16/28; C07K 2317/92; A61K 45/06; A61K 2039/505; A61K 2039/545; A61P 3/06
See application file for complete search history.

(56) References Cited

U.S. PATENT DOCUMENTS

| | | | | |
|---|---|---|---|---|
| 5,859,205 A * | 1/1999 | Adair | ................. | C07K 16/465 530/387.3 |
| 7,879,984 B2 * | 2/2011 | Martin | ................. | A61P 35/02 530/808 |
| 8,883,157 B1 * | 11/2014 | Clube | ................. | C07K 16/40 |
| 8,999,341 B1 * | 4/2015 | Clube | ................. | C12Q 1/6883 424/146.1 |
| 9,017,678 B1 | 4/2015 | Clube | | |
| 9,034,332 B1 * | 5/2015 | Clube | ................. | C07K 16/40 424/146.1 |
| 9,045,548 B1 * | 6/2015 | Clube | ................. | C07K 16/40 |
| 9,051,378 B1 * | 6/2015 | Clube | ................. | C07K 16/40 |
| 9,255,154 B2 | 2/2016 | Feldhaus et al. | | |
| 9,266,961 B2 * | 2/2016 | Wu | ................. | C07K 16/40 |
| 2012/0093818 A1 | 4/2012 | Jackson et al. | | |
| 2013/0004501 A1 * | 1/2013 | Towne | ................. | C07K 16/244 435/254.2 |

FOREIGN PATENT DOCUMENTS

| | | | |
|---|---|---|---|
| CN | 106062004 A | 10/2016 | |
| EP | 2650016 A1 | 10/2013 | |
| JP | 2016-528193 A | 9/2016 | |
| WO | WO 1998/050431 A2 | 11/1998 | |
| WO | WO 2006/106905 A1 | 10/2006 | |
| WO | WO 2007/110205 A2 | 10/2007 | |
| WO | WO 2008/003103 A2 | 1/2008 | |
| WO | WO 2010/077854 A1 | 7/2010 | |
| WO | WO 2011/004192 A1 | 1/2011 | |
| WO | WO 2011/143545 A1 | 11/2011 | |
| WO | WO 2013/157954 A1 | 10/2013 | |
| WO | WO 2017/063593 A1 | 5/2014 | |
| WO | WO 2014/209384 A1 | 12/2014 | |
| WO | WO 2015/092393 A2 | 6/2015 | |
| WO | WO 2015/103072 A1 | 7/2015 | |

OTHER PUBLICATIONS

Bowie Ju, et al. Deciphering the message in protein sequences: tolerance to amino acid substitutions. Science. Mar. 16, 1990;247(4948):1306-10. doi: 10.1126/science.2315699. PMID: 2315699. (Year: 1990).*
Portolano S, et al. Lack of promiscuity in autoantigen-specific H and L chain combinations as revealed by human H and L chain "roulette". J Immunol. Feb. 1, 1993;150(3):880-7. PMID: 8423344. (Year: 1993).*
Padlan EA. Anatomy of the antibody molecule. Mol Immunol. Feb. 1994;31(3):169-217. doi: 10.1016/0161-5890(94)90001-9. PMID: 8114766. (Year: 1994).*
Bork P, et al. Go hunting in sequence databases but watch out for the traps. Trends Genet. Oct. 1996;12(10):425-7. doi: 10.1016/0168-9525(96)60040-7. PMID: 8909140. (Year: 1996).*
Brown M, et al. Tolerance of single, but not multiple, amino acid replacements in antibody VH CDR 2: a means of minimizing B cell wastage from somatic hypermutation? J Immunol. May 1, 1996;156(9):3285-91. PMID: 8617951. (Year: 1996).*
MacCallum RM, et al. Antibody-antigen interactions: contact analysis and binding site topography. J Mol Biol. Oct. 11, 1996;262(5):732-45. doi: 10.1006/jmbi.1996.0548. PMID: 8876650. (Year: 1996).*
Metzler WJ, et al. Solution structure of human CTLA-4 and delineation of a CD80/CD86 binding site conserved in CD28. Nat Struct Biol. Jul. 1997;4(7):527-31. doi: 10.1038/nsb0797-527. PMID: 9228944. (Year: 1997).*

(Continued)

*Primary Examiner* — Misook Yu
*Assistant Examiner* — Alec Jon Peters
(74) *Attorney, Agent, or Firm* — MH2 Technology Law Group, LLP

(57) ABSTRACT

The invention relates to Proprotein Convertase Subtilisin Kexin type 9 (PCSK9) antagonists, such as antibodies and fragments, as well as methods, uses and combinations.

9 Claims, 48 Drawing Sheets
Specification includes a Sequence Listing.

(56) References Cited

OTHER PUBLICATIONS

Smith TF, et al. The challenges of genome sequence annotation or "the devil is in the details". Nat Biotechnol. Nov. 1997; 15(12): 1222-3. doi: 10.1038/nbt1197-1222. PMID: 9359093. (Year: 1997).*
Doerks T, et al. Protein annotation: detective work for function prediction. Trends Genet. Jun. 1998;14(6):248-50. doi: 10.1016/s0168-9525(98)01486-3. PMID: 9635409. (Year: 1998).*
Brenner SE. Errors in genome annotation. Trends Genet. Apr. 1999;15(4): 132-3. doi: 10.1016/s0168-9525(99)01706-0. PMID: 10203816. (Year: 1999).*
Attwood TK. Genomics. The Babel of bioinformatics. Science. Oct. 20, 2000;290(5491):471-3. doi: 10.1126/science.290.5491.471. PMID: 11183771. (Year: 2000).*
Bork P. Powers and pitfalls in sequence analysis: the 70% hurdle. Genome Res. Apr. 2000;10(4):398-400. doi: 10.1101/gr.10.4.398. PMID: 10779480. (Year: 2000).*
Skolnick J, et al. From genes to protein structure and function: novel applications of computational approaches in the genomic era. Trends Biotechnol. Jan. 2000;18(1):34-9. doi: 10.1016/s0167-7799(99)01398-0. PMID: 10631780. (Year: 2000).*
Vajdos FF, et al. Comprehensive functional maps of the antigen-binding site of an anti-ErbB2 antibody obtained with shotgun scanning mutagenesis. J Mol Biol. Jul. 5, 2002;320(2):415-28. doi: 10.1016/S0022-2836(02)00264-4. PMID: 12079396. (Year: 2002).*
Casset F, et al. A peptide mimetic of an anti-CD4 monoclonal antibody by rational design. Biochem Biophys Res Commun. Jul. 18, 2003;307(1):198-205. doi: 10.1016/s0006-291x(03)01131-8. PMID: 12850000. (Year: 2003).*
International Human Genome Sequencing Consortium. Finishing the euchromatic sequence of the human genome. Nature. Oct. 21, 2004;431(7011):931-45. doi: 10.1038/nature03001. PMID: 15496913. (Year: 2004).*
Zody MC et al. Analysis of the DNA sequence and duplication history of human chromosome 15. Nature. Mar. 30, 2006;440(7084): 671-5. doi: 10.1038/nature04601. PMID: 16572171. (Year: 2006).*
Boyd SD, et al. High-Throughput DNA Sequencing Analysis of Antibody Repertoires. Microbiol Spectr. Oct. 2014;2(5). doi: 10.1128/microbiolspec.AID-0017-2014. PMID: 26104353. (Year: 2014).*
Rabia LA, et al. Understanding and overcoming trade-offs between antibody affinity, specificity, stability and solubility. Biochem Eng J. Sep. 15, 2018;137:365-374. doi: 10.1016/j.bej.2018.06.003. Epub Jun. 5, 2018. PMID: 30666176; PMCID: PMC6338232. (Year: 2018).*
Chan et al., "A Proprotein convertase subtilisin/kexin type 9 neutralizing antibody reduces serum cholesterol in mice and nonhuman primates", Proc. Natl. Acad. Sci. USA, Jun. 16, 2009, 106(24): 9820-9825.
Search Report for Colombian Patent Application No. NC2021/0007653, dated Dec. 28, 2023.
International Search Report and Written Opinion for PCT International Patent Application No. PCT/GB2019/053607, mailed Jun. 23, 2020.
Anderson et al., 1997. Activation of the furin endoprotease is a multiple-step process: requirements for acidification and internal propeptide cleavage. EMBO J., 16, pp. 1508-1518.
Ason B. et al., 2011, "Improved efficacy for ezetimibe and rosuvastatin by attenuating the induction of PCSK9", J Lipid Res, 52(4): 679-687.
Ason, B. et al., 2014, "PCSK9 inhibition fails to alter hepatic LDLR, circulating cholesterol, and atherosclerosis in the absence of ApoE", J Lipid Res, 55(11):2370-9.
Benjannet et al., 2004. NARC-1/PCSK9 and its natural mutants: zymogen cleavage and effects on the low density lipoprotein (LDL) receptor and LDL cholesterol, J. Biol. Chem., 279 (2004), pp. 48865-48875.
Chothia, C. & Lesk, A. M., 1987, "Canonical structures for the hypervariable regions of immunoglobulins", J. Mal. Biol., 196, 901-917.

De Knijff, P. et al., 1991, "Familial dysbetalipoproteinemia associated with apolipoprotein E3-Leiden in an extended multigeneration pedigree", J. Clin. Invest. 88: 643-655.
DiGiammarino et al., "Design and generation of DVD-Ig™ molecules for dual-specific targeting", Meth. Mo. Biol., 2012, 889, 145-156.
Fu et al., 2000. Folding pathway mediated by an intramolecular chaperone. The inhibitory and chaperone functions of the subtilisin propeptide are not obligatorily linked. J. Biol. Chem., 275, pp. 16871-16878.
Henrich et al., 2003. The crystal structure of the proprotein processing proteinase furin explains its stringent specificity. Nat. Struct. Biol., 10, pp. 520-526.
Henrich et al., 2005. Proprotein convertase models based on the crystal structures of furin and kexin: explanation of their specificity. J. Mol. Biol., 345, pp. 211-227.
Horton et al., 2007. Molecular biology of PCSK9: its role in LDL metabolism, Trends Biochem. Sci., 32, pp. 71-77.
Kabat et al., (1971) Ann. NY Acad. Sci., 190:382-391.
Kabat, E. A. et al., 1991, "Sequences of Proteins of Immunological Interest", 5th edit., NIH Publication No. 91-3242, U.S. Department of Health and Human Services.
Kotowski et al., 2006. A spectrum of PCSK9 alleles contributes to plasma levels of low-density lipoprotein cholesterol. Am. J. Hum. Genet., 78, pp. 410-422.
Kuhnast, Set al, 2014, "Alirocumab inhibits atherosclerosis, improves the plaque morphology, and enhances the effects of a statin", J Lipid Res. Oct. 2014, 55(10): 2103-2112.
Lagace et al., 2006. Secreted PCSK9 decreases the number of LDL receptors in hepatocytes and in livers of parabiotic mice. J. Clin. Invest., 116, pp. 2995-3005.
Langer (1990) Science 249:1527-1533.
Lee et al, Nat Biotechnol. 2014, 32(4):356-63. doi:10.1038/nbt.2825, "Complete humanization of the mouse immunoglobulin loci enables efficient therapeutic antibody discovery".
Lee, Jeong Hyun, et al. "Antibodies to a conformational epitope on gp41 neutralize HIV-1 by destabilizing the Env spike.", Nature communications, 6, (2015).
Lefranc, M. P., 1997, "Unique database numbering system for immunogenetic analysis", Immunol. Today, 18, 50.
Ikemura et al., 1987. Requirement of pro-sequence for the production of active subtilisin E in Escherichia coli. J. Biol. Chem., 262, pp. 7859-7864.
Mathis (1995) Clinical Chemistry 41(9), 1391-1397.
Maxwell et al., 2005. Overexpression of PCSK9 accelerates the degradation of the LDLR in a post-endoplasmic reticulum compartment. Proc. Natl. Acad. Sci. USA, 102, pp. 2069-2074.
Naureckiene et al., 2003. Functional characterization of Narc 1, a novel proteinase related to proteinase K. Arch. Biochem. Biophys., 420, pp. 55-67.
Niederfellner, Gerhard, et al. "Epitope characterization and crystal structure of GA101 provide insights into the molecular basis for type 1/11 distinction of CD20 antibodies.", Blood, 118.2, (2011), 358-367.
Park et al., 2004. Post-transcriptional regulation of low density lipoprotein receptor protein by proprotein convertase subtilisin/kexin type 9a in mouse liver. J. Biol. Chem., 279, pp. 50630-50638.
Powell et al. "Compendium of excipients for parenteral formulations" PDA (1998) J Pharm Sci Technol 52:238-311.
Rashid et al., 2005. Decreased plasma cholesterol and hypersensitivity to statins in mice lacking Pcsk9. Proc. Natl. Acad. Sci. USA, 102, pp. 5374-5379.
Rawlings et al., 2006. MEROPS: the peptidase database. Nucleic Acids Res., 34, pp. D270-D272.
Sakai et al., 1998. Molecular identification of the sterol-regulated luminal protease that cleaves SREBPs and controls lipid composition of animal cells. Mol. Cell, 2, pp. 505-514.
Sefton (1987) CRC Crit. Ref. Biomed. Eng. 14:201.
Seidah and Prat, 2007. The proprotein convertases are potential targets in the treatment of dyslipidemia, J. Mol. Med., 10.1007/s00109-007-0172-7.

(56) References Cited

OTHER PUBLICATIONS

Seidah et al., 1999. Mammalian subtilisin/kexin isozyme SKI-1: a widely expressed proprotein convertase with a unique cleavage specificity and cellular localization. Proc. Natl. Acad. Sci. USA, 96, pp. 1321-1326.

Seidah, et al., 2003. The secretory proprotein convertase neural apoptosis-regulated convertase 1 (NARC-1): liver regeneration and neuronal differentiation. Proc. Natl. Acad. Sci. USA, 100, pp. 928-933.

Shield et al. (2002) JBC 277:26733.

Spiess, C., et al., Mal. Immunol. (2015).

Suckau, Detlev, et al. "Molecular epitope identification by limited proteolysis of an immobilized antigen-antibody complex and mass spectrometric peptide mapping.", Proceedings of the National Academy of Sciences, 87.24, (1990), 9848-9852.

Tangrea et al., 2002. Solution structure of the pro-hormone convertase 1 pro-domain from Mus musculus. J. Mol. Biol., 320, pp. 801-812.

Tsuyoshi Nozue: "Lipid Lowering Therapy and Circulating PCSK9 Concentration" Journal Of Atherosclerosis And Thrombosis, vol. 24, No. 9, Jan. 1, 2017 (Jan. 1, 2017), pp. 895-907.

Van den Hoek AM. et al., 2014, "APOE*3Leiden.CETP transgenic mice as model for pharmaceutical treatment of the metabolic syndrome", Diabetes Obes Metab. Jun. 2014;16(6):537-44.

Westerterp, M. et al., 2006, "Cholesteryl ester transfer protein decreases high-density lipoprotein and severely aggravates atherosclerosis in APOE*3-Leidenmice", Arterioscler. Thromb. Vase. Biol. 26:2552- 2559.

Wu et al. (1987) J. Biol. Chem. 262:4429-4432.

Zhao et al., 2006. Molecular characterization of loss-of-function mutations in PCSK9 and identification of a compound heterozygote. Am. J. Hum. Genet., 79, pp. 514-523.

\* cited by examiner

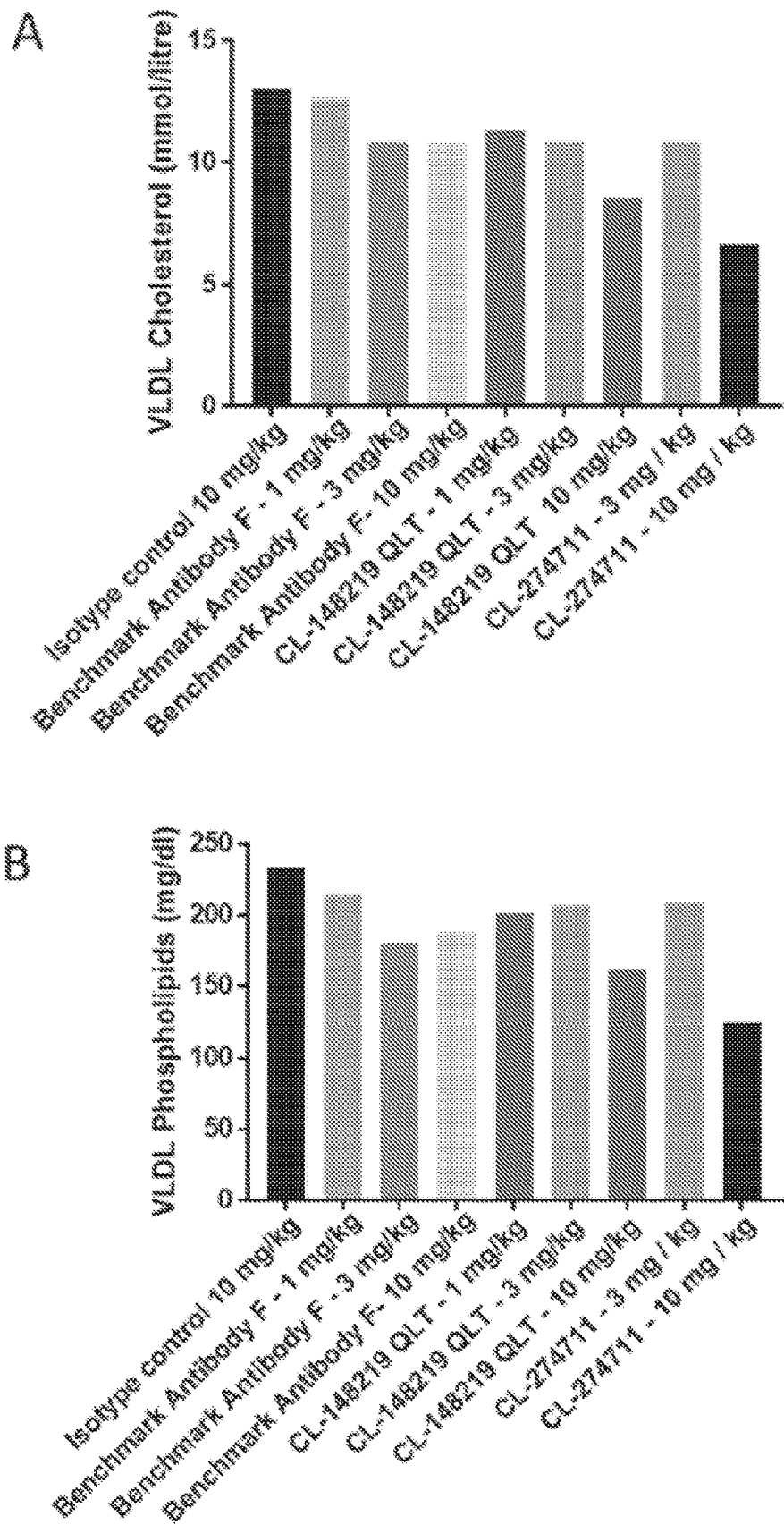
Figure 22a-b

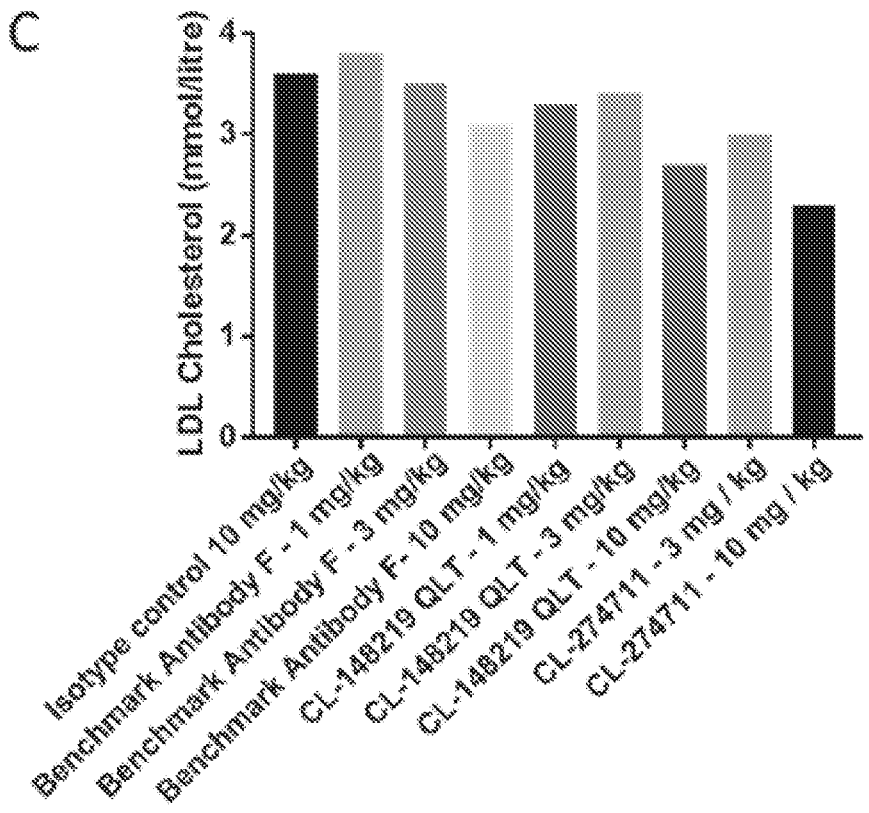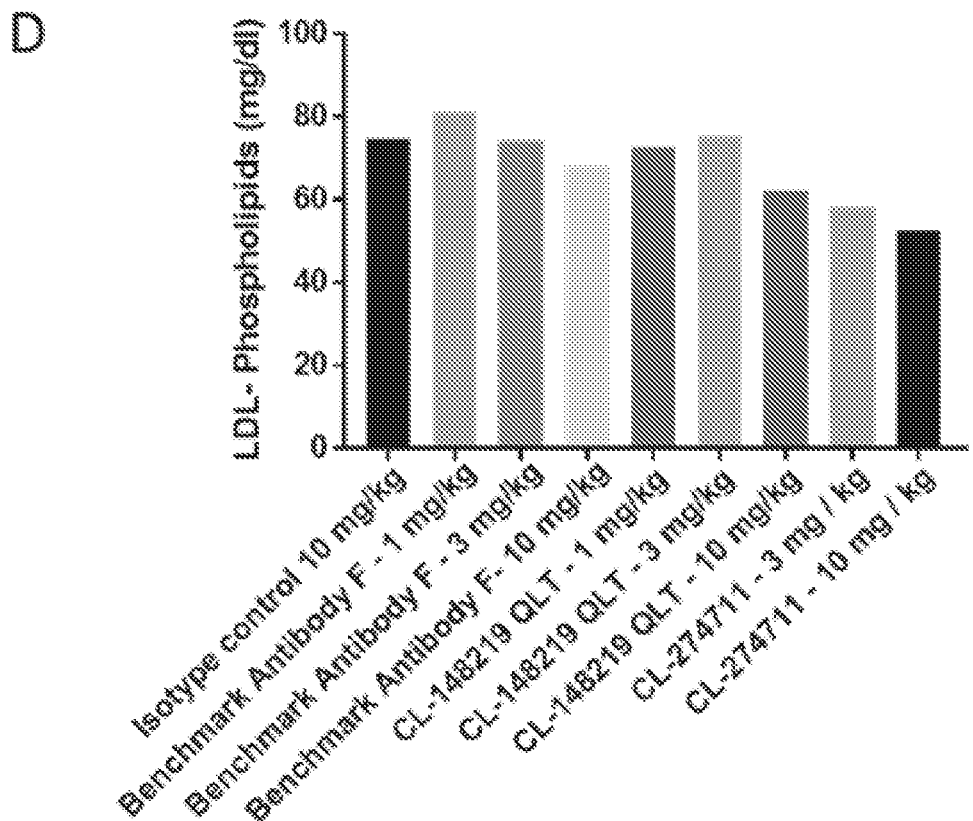
Figure 22c-d

PCSK9 ANTAGONISTS

FIELD OF THE INVENTION

The invention relates to Proprotein Convertase Subtilisin Kexin type 9 (PCSK9) antagonists, such as antibodies and fragments, as well as methods, uses and combinations.

BACKGROUND

Proprotein convertase subtilisin kexin type 9 (PCSK9) is a serine protease involved in regulating the levels of the low density lipoprotein receptor (LDLR) protein (Horton et al., 2007; Seidah and Prat, 2007). In vitro experiments have shown that adding PCSK9 to HepG2 cells lowers the levels of cell surface LDLR (Benjannet et al., 2004; Lagace et al., 2006; Maxwell et al., 2005; Park et al., 2004).

Experiments with mice have shown that increasing PCSK9 protein levels decreases levels of LDLR protein in the liver (Benjannet et al., 2004; Lagace et al., 2006; Maxwell et al., 2005; Park et al., 2004), while PCSK9 knockout mice have increased levels of LDLR in the liver (Rashid et al., 2005).

Additionally, various human PCSK9 mutations that result in either increased or decreased levels of plasma LDL have been identified (Kotowski et al., 2006; Zhao et al., 2006). PCSK9 has been shown to directly interact with the LDLR protein, be endocytosed along with the LDLR, and co-immunofluoresce with the LDLR throughout the endosomal pathway (Lagace et al., 2006).

PCSK9 is a prohormone-proprotein convertase in the subtilisin (S8) family of serine proteases (Seidah et al., 2003). Humans have nine prohormone-proprotein convertases that can be divided between the S8A and S8B subfamilies (Rawlings et al., 2006). Furin, PC1/PC3, PC2, PACE4, PC4, PC5/PC6 and PC7/PC8/LPC/SPC7 are classified in subfamily S8B. Crystal and NMR structures of different domains from mouse furin and PC1 reveal subtilisin-like pro- and catalytic domains, and a P domain directly C-terminal to the catalytic domain (Henrich et al., 2003; Tangrea et al., 2002). Based on the amino acid sequence similarity within this subfamily, all seven members are predicted to have similar structures (Henrich et al., 2005). SKI-1/S1P and PCSK9 are classified in subfamily S8A. Sequence comparisons with these proteins also suggest the presence of subtilisin-like pro- and catalytic domains (Sakai et al., 1998; Seidah et al., 2003; Seidah et al., 1999). In these proteins the amino acid sequence C-terminal to the catalytic domain is more variable and does not suggest the presence of a P domain.

Prohormone-proprotein convertases are expressed as zymogens and they mature through a multi step process. The function of the pro-domain in this process is two-fold. The pro-domain first acts as a chaperone and is required for proper folding of the catalytic domain (Ikemura et al., 1987). Once the catalytic domain is folded, autocatalysis occurs between the pro-domain and catalytic domain. Following this initial cleavage reaction, the pro-domain remains bound to the catalytic domain where it then acts as an inhibitor of catalytic activity (Fu et al., 2000). When conditions are correct, maturation proceeds with a second autocatalytic event at a site within the pro-domain (Anderson et al., 1997). After this second cleavage event occurs the pro-domain and catalytic domain dissociate, giving rise to an active protease.

Autocatalysis of the PCSK9 zymogen occurs between Gln152 and Ser153 (VFAQ|SIP (SEQ ID NO: 67)) (Naureckiene et al., 2003), and has been shown to be required for its secretion from cells (Seidah et al., 2003). A second autocatalytic event at a site within PCSK9's pro-domain has not been observed. Purified PCSK9 is made up of two species that can be separated by non-reducing SDS-PAGE; the pro-domain at 17 Kd, and the catalytic plus C-terminal domains at 65 Kd. PCSK9 has not been isolated without its inhibitory pro-domain, and measurements of PCSK9's catalytic activity have been variable (Naureckiene et al., 2003; Seidah et al., 2003).

In certain embodiments, a PCSK9 polypeptide includes terminal residues, such as, but not limited to, leader sequence residues, targeting residues, amino terminal methionine residues, lysine residues, tag residues and/or fusion protein residues. "PCSK9" has also been referred to as FH3, NARC1, HCHOLA3, proprotein convertase subtilisin/kexin type 9, and neural apoptosis regulated convertase 1. The PCSK9 gene encodes a proprotein convertase protein that belongs to the proteinase K subfamily of the secretory subtilase family. The term "PCSK9" denotes both the proprotein and the product generated following autocatalysis of the proprotein. When only the autocatalyzed product is being referred to (such as for an antigen binding protein or ligand that binds to the cleaved PCSK9), the protein can be referred to as the "mature," "cleaved", "processed" or "active" PCSK9. When only the inactive form is being referred to, the protein can be referred to as the "inactive", "pro-form", or "unprocessed" form of PCSK9. The term PCSK9 also encompasses PCSK9 molecules incorporating post-translational modifications of the PCSK9 amino acid sequence, such as PCSK9 sequences that have been glycosylated, PCSK9 sequences from which its signal sequence has been cleaved, PCSK9 sequence from which its pro domain has been cleaved from the catalytic domain but not separated from the catalytic domain (see, e.g., FIGS. 1A and 1B of US20120093818A1). PCSK9 controls expression of the low-density lipoprotein (LDL) receptor in the liver by promoting lysosomal degradation of the receptor. Inhibition of PCSK9 leads to increased hepatocyte LDL receptor expression and results in decreased plasma cholesterol levels through increased clearance of LDL particles by the liver. Treatment with monoclonal antibodies against PCSK9 is a clinically successful therapeutic intervention in patients diagnosed with hyperlipidemia or hypercholesterolemia that is unresponsive to statin treatment. Anti-PCSK9 antibody alirocumab is marketed by Regeneron Pharmaceuticals, Inc under the name Praluent™. Anti-PCSK9 antibody evolocumab is marketed by Amgen, Inc under the name Repatha™.

STATEMENT OF INVENTION

In a first configuration the invention provides:

An antibody or fragment comprising a binding site which specifically binds to Proprotein Convertase Subtilisin Kexin type 9 (PCSK9), wherein the binding site comprises a VH domain that is encoded by a nucleotide sequence that is derived from the recombination of a human VH gene segment, DH gene segment and JH gene segment, wherein the VH gene segment is selected from IGHV4-31, IGHV4-59, IGHV4-4 and IGHV3-9.

In a second configuration the invention provides:

An antibody or fragment which specifically binds to PCSK9 and comprises the CDRH3 sequence of an anti-PCSK9 antibody according to the invention, or said CDRH3 sequence comprising 3, 2 or 1 amino acid substitution(s).

In a third configuration the invention provides:

An antibody or fragment (optionally according to any preceding claim) which specifically binds to PCSK9 and comprises a VH domain which comprises a CDRH3 sequence of an antibody selected from CL-274711, CL-148219QLT, CL-274698, CL-148219 and CL-148489 (eg, CL-274711 or CL-148219QLT); or said sequence comprising 3, 2 or 1 amino acid substitution(s).

In a fourth configuration the invention provides:

An antibody or fragment comprising a binding site which specifically binds to PCSK9, wherein the binding site comprises a VH domain that comprises the amino acid sequence of a VH domain of an antibody selected from CL-274711, CL-148219QLT, CL-274698, CL-148219 and CL-148489 (eg, CL-274711 or CL-148219QLT); or an amino acid that is at least 70% identical thereto.

In a fifth configuration the invention provides:

An antibody or fragment (optionally according to any preceding claim) comprising a binding site which specifically binds to PCSK9, wherein the binding site comprises a VL domain that is encoded by a nucleotide sequence that is derived from the recombination of a human VL gene segment and JL gene segment, wherein the VL gene segment is selected from IGKV3-11, IGKV2-28 and IGKV2-29.

In a sixth configuration the invention provides:

An antibody or fragment which specifically binds to PCSK9 and comprises the CDRL3 sequence of an anti-PCSK9 antibody of the invention, said CDRL3 sequence comprising 3, 2 or 1 amino acid substitution(s).

In a seventh configuration the invention provides:

An antibody or fragment which specifically binds to PCSK9 and comprises a VL domain which comprises a CDRL3 (and optionally a CDRH3) sequence of an antibody selected from CL-274711, CL-148219QLT, CL-274698, CL-148219 and CL-148489 (eg, CL-274711 or CL-148219QLT); or said sequence(s) each comprising 3, 2 or 1 amino acid substitution(s).

In a eighth configuration the invention provides:

An antibody or fragment comprising a binding site which specifically binds to PCSK9, wherein the binding site comprises a VL domain that comprises the amino acid sequence of a VL domain of an antibody selected from CL-274711, CL-148219QLT, CL-274698, CL-148219 and CL-148489 (eg, CL-274711 or CL-148219QLT); or an amino acid that is at least 70% identical thereto.

In a ninth configuration the invention provides:

An antibody or fragment which specifically binds to PCSK9 and comprises the heavy chain amino acid sequence of an antibody selected from CL-274711, CL-148219QLT, CL-274698, CL-148219 and CL-148489 (eg, CL-274711 or CL-148219QLT); or an amino acid that is at least 70% identical thereto.

In a tenth configuration the invention provides:

An antibody or fragment which specifically binds to PCSK9 and comprises the light chain amino acid sequence of an antibody selected from CL-274711, CL-148219QLT, CL-274698, CL-148219 and CL-148489 (eg, CL-274711 or CL-148219QLT); or an amino acid that is at least 70% identical thereto.

In a eleventh configuration the invention provides:

An antibody or fragment which specifically binds to a human PCSK9 epitope that is identical to an epitope to which the antibody of the invention (eg, CL-274711 or CL-148219QLT) binds.

In a twelfth configuration the invention provides:

An antibody or fragment which competes for binding to human PCSK9 with the antibody of the invention.

In a thirteenth configuration the invention provides:

An anti-PCSK9 antibody or fragment of the invention for treating or preventing a PCSK9-mediated disease or condition (optionally hyperlipidaemia or hypercholesterolaemia) in a subject.

In a fourteenth configuration the invention provides:

A combination of an amount of an anti-PCSK9 antibody or fragment and an amount of a statin (optionally comprising multiple doses of said antibody and/or statin), wherein the antibody or fragment is according to the invention.

A combination of an amount of an anti-PCSK9 antibody or fragment and an amount of an ANGPTL3 inhibitor (eg, an anti-ANGPTL3 antibody, eg, evinacumab) (optionally comprising multiple doses of said antibody and/or statin), wherein the antibody or fragment is according to the invention. Optionally, the combination also comprises a statin.

In a fifteenth configuration the invention provides:

Use of the antibody, fragment or combination of the invention in the manufacture of a medicament for administration to a subject for treating or preventing a PCSK9-mediated disease or condition, optionally hyperlipidaemia or hypercholesterolaemia.

In a sixteenth configuration the invention provides:

A method of treating or preventing a PCSK9-mediated disease or condition in a subject (optionally hyperlipidaemia or hypercholesterolaemia), the method comprising administering to said subject a therapeutically effective amount of an antibody, fragment or combination of the invention, wherein the PCSK9-mediated disease or condition is thereby treated or prevented.

In a seventeenth configuration the invention provides:

A pharmaceutical composition comprising an antibody, fragment or combination of the invention and a pharmaceutically acceptable excipient, diluent or carrier.

In a eighteenth configuration the invention provides:

A nucleic acid that encodes a VH domain and/or a VL domain of an antibody or fragment of the invention In a nineteenth configuration the invention provides:

A nucleic acid that encodes a VH domain comprising the amino acid sequence of a VH domain of an antibody selected from CL-274711, CL-148219QLT, CL-274698, CL-148219 and CL-148489 (eg, CL-274711 or CL-148219QLT); or an amino acid that is at least 70% identical thereto.

In a twentieth configuration the invention provides:

A nucleic acid that encodes a heavy chain and/or a light chain of an antibody or fragment of the invention.

In a twenty-first configuration the invention provides:

A vector comprising the nucleic acid(s); optionally wherein the vector is a CHO or HEK293 vector.

In a twenty-second configuration the invention provides:

A host cell comprising the nucleic acid(s) or the vector.

In a twenty-third configuration the invention provides:

An antibody, fragment, combination, vector, host cell, use or method as herein described.

BRIEF DESCRIPTION OF THE DRAWINGS

FIG. 14a shows the phospholipid profiles for lipoprotein fractions after treatment with different anti-PCSK9 antibodies; FIG. 14b shows the cholesterol profiles for lipoprotein fractions after treatment with different anti-PCSK9 antibodies;

FIG. 22: Shows the lipoprotein profiles (A—VLDL Cholesterol, B—VLDL Phospholipids, C—LDL Cholesterol, D—LDL Phospholipids) following a single subcutaneous 1, 3 or 10 mg/kg dose of Benchmark Antibody F/CL-148219 QLT, 3 or 10 mg/kg of CL-274711 or 10 mg/kg dose of isotype control in APOE*3Leiden.CETP transgenic mice feed a Western-type diet containing 0.15% cholesterol and 15% saturated fat; FIG. 1. CL-148219 neuralised human PCSK9 internalisation more than benchmarks in a cell-based assay in vitro. HepG2 cells were treated with AF647-labelled human PCSK9 gain-of-function mutant in the presence of isotype control, benchmarks, or CL-148219, followed by treatment with BODIPY LDL. Cells were then collected and the fluorescent signals of AF647 was detected by CytoFlex™ flow cytometer.

DETAILED DESCRIPTION

Definitions

Figure 1:
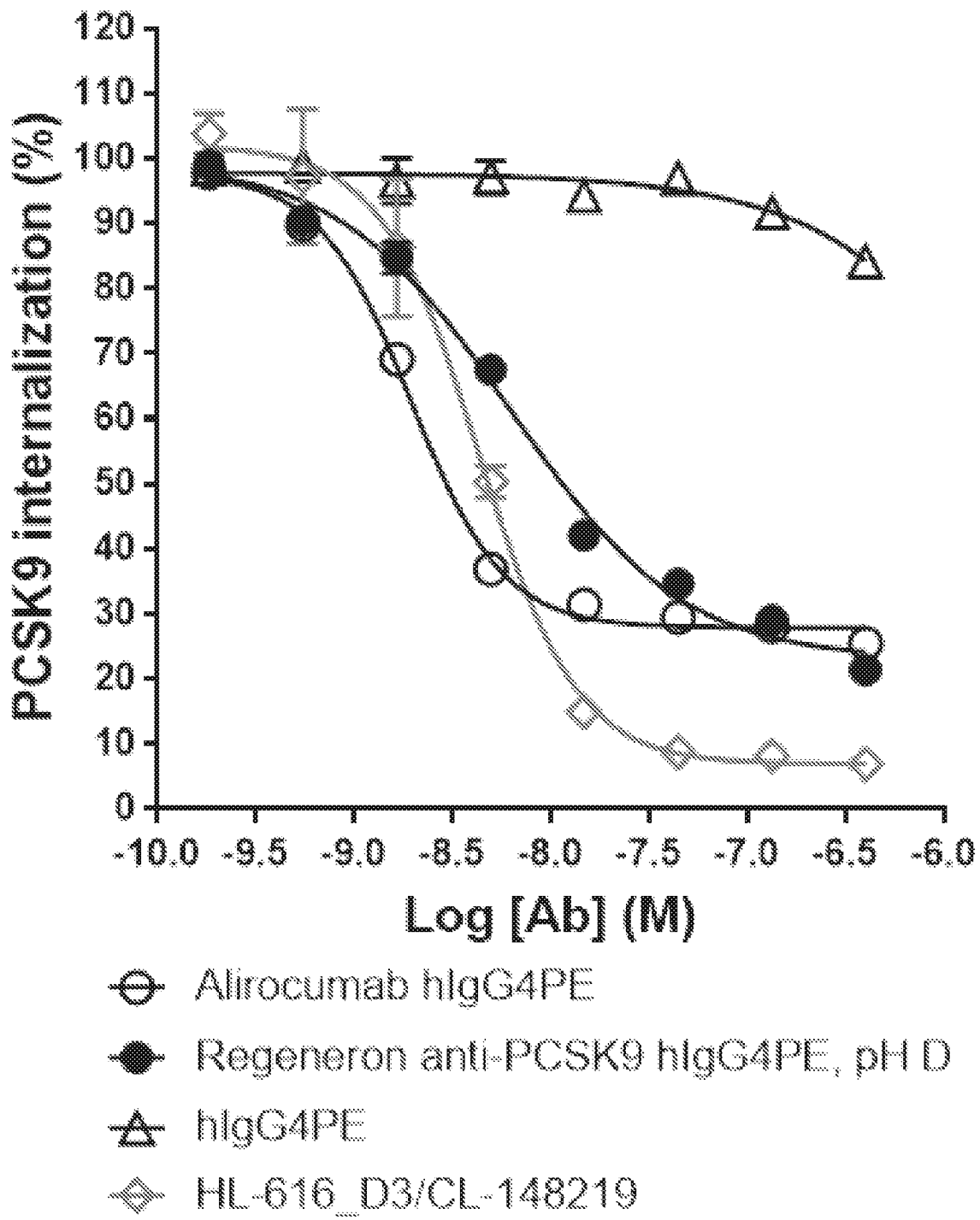
FIG. 1: CL-148219 hPCSK9 neutralisation versus benchmark antibodies.
Figure 2:
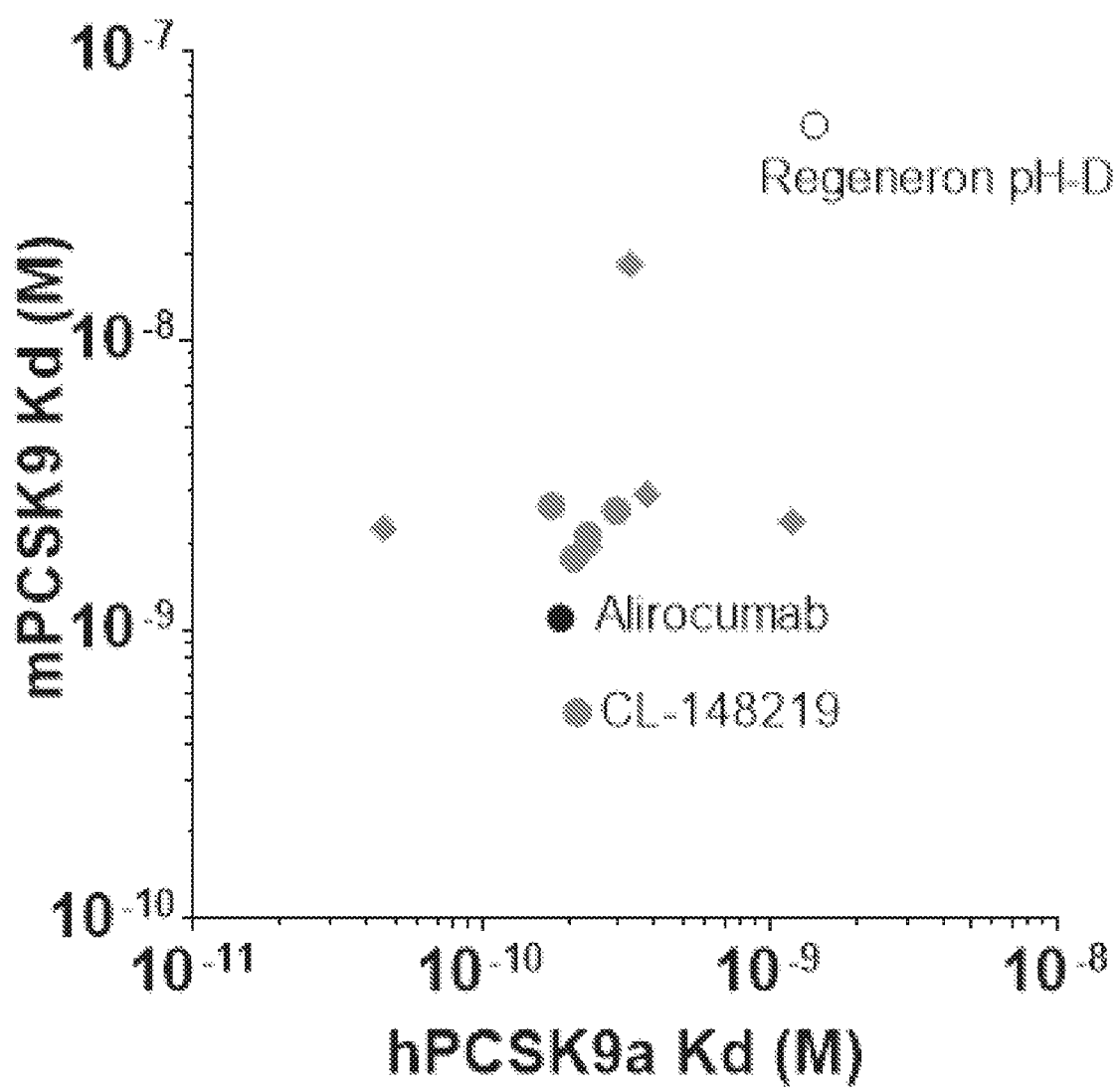
FIG. 2: CL-148219 restoration of LDL uptake versus benchmark antibodies.
Figure 3:
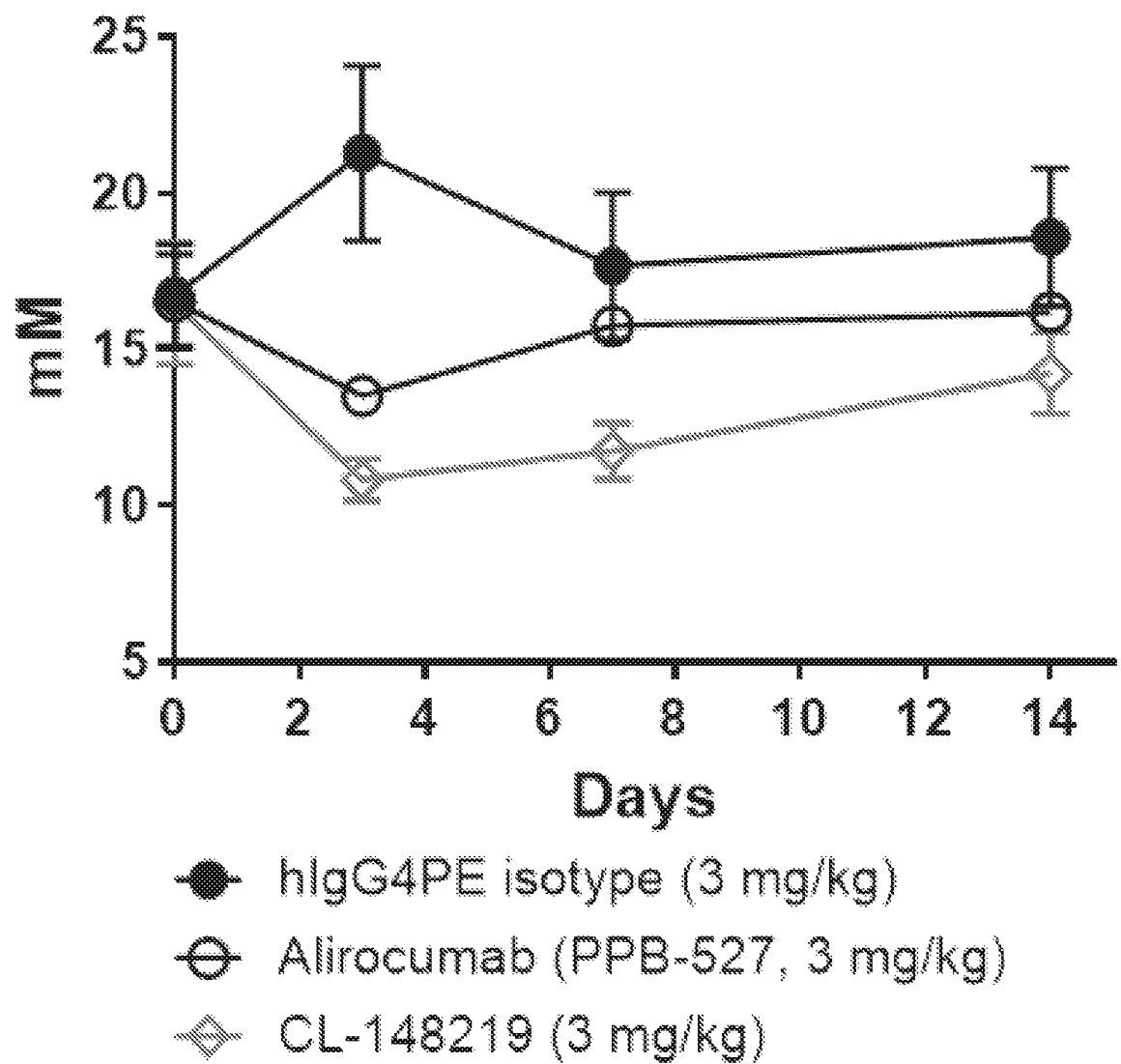
FIG. 3: CL-148219 affinity versus benchmark antibodies.
Figure 4:
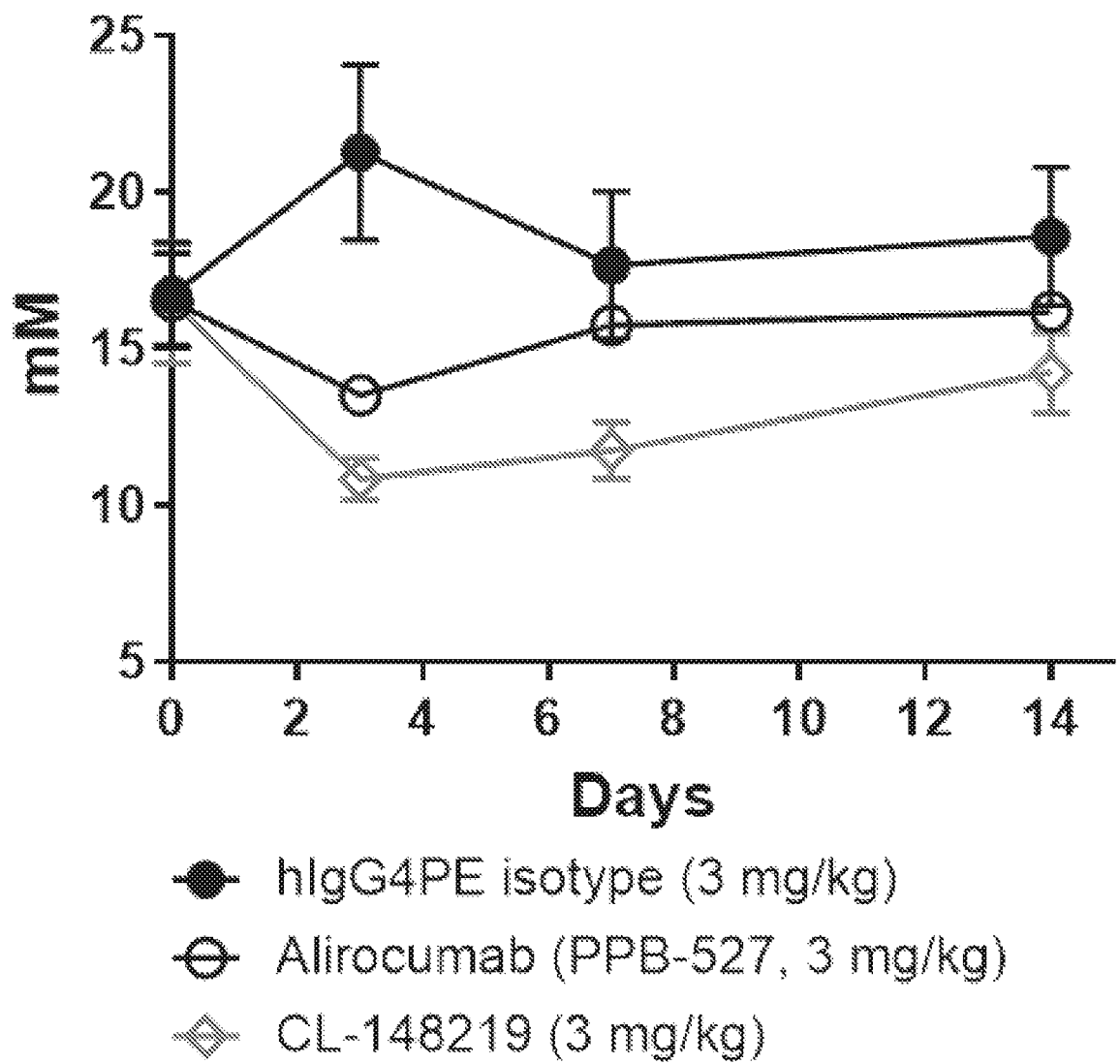
FIG. 4: CL-148219 plasma non-HDL reduction versus benchmark antibodies.
Figure 5:
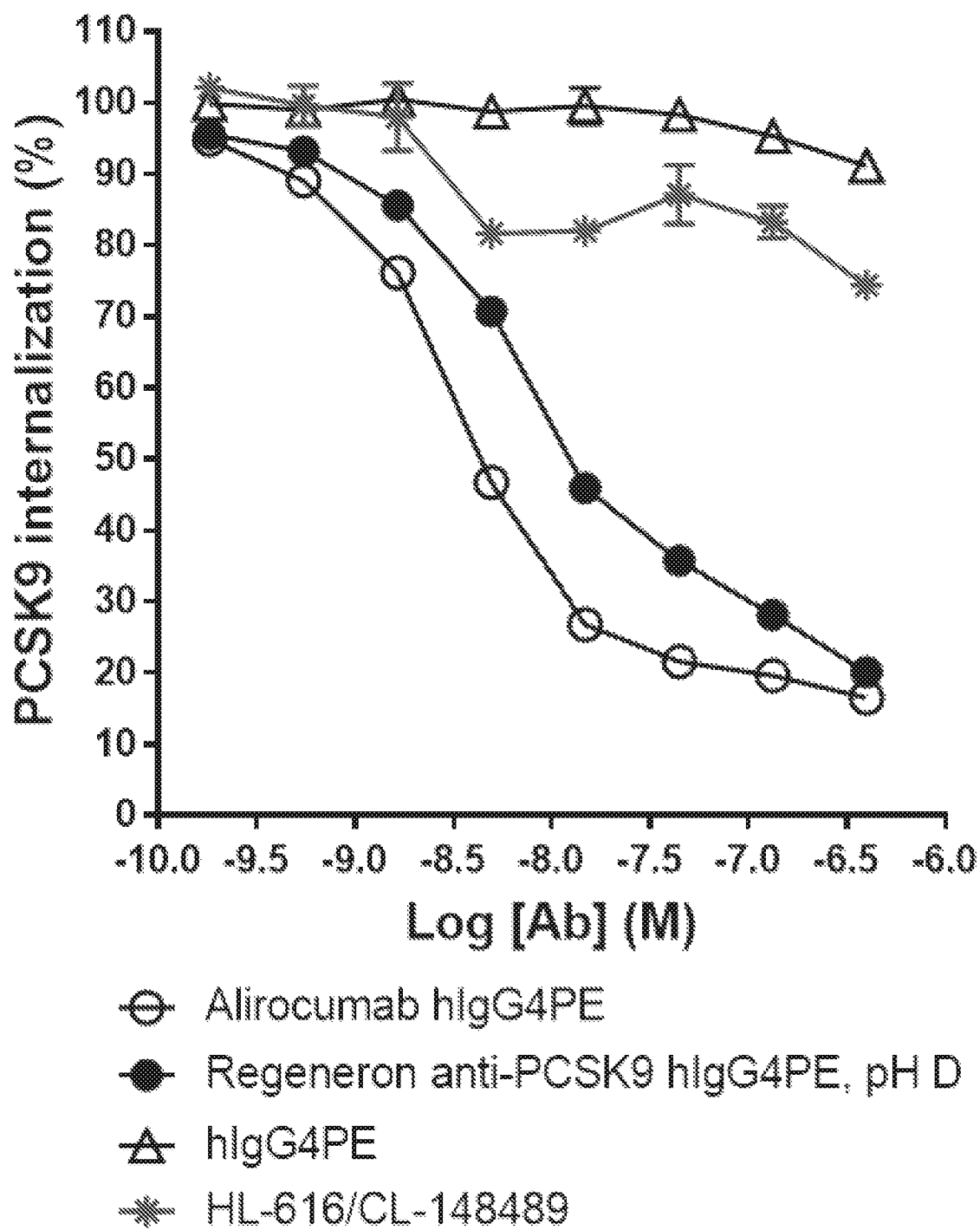
FIG. 5: CL-148489 hPCSK9 neutralisation versus benchmark antibodies.
Figure 6:
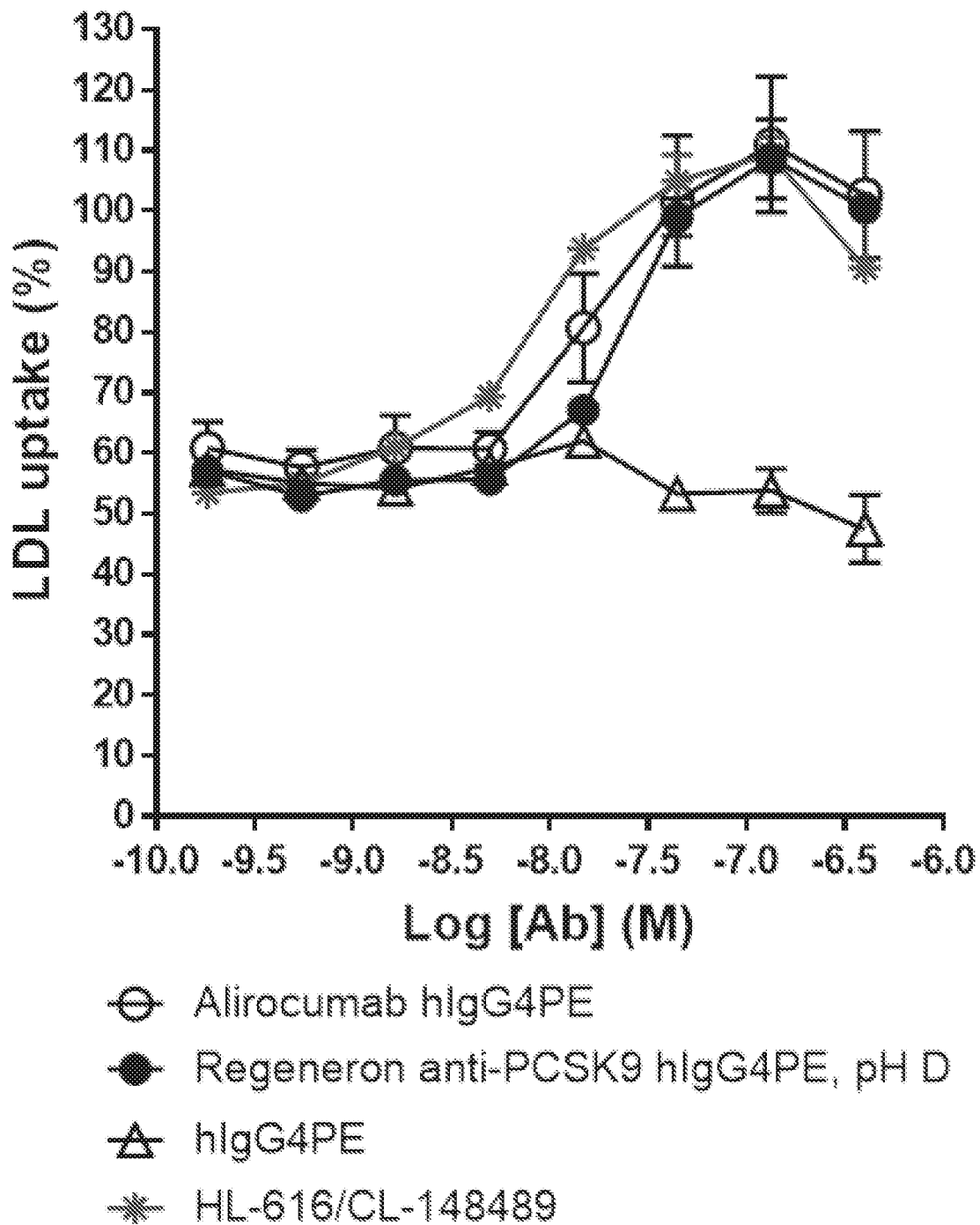
FIG. 6: CL-148489 restoration of LDL uptake versus benchmark antibodies.
Figure 7:
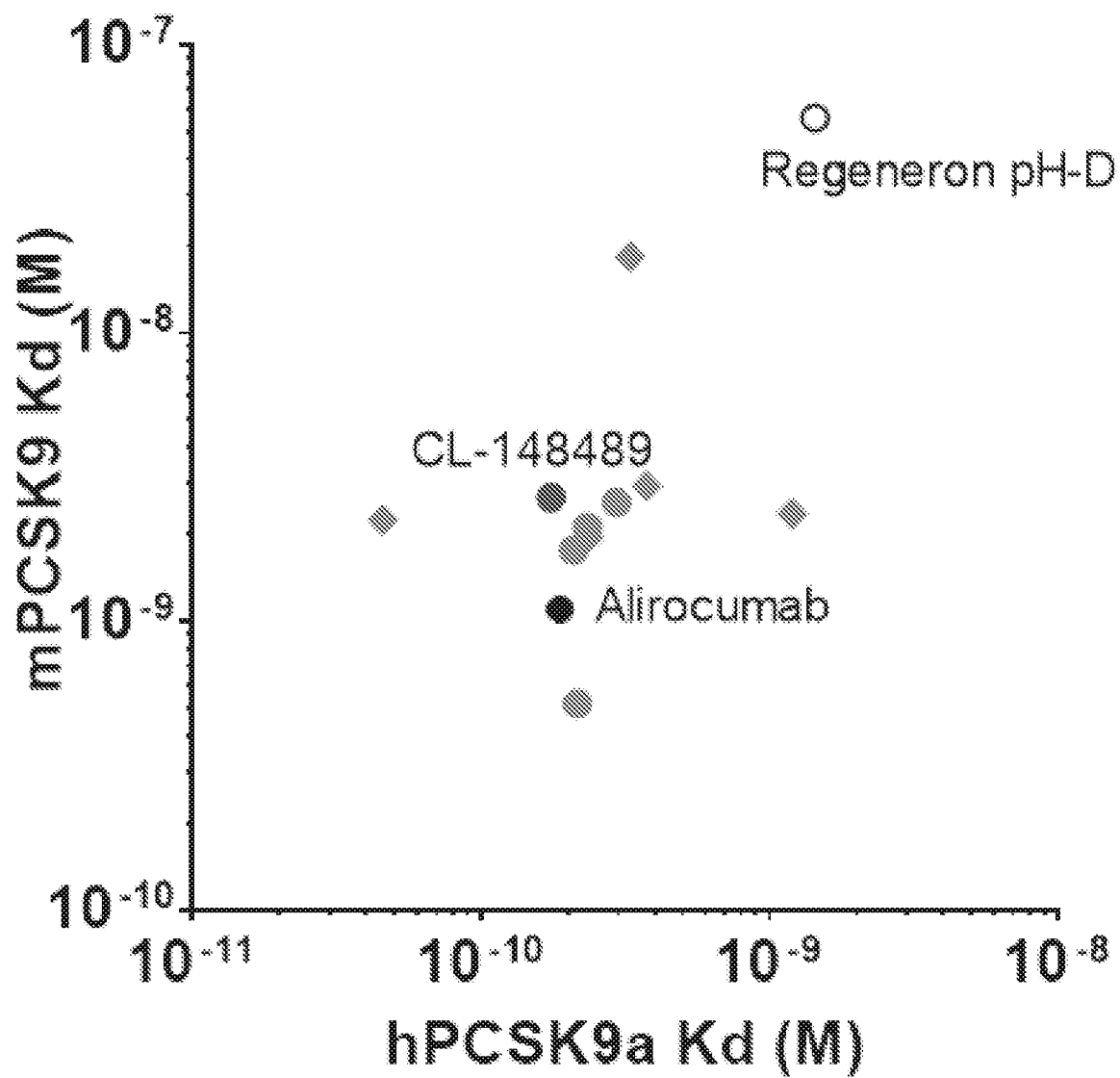
FIG. 7: CL-148489 affinity versus benchmark antibodies.
Figure 8:
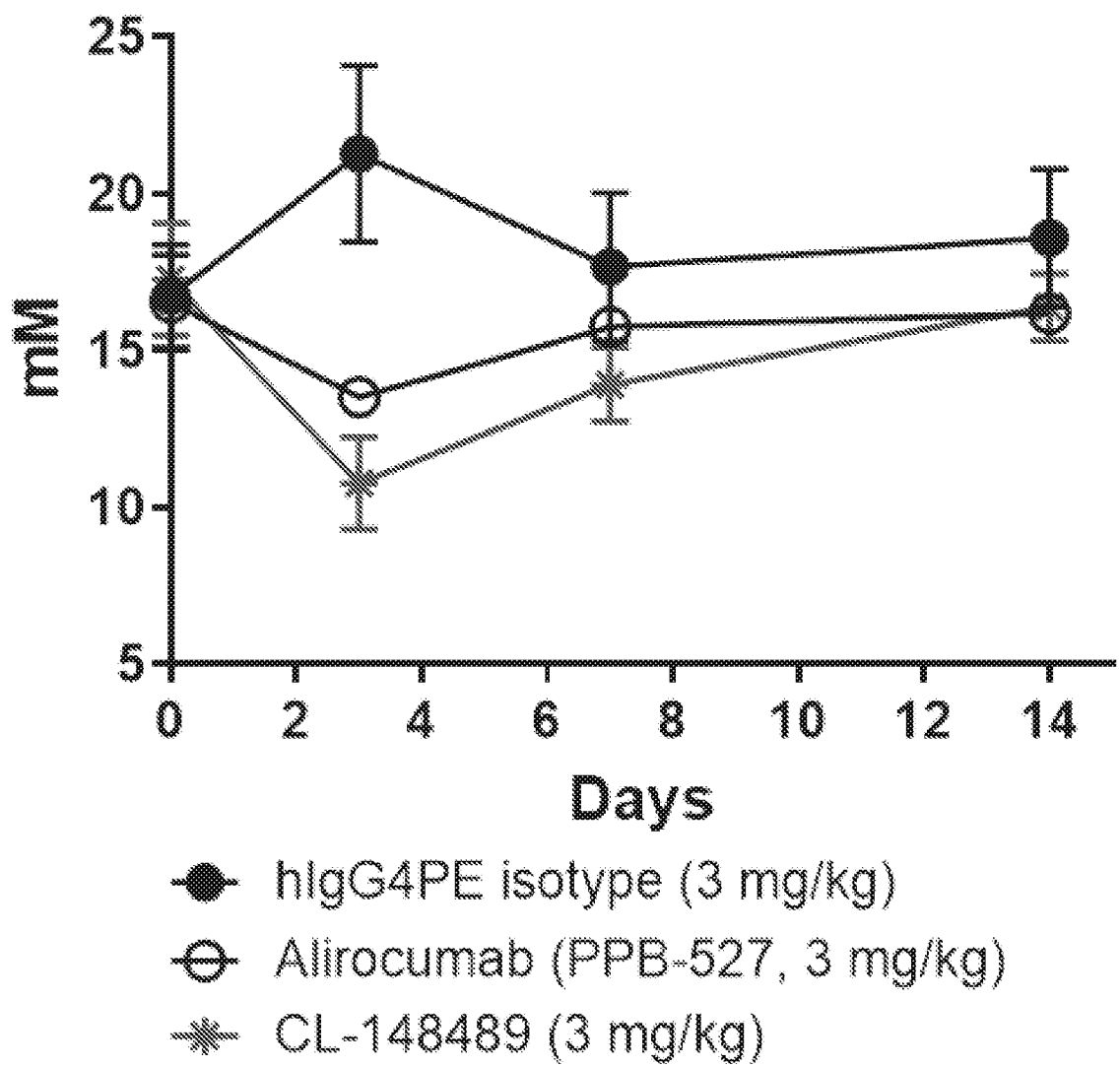
FIG. 8: CL-148489 plasma non-HDL reduction versus benchmark antibodies.

Unless otherwise defined herein, scientific and technical terms shall have the meanings that are commonly understood by those of ordinary skill in the art. Further, unless otherwise required by context, singular terms shall include pluralities and plural terms shall include the singular. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia and is used herein to indicate a non-limiting example. Thus, the abbreviation "e.g." is synonymous with the term "for example." In the specification and claims, the term "about" is used to modify, for example, the quantity of an ingredient in a composition, concentration, volume, process temperature, process time, yield, flow rate, pressure, and like values, and ranges thereof, employed in describing the embodiments of the disclosure. The term "about" refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

As used herein, "administer" or "administration" refers to the act of injecting or otherwise physically delivering a substance as it exists outside the body (e.g., an anti-hPCSK9 antibody provided herein) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

The term "antibody", "immunoglobulin" or "Ig" may be used interchangeably herein and means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies (including dual binding antibodies), chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. The term "antibody" can also refer to a Y-shaped glycoprotein with a molecular weight of approximately 150 kDa that is made up of four polypeptide chains: two light (L) chains and two heavy (H) chains. There are five types of mammalian Ig heavy chain isotypes denoted by the Greek letters alpha (α), delta (δ), epsilon (ε), gamma (γ), and mu (μ). The type of heavy chain defines the class of antibody, i.e., IgA, IgD, IgE, IgG, and IgM, respectively. The γ and α classes are further divided into subclasses on the basis of differences in the constant domain sequence and function, e.g., IgG1, hIgG2, mIgG2A, mIgG2B, IgG3, IgG4, IgA1 and IgA2. In mammals, there are two types of immunoglobulin light chains, λ and κ. The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. An example of antibodies are heavy chain-only (ie, H2) antibodies that comprise a dimer of a heavy chain (5'-VH-(optional Hinge)-CH2-CH3-3') and are devoid of a light chain.

The antibodies described herein may be oligoclonal, polyclonal, monoclonal (including full-length monoclonal antibodies), camelised, chimeric, CDR-grafted, multi-specific, bi-specific (including dual-binding antibodies), catalytic, chimeric, humanized, fully human, anti-idiotypic, including antibodies that can be labelled in soluble or bound form as well as fragments, variants or derivatives thereof, either alone or in combination with other amino acid sequences provided by known techniques. An antibody may be from any species. Antibodies described herein can be naked or conjugated to other molecules such as toxins, radioisotopes, etc.

The term "antigen binding site," "antigen binding domain," "antigen binding region," "antigen binding fragment," and similar terms refer to that portion of an antibody which comprises the amino acid residues that interact with an antigen and confer on the binding agent its specificity and affinity for the antigen (e.g. the complementarity determining regions (CDRs)). The antigen binding region can be derived from any animal species, such as rodents (e.g. rabbit, rat or hamster) and humans. Preferably, the antigen binding region will be of human origin.

Antigen binding fragments described herein can include single-chain Fvs (scFv), single-chain antibodies, single domain antibodies, domain antibodies, Fv fragments, Fab fragments, F(ab') fragments, F(ab')$_2$ fragments, antibody fragments that exhibit the desired biological activity, disulfide-stabilised variable region (dsFv), dimeric variable region (diabody), anti-idiotypic (anti-Id) antibodies (including, e.g. anti-Id antibodies to antibodies), intrabodies, linear antibodies, single-chain antibody molecules and multispecific antibodies formed from antibody fragments and epitope-binding fragments of any of the above. In particular, antibodies and antibody fragments described herein can include immunoglobulin molecules and immunologically active fragments of immunoglobulin molecules, i.e., molecules that contain an antigen-binding site. Digestion of antibodies with the enzyme, papain, results in two identical antigen-binding fragments, known also as "Fab" fragments, and a "Fc" fragment, having no antigen-binding activity but having the ability to crystallize. "Fab" when used herein refers to a fragment of an antibody that includes one constant and one variable domain of each of the heavy and light chains. The term "Fc region" herein is used to define a C-terminal region of an immunoglobulin heavy chain, including native-sequence Fc regions and variant Fc regions. The "Fc fragment" refers to the carboxy-terminal portions of both H chains held together by disulfides. The effector functions of antibodies are determined by sequences in the Fc region, the region which is also recognized by Fc receptors (FcR) found on certain types of cells. Digestion of antibodies with the enzyme, pepsin, results in a F(ab')$_2$ fragment in which the two arms of the antibody molecule remain linked and comprise two-antigen binding sites. The F(ab')$_2$ fragment has the ability to crosslink antigen.

The term "derived from the recombination of" in relation to gene segments will be readily apparent to the skilled person, who will understand that B-cells recombine their variable region gene segments to produce coding sequence for variable domains. For example "derived from the recombination of a human VH gene segment, DH gene segment and JH gene segment" relates to the recombination of one human VH gene segment, with one DH gene segment and one JH gene segment together to form a rearranged VDJ sequence encoding a heavy chain antibody variable domain. Junctional and somatic hypermutation may also be features of the process, whereby the resulting recombined VDJ sequence includes one or more nucleotide additions, substitutions or deletions (eg, p-additions and/or n-additions) that are not comprised by the germline V, D and J sequences. The equivalent will be said of $V_K$ and $J_K$ gene segments for a kappa light chain variable domain, and of Vλ and Jλ for a lambda light chain variable domain. It is intended that any post-translational modifications may additionally encompassed in variable domains.

"Fv" when used herein refers to the minimum fragment of an antibody that retains both antigen-recognition and antigen-binding sites. This region consists of a dimer of one heavy and one light chain variable domain in tight, non-covalent or covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an $F_V$ comprising only three CDRs specific for an antigen) has the ability to recognize and bind antigen, although at a lower affinity than the entire binding site.

The term "monoclonal antibody" as used herein refers to an antibody obtained from a population of substantially homogeneous antibodies, i.e. the individual antibodies comprising the population are identical except for possible naturally occurring mutations and/or post-translation modifications (e.g. isomerizations, amidations) that may be present in minor amounts. Monoclonal antibodies are highly specific and are directed against a single antigenic determinant or epitope. In contrast, polyclonal antibody preparations typically include different antibodies directed against different antigenic determinants (or epitopes). The term "monoclonal antibody" as used herein encompasses both intact and full-length monoclonal antibodies as well as antibody fragments (such as Fab, Fab', F(ab')$_2$, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, hybridoma, phage selection, recombinant expression, and transgenic animals. The monoclonal antibodies herein can include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies that exhibit the desired biological activity.

The term "humanised antibody" refers to a subset of chimeric antibodies in which a "hypervariable region" from a non-human immunoglobulin (the donor antibody) replaces residues from a hypervariable region in a human immunoglobulin (recipient antibody). In general, a humanized antibody will include substantially all of at least one, and typically two, variable domains, in which all or substantially all of the hypervariable loops correspond to those of a non-human immunoglobulin sequence, and all or substantially all of the framework regions are those of a human immunoglobulin sequence, although the framework regions may include one or more substitutions that improve antibody performance, such as binding affinity, isomerization, immunogenicity, etc.

The term "bispecific antibody" means an antibody which comprises specificity for two target molecules, and includes, but is not limited to, formats such as DVD-Ig (see DiGiammarino et al., "Design and generation of DVD-Ig™ molecules for dual-specific targeting", Meth. Mo. Biol., 2012, 889, 145-156), mAb$^2$ (see WO2008/003103, the description of the mAb$^2$ format is incorporated herein by reference), FIT-Ig (see WO2015/103072, the description of the FIT-Ig scaffold is incorporated herein by reference), mAb-dAb, dock and lock, Fab-arm exchange, SEEDbody, Triomab, LUZ-Y, Fcab, Kλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, TriBi minibody, scFv-CH3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG (L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv, scFv4-Ig and zybody. For a review of bispecific formats, see Spiess, C., et al., Mol. Immunol. (2015). In another embodiment, the bispecific molecule comprises an antibody which is fused to another non-Ig format, for example a T-cell receptor binding domain; an immunoglobulin superfamily domain; an agnathan variable lymphocyte receptor; a fibronectin domain (e.g. an Adnectin™); an antibody constant domain (e.g. a CH$_3$ domain, e.g., a CH$_2$ and/or CH$_3$ of an Fcab™) wherein the constant domain is not a functional CH$_1$ domain; an scFv; an (scFv)$_2$; an sc-diabody; an scFab; a centyrin and an epitope binding domain derived from a scaffold selected from CTLA-4 (Evibody™); a lipocalin domain; Protein A such as Z-domain of Protein A (e.g. an Affibody™ or SpA); an A-domain (e.g. an Avimer™ or Maxibody™); a heat shock protein (such as and epitope binding domain derived from GroEl and GroES); a transferrin domain (e.g. a trans-body); ankyrin repeat protein (e.g. a DARPin™); peptide aptamer; C-type lectin domain (e.g. Tetranectin™); human γ-crystallin or human ubiquitin (an affilin); a PDZ domain; scorpion toxin; and a kunitz type domain of a human protease inhibitor. See, eg, U.S. Pat. No. 5,731,568 and WO98/50431 (both incorporated herein by reference) for non-limiting examples of knob-in-hole technology.

The principle is to engineer paired CH3 domains of heterodimeric heavy chains so that one CH3 domain contains a "knob" and the other CH3 domains contains a "hole" at a sterically opposite position. Knobs are created by replacing small amino acid side chain at the interface between the CH3 domains, while holes are created by replacing large side chains with smaller ones. The knob is designed to insert into the hole, to favour heterodimerisation of the different CH3 domains while destabilising homodimer formation. In in a mixture of antibody heavy and light chains that assemble to form a bispecific antibody, the proportion of IgG molecules having paired heterodimeric heavy chains is thus increased, raising yield and recovery of the active molecule Mutations Y349C and/or T366W may be included to form "knobs" in an IgG CH3 domain. Mutations E356C, T366S, L368A and/or Y407V may be included to form "holes" in an IgG CH3 domain. Knobs and holes may be introduced into any human IgG CH3 domain, e.g., an IgG1, IgG2, IgG3 or IgG4 CH3 domain. A preferred example is IgG4. As noted, the IgG4 may include further modifications such as the "P" and/or "E" mutations. The IgG4 type a ("ra") sequence contains substitutions Y349C and T366W ("knobs"), and the IgG4 type b ("γb") sequence contains substitutions E356C, T366S, L368A, and Y407V ("holes"). Both ra and γb also contain the "P" substitution at position 228 in the hinge (S228P), to stabilise the hinge region of the heavy chain. Both ra and γb also contain the "E" substitution in the CH2 region at position 235 (L235S), to abolish binding to FcγR. Thus the relevant sequence of the IgG4-PE heavy chain is ppcpPcpapefEggps.

A further advance in bispecific IgG engineering was the idea of using a common light chain, as described in WO98/50431. Bispecific antibodies comprising two heavy-light chain pairs were described, in which the variable light chains of both heavy-light chain pairs had a common sequence. WO98/50431 described combining the common light chain approach with specific complementary interactions in the heavy chain heterodimerisation interface (such as knobs-into-holes) to promote heterodimer formation and hinder homodimer formation. In combination, these approaches enhance formation of the desired heterodimer relative to undesired heterodimers and homodimers. While knobs-into-holes technology involves engineering amino acid side chains to create complementary molecular shapes at the interface of the paired CH3 domains in the bispecific heterodimer, another way to promote heterodimer formation and hinder homodimer formation is to engineer the amino acid side chains to have opposite charges. Association of CH3 domains in the heavy chain heterodimers is favoured by the pairing of oppositely charged residues, while paired positive charges or paired negative charges would make homodimer formation less energetically favourable. WO2006/106905 described a method for producing a heteromultimer composed of more than one type of polypeptide (such as a heterodimer of two different antibody heavy chains) comprising a substitution in an amino acid residue forming an interface between said polypeptides such that heteromultimer association will be regulated, the method comprising:

(a) modifying a nucleic acid encoding an amino acid residue forming the interface between polypeptides from the original nucleic acid, such that the association between polypeptides forming one or more multimers will be inhibited in a heteromultimer that may form two or more types of multimers;

(b) culturing host cells such that a nucleic acid sequence modified by step (a) is expressed; and (c) recovering said heteromultimer from the host cell culture, wherein the modification of step (a) is modifying the original nucleic acid so that one or more amino acid residues are substituted at the interface such that two or more amino acid residues, including the mutated residue(s), forming the interface will carry the same type of positive or negative charge.

An example of this is to suppress association between heavy chains by introducing electrostatic repulsion at the interface of the heavy chain homodimers, for example by modifying amino acid residues that contact each other at the interface of the CH3 domains, including:

positions 356 and 439
positions 357 and 370
positions 399 and 409,
the residue numbering being according to the EU numbering system.

By modifying one or more of these pairs of residues to have like charges (both positive or both negative) in the CH3 domain of a first heavy chain, the pairing of heavy chain homodimers is inhibited by electrostatic repulsion. By engineering the same pairs or pairs of residues in the CH3 domain of a second (different) heavy chain to have an opposite charge compared with the corresponding residues in the first heavy chain, the heterodimeric pairing of the first and second heavy chains is promoted by electrostatic attraction.

Amino acids at the heavy chain constant region CH3 interface were modified to introduce charge pairs, the mutations being listed in Table 1 of WO2006/106905. It was reported that modifying the amino acids at heavy chain positions 356, 357, 370, 399, 409 and 439 to introduce charge-induced molecular repulsion at the CH3 interface had the effect of increasing efficiency of formation of the intended bispecific antibody. For example, one heavy chain constant region may be an IgG4 constant region containing mutation K439E (positively charged Lys replaced by negatively charged Glu) and the other heavy chain constant region may be an IgG4 constant region containing mutation E356K (negatively charged Glu replaced by positively charged Lys), using EU numbering. "Charge pairing" results from spatial proximity of residues 439 and 356 in an Fc region assembled from heterodimerisation of these two constant regions.

Where two different heavy chain constant regions are used, these may be connected to the two different VH domains of the antibody in either orientation.

WO2006/106905 also exemplified bispecific IgG antibodies in which the CH3 domains of IgG4 were engineered with knobs-into-holes mutations. Type a Type a (IgG4γa) was an IgG4 substituted at Y349C and T366W, and type b (IgG4γb) was an IgG4 substituted at E356C, T366S, L368A, and Y407V. In another example, introduction of charge pairs in the antibody VH and VL domains was used to inhibit the formation of "incorrect" VH-VL pairs (pairing of VH from one antibody with VL of the other antibody). In one example, Q residues in the VH and VL were changed to K or R (positive), or to E or D (negative), to inhibit hydrogen bonding between the Q side chains and to introduce electrostatic repulsion.

Further examples of charge pairs were disclosed in WO2013/157954, which described a method for producing a heterodimeric CH3 domain-comprising molecule from a single cell, the molecule comprising two CH3 domains capable of forming an interface. The method comprised providing in the cell (a) a first nucleic acid molecule encoding a first CH3 domain-comprising polypeptide chain, this chain comprising a K residue at position 366 according to the EU numbering system and (b) a second nucleic acid molecule encoding a second CH3 domain-comprising polypeptide chain, this chain comprising a D residue at position 351 according to the EU numbering system, the method further comprising the step of culturing the host cell, allowing expression of the two nucleic acid molecules and harvesting the heterodimeric CH3 domain-comprising molecule from the culture.

Further methods of engineering electrostatic interactions in polypeptide chains to promote heterodimer formation over homodimer formation were described in WO2011/143545.

Another example of engineering at the CH3-CH3 interface is strand-exchange engineered domain (SEED) CH3 heterodimers. The CH3 domains are composed of alternating segments of human IgA and IgG CH3 sequences, which form pairs of complementary SEED heterodimers referred to as "SEED-bodies" [WO2007/110205].

Bispecifics have also been produced with heterodimerised heavy chains that are differentially modified in the CH3 domain to alter their affinity for binding to a purification reagent such as Protein A. WO2010/151792 described a heterodimeric bispecific antigen-binding protein comprising a first polypeptide comprising, from N-terminal to C-terminal, a first epitope-binding region that selectively binds a first epitope, an immunoglobulin constant region that comprises a first CH3 region of a human IgG selected from IgG1, IgG2, and IgG4; and a second polypeptide comprising, from N-terminal to C-terminal, a second epitope-binding region that selectively binds a second epitope, an immunoglobulin constant region that comprises a second CH3 region of a human IgG selected from IgG1, IgG2, and IgG4, wherein the second CH3 region comprises a modification that reduces or eliminates binding of the second CH3 domain to Protein A.

The Fc region may thus comprise one or more mutations to promote differential purification of the active heterodimer from homodimer species. The CH3 of one heavy chain constant region may comprise the mutation His435Arg and/or Tyr436Phe (EU numbering) [ ] while the CH3 of the other heavy chain constant region lacks said mutations.

Emicizumab, for example, comprises an Fc region in which one CH3 comprises His435 and the other CH3 comprises His435Arg.

The bispecifics of the present invention may employ any of these bispecifics techniques and molecular formats as desired.

In one embodiment, the bispecific antibody is a mAb². A mAb² comprises a $V_H$ and $V_L$ domain from an intact antibody, fused to a modified constant region, which has been engineered to form an antigen-binding site, known as an "Fcab". The technology behind the Fcab/mAb² format is described in more detail in WO2008/003103, and the description of the mAb² format is incorporated herein by reference.

In another embodiment, the bispecific antibody is a "dual binding antibody". As used herein, the term "dual binding antibody" is a bispecific antibody wherein both antigen-binding domains are formed by a $V_H/V_L$ pair, and includes FIT-Ig (see WO2015/103072, incorporated herein by reference), mAb-dAb, dock and lock, Fab-arm exchange, SEED-body, Triomab, LUZ-Y, Fcab, Kλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, scFv-CH₃ KIH, scFv-CH-CL-scFv, F(ab')₂-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG (L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv and scFv4-Ig.

The term "hypervariable region", "CDR region" or "CDR" refers to the regions of an antibody variable domain which are hypervariable in sequence and/or form structurally defined loops. Generally, antigen binding sites of an antibody include six hypervariable regions: three in the $V_H$ (CDRH1, CDRH2, CDRH3), and three in the $V_L$ (CDRL1, CDRL2, CDRL3). These regions of the heavy and light chains of an antibody confer antigen-binding specificity to the antibody. CDRs may be defined according to the Kabat system (see Kabat, E. A. et al., 1991, "Sequences of Proteins of Immunological Interest", 5th edit., NIH Publication no. 91-3242, U.S. Department of Health and Human Services).

Other systems may be used to define CDRs, which as the system devised by Chothia et al (see Chothia, C. & Lesk, A. M., 1987, "Canonical structures for the hypervariable regions of immunoglobulins", J. Mol. Biol., 196, 901-917) and the IMGT system (see Lefranc, M. P., 1997, "Unique database numbering system for immunogenetic analysis", Immunol. Today, 18, 50). An antibody typically contains 3 heavy chain CDRs and 3 light chain CDRs. The term CDR or CDRs is used here to indicate one or several of these regions. A person skilled in the art is able to readily compare the different systems of nomenclature and determine whether a particular sequence may be defined as a CDR.

A "human antibody" is an antibody that possesses an amino-acid sequence corresponding to that of an antibody produced by a human and/or has been made using any of the techniques for making human antibodies and specifically excludes a humanized antibody comprising non-human antigen-binding residues. The term "specifically binds to" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g. by a radioimmunoassay (RIA).

An antibody or a fragment thereof that specifically binds to a hPCSK9 antigen may be cross-reactive with related antigens. Preferably, an antibody or a fragment thereof that specifically binds to a hPCSK9 antigen does not cross-react with other antigens (but may optionally cross-react with PCSK9 of a different species, e.g. rhesus, or murine). An antibody or a fragment thereof that specifically binds to a hPCSK9 antigen can be identified, for example, by immunoassays, BIAcore™, or other techniques known to those of skill in the art. An antibody or a fragment thereof binds specifically to a PCSK9 antigen when it binds to a hPCSK9 antigen with higher affinity than to any cross-reactive antigen as determined using experimental techniques, such as radioimmunoassays (RIA) and enzyme-linked immunosorbent assays (ELISAs). Typically, a specific or selective reaction will be at least twice background signal or noise and more typically more than 10 times (such as more than 15 times, more than 20 times, more than 50 times or more than 100 times) background. See, e.g. Paul, ed., 1989, Fundamental Immunology Second Edition, Raven Press, New York at pages 332-336 for a discussion regarding antibody specificity.

The term "aliphatic amino acid" means that the amino acid R groups are nonpolar and hydrophobic. Hydrophobicity increases with increasing number of C atoms in the hydrocarbon chain. Glycine, Alanine, Valine, Leucine and Isoleucine are aliphatic amino acids.

The term "aromatic amino acid" means that the amino acid R groups contain an aromatic ring system. Phenylalanine, Tyrosine and Tryptophan are aromatic amino acids.

The term "hydroxyl-containing amino acid" means that the amino acid R groups contain a hydroxyl group and are hydrophilic. Serine, Cysteine, Threonine and Methionine are hydroxyl-containing amino acids.

The term "basic amino acid" means that the amino acid R groups are nitrogen containing and are basic at neutral pH. Histidine, Lysine and Arginine are basic amino acids.

The term "cyclic amino acid" means that the amino acid R groups have an aliphatic cyclic structure. Proline is the only cyclic aliphatic amino acid.

The term "acidic amino acid" means that the amino acid R groups are polar and are negatively charged at physiological pH. Aspartate and Glutamate are acidic amino acids.

The term "amide amino acid" means that the amino acid R groups contain an amide group. Asparagine and Glutamine are amide amino acids.

As used herein, "authorization number" or "marketing authorization number" refers to a number issued by a regulatory agency upon that agency determining that a particular medical product and/or composition may be marketed and/or offered for sale in the area under the agency's jurisdiction. As used herein "regulatory agency" refers to one of the agencies responsible for evaluating, e.g. the safety and efficacy of a medical product and/or composition and controlling the sales/marketing of such products and/or compositions in a given area. The Food and Drug Administration (FDA) in the US and the European Medicines Agency (EPA) in Europe are but two examples of such regulatory agencies. Other non-limiting examples can include SDA, MPA, MHPRA, IMA, ANMAT, Hong Kong Department of Health-Drug Office, CDSCO, Medsafe, and KFDA.

As used herein, a "buffer" refers to a chemical agent that is able to absorb a certain quantity of acid or base without undergoing a strong variation in pH.

As used herein, the term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

As used herein, the term "composition" is intended to encompass a product containing the specified ingredients (e.g. an antibody of the invention) in, optionally, the specified amounts, as well as any product which results, directly or indirectly, from combination of the specified ingredients in, optionally, the specified amounts.

As used herein the term "comprising" or "comprises" is used with reference to antibodies, fragments, uses, compositions, methods, and respective component(s) thereof, that are essential to the method or composition, yet open to the inclusion of unspecified elements, whether essential or not.

The term "consisting of" refers to antibodies, fragments, uses, compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

In the context of a polypeptide, the term "derivative" as used herein includes a polypeptide that comprises an amino acid sequence of a hPCSK9 polypeptide, a fragment of a hPCSK9 polypeptide, or an antibody or fragment that specifically binds to a hPCSK9 polypeptide which has been altered by the introduction of amino acid residue substitutions, deletions or additions. The term "derivative" as used herein also includes a hPCSK9 polypeptide, a fragment of a hPCSK9 polypeptide, or an antibody that specifically binds to a hPCSK9 polypeptide which has been chemically modified, e.g. by the covalent attachment of any type of molecule to the polypeptide. For example, but not by way of limitation, a hPCSK9 polypeptide, a fragment of a hPCSK9 polypeptide, or a hPCSK9 antibody may be chemically modified, e.g. by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a hPCSK9 polypeptide, a fragment of a hPCSK9 polypeptide, or a hPCSK9 antibody may be chemically modified by chemical modifications using techniques known to those of skill in the art, including, but not limited to specific chemical cleavage, acetylation, formulation, metabolic synthesis of tunicamycin, etc. Further, a derivative of a hPCSK9 polypeptide, a fragment of a hPCSK9 polypeptide, or a hPCSK9 antibody may contain one or more non-classical amino acids. A polypeptide derivative possesses a similar or identical function as a hPCSK9 polypeptide, a fragment of a hPCSK9 polypeptide, or a hPCSK9 antibody described herein.

The term "effector function" (or "effector-enabled") as used herein refers to one or more of antibody dependent cell mediated cytotoxic activity (ADCC), complement-dependent cytotoxic activity (CDC) mediated responses, Fc-mediated phagocytosis or antibody dependent cellular phagocytosis (ADCP) and antibody recycling via the FcRn receptor.

An "effective amount" refers to an amount effective, at dosages and for periods of time necessary, to achieve the desired effect, including a therapeutic or prophylactic result. A "therapeutically effective amount" refers to the minimum concentration required to effect a measurable improvement or prevention of a particular disorder. A therapeutically effective amount herein may vary according to factors such as the disease state, age, sex, and weight of the patient, and the ability of the antibody to elicit a desired response in the individual. A therapeutically effective amount is also one in which toxic or detrimental effects of the antibody are outweighed by the therapeutically beneficial effects. A "prophylactically effective amount" refers to an amount effective, at the dosages and for periods of time necessary, to achieve the desired prophylactic result. In some embodiments, the effective amount of an antibody of the invention is from about 0.1 mg/kg (mg of antibody per kg weight of the subject) to about 100 mg/kg. In certain embodiments, an effective amount of an antibody provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg about 90 mg/kg or about 100 mg/kg (or a range therein). In some embodiments, "effective amount" as used herein also refers to the amount of an antibody of the invention to achieve a specified result (e.g. inhibition of a hPCSK9 biological activity of a cell). The term "epitope" as used herein refers to a localized region on the surface of an antigen, such as hPCSK9 polypeptide or hPCSK9 polypeptide fragment, that is capable of being bound to one or more antigen binding regions of an antibody, and that has antigenic or immunogenic activity in an animal, preferably a mammal, and most preferably in a human, that is capable of eliciting an immune response. An epitope having immunogenic activity is a portion of a polypeptide that elicits an antibody response in an animal. An epitope having antigenic activity is a portion of a polypeptide to which an antibody specifically binds as determined by any method well known in the art, for example, by the immunoassays described herein. Antigenic epitopes need not necessarily be immunogenic. Epitopes usually consist of chemically active surface groupings of molecules such as amino acids or sugar side chains and have specific three-dimensional structural characteristics as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a hPCSK9 epitope is a three-dimensional surface feature of a hPCSK9 polypeptide (e.g. in a trimeric form of a hPCSK9 polypeptide). In other embodiments, a hPCSK9 epitope is linear feature of a hPCSK9 polypeptide (e.g. in a trimeric form or monomeric form of the hPCSK9 polypeptide). Antibodies provided herein may specifically bind to an epitope of the monomeric (denatured) form of hPCSK9, an epitope of the trimeric (native) form of hPCSK9, or both the monomeric (denatured) form and the trimeric (native) form of hPCSK9. In specific embodiments, the antibodies provided herein specifically bind to an epitope of the trimeric form of hPCSK9 but do not specifically bind the monomeric form of hPCSK9.

The term "excipients" as used herein refers to inert substances which are commonly used as a diluent, vehicle, preservatives, binders, or stabilizing agent for drugs and includes, but not limited to, proteins (e.g. serum albumin, etc.), amino acids (e.g. aspartic acid, glutamic acid, lysine, arginine, glycine, histidine, etc.), fatty acids and phospholipids (e.g. alkyl sulfonates, caprylate, etc.), surfactants (e.g. SDS, polysorbate, nonionic surfactant, etc.), saccharides (e.g. sucrose, maltose, trehalose, etc.) and polyols (e.g. mannitol, sorbitol, etc.). See, also, Remington's Pharmaceutical Sciences (1990) Mack Publishing Co., Easton, Pa., which is hereby incorporated by reference in its entirety.

As used herein, "authorization number" or "marketing authorization number" refers to a number issued by a regulatory agency upon that agency determining that a particular medical product and/or composition may be marketed and/or offered for sale in the area under the agency's jurisdiction. As used herein "regulatory agency" refers to one of the agencies responsible for evaluating, e.g. the safety and efficacy of a medical product and/or composition and controlling the sales/marketing of such products and/or compositions in a given area. The Food and Drug Administration (FDA) in the US and the European Medicines Agency (EPA) in Europe are but two examples of such regulatory agencies. Other non-limiting examples can include SDA, MPA, MHPRA, IMA, ANMAT, Hong Kong Department of Health-Drug Office, CDSCO, Medsafe, and KFDA.

As used herein, "injection device" refers to a device that is designed for carrying out injections, an injection including the steps of temporarily fluidically coupling the injection device to a person's tissue, typically the subcutaneous tissue. An injection further includes administering an amount of liquid drug into the tissue and decoupling or removing the injection device from the tissue. In some embodiments, an injection device can be an intravenous device or IV device, which is a type of injection device used when the target tissue is the blood within the circulatory system, e.g., the blood in a vein. A common, but non-limiting example of an injection device is a needle and syringe.

As used herein, a "buffer" refers to a chemical agent that is able to absorb a certain quantity of acid or base without undergoing a strong variation in pH.

As used herein, "packaging" refers to how the components are organized and/or restrained into a unit fit for distribution and/or use. Packaging can include, e.g., boxes, bags, syringes, ampoules, vials, tubes, clamshell packaging, barriers and/or containers to maintain sterility, labeling, etc.

As used herein, "instructions" refers to a display of written, printed or graphic matter on the immediate container of an article, for example the written material displayed on a vial containing a pharmaceutically active agent, or details on the composition and use of a product of interest included in a kit containing a composition of interest. Instructions set forth the method of the treatment as contemplated to be administered or performed.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, PCSK9 fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a hPCSK9 polypeptide or an antibody that specifically binds to a hPCSK9 polypeptide. In a specific embodiment, a fragment of a hPCSK9 polypeptide or an antibody that specifically binds to a hPCSK9 antigen retains at least 1, at least 2, or at least 3 functions of the polypeptide or antibody.

The term "free" can refer to a polypeptide, for example, PCSK9 or fragments and variants thereof, that is combined with a buffer, wherein the polypeptide is not associated with a cell surface or cell membrane. As such, the term "free" can refer to a polypeptide that is capable of surface expression (i.e. includes one or more transmembrane domains or membrane association domains), but that is not, in its present state, expressed on the surface of a cell or bound to a protein that is expressed on the surface of a cell. A free polypeptide can also refer to a free recombinant or native or unbound polypeptide. In the context of phage display, a free antigen can be selected in solution (referred to herein as a "soluble selection") or adsorbed to a surface, for example, adsorbed to the surface of a 96-well plate (referred to herein as "biopanning selection").

The term "fusion protein" as used herein refers to a polypeptide that comprises an amino acid sequence of an antibody and an amino acid sequence of a heterologous polypeptide or protein (i.e. a polypeptide or protein not normally a part of the antibody (e.g. a non-anti-PCSK9 antigen antibody)). The term "fusion" when used in relation to PCSK9 or to an anti-PCSK9 antibody refers to the joining of a peptide or polypeptide, or fragment, variant and/or derivative thereof, with a heterologous peptide or polypeptide. Preferably, the fusion protein retains the biological activity of the PCSK9 or anti-PCSK9 antibody. In certain embodiments, the fusion protein comprises a PCSK9 antibody VH domain, VL domain, VH CDR (one, two or three VH CDRs), and/or VL CDR (one, two or three VL CDRs), wherein the fusion protein specifically binds to a PCSK9 epitope.

The term "heavy chain" when used with reference to an antibody refers to five distinct types, called alpha ($\alpha$), delta ($\delta$), epsilon ($\epsilon$), gamma ($\gamma$) and mu ($\mu$), based on the amino acid sequence of the heavy chain constant domain. These distinct types of heavy chains are well known and give rise to five classes of antibodies, IgA, IgD, IgE, IgG and IgM, respectively, including four subclasses of IgG, namely IgG1, IgG2, IgG3 and IgG4. Preferably the heavy chain is a human heavy chain. In the human population, multiple heavy chain constant region alleles, of each immunoglobulin or immunoglobulin subclass, exist. The nucleotide and amino acid sequences of these allelic variants are accessible on publicly available databases such as IMGT, ENSEMBL Swiss-Prot and Uniprot. Allelic variants may also be identified in various genome sequencing projects. In one embodiment, the antibodies and antibody fragments disclosed herein comprise a heavy chain encoded by a IgG1 constant region allele, which includes, but is not limited to, human IGHG1*01 (Seq ID Nos:340, 341 & 537), IGHG1*02 (Seq ID Nos:340, 341 &537), IGHG1*03 (Seq ID Nos:523 & 524), IGHG1*04 (Seq ID Nos:525 & 526) and IGHG1*05 (Seq ID Nos:340, 341 & 537). In one embodiment, the antibodies and antibody fragments disclosed herein comprise a protein encoded by a IgG2 constant region allele, which includes, but is not limited to, human IGHG2*01 (Seq ID Nos:527 & 528), IGHG2*02 (Seq ID Nos:529 & 530), IGHG2*03 (Seq ID Nos:527 & 528), IGHG2*04 (Seq ID Nos:531 & 532), IGHG2*05 (Seq ID Nos:527 & 528) and IGHG2*06 (Seq ID Nos:533 & 534). In one embodiment, the antibodies or antibody fragments disclosed herein comprise a protein encoded by a IgG3 constant region allele, which includes but is not limited to human IGHG3*01, IGHG3*02, IGHG3*03, IGHG3*04, IGHG3*05, IGHG3*06, IGHG3*07, IGHG3*08, IGHG3*09, IGHG3*10, IGHG3*11, IGHG3*12, IGHG3*13, IGHG3*14, IGHG3*15, IGHG3*16, IGHG3*17, IGHG3*18 and IGHG3*19. In one embodiment, the antibodies or antibody fragments disclosed herein comprise a protein encoded by a IgG4 constant region allele, which includes but is not limited to human IGHG4*01 (see, eg, the sequence table herein), IGHG4*02 (see, eg, the sequence table herein), IGHG4*03 (see, eg, the sequence table herein) and IGHG4*04 (see, eg, the sequence table herein). In another example, the heavy chain is a disabled IgG isotype, e.g. a disabled IgG4. In certain embodiments, the antibodies of the invention comprise a human gamma 4 constant region. In another embodiment, the heavy chain constant region does not bind Fc-γ receptors, and e.g. comprises a Leu235Glu mutation. In another embodiment, the heavy chain constant region comprises a Ser228Pro mutation to increase stability.

In another embodiment, the heavy chain constant region is IgG4-PE (see, eg, the sequence table herein). In another embodiment, the antibodies and antibody fragments disclosed herein comprise a heavy chain constant region encoded by a murine IgG1 constant region allele, which includes but is not limited to mouse IGHG1*01 or IGHG1*02. In one embodiment, the antibodies and antibody fragments disclosed herein comprise a heavy chain constant region encoded by a murine IgG2 constant region allele, which includes, but is not limited to, mouse IGHG2A*01, IGHG2A*02, IGHG2B*01, IGHG2B*02, IGHG2C*01, IGHG2C*02 or IGHG2C*03. In one embodiment, the antibodies or antibody fragments disclosed herein comprise a protein encoded by a murine IgG3 constant region allele, which includes but is not limited to mouse IGHG3*01.

The term "host" as used herein refers to an animal, preferably a mammal, and most preferably a human.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "in combination" in the context of the administration of other therapies refers to the use of more than one therapy. The use of the term "in combination" does not restrict the order in which therapies are administered to a subject with a disease. A first therapy can be administered before (e.g. 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g. 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a PCSK9-mediated disease. Any additional therapy can be administered in any order with the other additional therapies. In certain embodiments, the antibodies of the invention can be administered in combination with one or more therapies (e.g. therapies that are not the antibodies of the invention that are currently administered to prevent, treat, manage, and/or ameliorate a PCSK9-mediated disease. Non-limiting examples of therapies that can be administered in combination with an antibody of the invention include analgesic agents, anaesthetic agents, antibiotics, or immunomodulatory agents or any other agent listed in the U.S. Pharmacopoeia and/or Physician's Desk Reference.

As used herein, "injection device" refers to a device that is designed for carrying out injections, an injection including the steps of temporarily fluidically coupling the injection device to a person's tissue, typically the subcutaneous tissue. An injection further includes administering an amount of liquid drug into the tissue and decoupling or removing the injection device from the tissue. In some embodiments, an injection device can be an intravenous device or IV device, which is a type of injection device used when the target tissue is the blood within the circulatory system, e.g. the blood in a vein. A common, but non-limiting example of an injection device is a needle and syringe. As used herein, "instructions" refers to a display of written, printed or graphic matter on the immediate container of an article, for example the written material displayed on a vial containing a pharmaceutically active agent, or details on the composition and use of a product of interest included in a kit containing a composition of interest. Instructions set forth the method of the treatment as contemplated to be administered or performed.

An "isolated" or "purified" antibody or protein is one that has been identified, separated and/or recovered from a component of its production environment (e.g. natural or recombinant). For example, the antibody or protein is substantially free of cellular material or other contaminating proteins from the cell or tissue source from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). When the antibody is recombinantly produced, it is also preferably substantially free of culture medium, i.e. culture medium represents less than about 20%, 10%, or 5% of the volume of the protein preparation. When the antibody is produced by chemical synthesis, it is preferably substantially free of chemical precursors or other chemicals, i.e., it is separated from chemical precursors or other chemicals which are involved in the synthesis of the protein. Accordingly, such preparations of the antibody have less than about 30%, 20%, 10%, 5% (by dry weight) of chemical precursors or compounds other than the antibody of interest. In a preferred embodiment, antibodies of the invention are isolated or purified.

The terms "Kabat numbering," and like terms are recognized in the art and refer to a system of numbering amino acid residues which are more variable (i.e. hypervariable) than other amino acid residues in the heavy chain variable regions of an antibody, or an antigen binding portion thereof (Kabat et al., (1971) Ann. NY Acad. Sci., 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3.

"Label" or "labelled" as used herein refers to the addition of a detectable moiety to a polypeptide, for example, a radiolabel, fluorescent label, enzymatic label, chemiluminescent label or a biotinyl group or gold. Radioisotopes or radionuclides may include $^{3}H$, $^{14}C$, $^{15}N$, $^{35}S$, $^{90}Y$, $^{99}Tc$, $^{115}In$, $^{125}I$, $^{131}I$, fluorescent labels may include rhodamine, lanthanide phosphors or FITC and enzymatic labels may include horseradish peroxidase, 3-galactosidase, luciferase, alkaline phosphatase. Additional labels include, by way of illustration and not limitation: enzymes, such as glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase; dyes (e.g. cyanine dyes, e.g. Cy5™, Cy5.5™. or Cy7™); additional fluorescent labels or fluorescers include, such as fluorescein and its derivatives, fluorochrome, GFP (GFP for "Green Fluorescent Protein"), other fluorescent proteins (e.g. mCherry, mTomato), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cisbio Assays); chemoluminescent labels or chemiluminescers, such as isoluminol, luminol and the dioxetanes; sensitisers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of Pseudomonas exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

The term "light chain" when used in reference to an antibody refers to the immunoglobulin light chains, of which there are two types in mammals, lambda (λ) and kappa (κ). Preferably, the light chain is a human light chain. Preferably the light chain constant region is a human constant region. In the human population, multiple light chain constant region alleles exist. The nucleotide and amino acid sequences of these allelic variants are accessible on publicly available databases such as IMGT, ENSEMBL, Swiss-Prot and Uniprot. In one embodiment, the antibodies or antibody fragments disclosed herein comprise a protein encoded by a human K constant region allele, which includes, but is not limited to, IGKC*01 (see, eg, the sequence table herein), IGKC*02 (see, eg, the sequence table herein), IGKC*03 (see, eg, the sequence table herein), IGKC*04 (see, eg, the sequence table herein) and IGKC*05 (see, eg, the sequence table herein). In one embodiment, the antibodies or antibody fragments disclosed herein comprise a protein encoded by a human A constant region allele, which includes but is not limited to IGLC1*01 (see, eg, the sequence table herein), IGLC1*02 (see, eg, the sequence table herein), IGLC2*01 (see, eg, the sequence table herein), IGLC2*02 (see, eg, the sequence table herein), IGLC2*03 (see, eg, the sequence table herein), IGLC3*01 (see, eg, the sequence table herein), IGLC3*02 (see, eg, the sequence table herein), IGLC3*03 (see, eg, the sequence table herein), IGLC3*04 (see, eg, the sequence table herein), IGLC6*01 (see, eg, the sequence table herein), IGLC7*01 (see, eg, the sequence table herein), IGLC7*02 (see, eg, the sequence table herein), IGLC7*03 (see, eg, the sequence table herein). In another embodiment, the antibodies and antibody fragments disclosed herein comprise a light chain constant region encoded by a mouse K constant region allele, which includes, but is not limited to, IGKC*01, IGKC*03 or IGKC*03. In another embodiment, the antibodies and antibody fragments disclosed herein comprise a light chain constant region encoded by a mouse A constant region allele, which includes, but is not limited to, IGLC1*01, IGLC2*01 or IGLC3*01.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEG ALIGN™ (DNASTAR) software. In one embodiment, the % homology is about 70%. In one embodiment, the % homology is about 75%. In one embodiment, the % homology is about 80%. In one embodiment, the % homology is about 85%. In one embodiment, the % homology is about 90%. In one embodiment, the % homology is about 92%. In one embodiment, the % homology is about 95%. In one embodiment, the % homology is about 97%. In one embodiment, the % homology is about 98%. In one embodiment, the % homology is about 99%. In one embodiment, the % homology is 100%.

The term "naturally occurring" or "native" when used in connection with biological materials such as nucleic acid molecules, polypeptides, host cells, and the like, refers to those which are found in nature and not manipulated by a human being.

As used herein, "packaging" refers to how the components are organized and/or restrained into a unit fit for distribution and/or use. Packaging can include, e.g. boxes, bags, syringes, ampoules, vials, tubes, clamshell packaging, barriers and/or containers to maintain sterility, labelling, etc. The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

As used herein, the term "polynucleotide," "nucleotide," nucleic acid" "nucleic acid molecule" and other similar terms are used interchangeable and include DNA, RNA, mRNA and the like. As used herein, the terms "prevent", "preventing", and "prevention" refer to the total or partial inhibition of the development, recurrence, onset or spread of a hPCSK9-mediated disease and/or symptom related thereto, resulting from the administration of a therapy or combination of therapies provided herein (e.g. a combination of prophylactic or therapeutic agents, such as an antibody of the invention).

The term "soluble" refers to a polypeptide, such as PCSK9 and variants or fragments thereof, that is lacking one or more transmembrane or cytoplasmic domains found in the native or membrane-associated form. In one embodiment, the "soluble" form of PCSK9 lacks both the transmembrane domain and the cytoplasmic domain.

The term "subject" or "patient" refers to any animal, including, but not limited to, mammals. As used herein, the term "mammal" refers to any vertebrate animal that suckle their young and either give birth to living young (eutharian or placental mammals) or are egg-laying (metatharian or nonplacental mammals). Examples of mammalian species include, but are not limited to, humans and other primates, including non-human primates such as chimpanzees and other apes and monkey species; farm animals such as cattle, sheep, pigs, goats and horses; domestic mammals such as dogs and cats; laboratory animals including rodents such as mice, rats (including cotton rats) and guinea pigs; birds, including domestic, wild and game birds such as chickens, turkeys and other gallinaceous birds, ducks, geese, and the like.

As used herein "substantially all" refers to refers to at least about 60%, at least about 70%, at least about 75%, at least about 80%, at least about 85%, at least about 90%, at least about 95%, at least about 98%, at least about 99%, or about 100%.

As used herein, the term "therapeutic agent" refers to any agent that can be used in the treatment, management or amelioration of a PCSK9-mediated disease and/or a symptom related thereto. In certain embodiments, the term "therapeutic agent" refers to an antibody of the invention. In certain other embodiments, the term "therapeutic agent" refers to an agent other than an antibody of the invention. Preferably, a therapeutic agent is an agent which is known to be useful for, or has been or is currently being used for the treatment, management or amelioration of a PCSK9-mediated disease or one or more symptoms related thereto. In specific embodiments, the therapeutic agent is a fully human anti-PCSK9 antibody, such as a fully human anti-PCSK9 monoclonal antibody.

As used herein, the term "therapy" refers to any protocol, method and/or agent that can be used in the prevention, management, treatment and/or amelioration of a PCSK9-mediated disease (e.g. cancer). In certain embodiments, the terms "therapies" and "therapy" refer to a biological therapy, supportive therapy, and/or other therapies useful in the prevention, management, treatment and/or amelioration of a PCSK9-mediated disease known to one of skill in the art such as medical personnel.

The terms "treat", "treatment" and "treating" refer to the reduction or amelioration of the progression, severity, and/or duration of a hPCSK9-mediated disease (e.g. cancer) resulting from the administration of one or more therapies (including, but not limited to, the administration of one or more prophylactic or therapeutic agents, such as an antibody of the invention). In specific embodiments, such terms refer to the reduction or inhibition of the binding of hPCSK9 to a BMP receptor or HJV, and/or the inhibition or reduction of one or more symptoms associated with a PCSK9-mediated disease, such as hyperlipidaemia or hypercholesterolaemia.

The term "variable region" or "variable domain" refers to a portion of the light and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complimentarily determining regions (CDRs) while the more highly conserved regions in the variable domain are called framework regions (FR). The CDRs of the PCSK9 and heavy chains are primarily responsible for the interaction of the antibody with antigen. Numbering of amino acid positions used herein is according to the EU Index, as in Kabat et al. (1991) Sequences of proteins of immunological interest. (U.S. Department of Health and Human Services, Washington, D.C.) $5^{th}$ ed. ("Kabat et al."). In preferred embodiments, the variable region is a human variable region.

Definitions of common terms in cell biology and molecular biology can be found in "The Merck Manual of Diagnosis and Therapy", $19^{th}$ Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (Eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et al., ed., John Wiley and Sons, Inc.), Current Protocols in Cell Biology (CPCB) (Juan S. Bonifacino et al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties. Other terms are defined herein within the description of the various aspects of the invention.

Anti-PCSK9 Antibodies & Fragments

The invention provides various anti-PCSK9 antibodies and fragments (such as Fab or scFv fragments), uses, methods and combinations (eg, with statin). Examples are set out in the following numbered Clauses.

1. An antibody or fragment comprising a binding site which specifically binds to Proprotein Convertase Subtilisin Kexin type 9 (PCSK9), wherein the binding site comprises a $V_H$ domain that is encoded by a nucleotide sequence that is derived from the recombination of a human $V_H$ gene segment, DH gene segment and JH gene segment, wherein the $V_H$ gene segment is selected from IGHV4-59 and IGHV3-9.

For example, the VH gene segment is IGHV4-59*01 and the DH gene segment and JH gene segments are human gene segments. For example, the $V_H$ gene segment is IGHV3-9*01 and the DH gene segment and JH gene segments are human gene segments.

In an example, specific binding is with a KD, $K_{off}$ and/or $K_{on}$ as described further below. In an example, specific binding is with a KD from 1 µM to 5 nM.

The skilled person is familiar with databases and other sources for human and other species of antibody gene segments. For example, the IMGT database (www IMGT.org) is a suitable source, eg, the version as at 1 Sep. 2018.

Reference is made to the Examples, showing antibodies that are based on IGHV4-59 and IGHV3-9. Surprisingly, this human VH gene segment produces anti-PCSK9 antibodies which have desirable anti-PCSK9 properties, such as those described in, eg, in the Examples.

For example, the antibody or fragment of the invention is for administration to a subject for decreasing plasma total cholesterol and plasma non-HDL-cholesterol in a dose-dependent fashion in the subject.

For example, the antibody or fragment of the invention is for administration to a subject for decreasing plasma total cholesterol in the subject.

For example, the antibody or fragment of the invention is for administration to a subject for decreasing plasma non-HDL-cholesterol (optionally in a dose-dependent fashion) in the subject.

For example, the antibody or fragment of the invention is for administration to a subject for administration to a subject for decreasing plasma triglyceride levels) in the subject.

In an embodiment of any of these examples, HDL-cholesterol is not reduced or is not significantly reduced in the subject.

The examples show beneficial dosing of the antibodies of the invention compared to alirocumab benchmark. For example, the antibody or fragment of the invention is for administration to a subject for treating or preventing a PCSK9-mediated disease or condition (eg, heterozygous familial hypercholesterolaemia (HeFH) or homozygous familial hypercholesterolaemia (HoFH)), wherein the antibody or fragment is administered at a dose that is less than 75 mg every 2 weeks or 300 mg every 4 weeks. For example, the antibody or fragment of the invention is for administration to a subject for treating or preventing a PCSK9-mediated disease or condition (eg, heterozygous familial hypercholesterolaemia (HeFH) or homozygous familial hypercholesterolaemia (HoFH)), wherein the antibody or fragment is administered at a dose that is less than 140 mg every 2 weeks or less than 420 mg every 4 weeks. For example, the antibody or fragment of the invention is for administration to a subject for treating or preventing a PCSK9-mediated disease or condition (eg, heterozygous familial hypercholesterolaemia (HeFH) or homozygous familial hypercholesterolaemia (HoFH)), wherein the antibody or fragment is administered at a dose that is less than 2 weekly dose of Praluent or Repatha. For example, the antibody or fragment of the invention is for administration to a subject for treating or preventing a PCSK9-mediated disease or condition (eg, heterozygous familial hypercholesterolaemia (HeFH) or homozygous familial hypercholesterolaemia (HoFH)), wherein the antibody or fragment is administered at a dose that is less than 4 weekly dose of Praluent or Repatha. For example, the antibody or fragment of the invention is for administration to a subject for treating or preventing a PCSK9-mediated disease or condition (eg, heterozygous familial hypercholesterolaemia (HeFH) or homozygous familial hypercholesterolaemia (HoFH)), wherein the antibody or fragment is administered at a 2 weekly or 4 weekly dose that is less than 70, 65, 60, 50, 40, 30 or 25 mg.

The recommended starting dose of Praluent™ is 75 mg once every 2 weeks administered subcutaneously, since the majority of patients achieve sufficient LDL-C reduction with this dosage or 2×150 mg every 4 weeks.

The recommended subcutaneous dosage of Repatha™ in adults with established cardiovascular disease or in adults with primary hyperlipidemia (including heterozygous familial hypercholesterolemia [HeFH]) is either 140 mg every 2 weeks or 420 mg once monthly, based on patient preference for dosing frequency and injection volume. The recommended subcutaneous dosage of Repatha™ in patients with HoFH is 420 mg once monthly.

For example, the antibody or fragment comprises a CDRH3 sequence of an antibody selected from CL-274711, CL-148219QLT, CL-274698, CL-148219 and CL-148489 (eg, CL-274711 or CL-148219QLT) and optionally a CDRL3 of said selected antibody. For example, the antibody or fragment comprises a CDRH1 and CDRH3 sequence of an antibody selected from CL-274711, CL-148219QLT, CL-274698, CL-148219 and CL-148489 (eg, CL-274711 or CL-148219QLT) and optionally a CDRL2 of said selected antibody. For example, the antibody or fragment comprises a CDRH1 and CDRH2 sequence of an antibody selected from CL-274711, CL-148219QLT, CL-274698, CL-148219 and CL-148489 (eg, CL-274711 or CL-148219QLT). For example, the antibody or fragment comprises a CDRH2 and CDRH3 sequence of an antibody selected from CL-274711, CL-148219QLT, CL-274698, CL-148219 and CL-148489 (eg, CL-274711 or CL-148219QLT). For example, the antibody or fragment comprises an anti-PCSK9 binding site, wherein the binding site comprises a VH domain comprising the CDRH3 sequence of CL-58838 paired with a VL domain of CL-58838.

For example, the antibody or fragment comprises an anti-PCSK9 binding site, wherein the binding site comprises a VH domain comprising SEQ ID NO: 1 optionally paired with a VL domain comprising respectively SEQ ID NO: 33. For example, the antibody or fragment comprises an anti-PCSK9 binding site, wherein the binding site comprises a VH domain comprising SEQ ID NO: 65 paired with a VL domain comprising SEQ ID NO: 95.

For example, the antibody or fragment comprises an anti-PCSK9 binding site, wherein the binding site comprises a VH domain of an antibody selected from CL-274711, CL-148219QLT, CL-274698, CL-148219 and CL-148489 (eg, CL-274711 or CL-148219QLT), optionally paired with a VL domain of the selected antibody. For example, the antibody or fragment comprises an anti-PCSK9 binding site, wherein the binding site comprises a VH domain of CL-58838 paired with a VL domain of CL-58838.

2. The antibody or fragment according to Clause 1, wherein (i) the VH gene segment is IGHV4-59 (eg, IGHV4-59*01) and the DH gene segment is human gene segment IGHD3-10 (eg, IGHD3-10*01); or (ii) the VH gene segment is IGHV3-9 (eg, IGHV3-9*01) and the DH gene segment is human gene segment IGHD3-9 (eg, IGHD3-9*01).

3. The antibody or fragment according to Clause 1 or 2, wherein the JH gene segment is a human gene segment is JH6 (eg, JH6*02).
4. An antibody or fragment which specifically binds to Proprotein Convertase Subtilisin Kexin type 9 (PCSK9) and comprises the CDRH3 sequence of an anti-PCSK9 antibody according to any preceding Clause.
5. An antibody or fragment which specifically binds to Proprotein Convertase Subtilisin Kexin type 9 (PCSK9) and comprises a VH domain which comprises the CDRH3 sequence of any anti-PCSK9 antibody disclosed herein (eg, CL-148219 or CL-148489), or said CDRH3 sequence comprising 3, 2 or 1 amino acid substitution(s).
6. An antibody or fragment (optionally according to any preceding Clause) which specifically binds to Proprotein Convertase Subtilisin Kexin type 9 (PCSK9) and comprises a VH domain which comprises a CDRH3 sequence of an antibody selected from CL-274711, CL-148219QLT, CL-274698, CL-148219 and CL-148489 (eg, CL-274711 or CL-148219QLT); or said sequence comprising 3, 2 or 1 amino acid substitution(s).

Optionally, the VH domain comprises a CDRH3 sequence selected from the CDRH3 sequences disclosed herein, or said selected sequence comprising 3, 2 or 1 amino acid substitution(s).

7. The antibody or fragment according to Clause 6, wherein the VH domain comprises (i) a CDRH3 sequence of an antibody selected from CL-274711, CL-148219QLT, CL-274698, CL-148219 and CL-148489 (eg, CL-274711 or CL-148219QLT); or said CDRH3 sequence comprising 3, 2 or 1 amino acid substitution(s); and (ii) a CDRH1 sequence of said selected antibody; or said CDRH1 sequence comprising 3, 2 or 1 amino acid substitution(s).
8. The antibody or fragment according to Clause 6 or 7, wherein the VH domain comprises (iii) a CDRH3 sequence of an antibody selected from CL-274711, CL-148219QLT, CL-274698, CL-148219 and CL-148489 (eg, CL-274711 or CL-148219QLT); or said CDRH3 sequence comprising 3, 2 or 1 amino acid substitution(s); and (iv) a CDRH2 sequence of said selected antibody; or said CDRH2 sequence comprising 3, 2 or 1 amino acid substitution(s).
9. An antibody or fragment (optionally according to any preceding Clause) comprising a binding site which specifically binds to Proprotein Convertase Subtilisin Kexin type 9 (PCSK9), wherein the binding site comprises a VH domain that comprises the amino acid sequence of a VH domain of an antibody selected from CL-274711, CL-148219QLT, CL-274698, CL-148219 and CL-148489 (eg, CL-274711 or CL-148219QLT); or an amino acid that is at least 70, 80, 85, 90, 95, 96, 97, 98 or 99% identical thereto.

For example, the identity is at least 85%. For example, the identity is at least 90%. For example, the identity is at least 95%.

Optionally the VH domain of the antibody or fragment of comprises a VH amino acid sequence of disclosed herein, or a heavy chain variable domain amino acid sequence that is at least 70, 80, 85, 90, 95, 96, 97, 98 or 99% identical thereto. For example, the identity is at least 85%. For example, the identity is at least 90%. For example, the identity is at least 95%, 10. The antibody or fragment according to any preceding Clause comprising first and second copies of said VH domain.

In an example, the antibody or fragment comprises a binding site comprising a VH domain of the invention paired with a VL domain of the invention, wherein the binding site is capable of specifically binding to PCSK9 (eg, mature PCSK9, eg human and/or cynomolgus monkey PCSK9). For example, the antibody or fragment comprise two of such binding sites.

11. An antibody or fragment (optionally according to any preceding Clause) comprising a binding site which specifically binds to Proprotein Convertase Subtilisin Kexin type 9 (PCSK9), wherein the binding site comprises a VL domain that is encoded by a nucleotide sequence that is derived from the recombination of a human VL gene segment and JL gene segment, wherein the VL gene segment is selected from IGKV2-28 (eg, IGKV2-28*01) and IGKV2-29 (eg, IGKV2-29*01).
12. The antibody or fragment according to Clause 11, wherein the VL is a $V_K$ and the JL gene segment is a human gene segment selected from IGKJ3 and IGKJ4.

Optionally, the JL gene segment is selected from IGKJ3*01 and IGKJ4*01.

13. An antibody or fragment which specifically binds to Proprotein Convertase Subtilisin Kexin type 9 (PCSK9) and comprises the CDRL3 sequence of an anti-PCSK9 antibody according to Clause 11 or 12.
14. An antibody or fragment (optionally according to any preceding Clause) which specifically binds to Proprotein Convertase Subtilisin Kexin type 9 (PCSK9) and comprises a VL domain which comprises the CDRL3 sequence of any anti-PCSK9 antibody disclosed herein (eg, CL-148219 or CL-148489) or said selected CDRL3 sequence comprising 3, 2 or 1 amino acid substitution(s).
15. The antibody or fragment of Clause 14, comprising a VH domain which comprises the CDRH3 sequence of said selected antibody.
16. An antibody or fragment (optionally according to any preceding Clause) which specifically binds to Proprotein Convertase Subtilisin Kexin type 9 (PCSK9) and comprises a VL domain which comprises a CDRL3 sequence selected from a CDRL3 sequence disclosed herein, or said selected CDRL3 sequence comprising 3, 2 or 1 amino acid substitution(s).
17. An antibody or fragment (optionally according to any preceding Clause) which specifically binds to Proprotein Convertase Subtilisin Kexin type 9 (PCSK9) and comprises a VL domain which comprises a CDRL3 (and optionally a CDRH3) sequence of an antibody selected from CL-274711, CL-148219QLT, CL-274698, CL-148219 and CL-148489 (eg, CL-274711 or CL-148219QLT); or said sequence(s) each comprising 3, 2 or 1 amino acid substitution(s).
18. The antibody or fragment according to Clause 17, wherein the VL domain comprises (i) a CDRL3 sequence (and optionally a CDRH3) of an antibody selected from CL-274711, CL-148219QLT, CL-274698, CL-148219 and CL-148489 (eg, CL-274711 or CL-148219QLT); or said CDR3 sequence(s) each comprising 3, 2 or 1 amino acid substitution(s); and (ii) a CDRL1 (and optionally a CDRH1) sequence of said selected antibody; or said CDR1 sequence(s) each comprising 3, 2 or 1 amino acid substitution(s).

19. The antibody or fragment according to Clause 17 or 18, wherein the VL domain comprises (iii) a CDRL3 (and optionally a CDRH3) sequence of an antibody selected from CL-274711, CL-148219QLT, CL-274698, CL-148219 and CL-148489 (eg, CL-274711 or CL-148219QLT); or said CDR3 sequence(s) each comprising 3, 2 or 1 amino acid substitution(s); and (iv) a CDRL2 (and optionally a CDRH2) sequence of said selected antibody; or said CDR2 sequence(s) each comprising 3, 2 or 1 amino acid substitution(s).

20. An antibody or fragment (optionally according to any preceding Clause) comprising a binding site which specifically binds to Proprotein Convertase Subtilisin Kexin type 9 (PCSK9), wherein the binding site comprises a VL domain that comprises the amino acid sequence of a $V_L$ domain of an antibody selected from CL-274711, CL-148219QLT, CL-274698, CL-148219 and CL-148489 (eg, CL-274711 or CL-148219QLT); or an amino acid that is at least 70, 80, 85, 90, 95, 96, 97, 98 or 99% identical thereto.

For example, the identity is at least 85%. For example, the identity is at least 90%. For example, the identity is at least 95%.

21. The antibody or fragment according to any preceding Clause comprising first and second copies of said VL domain.

In an example, the antibody or fragment comprises a binding site comprising a VL domain of the invention paired with a VH domain, wherein the binding site is capable of specifically binding to PCSK9 (eg, mature PCSK9, eg human and/or cynomolgus monkey PCSK9). For example, the antibody or fragment comprise two of such binding sites.

22. An antibody or fragment (optionally according to any preceding Clause) which specifically binds to Proprotein Convertase Subtilisin Kexin type 9 (PCSK9) and comprises the heavy chain amino acid sequence of an antibody selected from CL-274711, CL-148219QLT, CL-274698, CL-148219 and CL-148489 (eg, CL-274711 or CL-148219QLT); or an amino acid that is at least 70, 80, 85, 90, 95, 96, 97, 98 or 99% identical thereto.

In an example, the heavy chain sequence comprises the VH amino acid sequence of CL-148219 or CL-148489 fused to an antibody heavy chain constant region disclosed herein, eg, an IgG4-PE constant region, eg, SEQ ID NO: 3. Additionally or alternatively, in an example, the light chain sequence comprises the $V_L$ amino acid sequence of CL-148219 or CL-148489 fused to an antibody light chain constant region disclosed herein, eg, a kapa constant region, eg, SEQ ID NO: 156.

For example, the identity is at least 85%. For example, the identity is at least 90%. For example, the identity is at least 95%.

23. An antibody or fragment (optionally according to any preceding Clause) which specifically binds to Proprotein Convertase Subtilisin Kexin type 9 (PCSK9) and comprises the light chain amino acid sequence of an antibody selected from CL-274711, CL-148219QLT, CL-274698, CL-148219 and CL-148489 (eg, CL-274711 or CL-148219QLT); or an amino acid that is at least 70, 80, 85, 90, 95, 96, 97, 98 or 99% identical thereto.

For example, the identity is at least 85%. For example, the identity is at least 90%. For example, the identity is at least 95%.

24. The antibody or fragment of Clause 23, comprising the light chain amino acid sequence of said selected antibody; or an amino acid that is at least 70, 80, 85, 90, 95, 96, 97, 98 or 99% identical thereto.

For example, the identity is at least 85%. For example, the identity is at least 90%. For example, the identity is at least 95%.

25. An antibody or fragment (optionally according to any preceding Clause) which specifically binds to a human PCSK9 epitope that is identical to an epitope to which the antibody of any preceding Clause binds.

26. The antibody or fragment according to Clause 25, wherein the epitope is identified by unrelated amino acid scanning, or by X-ray crystallography.

Contact amino acid residues involved in the interaction of antibody and antigen may be determined by various known methods to those skilled in the art.

In one embodiment, sequential replacement of the amino acids of the antigen sequence (using standard molecular biology techniques to mutate the DNA of the coding sequence of the antigen), in this case PCSK9 with Alanine (a.k.a Alanine scan), or another unrelated amino acid, may provide residues whose mutation would reduce or ablate the ability of the antibody to recognise the antigen in question. Binding may be assessed using standard techniques, such as, but not limited to, SPR, HTRF, ELISA (which are described elsewhere herein). Other substitutions could be made to enhance the disruption of binding such as changing the charge on the side chain of antigen sequence amino acids (e.g. Lysine change to glutamic acid), switching polar and non-polar residues (e.g. Serine change to leucine). The alanine scan or other amino substitution method may be carried out either with recombinant soluble antigen, or where the target is a cell membrane target, directly on cells using transient or stable expression of the mutated versions.

In one embodiment, protein crystallography may be used to determine contact residues between antibody and antigen (i.e. to determine the epitope to which the antibody binds), crystallography allows the direct visualisation of contact residues involved in the antibody-antigen interaction. As well as standard X-ray crystallography, cryo-electro microscopy has been used to determine contact residues between antibodies and HIV capsid protein (see Lee, Jeong Hyun, et L. "Antibodies to a conformational epitope on gp41 neutralize HIV-1 by destabilizing the Env spike.", Nature communications, 6, (2015)).

In one embodiment, if the antibody recognises a linear epitope, short peptides based on the antigen sequence can be produced and binding of the antibody to these peptides can be assessed using standard techniques, such as, but not limited to, SPR, HTRF, ELISA (which are described elsewhere herein). Further investigation of the epitope could be provided by performing an Alanine scan on any peptides that show binding. Alternative to linear peptides, conformational scans could be carried out using Pepscan technology (http://www.pepscan.com/) using their chemical linkage of peptides onto scaffolds, which has been used to determine discontinuous epitopes on CD20 targeting antibodies (Niederfellner, Gerhard, et al. "Epitope characterization and crystal structure of GA101 provide insights into the molecular basis for type I/II distinction of CD20 antibodies.", Blood, 118.2, (2011), 358-367).

In one embodiment, limited proteolytic digestion and mass spectrophotometry can be used to identify binding epitopes. The antibody-antigen complex is digested by a protease, such as, but not limited to, trypsin. The digested complex peptides are compared to antibody-alone and antigen-alone digestion mass spectrophotometry to determine if a particular epitope is protected by the complexation. Further work involving amino acid substitution, competition binding, may then be employed to narrow down to individual amino acid residues involved in the interaction (see, for example, Suckau, Detlev, et al. "Molecular epitope identification by limited proteolysis of an immobilized antigen-antibody complex and mass spectrometric peptide mapping.", Proceedings of the National Academy of Sciences, 87.24, (1990), 9848-9852).

Thus, in one embodiment, the contact residues of the epitope are identified with an unrelated amino acid scan (e.g. alanine scan). In another embodiment, an unrelated amino acid scan (e.g. alanine scan) is carried out using a technique selected from SPR, HTRF, ELISA, X-ray crystallography, cryo-electro microscopy and a combination of limited proteolytic digestion and mass spectrometry.

In one embodiment, the unrelated amino acid scan (e.g. alanine scan) is carried out using HTRF. In one embodiment, the unrelated amino acid scan (e.g. alanine scan) is carried out using ELISA. When the alanine scan is carried out with either ELISA or HTRF, an amino acid residue is identified as contributing to the epitope if the reduction in signal is at least 25%. In one embodiment, the reduction in signal is at least 30%. In one embodiment, the reduction in signal is at least 35%. In one embodiment, the reduction in signal is at least 40%. In one embodiment, the reduction in signal is at least 45%. In one embodiment, the reduction in signal is at least 50%. In one embodiment, the reduction in signal is at least 55%. In one embodiment, the reduction in signal is at least 60%. In one embodiment, the reduction in signal is at least 70%. In one embodiment, the reduction in signal is at least 75%. In one embodiment, the reduction in signal is at least 80%. In one embodiment, the reduction in signal is at least 85%. In one embodiment, the reduction in signal is at least 90%.

When the alanine scan is carried out with SPR, an amino acid residue is identified as contributing to the epitope if there is at least a 10-fold reduction in affinity. In one embodiment, the reduction in affinity is at least 15-fold. In one embodiment, the reduction in affinity is at least 20-fold. In one embodiment, the reduction in affinity is at least 30-fold. In one embodiment, the reduction in affinity is at least 40-fold. In one embodiment, the reduction in affinity is at least 50-fold. In one embodiment, the reduction in affinity is at least 100-fold.

In one embodiment, the contact residues of the epitope are identified by X-ray crystallography. In one embodiment, the contact residues of the epitope are identified by cryo-electro microscopy. In one embodiment, the contact residues of the epitope are identified by a combination of limited proteolytic digestion and mass spectrometry.

27. The antibody or fragment according to Clause 26, wherein the contact residues of the epitope are defined by a reduction in affinity of at least 10-fold in an unrelated amino acid scan, e.g. an alanine scan as determined by SPR.

In one embodiment, the reduction in affinity is at least 15-fold. In one embodiment, the reduction in affinity is at least 20-fold. In one embodiment, the reduction in affinity is at least 30-fold. In one embodiment, the reduction in affinity is at least 40-fold. In one embodiment, the reduction in affinity is at least 50-fold. In one embodiment, the reduction in affinity is at least 100-fold.

SPR may be carried out as described herein.

28. An antibody or fragment (optionally according to any preceding Clause) which competes for binding to human PCSK9 with the antibody of any preceding Clause.

Optionally, competition is determined by surface plasmon resonance (SPR) or ELISA. The skilled person will be familiar with these techniques and standard conditions, for example.

In one embodiment, the antibody or fragment competes (e.g. in a dose-dependent manner) with hPCSK9 (or a fusion protein thereof) for binding to cell surface-expressed hPCSK9. In one embodiment, the antibody or fragment competes (e.g. in a dose-dependent manner) with hPCSK9 (or a fusion protein thereof) for binding to soluble hPCSK9.

Optionally, the competition for binding to hPCSK9 is conducted using SPR. SPR may be carried out as described herein.

29. The antibody or fragment according to any preceding Clause which specifically binds to human PCSK9 comprising any one of SEQ ID NOs: 189-192; and/or a cynomolgus PCSK9 comprising SEQ ID NO: 193; and/or a mouse PCSK9 comprising SEQ ID NO: 194.

Optionally, the antibody or fragment of the invention specifically binds to the amino acid sequence of SEQ ID NO: 189. Optionally, the antibody or fragment of the invention specifically binds to the amino acid sequence of SEQ ID NO: 193. Optionally, the antibody or fragment of the invention specifically binds to the amino acid sequence of SEQ ID NO: 194.

In an example, PCSK9 herein is a human, mouse or cynomolgus monkey PCSK9.

In one embodiment, the antibody or fragment binds to cynomolgus PCSK9 with an affinity of less than 1 nM (e.g. from 1 nM to 0.01 pM or from 1 nM to 0.1 pM, or from 1 nM to 1 pM). In one embodiment, the antibody or fragment binds to cynomolgus PCSK9 with an affinity of less than 10 nM (e.g. from 10 nM to 0.01 pM or from 10 nM to 0.1 pM, or from 10 nM to 1 pM). In one embodiment, the antibody or fragment binds to cynomolgus PCSK9 with an affinity of less than 0.1 nM (e.g. from 0.1 nM to 0.01 pM or from 0.1 nM to 0.1 pM, or from 0.1 nM to 1 pM). In one embodiment, the antibody or fragment binds to cynomolgus PCSK9 with an affinity of less than 0.01 nM (e.g. from 0.011 nM to 0.01 pM or from 0.01 nM to 0.1 pM).

In one embodiment, the antibody or fragment binds to cynomolgus PCSK9 with an affinity of within 2-fold of the affinity to hPCSK9. In one embodiment, the antibody or fragment binds to cynomolgus PCSK9 with an affinity of within 4-fold of the affinity to hPCSK9. In one embodiment, the antibody or fragment binds to cynomolgus PCSK9 with an affinity of within 5-fold of the affinity to hPCSK9. In one embodiment, the antibody or fragment binds to cynomolgus PCSK9 with an affinity of within 6-fold of the affinity to hPCSK9. In one embodiment, the antibody or fragment binds to cynomolgus PCSK9 with an affinity of within 8-fold of the affinity to hPCSK9. In one embodiment, the antibody or fragment binds to cynomolgus PCSK9 with an affinity of within 10-fold of the affinity to hPCSK9. "hPCSK9" herein is a human PCSK9, eg, a human PCSK9 disclosed herein, eg, comprising SEQ ID NO: 562.

In one embodiment, the antibody or fragment does not detectably bind to cynomolgus PCSK9. In one embodiment, the antibody or fragment does not detectably bind to murine (eg, mouse and/or rat) PCSK9.

In one embodiment, the antibody or fragment binds to murine (eg, mouse and/or rat) PCSK9 with an affinity of less than 1 nM (e.g. from 1 nM to 0.01 pM or from 1 nM to 0.1 pM, or from 1 nM to 1 pM). In one embodiment, the antibody or fragment binds to murine PCSK9 with an affinity of less than 10 nM (e.g. from 10 nM to 0.01 pM or from 10 nM to 0.1 pM, or from 10 nM to 1 pM). In one embodiment, the antibody or fragment binds to murine PCSK9 with an affinity of less than 0.1 nM (e.g. from 0.1 nM to 0.01 pM or from 0.1 nM to 0.1 pM, or from 0.1 nM to 1 pM). In one embodiment, the antibody or fragment binds to murine PCSK9 with an affinity of less than 0.01 nM (e.g. from 0.011 nM to 0.01 pM or from 0.01 nM to 0.1 pM).

Optionally, the antibody or fragment comprises an effector-enabled or effector-disabled constant region, such as a human constant region, for example an effector-null human constant region, e.g. an IgG4 constant region or an IgG1 constant region, optionally wherein the constant region is IgG4-PE, or a disabled IgG1. Optionally, the antibody or fragment comprises a murine (eg, mouse and/or rat) constant region. Optionally, the antibody or fragment comprises any of the heavy chain constant region sequences described herein.

Optionally, the constant region has CDC and/or ADCC activity.

30. The antibody or fragment according to any preceding Clause, wherein the antibody or fragment comprises a human constant region, e.g. an IgG4 constant region or an IgG1 constant region.

For example, the constant region comprises a heavy chain constant region disclosed herein.

In an example (optionally in addition to the heavy chain region as per the paragraph immediately above), the constant region comprises a light chain constant region, the light chain constant region comprising a light chain constant region amino acid sequence disclosed herein.

31. The antibody or fragment according to Clause 30, wherein the constant region is an IgG4-PE constant region.

The anti-PCSK9 antibody or fragment according to the invention may comprise a constant region, such as a human constant region, for example an effector-null human constant region, e.g. an IgG4 constant region or an IgG1 constant region, optionally wherein the constant region is IgG4-PE, or a disabled IgG1 as defined in the sequence table herein.

In other embodiments, the antibody or fragment is any of the isotypes or constant regions as defined herein. In one embodiment, the constant region is wild-type human IgG1. For example, the constant region is an effector-enabled IgG1 constant region, optionally having ADCC and/or CDC activity. In one embodiment, the constant region is engineered for enhanced ADCC and/or CDC and/or ADCP. In another embodiment, the constant region is engineered for enhanced effector function.

The IgG4 constant region may be any of the IgG4 constant region amino acid sequences or encoded by any of the nucleic acid sequences of the sequence table herein. A heavy chain constant region may be an IgG4 comprising both the Leu235Glu mutation and the Ser228Pro mutation. This "IgG4-PE" heavy chain constant region (see the sequence table for an example) is effector null.

An alternative effector null human constant region is a disabled IgG1 being an IgG1*01 allele comprising the L235A and/or G237A mutations (e.g. LAGA, see the sequence table). In one embodiment, the antibodies or antibody fragments disclosed herein comprise an IgG1 heavy chain constant region, wherein the sequence contains alanine at position 235 and/or 237 (EU index numbering).

The potency of Fc-mediated effects may be enhanced by engineering the Fc domain by any of the techniques as will be apparent to the skilled person. In another embodiment, the antibodies and fragments disclosed herein may comprise a triple mutation (M252Y/S254T/T256E) which enhances binding to FcRn.

32. The antibody or fragment according to any preceding Clause (eg, a bispecific antibody), further comprising an antigen-binding site that specifically binds another target antigen (eg, ANGPTL3, eg, human ANGPTL3).

In an example, the further binding site is an agonist binding site for said another antigen. In an example, the further binding site is an antagonist binding site for said another antigen.

In an example, the further binding site is an antibody binding site comprising a VH and a VL; a binding site comprised by a constant domain of the antibody (eg, an Fcab binding site) or a non-immunoglobulin binding site (eg, a fibronectin domain). Optionally, the antigen-binding site is any antigen-binding site disclosed herein.

For example, the antibody or fragment is a bispecific antibody or fragment. For example, the antibody or fragment is a dual binding antibody or fragment, or a fusion protein comprising an antibody or fragment thereof as defined in any preceding Clause. A dual binding antibody has the meaning as set out above.

In an example, the antibody or fragment comprises a bispecific format selected from DVD-Ig, mAb$^2$, FIT-Ig, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-CH$_3$, Diabody-CH$_3$, minibody, knobs-in-holes, knobs-in-holes with common light chain, knobs-in-holes with common light chain and charge pairs, charge pairs, charge pairs with common light chain, in particular mAb$^2$, knob-in-holes, knob-in-holes with common light chain, knobs-in-holes with common light chain and charge pairs and FIT-Ig, e.g. mAb$^2$ and FIT-Ig.

In one embodiment, the bispecific format is selected from DVD-Ig, mAb$^2$, FIT-Ig, mAb-dAb, dock and lock, Fab-arm exchange, SEEDbody, Triomab, LUZ-Y, Fcab, Kλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH$_3$, Diabody-CH$_3$, Triple body, Miniantibody, minibody, TriBi minibody, scFv-CH$_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG (L,H)-Fv, IgG(H)-V, V(H)—IgG, IgG(L)-V, V(L)-IgG, KIH IgG-scFab, 2scFv-IgG, IgG-2scFv, scFv4-Ig and zybody.

In one embodiment, the bispecific format is selected from DVD-Ig, FIT-Ig, mAb-dAb, dock and lock, Fab-arm exchange, SEEDbody, Triomab, LUZ-Y, Fcab, Kλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH$_3$, Diabody-CH$_3$, Triple body, Miniantibody, minibody, TriBi minibody, scFv-CH$_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG (L,H)-Fv, IgG(H)-V, V(H)—IgG, IgG(L)-V, V(L)-IgG, KIH IgG-scFab, 2scFv-IgG, IgG-2scFv, scFv4-Ig and zybody, for example DVD-Ig, FIT-Ig, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-CH$_3$, Diabody-CH$_3$, minibody, knobs-in-holes, knobs-in-holes with common light chain, knobs-in-holes with common light chain and charge pairs, charge pairs, charge pairs with common light chain, in particular knob-in-holes, knob-in-holes with common light chain, knobs-in-holes with common light chain and charge pairs and FIT-Ig, e.g. FIT-Ig.

In one embodiment, the bispecific format is selected from DVD-Ig, mAb$^2$, mAb-dAb, dock and lock, Fab-arm exchange, SEEDbody, Triomab, LUZ-Y, Fcab, Kλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH$_3$, Diabody-CH$_3$, Triple body, Miniantibody, minibody, TriBi minibody, scFv-CH$_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG (L,H)-Fv, IgG(H)-V, V(H)—IgG, IgG(L)-V, V(L)-IgG, KIH IgG-scFab, 2scFv-IgG, IgG-2scFv, scFv4-Ig and zybody, for example DVD-Ig, mAb$^2$, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-CH$_3$, Diabody-CH$_3$, minibody, knobs-in-holes, knobs-in-holes with common light chain, knobs-in-holes with common light chain and charge pairs, charge pairs, charge pairs with common light chain, in particular mAb$^2$, knob-in-holes, knob-in-holes with common light chain and charge pairs, and knob-in-holes with common light chain, e.g. mAb$^2$.

In one embodiment, the bispecific format is selected from DVD-Ig, mAb-dAb, dock and lock, Fab-arm exchange, SEEDbody, Triomab, LUZ-Y, Fcab, Kλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH$_3$, Diabody-CH$_3$, Triple body, Miniantibody, minibody, TriBi minibody, scFv-CH$_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv, scFv4-Ig and zybody, for example DVD-Ig, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-CH$_3$, Diabody-CH$_3$, minibody, knobs-in-holes, knobs-in-holes with common light chain, knobs-in-holes with common light chain and charge pairs, charge pairs, charge pairs with common light chain, in particular knob-in-holes, knobs-in-holes with common light chain and charge pairs, and knob-in-holes with common light chain.

33. An anti-PCSK9 antibody or fragment as defined in any preceding Clause for treating or preventing a PCSK9-mediated disease or condition (eg, hyperlipidaemia or hypercholesterolaemia) in a subject.

In an example, the subject is a human. In an alternative, the subject is a non-human animal. In an example, the subject is an adult human. In an example, the subject is a paediatric human. In an example, the subject is a human CKD patient on dialysis treatment. In an example, the subject is a human having end-stage renal disease.

In an example, the antibody or fragment herein is for treating or preventing a disease or condition selected from hypercholesterolemia, hyperlipidemia, hypercholesterolemia, dyslipidemia, cholestatic liver disease, nephrotic syndrome, hypothyroidism, obesity, diabetes, atherosclerosis or a cardiovascular disease. In an example, the disease or condition is selected from a lipid disorder, hyperlipoproteinemia, hyperlipidemia; dyslipidemia; hypercholesterolemia, a heart attack, a stroke, coronary heart disease, atherosclerosis, peripheral vascular disease, claudication, type II diabetes, high blood pressure, and a cardiovascular disease or condition. For example, the disease or condition is hyperlipidaemia. For example, the disease or condition is hypercholesterolaemia. For example, the disease or condition is diabetes. For example, the disease or condition is stroke. For example, the disease or condition is atherosclerosis. For example, the disease or condition is a CNS disorder. For example, the disease or condition is a neurological disorder. For example, the disease or condition is depression.

In an example, the disease or condition is in a human. In an example, the disease or condition is in an animal.

In an example, the PCSK9-mediated disease or condition is a neurodegenerative disease, disorder or condition, e.g. selected from Alzheimer's disease, amyotrophic lateral sclerosis, Parkinson's disease, Huntington's disease, primary progressive multiple sclerosis, secondary progressive multiple sclerosis, corticobasal degeneration, Rett syndrome, a retinal degeneration disorder selected from age-related macular degeneration and retinitis pigmentosa; anterior ischemic optic neuropathy, glaucoma, uveitis, depression, trauma-associated stress or post-traumatic stress disorder, frontotemporal dementia, Lewy body dementias, mild cognitive impairments, posterior cortical atrophy, primary progressive aphasia and progressive supranuclear palsy or aged-related dementia, in particular, the neurodegenerative disease, disorder or condition is selected from Alzheimer's disease, amyotrophic lateral sclerosis, Parkinson's disease and Huntington's disease, for example, Alzheimer's disease.

In an example, the antibody, fragment, combination of the invention is administered intravenously to the subject; or is for administration intravenously to the subject. In an example, the antibody, fragment, combination of the invention is administered subcutaneously to the subject; or is for administration subcutaneously to the subject.

34. The antibody or fragment of Clause 33, wherein the antibody or fragment is administered to the subject simultaneously or sequentially with a statin.
35. A combination of an amount of an anti-PCSK9 antibody or fragment and an amount of a statin (eg, comprising multiple doses of said antibody and/or statin), wherein the antibody or fragment is according to any one of Clauses 1 to 34.

There is also provided: A medical kit comprising the combination, a first sterile container comprising said amount of antibody or fragment, and a second sterile container comprising said amount of statin, and optionally instructions for using the combination to treat hyperlipidaemia or hypercholesterolaemia in a subject.

There is also provided: A medical kit comprising the combination, a first sterile container comprising said amount of antibody or fragment, and a second sterile container comprising said amount of a ANGPTL3 inhibitor, and optionally instructions for using the combination to treat hyperlipidaemia or hypercholesterolaemia in a subject.

In an example, the combination is for treating or preventing hyperlipidaemia or hypercholesterolaemia in a subject, wherein over a 4 consecutive week period a total dose of the antibody and total dose of statin are administered to said subject in a ratio of X:Y, wherein X is from 10 to $2\times10^6$ and Y=4, eg, X is from 10 to $2\times10^6$ micrograms and Y=4 micrograms.

36. The antibody, fragment or combination according to the invention for use in a method of treating or preventing hypercholesterolaemia in a subject that has previously been on a statin treatment regime at a first dose, wherein the method comprises reducing the dose of statin that is administered to the subject or administering no statin to the subject, wherein the method comprises administering the antibody or fragment to the subject.
37. The combination of clause 35 or 36, wherein comprising statin at a daily dose of 10 to 20 mg (eg, 10 mg); or <60 mg (eg, 40 mg).
38. The antibody, fragment or combination of any preceding clause for administering to a human or animal subject suffering from elevated cholesterol, for lowering plasma low density lipoprotein cholesterol (LDL-C) level in the subject after the subject has received the anti-PCSK9 antibody or fragment.
39. Use of the antibody, fragment or combination as defined in any preceding Clause in the manufacture of a medicament for administration to a subject for treating or preventing a PCSK9-mediated disease or condition, e.g. hyperlipidaemia or hypercholesterolaemia.
40. A method of treating or preventing a PCSK9-mediated disease or condition in a subject (e.g. hyperlipidaemia or hypercholesterolaemia), the method comprising administering to said subject a therapeutically effective amount of an antibody, fragment or combination as defined in any one of Clauses 1 to 38, wherein the PCSK9-mediated disease or condition is thereby treated or prevented.

The disease or condition can be any disclosed herein.

41. The use according to Clause 39 or the method according to Clause 40, wherein the PCSK9-mediated disease or condition is hyperlipidaemia or hypercholesterolaemia.
42. The antibody, fragment, combination, use or the method according to any one of Clauses 33 to 41, further comprising administering to the subject a further therapy, for example a further therapeutic agent, optionally wherein the further therapeutic agent is selected from the group consisting of a:
    a. Statin;
    b. An ANGPTL3 inhibitor (eg, an anti-ANGPTL3 antibody, eg, evinacumab)
    c. Fibrate;
    d. Bile acid sequestrant;
    e. Nicotinic acid; and
    f. Niacin.

The disclosure includes generic versions of the branded drugs instead and the disclosure of these generic drugs is included by reference herein for possible use in the invention, eg, as part of a combination.

43. A pharmaceutical composition comprising an antibody, fragment or combination as defined in any one of Clauses 1 to 38 and a pharmaceutically acceptable excipient, diluent or carrier and optionally in combination with a further therapeutic agent selected from those mentioned above (eg, in Clause 42).
44. The pharmaceutical composition according to Clause 43 for treating and/or preventing a PCSK9-mediated condition or disease, e.g. hyperlipidaemia or hypercholesterolaemia.
45. The pharmaceutical composition according to Clause 43 or 44 in combination with a label or instructions for use to treat and/or prevent said disease or condition in a human; optionally wherein the label or instructions comprise a marketing authorisation number (e.g., an FDA or EMA authorisation number); optionally wherein the kit comprises an IV or injection device that comprises the antibody or fragment.
46. A nucleic acid that encodes a VH domain and/or a VL domain of an antibody or fragment as defined in any one of Clauses 1 to 32.
47. A nucleic acid that encodes a VH domain comprising the amino acid sequence of a VH domain of an antibody selected from CL-274711, CL-148219QLT, CL-274698, CL-148219 and CL-148489 (eg, CL-274711 or CL-148219QLT); or an amino acid that is at least 70, 80, 85, 90, 95, 96, 97, 98 or 99% identical thereto.

For example, the identity is at least 85%. For example, the identity is at least 90%. For example, the identity is at least 95%.

Optionally, there is provided a nucleic acid that encodes a VH domain comprising the amino acid sequence of SEQ ID NO: 114, or an amino acid that is at least 70, 80, 85, 90, 95, 96, 97, 98 or 99% identical thereto. For example, the identity is at least 85%. For example, the identity is at least 90%. For example, the identity is at least 95%.

48. A nucleic acid that encodes a VL domain comprising the amino acid sequence of a VL domain of an antibody selected from CL-274711, CL-148219QLT, CL-274698, CL-148219 and CL-148489 (eg, CL-274711 or CL-148219QLT); or an amino acid that is at least 70, 80, 85, 90, 95, 96, 97, 98 or 99% identical thereto.

Optionally, the nucleic acid also encodes a VH domain comprising the amino acid sequence of a VH domain of the selected antibody; or an amino acid that is at least 70, 80, 85, 90, 95, 96, 97, 98 or 99% identical thereto. For example, the identity is at least 85%. For example, the identity is at least 90%. For example, the identity is at least 95%.

49. A nucleic acid (eg, in a host cell, eg, a CHO or HEK293 or Cos cell) comprising a nucleotide sequence that is at least 70% identical to the sequence of SEQ ID NO: 2 or 66.

Herein in any instance where % identity is mentioned, in an example there is 100% identity.

50. A nucleic acid that encodes a heavy chain and/or a light chain of an antibody or fragment as defined in any one of Clauses 1 to 32.
51. A nucleic acid that encodes a heavy chain comprising a VH amino acid sequence that is at least 70% identical to SEQ ID NO: 22 or 66; and a C region amino acid sequence that is at least 70% identical to a IGHG4 sequence, optionally at least 70% identical to SEQ ID NO: 3 or 152.
52. A nucleic acid that encodes a light chain comprising a VL amino acid sequence that is at least 70% identical to SEQ ID NO: 93 or 95; and a C region amino acid sequence that is at least 70% identical to a IGKC sequence, optionally at least 70% identical to SEQ ID NO: 156.
53. A nucleic acid (eg, in a host cell, eg, a CHO or HEK293 or Cos cell) comprising a. a nucleotide sequence that is at least 70% identical to a heavy chain sequence of an antibody selected from CL-274711, CL-148219QLT, CL-274698, CL-148219 and CL-148489 (eg, CL-274711 or CL-148219QLT); and/or b. a nucleotide sequence that is at least 70% identical to a light chain sequence of an antibody selected respectively from CL-274711, CL-148219QLT, CL-274698, CL-148219 and CL-148489 (eg, CL-274711 or CL-148219QLT).

54. A vector comprising the nucleic acid(s) (eg, the nucleic acid(s) of any one of clauses 46 to 53); optionally wherein the vector is a CHO or HEK293 vector.

All of the nucleic acids of the invention herein are expressible in a host cell, eg, a CHO or HEK293 or Cos cell, such as for expressing a variable domain or chain of an antibody or fragment of the invention.

55. A host cell comprising the nucleic acid(s) (eg, the nucleic acid(s) of any one of Clauses 46 to 53) or the vector of Clause 54.

In an example, the antibody or fragment comprises a HCDR3 length of 9, 10, 11 or 12 residues, eg, 10, eg, 11. In an example, the antibody or fragment comprises a LCDR3 length of 7, 8 or 9 residues, eg, 8, eg, 9. In an example, each $V_H$ domain of the antibody or fragment comprises from 1-11 non-germline residues, eg, 1, 2, 3, 4, 5, 6, 7, 8, 9, 10 or 11 non-germline residues. In an example, each $V_L$ domain of the antibody or fragment comprises from 3-8 non-germline residues, eg, 3, 4, 5, 6, 7 or 8 non-germline residues.

In an embodiment, a CDR sequence herein is determined according to Kabat. In an alternative, the CDR sequence is determined according to IMGT.

In an example, the selected antibody is CL-148219. In an example, the selected antibody is CL-148489.

In an example, the selected antibody comprises the heavy chain of CL-148219 or CL-148489.

In an example, the heavy chain of the antibody or fragment of the invention is a human gamma-1, gamma-2, gamma-3, gamma-4, mu, delta, epsilon or alpha isotype, preferably a gamma isotype (eg, an IgG4 isotype). In an example, the light chain of the antibody or fragment of the invention comprises a human kappa constant region. Alternatively, in an example, the light chain of the antibody or fragment of the invention comprises a human lambda constant region.

Optionally, the antibody is a 4-chain antibody comprising a dimer of a heavy chain associated with a dimer of a light chain. In an example, the heavy chain comprises one or heavy chain CDRs or a CDR combination as disclosed herein and/or the light chain comprises one or heavy chain CDRs or a CDR combinations as disclosed herein, such as from the same selected antibody. In an example, the heavy chain comprises a VH domain as disclosed herein and/or the light chain comprises a VL as disclosed herein, such as from the same selected antibody. In an example, the heavy chain and the light chain are from the same selected antibody, eg, any antibody disclosed in the sequence table herein or the tables in the Examples herein.

In an example, the selected antibody comprises the light (and optionally the heavy) chain(s) of CL-148219 or CL-148489.

In an example, the selected antibody comprises the variable domains of CL-148219 or CL-148489.

In an example, the selected antibody comprises the VH domains of CL-148219 or CL-148489.

In an example, the selected antibody comprises the VH and VL domains of CL-148219 or CL-148489.

Optionally, the VH is encoded by a nucleotide sequence that is derived from the recombination of a human IGHV4-59 (eg, IGHV4-59*01) a D gene segment (eg, IGHD3-10, eg, IGHD3-10*01) and a IGHJ6 (eg, IGHJ6*02) gene segment. Optionally additionally or alternatively the VL is encoded by a nucleotide sequence that is derived from the recombination of a human IGKV2-28 (eg IGKV2-28*01) and IGKJ3 (eg, IGKJ3*01).

Optionally, the VH is encoded by a nucleotide sequence that is derived from the recombination of a human IGHV3-9 (eg, IGHV3-9*01) a D gene segment (eg, IGHD3-9, eg, IGHD3-9*01) and a IGHJ6 (eg, IGHJ6*02) gene segment. Optionally additionally or alternatively the VL is encoded by a nucleotide sequence that is derived from the recombination of a human IGKV2-29 (eg IGKV2-29*01 or IGKV2D-29*01) and IGKJ4 (eg, IGKJ4*01).

In an example, the antibody or fragment comprises a HCDR3 length of 9-12 residues and/or the antibody or fragment comprises a LCDR3 length of 7-9 residues. In an example, the antibody or fragment comprises a HCDR3 length of 9, 10, 11 or 12 residues, eg, 10, eg, 11. In an example, the antibody or fragment comprises a LCDR3 length of 7, 8 or 9 residues, eg, 8, eg, 9. In an example, each VH domain of the antibody or fragment comprises from 1-11 non-germline residues, eg, 1, 2, 3, 4, 5, 6, 7, 8, 9, 10 or 11 non-germline residues. In an example, each VL domain of the antibody or fragment comprises from 3-8 non-germline residues, eg, 3, 4, 5, 6, 7 or 8 non-germline residues.

Optionally, the antibody or fragment competes with CL-148219 (eg, CL-148219 in IgG format, eg, IgG4-PE) for binding to PCSK9 (eg, human PCSK9) as determined by SPR.

Optionally, the antibody or fragment competes with CL-148489 (eg, CL-148489 in IgG format, eg, IgG4-PE) for binding to PCSK9 (eg, human PCSK9) as determined by SPR.

Optionally, the amino acid substitutions are conservative amino acid substitutions, optionally wherein each conservative substitution is from group (1) to (6):
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Any SPR herein is, for example, surface plasmon resonance (SPR) at 37° C. and pH 7.6.

Optionally, any PCSK9 herein is (for example, in in vitro testing) human PCSK9.

In an example, the antibody or fragment of the invention binds to human PCSK9 with a Ka of eg, $5\times10^6$ $M^{-1}\times s^{-1}$; or about $5\times10^6$ $M^{-1}\times s^{-1}$. In an example, the antibody or fragment of the invention binds to human PCSK9 with a Kd of eg, 4 or 5 $s^{-1}$; or about 4 or 5 $s^{-1}$. In an example, the antibody or fragment of the invention binds to human PCSK9 with a KD of eg, 0.07 or 0.14 nM; or about 0.07 or 0.14 nM. In an embodiment, the fragment is a Fab fragment. In an embodiment, the fragment is a scFv.

As used herein, "inhibits", "inhibition", "inhibiting" and the like, as used herein refers to the ability of an antagonist (e.g. an antibody or fragment thereof) to bind to an epitope (eg, of hPCSK9) which either partially or completely prevents the binding of another antigen If the epitope to which the antagonist binds completely blocks the binding site of the ligand, then ligand binding is completely prevented (which may be a physical blocking—in the case of overlapping epitopes—or steric blocking—where the antagonist is large such that it prevents the ligand binding to its distinct epitope), and the ligand is not removed from circulation. The concentration of circulating ligand may therefore appear to be increased. If the epitope to which the antagonist binds partially blocks the binding site of the ligand, the ligand may be able to bind, but only weakly (in the case of partial inhibition), or in a different orientation to the natural binding interaction. In this case, some of the ligand may be removed from circulation, but not as much as when the ligand binding site is completely free and available for binding. Inhibition thus refers to the physical interaction of ligand and receptor. Inhibition can be measured by HTRF, which is described in more detail elsewhere herein and in Mathis (1995) Clinical Chemistry 41(9), 1391-1397. Inhibition can also be measured by flow cytometry, where receptor is expressed on cells, or by ELISA, where receptor is adsorbed onto plates.

Optionally, the antibody of the invention has an affinity (KD) for binding PCSK9 of from 1 pM to 5 nM, optionally wherein binding is determined by SPR using a Fab of said antibody at 37° C. at pH 7.6.

Optionally, the antibody has off-rate ($K_{off}$) for binding PCSK9 of from $1\times10^{-5}$ to $1\times10^{-3}S^{-1}$, optionally wherein binding is determined by SPR using a Fab of said antibody at 37° C. at pH 7.6.

Optionally, the antibody has on-rate ($K_{on}$) for binding PCSK9 of from $1\times10^5$ to $1\times10^7$ $M^{-1}S^{-1}$, optionally wherein binding is determined by SPR using a Fab of said antibody at 37° C. at pH 7.6.

In an example, the antibody (eg, as a Fab) or fragment has an affinity (KD) for binding PCSK9 (eg, human PCSK9) of
  (a) from 2, 3, 4, 5 or 10 pM to 3, 4 or 5 nM;
  (b) from 1-10 pM to 5 nM;
  (c) from 10 pM to 3, 4 or 5 nM;
  (d) from 50 or 80 pM to 200 nM;
  (e) from 50 or 80 pM to 150 nM; or
  (f) from 50 or 80 pM to 100 nM.

In an example, the KD is (or is about) 5-15 pM (eg, 10 pM). In an example, the KD is (or is about) 2-5 nM (eg, 3 nM). In an example, the KD is (or is about) 100-400 pM (eg, 140 or 390 pM).

In an example, the antibody (eg, as a Fab) or fragment has an off-rate ($K_{off}$) for binding PCSK9 (eg, human PCSK9) of
  (a) from $1\times10^{-5}$ to $5\times10^{-4}S^{-1}$;
  (b) from $1\times10^{-5}$ to $6\times10^{-4}S^{-1}$;
  (c) from $1\times10^{-5}$ to $7\times10^{-4}$ $S^{-1}$;
  (d) from $1\times10^{-5}$ to $8\times10^{-4}S^{-1}$;
  (e) from $2\times10^{-5}$ to $1\times10^{-3}$ $S^{-1}$;
  (f) from $2\times10^{-5}$ to $5\times10^{-4}$ $S^{-1}$;
  (g) from $2\times10^{-5}$ to $6\times10^{-4}$ $S^{-1}$;
  (h) from $2\times10^{-5}$ to $7\times10^{-4}S^{-1}$; or
  (i) from $2\times10^{-5}$ to $8\times10^{-4}S^{-1}$.

In an example, the $K_{off}$ is (or is about) $5\times10^{-4}S^{-1}$ (eg, when the KD is (or is about) from 2 nM to 400 pM; when the KD is (or is about) 2-5 nM (eg, 3 nM); or when the KD is (or is about) 100-400 pM (eg, 140 or 390 pM)). In an example, the $K_{off}$ is (or is about) $3\times10^{-5}$ $S^{-1}$ (eg, when the KD is (or is about) from 5-15 pM (eg, 10 pM)).

In an example, the antibody (eg, as a Fab) or fragment has an on-rate ($K_{on}$) for binding PCSK9 (eg, human PCSK9) of
  (a) from $1\times10^5$ to $1\times10^6$ $M^{-1}S^{-1}$;
  (b) from $1\times10^5$ to $2\times10^6$ $M^{-1}S^{-1}$;
  (c) from $1\times10^5$ to $3\times10^6$ $M^{-1}S^{-1}$;
  (d) from $1\times10^5$ to $4\times10^6$ $M^{-1}S^{-1}$;
  (e) from $1\times10^5$ to $5\times10^6$ $M^{-1}S^{-1}$;
  (f) from $2\times10^5$ to $5\times10^6$ $M^{-1}S^{-1}$;
  (g) from $3\times10^5$ to $5\times10^6$ $M^{-1}S^{-1}$;
  (h) from $4\times10^5$ to $5\times10^6$ $M^{-1}S^{-1}$;
  (i) from $5\times10^5$ to $5\times10^6$ $M^{-1}S^{-1}$; or
  (j) from $6\times10^5$ to $5\times10^6$ $M^{-1}S^{-1}$.

In an example, the $K_{on}$ is (or is about) 1 or $2\times10^{-5}$ $M^{-1}S^{-1}$ (eg, when the KD is 2-5 nM (eg, 3 nM)). In an example, the $K_{on}$ is (or is about) 1-4, 1, 2, 3 or $4\times10^{-6}$ $M^{-1}S^{-1}$ (eg, when the KD is (or is about) from 5-400 pM (eg, 140 or 390 pM) or 5-15 pM (eg, 10 pM)).

As provided in the Clauses or other aspects herein, an anti-PCSK9 antibody or fragment may bind to PCSK9, e.g. human PCSK9 with a $K_D$ of less than 50 nM, less than 40 nM, less than 30 nM as determined by surface plasmon resonance. Another embodiment, anti-PCSK9 antibody or fragment may bind to PCSK9, e.g. human PCSK9 with a $K_D$ of less than 20 nM, less than 15 nM, less than 10 nM as determined by surface plasmon resonance. The anti-PCSK9 antibody or fragment may bind to PCSK9, e.g. human PCSK9 with a $K_D$ of less than 8 nM, less than 5 nM, less than 4 nM, less than 3 nM, less than 2 nM or less than 1 nM as determined by surface plasmon resonance. The $K_D$ may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less.

In another embodiment, the $K_D$ is within a range of 0.01 to 1 nM, or a range of 0.05 to 2 nM, or a range of 0.05 to 1 nM. The $K_D$ may be with regard to hPCSK9, cynomolgus monkey (ie, "cyno") PCSK9 and/or mouse PCSK9.

In another embodiment, the anti-PCSK9 antibodies described herein have a $K_{ON}$ rate (e.g. as measured by SPR, e.g. at 25° C. or at 37° C.) of approximately 0.5 to 10 μM, for example approximately 1 to 8 μM or approximately 1 to 7 μM. In another embodiment, the $K_{ON}$ rate is approximately 1 to 5 μM, e.g. approximately 1 μM, approximately 1.5 μM, approximately 2 μM, approximately 2.5 μM or approximately 3 μM. In another embodiment, the $K_{ON}$ rate is approximately 3.5 μM, approximately 4 μM, approximately 4.5 μM, approximately 5 μM or approximately 5.5 μM.

In another embodiment, the anti-PCSK9 antibodies described herein have a $K_{OFF}$ rate (e.g. as measured by SPR, e.g. at 25° C. or at 37° C.) of approximately 0.01 to 100 mM, for example approximately 0.1 to 50 mM or approximately 0.5 to 50 mM. In another embodiment, the $K_{OFF}$ rate is approximately 0.5 to 10 mM, or approximately 0.5 to 10 mM, e.g. approximately 1 mM, approximately 2 mM, approximately 3 mM, approximately 4 mM or approximately 5 mM. In another embodiment, the $K_{OFF}$ rate is approximately 0.6 mM, approximately 0.7 mM, approximately 0.8 mM or approximately 0.9 mM.

Optionally, the antibody of the invention comprises a human IgG4 constant region.

Preferably, an antibody or a fragment thereof that specifically binds to a hPCSK9 does not cross-react with other antigens (but may optionally cross-react with different PCSK9 species, e.g., rhesus, cynomolgus, or murine). An antibody or a fragment thereof that specifically binds to a PCSK9 antigen can be identified, for example, by immunoassays, BIAcore™, or other techniques known to those of skill in the art. An antibody or a fragment thereof binds specifically to a hPCSK9 antigen when it binds to a hPCSK9 antigen with higher affinity than to any cross-reactive antigen as determined using experimental techniques, such as radioimmunoassays (RIA) and enzyme-linked immunosorbent assays (ELISAs). Typically, a specific or selective reaction will be at least twice background signal or noise and more typically more than 10 times background. See, e.g. Paul, ed., 1989, Fundamental Immunology Second Edition, Raven Press, New York at pages 332-336 for a discussion regarding antibody specificity.

Contact amino acid residues involved in the interaction of antibody and antigen, such as PCSK9, may be determined by various known methods to those skilled in the art.

In one embodiment, if the antibody recognises a linear epitope, short peptides based on the antigen sequence can be produced and binding of the antibody to these peptides can be assessed using standard techniques.

In one embodiment, limited proteolytic digestion and mass spectrophotometry can be used to identify binding epitopes.

In one embodiment, the contact residues of the epitope are identified by X-ray crystallography. In one embodiment, the contact residues of the epitope are identified by cryo-electro microscopy. In one embodiment, the contact residues of the epitope are identified by a combination of limited proteolytic digestion and mass spectrometry.

In another embodiment, the anti-PCSK9 antibodies (and fragments) described in herein provide improved transient expression levels over other anti-PCSK9 antibodies and fragments. Thus, in one embodiment, the anti-PCSK9 antibody (or fragment) is expressed in a HEK293 cell, e.g. a HEK293T cell, at an expression level of approximately 100 µg/mL, or in a range of approximately 100 to 350 µg/mL. In another embodiment, the expression level is above approximately 350 µg/mL.

In another embodiment, the anti-PCSK9 antibody (or fragment) is expressed in a CHO cell, e.g. an Expi-CHO cell, at an expression level of approximately 100 µg/mL, or in a range of approximately 100 to 350 µg/mL. In another embodiment, the expression level is above approximately 350 µg/mL.

In another embodiment, the anti-PCSK9 antibody (or fragment) is expressed in a CHO cell, e.g. an Expi-CHO cell or a CHO-E7 EBNA cell, at an expression level of approximately 100 µg/mL, or in a range of approximately 100 to 350 µg/mL. In another embodiment, the expression level is above approximately 350 µg/mL. The antibody for example, comprises the VH and VL domains of any one of CL-58838, formatted as a human IgG1 or human IgG4 (eg, IgG4-PE).

In any of these expression systems, the expression is carried out of a scale of between approximately 0.5 mL and 3 mL, for example between approximately 0.5 mL and 2 mL. In any of these expression systems, the anti-PCSK9 antibody (or fragment) may be expressed from a pTT5 vector. In any of these expression systems, the anti-PCSK9 antibody (or fragment) may be expressed in conjunction with a lipid transfection reagent, and may optionally be expressed in a CHO cell, e.g. an Expi-CHO cell. In any of these expression systems, the anti-PCSK9 antibody (or fragment) may be expressed in conjunction with a PEI transfection reagent, and may optionally be expressed in a CHO cell, e.g. an CHO-E7 EBNA cell. In any of these expression systems, the anti-PCSK9 antibody (or fragment) may be expressed in conjunction with a helper plasmid (e.g. an AKT helper plasmid), and may optionally be expressed in a CHO cell, e.g. an CHO-E7 EBNA cell.

In any of these expression systems, the expression level is between approximately 100 µg/mL and approximately 1500 µg/mL, for example between approximately 100 µg/mL and approximately 1000 µg/mL, or between approximately 200 µg/mL and approximately 1000 µg/mL, or between approximately 350 µg/mL and approximately 1000 µg/mL. In any of these expression systems, the lower limit of expression may be approximately 100 µg/mL, approximately 200 µg/mL, approximately 300 µg/mL, or approximately 400 µg/mL. In another embodiment, the lower limit of expression may be approximately 500 µg/mL, approximately 600 µg/mL, approximately 700 µg/mL, or approximately 800 µg/mL. In any of these expression systems, the upper limit of expression may be approximately 2000 µg/mL, approximately 1800 µg/mL, approximately 1600 µg/mL, or approximately 1500 µg/mL. In another embodiment, the upper limit of expression may be approximately 1250 µg/mL, approximately 1000 µg/mL, approximately 900 µg/mL, or approximately 800 µg/mL.

In another embodiment, the expression system is a Lonza expression system, e.g. Lonza X-Ceed® system. In the Lonza expression system, the expression may be carried out at a scale of approximately 30 mL to 2 L, for example 50 mL to 1 L, or 1 L to 2 L. In the Lonza expression system, the anti-PCSK9 antibody (or fragment) may be expressed in conjunction with electroporation, and optionally without any helper plasmids. In the Lonza expression system, the anti-PCSK9 antibody (or fragment) may be expressed at a level of approximately 1 g/L, or approximately 900 mg/L, or approximately 800 mg/L, or approximately 700 mg/L. In another embodiment, In the Lonza expression system, the anti-PCSK9 antibody (or fragment) may be expressed at a level of approximately 600 mg/L or approximately 500 mg/L or approximately 400 mg/L. In the Lonza expression system, the anti-PCSK9 antibody (or fragment) may be expressed at a level of between approximately 400 mg/L and approximately 2 g/L, for example between approximately 500 mg/L and approximately 1.5 g/L, or between approximately 500 mg/L and approximately 1 g/L. In another embodiment, the expression level is above 1 g/L. In another embodiment, the anti-PCSK9 antibodies provide improved half-life over other anti-PCSK9 antibodies.

In one embodiment, the antibody or fragment is a human antibody or fragment. In one embodiment, the antibody or fragment is a fully human antibody or fragment. In one embodiment, the antibody or fragment is a fully human monoclonal antibody or fragment.

in one embodiment, the antibody or fragment is a humanised antibody or fragment. In one embodiment, the antibody or fragment is a humanised monoclonal antibody or fragment.

Contact amino acid residues involved in the interaction of antibody and antigen may be determined by various known methods to those skilled in the art, such as alanine scanning, protein crystallography, mass spectrophotometry or any other technique as will be apparent to the skilled addressee.

In one embodiment, the recited CDR comprises one amino acid substitution, which may be a conservative amino acid substitution. In one embodiment, the recited CDR comprises two amino acid substitutions, which may be conservative amino acid substitutions. In one embodiment, the recited CDR comprises three amino acid substitutions, which may be conservative amino acid substitutions. In one embodiment, the recited CDR comprises four amino acid substitutions, which may be conservative amino acid substitutions. In one embodiment, the recited CDR comprises five amino acid substitutions, which may be conservative amino acid substitutions. In one embodiment, the recited CDR comprises six amino acid substitutions, which may be conservative amino acid substitutions.

Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g. substituting a charged or hydrophobic amino; acid with alanine), or alternatively, in which a naturally-occurring amino acid is substituted with a non-conventional amino acid.

In one embodiment, the conservative amino acid substitutions are as described herein. For example, the substitution may be of Y with F, T with S or K, P with A, E with D or Q, N with D or G, R with K, G with N or A, T with S or K, D with N or E, I with L or V, F with Y, S with T or A, R with K, G with N or A, K with R, A with S, K or P. In another embodiment, the conservative amino acid substitutions may be wherein Y is substituted with F, T with A or S, I with L or V, W with Y, M with L, N with D, G with A, T with A or S, D with N, I with L or V, F with Y or L, S with A or T and A with S, G, T or V.

In an embodiment, the present invention provides a pharmaceutical composition comprising an anti-PCSK9 antagonist (eg, an antibody, or PCSK9-binding fragment thereof) of the present invention, and an acceptable carrier, diluent, or excipient. More particularly, the compositions of the present invention further comprise one or more additional therapeutic agents, eg, a statin. As referred to herein, a "statin" (also known as HMG-CoA reductase inhibitors) are inhibitors of the enzyme HMG-coA reductase, which mediates cholesterol production in the liver. Statins, by competitively binding HMG-CoA reductase, prevent the binding of HMG-CoA to the enzyme and thereby inhibit the activity of the reductase (e.g. the production of mevalonate). Non-limiting examples of statins can include atorvastatin (LIPITOR™), fluvastatin (LESCOL™), lovastatin (MEVACOR™, ALTOCOR™), pitavastatin (LIVALO™), pravastatin (PRAVACHOL™), rosuvastatin (CRESTOR™), and simvastatin (ZOCOR™).

Statins can be administered in combination with other agents, e.g. the combination of ezetimibe and simvastatin.

In an example, the anti-PCSK9 antagonist, antibody or fragment binds to PCSK9 with a KD of less than about $1 \times 10^{-8}$ M, preferably, less than about $1 \times 10^{-9}$ M as determined by common methods known in the art, eg, by use of a surface plasmon resonance (SPR) biosensor at 37° C.

"Effective amount" means the amount of an antagonist (eg, antibody) of the present invention or pharmaceutical composition of the present invention that will elicit the biological or medical response or desired therapeutic effect on a subject, mammal or human that is being sought by the researcher, medical doctor, or other clinician. An effective amount may vary according to factors such as the disease state, age, sex, and weight of the individual, and the ability of the antibody and/or statin to elicit a desired response in the individual. An effective amount is also one in which any toxic or detrimental effect is outweighed by the therapeutically beneficial effects.

An anti-PCSK9 antagonist antibody, or antigen-binding fragment thereof, of the present invention, combination or pharmaceutical composition comprising the same, may be administered by parenteral routes (eg, subcutaneous, intravenous, intraperitoneal, intramuscular, or transdermal). Administration may be to a subject alone or in combination with a pharmaceutically acceptable carrier and/or diluent in single or multiple doses. Pharmaceutical compositions, combinations or antagonists of the present invention can be prepared by methods well known in the art (e.g., Remington: *The Science and Practice of Pharmacy,* 19$^{th}$ ed. (1995), A. Gennaro et al., Mack Publishing Co.) and may comprise or be combined with one or more pharmaceutically acceptable carriers, diluents, or excipients.

In an embodiment, the subject is a human male, eg, an adult or infant. In an embodiment, the subject is a human female, eg, an adult or infant, eg, a non-pregnant female or pregnant female. I an example, the human is a dialysis patient. The infant may be a human that is >1 month old. In an example, the subject is an adult human with established cardiovascular disease or with primary hyperlipidemia (eg, heterozygous familial hypercholesterolemia [HeFH]). In an example, the subject is an human with HoFH, eg, an adult human.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

The invention may comprise simultaneously or sequentially administering the anti-PCSK9 antagonist and statin. In an example, antagonist and statin are administered no more than 1 month, 4 weeks, 3 weeks, 2 weeks, 1 week, 10 days, 9 days, 8 days, 7 days, 6 days, 5 days, 4 days, 3 days, 2 days or 1 day apart. As exemplified herein, administration of the antagonist and statin can be effective if no more than 7 days (eg, no more than one day) apart. In an example, the anti-PCSK9 antagonist and statin are administered to the subject no more than 10, 14, 21 or 28 days apart.

In an example, the statin is administered 2, 3 or 4 times weekly. In another example, the statin is administered 1, 2, 3 or 4 times monthly or in a 8 week period.

In an example, the statin and/or antibody or fragment is administered to the subject intraveneously or subcutaneously.

In an example, the hyperlipidaemia or hypercholesterolaemia is in a subject receiving or having received statin treatment, eg, a patient that is a low or non-responder to statin treatment.

In an embodiment, the present invention provides the use of an anti-PCSK9 antagonist and a statin for the manufacture of a medicament. In a further embodiment, the present invention provides the use of an anti-PCSK9 antagonist and a statin for the manufacture of a medicament for the treatment or prevention of hyperlipidaemia or hypercholesterolaemia, eg, moderate to severe hyperlipidaemia or hypercholesterolaemia, eg, in a subject that is a low or no-responder to statin treatment.

In an example the anti-PCSK9 antibody of the invention is an antibody that competes with a reference antibody in an HTRF assay. For example, wherein in the HTRF assay the antibody of the invention is a labelled antibody that is pre-incubated with human PCSK9 and subsequently combined with unlabelled reference antibody (according to part I or II), wherein competition between the antibodies is detected by the assay. In an example, the assay uses AlexaFluor™ 647 labelled antibody of the invention. In an alternative, the human PCSK9 is labelled (eg, with AlexaFluor™ 647, the test antibody is labelled with biotin for binding to Eu3+cryptate-streptavidin, and the reference antibody is unlabelled). Example reference antibodies are preferably CL-274711, CL-148219QLT, CL-274698, CL-148219 and CL-148489 (eg, CL-274711 or CL-148219QLT). Alternatives are alirocumab or evolocumab.

Optionally, the anti-PCSK9 antibody of the invention (test antibody) competes in an HTRF assay with the reference antibody for binding human PCSK9 (or binds the same epitope of human PCSK9 as the reference antibody), wherein the assay uses a directly or indirectly labelled test antibody directly or indirectly labelled with a donor (such as for example Eu3+cryptate) or an acceptor fluorophore (such as for example AlexaFluor™ 647) and a target PCSK9 labelled with either a donor or acceptor fluorophore to enable energy transfer between donor and acceptor, whereby a fluorescence signal is produced and detected. In an example, where AlexaFluor™ 647 labelling is used, competition is detected by a reduction in fluorescence signal at 665 nM of at least 20% when the test antibody is in the presence of the reference antibody versus signal without the reference antibody. Optionally, the reduction in signal at 665 nM is at least 20, 30, 40, 50, 60, 70, 80 or 90%.

In an example, the antibody or fragment is for reducing the total dose of administered over a 4 week period to a human or animal subject for treating or preventing hyperlipidaemia or hypercholesterolaemia or any other disease or condition disclosed herein.

In an example, the antibody or fragment is for reducing to ½ to ⅓ the total dose required in a control subject receiving identical treatment over the 4 week period except for administration of statin without administration of an anti-PCSK9 antagonist (eg, antibody or fragment) to a human or animal subject for treating or preventing hyperlipidaemia or hypercholesterolaemia or any other disease or condition disclosed herein.

In an example, the antibody or fragment is for sparing by ½ to ⅓ the administration of statin administered to a human or animal subject over a treatment period, eg, a 4 week period, for treating or preventing hyperlipidaemia or hypercholesterolaemia osteoporosis or any other disease or condition disclosed herein.

Optionally, the antibody is an IgG4 antibody.

Optionally, the dose of statin administered to the subject is not effective when administered in the absence of the anti-PCSK9 antagonist (eg, antibody or fragment of the invention).

In an example, the subject herein is refractory to a dose of statin, but is responsive for treatment of hyperlipidaemia or hypercholesterolaemia or another disease or condition when administered the antibody or fragment of the invention and the statin dose.

Thus, in an example, the antibody or fragment of the invention is for administration in combination with a dose of a statin to a human or animal subject for treating a PCSK9-related disease or condition in the subject, wherein the subject is treated with the combination, but is not treatable for the disease or condition by administration of the dose of statin in the absence of administration of said antibody or fragment.

The disease or condition may be hyperlipidaemia or hypercholesterolaemia or any other disease or condition disclosed herein, for example selected from a lipid disorder, hyperlipoproteinemia, hyperlipidemia; dyslipidemia; hypercholesterolemia, a heart attack, a stroke, coronary heart disease, atherosclerosis, peripheral vascular disease, claudication, type II diabetes, high blood pressure, and a cardiovascular disease or condition.

The invention provides a antibody or fragment which specifically binds to PCSK9. Optionally, the antibody or fragment comprises a CDRH1 sequence as disclosed herein or a sequence that is at least 70, 80, 85, 90, 95, 96, 97, 98 or 99% identical thereto. Optionally, the antibody or fragment comprises a CDRH2 sequence as disclosed herein or a sequence that is at least 70, 80, 85, 90, 95, 96, 97, 98 or 99% identical thereto. Optionally, the antibody or fragment comprises a CDRH3 sequence as disclosed herein or a sequence that is at least 70, 80, 85, 90, 95, 96, 97, 98 or 99% identical thereto. Optionally, the antibody or fragment comprises a CDRL1 sequence as disclosed herein or a sequence that is at least 70, 80, 85, 90, 95, 96, 97, 98 or 99% identical thereto. Optionally, the antibody or fragment comprises a CDRL2 sequence as disclosed herein or a sequence that is at least 70, 80, 85, 90, 95, 96, 97, 98 or 99% identical thereto. Optionally, the antibody or fragment comprises a CDRL3 sequence as disclosed herein or a sequence that is at least 70, 80, 85, 90, 95, 96, 97, 98 or 99% identical thereto.

Optionally, the antibody or fragment comprises the CDRH1 sequence of CL-148219 or a sequence that is at least 70, 80, 85, 90, 95, 96, 97, 98 or 99% identical thereto; the CDRH2 sequence of CL-148219 or a sequence that is at least 70, 80, 85, 90, 95, 96, 97, 98 or 99% identical thereto; and the CDRH3 sequence of CL-148219 or a sequence that is at least 70, 80, 85, 90, 95, 96, 97, 98 or 99% identical thereto. Optionally, the antibody or fragment comprises the CDRL1 sequence of CL-148219 or a sequence that is at least 70, 80, 85, 90, 95, 96, 97, 98 or 99% identical thereto; the CDRL2 sequence of CL-148219 or a sequence that is at least 70, 80, 85, 90, 95, 96, 97, 98 or 99% identical thereto; and the CDRL3 sequence of CL-148219 or a sequence that is at least 70, 80, 85, 90, 95, 96, 97, 98 or 99% identical thereto.

Optionally, the antibody or fragment comprises the CDRH1 sequence of CL-148489 or a sequence that is at least 70, 80, 85, 90, 95, 96, 97, 98 or 99% identical thereto; the CDRH2 sequence of CL-148489 or a sequence that is at least 70, 80, 85, 90, 95, 96, 97, 98 or 99% identical thereto; and the CDRH3 sequence of CL-148489 or a sequence that is at least 70, 80, 85, 90, 95, 96, 97, 98 or 99% identical thereto. Optionally, the antibody or fragment comprises the CDRL1 sequence of CL-148489 or a sequence that is at least 70, 80, 85, 90, 95, 96, 97, 98 or 99% identical thereto; the CDRL2 sequence of CL-148489 or a sequence that is at least 70, 80, 85, 90, 95, 96, 97, 98 or 99% identical thereto; and the CDRL3 sequence of CL-148489 or a sequence that is at least 70, 80, 85, 90, 95, 96, 97, 98 or 99% identical thereto.

Optionally, the antibody or fragment comprises the VH FR1 sequence of CL-148219 or a sequence that is at least 70, 80, 85, 90, 95, 96, 97, 98 or 99% identical thereto; the VH FR2 sequence of CL-148219 or a sequence that is at least 70, 80, 85, 90, 95, 96, 97, 98 or 99% identical thereto; the VH FR3 sequence of CL-148219 or a sequence that is at least 70, 80, 85, 90, 95, 96, 97, 98 or 99% identical thereto; and the VH FR4 sequence of CL-148219 or a sequence that is at least 70, 80, 85, 90, 95, 96, 97, 98 or 99% identical thereto. Additionally or alternatively, optionally the antibody or fragment comprises the VL FR1 sequence of CL-148219 or a sequence that is at least 70, 80, 85, 90, 95, 96, 97, 98 or 99% identical thereto; the VL FR2 sequence of CL-148219 or a sequence that is at least 70, 80, 85, 90, 95, 96, 97, 98 or 99% identical thereto; the VL FR3 sequence of CL-148219 or a sequence that is at least 70, 80, 85, 90, 95, 96, 97, 98 or 99% identical thereto; and the VL FR4 sequence of CL-148219 or a sequence that is at least 70, 80, 85, 90, 95, 96, 97, 98 or 99% identical thereto.

Optionally, the antibody or fragment comprises the VH FR1 sequence of CL-148489 or a sequence that is at least 70, 80, 85, 90, 95, 96, 97, 98 or 99% identical thereto; the VH FR2 sequence of CL-148489 or a sequence that is at least 70, 80, 85, 90, 95, 96, 97, 98 or 99% identical thereto; the VH FR3 sequence of CL-148489 or a sequence that is at least 70, 80, 85, 90, 95, 96, 97, 98 or 99% identical thereto; and the VH FR4 sequence of CL-148489 or a sequence that is at least 70, 80, 85, 90, 95, 96, 97, 98 or 99% identical thereto. Additionally or alternatively, optionally the antibody or fragment comprises the VL FR1 sequence of CL-148489 or a sequence that is at least 70, 80, 85, 90, 95, 96, 97, 98 or 99% identical thereto; the VL FR2 sequence of CL-148489 or a sequence that is at least 70, 80, 85, 90, 95, 96, 97, 98 or 99% identical thereto; the VL FR3 sequence of CL-148489 or a sequence that is at least 70, 80, 85, 90, 95, 96, 97, 98 or 99% identical thereto; and the VL FR4 sequence of CL-148489 or a sequence that is at least 70, 80, 85, 90, 95, 96, 97, 98 or 99% identical thereto.

In an example, each CDR and FR1-4 herein is according to IMGT nomenclature. In an alternative, each CDR and FR1-4 herein is according to Kabat nomenclature.

Optionally, the antibody or fragment comprises a human gamma-1 heavy chain constant region, eg, comprising a gamma-1 heavy chain constant region sequence disclosed herein or a sequence that is at least 70, 80, 85, 90, 95, 96, 97, 98 or 99% identical thereto. For example, said C region comprises SEQ ID NO: 126 or a sequence that is at least 70, 80, 85, 90, 95, 96, 97, 98 or 99% identical thereto.

Optionally, the antibody or fragment comprises a human gamma-2 heavy chain constant region, eg, comprising a sequence gamma-2 heavy chain constant region sequence disclosed herein or a sequence that is at least 70, 80, 85, 90, 95, 96, 97, 98 or 99% identical thereto. For example, said C region comprises SEQ ID NO: 136 or a sequence that is at least 70, 80, 85, 90, 95, 96, 97, 98 or 99% identical thereto.

Optionally, the antibody or fragment comprises a human gamma-3 heavy chain constant region.

Optionally, the antibody or fragment comprises a human gamma-4 heavy chain constant region, eg, comprising a sequence gamma-4 heavy chain constant region sequence disclosed herein or a sequence that is at least 70, 80, 85, 90, 95, 96, 97, 98 or 99% identical thereto. For example, said C region comprises SEQ ID NO: 3, 144, 152 or 154 or a sequence that is at least 70, 80, 85, 90, 95, 96, 97, 98 or 99% identical thereto.

Optionally, the antibody or fragment comprises a human kappa light chain constant region, eg, comprising a kappa light chain constant region sequence disclosed herein or a sequence that is at least 70, 80, 85, 90, 95, 96, 97, 98 or 99% identical thereto. For example, said C region comprises SEQ ID NO: 156 or a sequence that is at least 70, 80, 85, 90, 95, 96, 97, 98 or 99% identical thereto. In an embodiment, the antibody or fragment comprises a human gamma-4 heavy chain constant region, eg, a IgG4-PE constant region.

Optionally, the antibody or fragment comprises a human lambda light chain constant region, eg, comprising a lambda light chain constant region sequence disclosed herein or a sequence that is at least 70, 80, 85, 90, 95, 96, 97, 98 or 99% identical thereto. For example, said C region comprises SEQ ID NO: 166 or a sequence that is at least 70, 80, 85, 90, 95, 96, 97, 98 or 99% identical thereto.

In an embodiment, the antibody or fragment comprises a human gamma-4 heavy chain constant region, eg, a IgG4-PE constant region.

Target binding ability, specificity and affinity (Kd, $K_{off}$ and/or $K_{on}$) can be determined by any routine method in the art, eg, by surface plasmon resonance (SPR). The term "Kd", as used herein, is intended to refer to the equilibrium dissociation constant of a particular antibody-antigen interaction.

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (eg, using Hepes buffered saline at pH7.6 (also referred to as HBS-EP)).

In one embodiment, the SPR is carried out at a physiological salt level, eg, 150 mM NaCl.

In one embodiment, the SPR is carried out at a detergent level of no greater than 0.05% by volume, eg, in the presence of P20 (polysorbate 20; eg, Tween-20™) at 0.05% and EDTA at 3 mM.

In one example, the SPR is carried out at 25° C. or 37° C. in a buffer at pH7.6, 150 mM NaCl, 0.05% detergent (eg, P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the ligand (eg, antibody) is determined using SPR by
1. Coupling anti-mouse (or other relevant human, rat or non-human vertebrate antibody constant region species-matched) IgG (eg, Biacore™ BR-1008-38) to a biosensor chip (eg, GLM chip) such as by primary amine coupling;
2. Exposing the anti-mouse IgG (or other matched species antibody) to a test IgG antibody to capture test antibody on the chip;
3. Passing the test antigen over the chip's capture surface at 1024 nM, 256 nM, 64 nM, 16 nM, 4 nM with a 0nM (i.e. buffer alone); and
4. And determining the affinity of binding of test antibody to test antigen using surface plasmon resonance, eg, under an SPR condition discussed above (eg, at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH1.7. This removes the captured antibody and allows the surface to be used for another interaction. The binding data can be fitted to 1:1 model inherent using standard techniques, eg, using a model inherent to the ProteOn XPR36™ analysis software.

In an example, the antagonist (eg, antibody or fragment) of the invention is contained in a medical container, eg, a vial, syringe, IV container or an injection device (eg, an intraocular or intravitreal injection device). In an example, the antagonist is in vitro, eg, in a sterile container. In an example, the invention provides a kit comprising the antagonist of the invention, packaging and instructions for use in treating or preventing or diagnosing in a human a disease or condition mediated by PCSK9.

In an example, the instructions indicate that the human should be genotyped for a PCSK9 variant sequence of the invention before administering the antagonist to the human. In an example, the instructions indicate that the human should be phenotyped for a PCSK9 variant of the invention before administering the ligand to the human. In an example, the human is of Chinese (eg, Han) ethnicity and the instructions are in Chinese (eg, Mandarin).

In an example, the antagonist is (or has been determined as) a neutraliser of PCSK9. In an example, determination is carried out in a human (eg, in a clinical trial). In an example, determination is carried out in a non-human, eg, in a mouse, rat, rabbit, pig, dog, sheep or non-human primate (eg, Cynomolgous monkey, rhesus monkey or baboon).

Variants of PCSK9 can include the forms described in WO2015092393 as a, f, c, r, p, m, e h, aj, and q. Sequences of these variants are provided therein, see, e.g, SEQ ID NOs:1-27 and in Table 1, 2 or 6. The disclosure of this reference and these sequences are incorporated herein by reference for possible use in the present invention. In an example, the antagonist specifically binds to a PCSK9 variant disclosed in WO2015092393. In an example, additionally or alternatively the human subject expresses such a PCSK9 variant.

In an example, the antagonist specifically binds to PCSK9 variants comprising a E670G amino acid. In an example, additionally or alternatively the human subject expresses such a PCSK9 variant.

In an example, the antagonist specifically binds to PCSK9 variants comprising a 1474V amino acid. In an example, additionally or alternatively the human subject expresses such a PCSK9 variant.

Antagonists of the invention are useful, for instance, in specific binding assays, for genotyping or phenotyping humans, affinity purification of the PCSK9 and in screening assays to identify other antagonists of PCSK9 activity. Some of the antagonists of the invention are useful for inhibiting binding of PCSK9 to a cognate human receptor or protein, or inhibiting PCSK9-mediated activities.

The invention encompasses anti-PCSK9 (eg, PCSK9) antibody antagonists having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, modification of galactosylation can be made in order to modify complement dependent cytotoxicity (CDC).

In an example, the invention features a pharmaceutical composition comprising a antagonist of the invention, wherein the antagonist is or comprises a recombinant human antibody or fragment thereof which specifically binds the PCSK9 (eg, a rare variant as described herein) and a pharmaceutically acceptable carrier. In one embodiment, the invention features a composition which is a combination of an antibody antagonist or antigen-binding fragment of an antibody of the invention, and a second therapeutic agent. The second therapeutic agent may be any of an anti-inflammatory agent, an anti-angiogenesis agent, a painkiller, a diuretic, a chemotherapeutic agent, an anti-neoplastic agent, a vasodilator, a vasoconstrictor, a statin, a beta blocker, a nutrient, an adjuvant, an anti-obesity agent and an anti-diabetes agent.

In an example, the invention features a method for inhibiting PCSK9 activity using the anti-PCSK9 antagonist of the invention (eg, an antibody or antigen-binding portion of the antibody of the invention), wherein the therapeutic method comprises administering a therapeutically effective amount of a pharmaceutical composition comprising the antagonist. The disorder treated is any disease or condition which is improved, ameliorated, inhibited or prevented by removal, inhibition or reduction of PCSK9 activity.

Paragraphs:

The invention provides the following aspects set out in Paragraphs 1 et seq.

1. An antibody or fragment comprising a binding site which specifically binds to Proprotein Convertase Subtilisin Kexin type 9 (PCSK9), wherein the binding site comprises a VH domain that is encoded by a nucleotide sequence that is derived from the recombination of a human VH gene segment, DH gene segment and JH gene segment, wherein the VH gene segment is selected from IGHV4-31, IGHV4-59, IGHV4-4 and IGHV3-9.

2. The antibody or fragment according to Paragraph 1, wherein (i) the VH gene segment is IGHV4-31 and the DH gene segment is human gene segment IGHD3-9; or (ii) the VH gene segment is IGHV4-59 and the DH gene segment is human gene segment IGHD3-10; or (iii) the VH gene segment is IGHV4-4 and the DH gene segment is human gene segment IGHD2-15; or (iv) the VH gene segment is IGHV3-9 and the DH gene segment is human gene segment IGHD3-9.

3. The antibody or fragment according to Paragraph 1 or 2, wherein the JH gene segment is human gene segment IGHJ6.

4. The antibody or fragment according to any preceding Paragraph, wherein the binding site comprises a CDRH3 sequence selected from SEQ ID NO: 271, 285, 15, 77, 29, 91, 211 and 225.

5. The antibody or fragment according to any preceding Paragraph, wherein the binding site comprises a VH domain comprising SEQ ID NO: 259, 1, 65 or 199.

6. The antibody or fragment according to any preceding Paragraph, wherein the binding site comprises a VH domain comprising SEQ ID NO: 259 paired with a VL domain comprising SEQ ID NO: 289.

7. The antibody or fragment according to any one of Paragraphs 1 to 5, wherein the binding site comprises a VH domain comprising SEQ ID NO: 319 paired with a VL domain comprising SEQ ID NO: 349.

8. An antibody or fragment which specifically binds to PCSK9 and comprises the CDRH3 sequence of an anti-PCSK9 antibody according to any preceding Paragraph, or said CDRH3 sequence comprising 3, 2 or 1 amino acid substitution(s).

9. An antibody or fragment (optionally according to any preceding Paragraph) which specifically binds to PCSK9 and comprises a VH domain which comprises a CDRH3 sequence of an antibody selected from CL-274711, CL-148219QLT, CL-274698, CL-148219 and CL-148489 (eg, CL-274711 or CL-148219QLT); or said sequence comprising 3, 2 or 1 amino acid substitution(s).

10. The antibody or fragment according to Paragraph 9, wherein the VH domain comprises (i) a CDRH3 sequence of an antibody selected from CL-274711, CL-148219QLT, CL-274698, CL-274711, CL-148219QLT, CL-274698, CL-148219 and CL-148489 (eg, CL-274711 or CL-148219QLT); or said CDRH3 sequence comprising 3, 2 or 1 amino acid substitution(s); and (ii) a CDRH1 sequence of said selected antibody; or said CDRH1 sequence comprising 3, 2 or 1 amino acid substitution(s).

11. The antibody or fragment according to Paragraph 9 or 10, wherein the VH domain comprises (iii) a CDRH3 sequence of an antibody selected from CL-274711, CL-148219QLT, CL-274698, CL-148219 and CL-148489 (eg, CL-274711 or CL-148219QLT); or said CDRH3 sequence comprising 3, 2 or 1 amino acid substitution(s); and (iv) a CDRH2 sequence of said selected antibody; or said CDRH2 sequence comprising 3, 2 or 1 amino acid substitution(s).

12. An antibody or fragment (optionally according to any preceding Paragraph) comprising a binding site which specifically binds to PCSK9, wherein the binding site comprises a VH domain that comprises the amino acid sequence of a VH domain of an antibody selected from CL-274711, CL-148219QLT, CL-274698, CL-148219 and CL-148489 (eg, CL-274711 or CL-148219QLT); or an amino acid that is at least 70% identical thereto.

13. The antibody or fragment according to Paragraph 9, 10, 11 or 12, wherein the selected antibody is CL-274711 or CL-148219QLT.

14. The antibody or fragment according to any preceding Paragraph comprising first and second copies of said VH domain.

15. An antibody or fragment (optionally according to any preceding Paragraph) comprising a binding site which specifically binds to PCSK9, wherein the binding site comprises a VL domain that is encoded by a nucleotide sequence that is derived from the recombination of a human VL gene segment and JL gene segment, wherein the VL gene segment is selected from IGKV3-11, IGKV2-28 and IGKV2-29.

16. The antibody or fragment according to Paragraph 15, wherein the JL gene segment is a human gene segment selected from IGKJ4, IGJK3 and IGKJ1.

17. An antibody or fragment which specifically binds to PCSK9 and comprises the CDRL3 sequence of an anti-PCSK9 antibody according to any preceding Paragraph, or said CDRL3 sequence comprising 3, 2 or 1 amino acid substitution(s).

18. An antibody or fragment (optionally according to any preceding Paragraph) which specifically binds to PCSK9 and comprises a VL domain which comprises a CDRL3 sequence selected from SEQ ID NO: 301, 315, 47, 107, 61, 121, 241 and 255, or said selected CDRL3 sequence comprising 3, 2 or 1 amino acid substitution(s).

19. An antibody or fragment (optionally according to any preceding Paragraph) which specifically binds to PCSK9 and comprises a VL domain which comprises a CDRL3 (and optionally a CDRH3) sequence of an antibody selected from CL-274711, CL-148219QLT, CL-274698, CL-148219 and CL-148489 (eg, CL-274711 or CL-148219QLT); or said sequence(s) each comprising 3, 2 or 1 amino acid substitution(s).

20. The antibody or fragment according to Paragraph 19, wherein the VL domain comprises (i) a CDRL3 sequence (and optionally a CDRH3) of an antibody selected from CL-274711, CL-148219QLT, CL-274698, CL-148219 and CL-148489 (eg, CL-274711 or CL-148219QLT); or said CDR3 sequence(s) each comprising 3, 2 or 1 amino acid substitution(s); and (ii) a CDRL1 (and optionally a CDRH1) sequence of said selected antibody; or said CDR1 sequence(s) each comprising 3, 2 or 1 amino acid substitution(s).

21. The antibody or fragment according to Paragraph 19 or 20, wherein the VL domain comprises (iii) a CDRL3 (and optionally a CDRH3) sequence of an antibody selected from CL-274711, CL-148219QLT, CL-274698, CL-148219 and CL-148489 (eg, CL-274711 or CL-148219QLT); or said CDR3 sequence(s) each comprising 3, 2 or 1 amino acid substitution(s); and (iv) a CDRL2 (and optionally a CDRH2) sequence of said selected antibody; or said CDR2 sequence(s) each comprising 3, 2 or 1 amino acid substitution(s).

22. An antibody or fragment (optionally according to any preceding Paragraph) comprising a binding site which specifically binds to PCSK9, wherein the binding site comprises a VL domain that comprises the amino acid sequence of a VL domain of an antibody selected from CL-274711, CL-148219QLT, CL-274698, CL-148219 and CL-148489 (eg, CL-274711 or CL-148219QLT); or an amino acid that is at least 70% identical thereto.

23. An antibody or fragment (optionally according to any preceding Paragraph) which specifically binds to PCSK9 and comprises the heavy chain amino acid sequence of an antibody selected from CL-274711, CL-148219QLT, CL-274698, CL-148219 and CL-148489 (eg, CL-274711 or CL-148219QLT); or an amino acid that is at least 70% identical thereto.

24. An antibody or fragment (optionally according to any preceding Paragraph) which specifically binds to PCSK9 and comprises the light chain amino acid sequence of an antibody selected from CL-274711, CL-148219QLT, CL-274698, CL-148219 and CL-148489 (eg, CL-274711 or CL-148219QLT); or an amino acid that is at least 70% identical thereto.

25. The antibody or fragment of Paragraph 23, comprising the light chain amino acid sequence of said selected antibody; or an amino acid that is at least 70% identical thereto.

26. An antibody or fragment (optionally according to any preceding Paragraph) which specifically binds to a human PCSK9 epitope that is identical to an epitope to which the antibody of any preceding Paragraph binds.

27. The antibody or fragment according to Paragraph 26, wherein the epitope is identified by unrelated amino acid scanning, or by X-ray crystallography.

28. The antibody or fragment according to Paragraph 27, wherein the contact residues of the epitope are defined by a reduction in affinity of at least 10-fold in an unrelated amino acid scan, e.g. an alanine scan as determined by SPR.

29. An antibody or fragment (optionally according to any preceding Paragraph) which competes for binding to human PCSK9 with the antibody of any preceding Paragraph.

30. The antibody or fragment according to any preceding Paragraph which specifically binds to a PCSK9 comprising an amino acid sequence selected from SEQ ID NOs: 189-194.

31. The antibody or fragment according to any preceding Paragraph, wherein the antibody or fragment comprises a human constant region, optionally an IgG4 constant region or an IgG1 constant region.

32. The antibody or fragment according to Paragraph 31, wherein the constant region is an IgG4-PE constant region, optionally the constant region comprises the amino acid sequence of SEQ ID NO: 3 or 152.

33. The antibody or fragment according to any preceding Paragraph further comprising an antigen-binding site that specifically binds another target antigen, optionally ANGPTL3.

34. An anti-PCSK9 antibody or fragment as defined in any preceding Paragraph for treating or preventing a PCSK9-mediated disease or condition (optionally hypercholesterolaemia) in a subject.

35. The anti-PCSK9 antibody or fragment of Paragraph 34, wherein the disease or condition is selected from hypercholesterolemia, hyperlipidemia, hypercholesterolemia, dyslipidemia, cholestatic liver disease, nephrotic syndrome, hypothyroidism, obesity, diabetes, atherosclerosis or a cardiovascular disease.

36. The antibody or fragment of Paragraph 34 or 35, wherein the antibody or fragment is administered to the subject simultaneously or sequentially with a statin.

37. A combination of an amount of an anti-PCSK9 antibody or fragment and an amount of a statin (optionally comprising multiple doses of said antibody and/or statin), wherein the antibody or fragment is according to any one of Paragraphs 1 to 36.

38. The antibody, fragment or combination according to any one of Paragraphs 1 to 37 for use in a method of treating or preventing hypercholesterolaemia in a subject that has previously been on a statin treatment regime at a first dose, wherein the method comprises reducing the dose of statin that is administered to the subject or administering no statin to the subject, wherein the method comprises administering the antibody or fragment to the subject.

39. The combination of Paragraph 37 or 38, wherein comprising statin at a daily dose of 10 to 20 mg (eg, 10 mg); or <60 mg (eg, 40 mg).

40. The antibody, fragment or combination of any preceding Paragraph for administering to a human or animal subject suffering from elevated cholesterol, for lowering plasma low density lipoprotein cholesterol (LDL-C) level in the subject after the subject has received the anti-PCSK9 antibody or fragment.

41. Use of the antibody, fragment or combination as defined in any preceding Paragraph in the manufacture of a medicament for administration to a subject for treating or preventing a PCSK9-mediated disease or condition, optionally hypercholesterolaemia.

42. A method of treating or preventing a PCSK9-mediated disease or condition in a subject (optionally hypercholesterolaemia), the method comprising administering to said subject a therapeutically effective amount of an antibody, fragment or combination as defined in any one of Paragraphs 1 to 40, wherein the PCSK9-mediated disease or condition is thereby treated or prevented.

43. The use according to Paragraph 41 or the method according to Paragraph 42, wherein the PCSK9-mediated disease or condition is hypercholesterolaemia.

44. The antibody, fragment, combination, use or the method according to any one of Paragraphs 34 to 43, further comprising administering to the subject a further therapy, for example a further therapeutic agent, optionally wherein the further therapeutic agent is selected from the group consisting of a:
   a. Statin;
   b. An ANGPTL3 inhibitor (eg, an anti-ANGPTL3 antibody, eg, evinacumab)
   c. Fibrate;
   d. Bile acid sequestrant;
   e. Nicotinic acid; and
   f. Niacin.

45. A pharmaceutical composition comprising an antibody, fragment or combination as defined in any one of Paragraphs 1 to 40 and 44 and a pharmaceutically acceptable excipient, diluent or carrier and optionally in combination with a further therapeutic agent selected from an agent recited in Paragraph 44.

46. The pharmaceutical composition according to Paragraph 45 for treating and/or preventing a PCSK9-mediated condition or disease, optionally hypercholesterolaemia.

47. The pharmaceutical composition according to Paragraph 45 or 46 in combination with a label or instructions for use to treat and/or prevent said disease or condition in a human; optionally wherein the label or instructions comprise a marketing authorisation number (optionally an FDA or EMA authorisation number); optionally wherein the kit comprises an IV or injection device that comprises the antibody or fragment.

48. A nucleic acid that encodes a VH domain and/or a VL domain of an antibody or fragment as defined in any one of Paragraphs 1 to 33.

49. A nucleic acid that encodes a VH domain comprising the amino acid sequence of a VH domain of an antibody selected from CL-274711, CL-148219QLT, CL-274698, CL-148219 and CL-148489 (eg, CL-274711 or CL-148219QLT); or an amino acid that is at least 70% identical thereto.

50. A nucleic acid that encodes a VL domain comprising the amino acid sequence of a VL domain of an antibody selected from CL-274711, CL-148219QLT, CL-274698, CL-148219 and CL-148489 (eg, CL-274711 or CL-148219QLT); or an amino acid that is at least 70% identical thereto.

51. A nucleic acid comprising a nucleotide sequence that is at least 70% identical to the sequence of SEQ ID NO: 260 or 320.
Alternatively:
   A nucleic acid comprising a nucleotide sequence that is at least 70% identical to the sequence of SEQ ID NO: 2, 66 or 200.

52. A nucleic acid that encodes a heavy chain and/or a light chain of an antibody or fragment as defined in any one of Paragraphs 1 to 33.

53. A nucleic acid that encodes a heavy chain comprising a VH amino acid sequence that is at least 70% identical to SEQ ID NO: 259 or 319; and a C region amino acid sequence that is at least 70% identical to a IGHG4 sequence, optionally at least 70% identical to SEQ ID NO: 3 or 152.
Alternatively:
   A nucleic acid that encodes a heavy chain comprising a VH amino acid sequence that is at least 70% identical to SEQ ID NO: 1, 65, and a C region amino acid sequence that is at least 70% identical to a IGHG4 sequence, optionally at least 70% identical to SEQ ID NO: 3 or 152.

54. A nucleic acid that encodes a light chain comprising a VL amino acid sequence that is at least 70% identical to SEQ ID NO: 289 or 349; and a C region amino acid sequence that is at least 70% identical to a IGKC sequence, optionally at least 70% identical to SEQ ID NO: 156.
Alternatively:
   A nucleic acid that encodes a light chain comprising a VL amino acid sequence that is at least 70% identical to SEQ ID NO: 33, 95 and 229; and a C region amino acid sequence that is at least 70% identical to a IGKC sequence, optionally at least 70% identical to SEQ ID NO: 156.

55. A nucleic acid (eg, in a host cell, eg, a CHO or HEK293 or Cos cell) comprising
   a. a nucleotide sequence that is at least 70% identical to a heavy chain sequence of an antibody selected from CL-274711, CL-148219QLT, CL-274698, CL-148219 and CL-148489 (eg, CL-274711 or CL-148219QLT); and/or
   b. a nucleotide sequence that is at least 70% identical to a light chain sequence of an antibody selected respectively from CL-274711, CL-148219QLT, CL-274698, CL-148219 and CL-148489 (eg, CL-274711 or CL-148219QLT).

56. A vector comprising the nucleic acid(s) (eg, the nucleic acid(s) of any one of Paragraphs 48 to 55); optionally wherein the vector is a CHO or HEK293 vector.

57. A host cell comprising the nucleic acid(s) (eg, the nucleic acid(s) of any one of Paragraphs 48 to 55) or the vector of Paragraph 56.

58. An antibody, fragment, combination, vector, host cell, use or method as herein described.

In any embodiment herein, preferably the selected antibody is CL-274711.

Therapeutic Administration and Formulations

The invention provides therapeutic compositions comprising the anti-PCSK9 antagonist, eg, antibodies or antigen-binding fragments thereof, of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the size of a subject to be administered, target disease, conditions, route of administration, and the like. When the antagonist, eg, antibody, of the present invention is used for treating various conditions and diseases associated with the PCSK9 in an adult patient, it is advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted.

Various delivery systems are known and can be used to administer the antagonist or pharmaceutical composition of the invention, for example a antagonist provided by e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The antagonist or composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The antagonist or pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the antagonist or pharmaceutical composition can be delivered in a controlled release system. In one embodiment, a pump may be used (see Langer, supra; Sefton (1987) CRC Crit. Ref Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a antagonist or pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25 pen, HUMALOG™ pen, HUMALIN 70/30™ pen (Eli Lilly and Co., Indianapolis, Ind.), NOVOPENT™ I, II and Ill (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENT™, OPTIPEN PRO™, OPTIPEN STARLET™, and OPTICLIKT™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the antagonist(s). Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", or "reduction" are all used herein to mean a decrease by a statistically significant amount. In some embodiments, "reduce," "reduction" or "decrease" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" does not encompass a complete reduction as compared to a reference level. A decrease can be preferably down to a level accepted as within the range of normal for an individual without a given disorder. However, for example, for the purposes of lowering or reducing cholesterol level, for example, a reduction by about 5-10 points can be considered a "decrease" or "reduction."

In certain aspects of all embodiments of the invention, the term "inhibition" is used. Inhibition refers and refers to decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more including 100% inhibition as compared to a reference level. "Complete inhibition" refers to a 100% inhibition as compared to a reference level.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. For the removal of doubt, "substantially" can refer to at least a 90% extent or degree of a characteristic or property of interest, e.g. at least 90%, at least 92%, at least 95%, at least 98%, at least 99% or greater.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

It will be understood that particular configurations, aspects, examples, clauses and embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non-limiting Examples

EXAMPLES

Plasma LDL cholesterol (LDL-C) is a main risk factor of cardiovascular diseases, which cause 4 million deaths annually in Europe. Clearance of plasma LDL-C is primarily carried out in liver by LDL receptor (LDLR). LDLR constantly internalises LDL-C from plasma into hepatocytes and continues LDL-C uptake by recycling back to the cell surface. The surface level of LDLR is negatively regulated by PCSK9, which directly binds to LDLR and facilitates lysosome-mediated degradation of LDLR. Diminished surface exposure of LDLR to LDL-C reduces LDL-C internalisation in hepatocytes and thus increases plasma LDL-C, which may lead to plaque forming and clogging in blood stream. Recently targeting PCSK9 emerges as a promising strategy to control plasma LDL-C level.

We discovered monoclonal antibodies that block PCSK9 function and have therapeutic potential. We first immunised Kymice™ (see, eg, WO2011/004192 and Lee et al, Nat Biotechnol. 2014 April; 32(4):356-63. doi: 10.1038/nbt.2825. Epub 2014 Mar. 16, "Complete humanization of the mouse immunoglobulin loci enables efficient therapeutic antibody discovery") with both human and mouse PCSK9 proteins to generate cross-reactive antibodies. To avoid the unwanted effect of a His tag, we made a cell line that actively secretes the native form of both human and mouse PCSK9 protein without His tag for immunisation. Following immunisation, antibody sequences were retrieved from antigen-specific B cells by Next Generation Sequencing and analyzed in silico to identify favourable antibodies to progress. After expression, antibodies were screened and selected based on cross-reactive binding, affinity, and function by a sequential in vitro screening cascade. Binding to human PCSK9 variants was confirmed to ensure efficacy in the majority of human population. Biophysical features of selected antibodies were characterised from the perspective of developability. In a mouse model of hyperlipidemia, two outstanding antibodies (CL-274711, CL-148219QLT, CL-274698, CL-148219 and CL-148489 (eg, CL-274711 or CL-148219QLT)) showed superior function in decreasing plasma non-HDL cholesterol without changing HDL cholesterol and sustained effect with longer duration compared to benchmark antibodies. In conclusion, we successfully elicited cross-reactive antibodies against PCSK9 and identified at least two superior fully human monoclonal antibodies to block PCSK9 function in vitro and in vivo.

Example 1: Identification of Antibodies by In Vitro Assays

Five immunisation campaigns were conducted in Kymice™ and in vitro assays were conducted including the following selection criteria:—
   (a) Cross-reactive binders against human PCSK9 (hPCSK9), cynomolgus monkey PCSK9 (cynoPCSK9) and mouse PCSK9 (mPCSK9) were selected;
   (b) Antibody affinity against hPCSK9a and mPCSK9 were determined and antibodies with higher affinity were prioritized;
   (c) In a cell-based assay in vitro, neutralisation of antibodies was demonstrated to reduce internalisation of fluorescent hPCSK9 in a human liver cell line (HepG2); and
   (d) Simultaneously, functionality of antibodies to restore LDL uptake in HepG2 cells was determined in the same in vitro cell-based assay as in (c).

Two antibodies (CL-274711, CL-148219QLT, CL-274698, CL-148219 and CL-148489 (eg, CL-274711 or CL-148219QLT)) showed particularly promising function both in vitro and in vivo (Example 2).

CL-148219

Compared to the benchmarks, CL-148219 showed stronger neutralisation activity with higher capacity to restore LDL uptake in vitro, suggesting CL-148219 may directly blocks the interaction between PCSK9 and LDLR. In a mouse model of hyperlipidemia (E3L.CETP mice; de Knijff, Westerterp, Ason, van den Hoek and Kühnast), CL-148219 reduced plasma non-HDL cholesterol superior to benchmark Ab with longer duration of effect. See FIGS. 1-4.

CL-148489

In the in vitro cell-based assay, CL-148489 neutralised hPCSK9 moderately but contained significant capacity to restore LDL uptake, suggesting this antibody may indirectly interfere the binding of PCSK9 to LDLR, possibly via blocking HSPG binding to PCSK9. This antibody also reduced plasma non-HDL cholesterol in a mouse model of hyperlipidemia (E3L.CETP mice) better than benchmarks with similar duration of effect. See FIGS. 5-8.

The benchmarks were: alirocumab hIgG4-PE (SEQ ID Nos: 195 and 196) and "Regeneron pH-D" (a pH-dependent (differential PCSK9 binding inside versus outside lysosome) anti-PCSK9 hIgG4-PE antibody) (SEQ ID Nos: 197 and 198).

The antibodies' VH and VL regions were derived from the recombination of the following gene segments:—

| | | |
|---|---|---|
| CL-148219 VH | VH | IGHV4-59*01 |
| | D | IGHD3-10*01 |
| | JH | IGHJ6*02 |
| CL-148219 VL | VL | IGKV2-28*01 |
| | JL | IGKJ3*01 |
| CL-148489 VH | VH | IGHV3-9*01 |
| | D | IGHD3-9*01 |
| | JH | IGHJ6*02 |
| CL-148489 VL | VL | IGKV2D-29*01 |
| | JL | IGKJ4*01 |

REFERENCES de Knijff, P. et al, 1991, "Familial dysbetalipoproteinemia associated with apolipoprotein E3-Leiden in an extended multigeneration pedigree", J. Clin. Invest. 88: 643-655;

Westerterp, M. et al, 2006, "Cholesteryl ester transfer protein decreases high-density lipoprotein and severely aggravates atherosclerosis in APOE*3-Leidenmice", Arterioscler. Thromb. Vasc. Biol. 26: 2552-2559;

Ason, B. et al, 2011, "PCSK9 inhibition fails to alter hepatic LDLR, circulating cholesterol, and atherosclerosis in the absence of ApoE", J Lipid Res. 2011 April, 52(4): 679-687;

van den Hoek AM. et al, 2014, "APOE*3Leiden.CETP transgenic mice as model for pharmaceutical treatment of the metabolic syndrome", Diabetes Obes Metab. 2014 June; 16(6):537-44; and Kühnast, S et al, 2014, "Alirocumab inhibits atherosclerosis, improves the plaque morphology, and enhances the effects of a statin", J Lipid Res. 2014 October, 55(10): 2103-2112.

Example 2: In Vivo Assays

In this study we used APOE*3Leiden.cholesteryl ester transfer protein (CETP) mice, which contain mouse ApoE, human mutant APOE3*Leiden, and a functional LDLR. These mice have shown excellent translational value with the increases in cholesterol seen in the model treatable by the same therapies which are effective in patients and showing a similar maximum reduction in LDL levels to those obtainable in the clinic.

CETP mice were fed a high fat diet for 4 weeks and then received a single dose of antibody, isotype control or standard of care (alirocumab, an FDA approved PCSK9 inhibitor) on day 0. The mice then received a second higher dose (half log), on day 18. Individual animal cholesterol levels were measured on day 0, 3, 7, 14, 21 and 28. A full lipid profile was carried out on a pooled group sample from the terminal bleed at day 28.

Of the 10 of our antibodies tested two (CL-148219 and CL148489) reduced cholesterol levels by more than the equivalent dose of alirocumab with one those CL-148219 showing a longer duration of effect. In summary we have identified two potentially best in class PCSK9 inhibitors.

Methods

Figure 9:
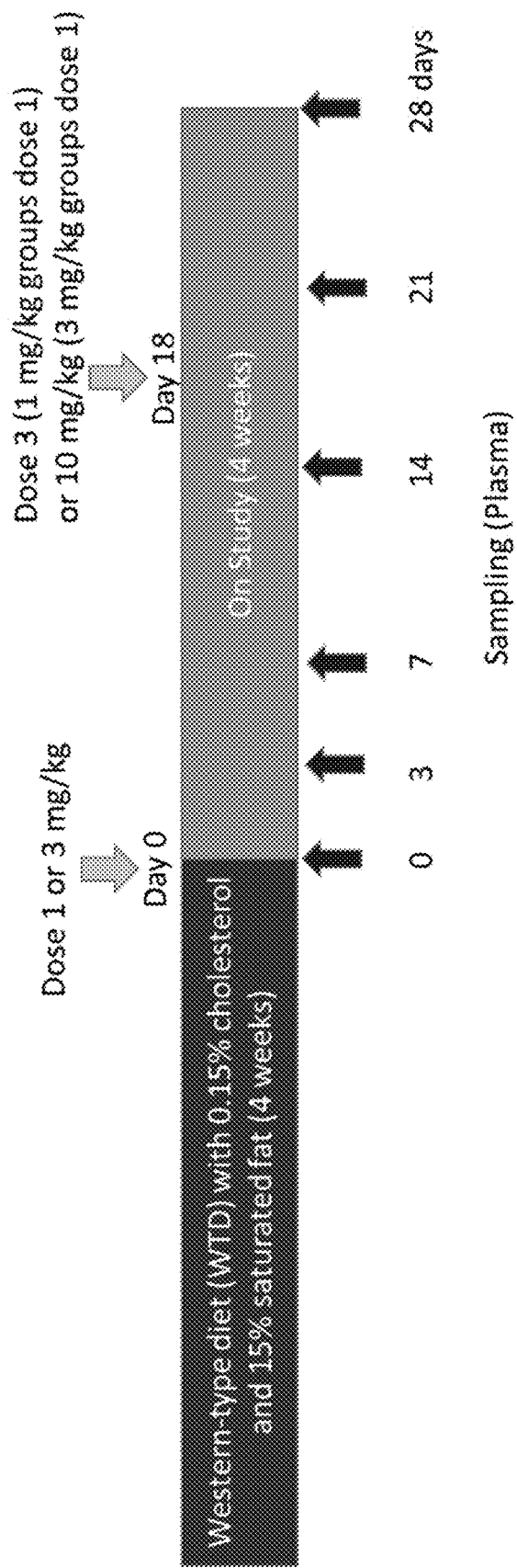
FIG. 9: Study design.

See FIG. 9 for the study design. One hundred and twenty-eight female, 8-14 weeks of age, APOE*3Leiden.CETP transgenic mice were put on Western-type diet (WTD) with 0.15% cholesterol and 15% saturated fat. After 4 weeks run-in period 24 low-responder mice were removed from the study and the animals placed into groups (n=6-8), matched on age, body weight, plasma cholesterol, triglycerides and HDL-cholesterol after 4 h fasting (t=0). The mice were dosed subcutaneously at t=0 with 3 mg/kg of isotype control, benchmark or our anti-PCSK9 antibodies. Four of our antibodies, identified as excellent from prior in vitro screening, had an additional dose group of 1 mg/kg at t=0. At t=18 days the mice received a 2nd subcutaneous dose of the same antibody at a $\%_z$ log higher dose than the first dose (i.e. first dose 3 mg/kg, 2nd dose 10 mg/kg).

Body weight and food intake were measured twice weekly. On day 0, 3, 7, 14, 21 and 28 post the initial dose 4 h fasted plasma samples were collected for the determination of plasma total cholesterol, HDL-cholesterol and triglycerides. Plasma non-HDL-cholesterol values were calculated. At t=28 days, after the last blood collection, mice were sacrificed, and plasma and liver tissue collected. Lipoprotein profiles were determined on FPLC fractions from group pooled plasma samples.

Statistics: Two way annova and Dunnetts post-hoc analysis—Graphpad Prismi™.

Results

Figure 10:
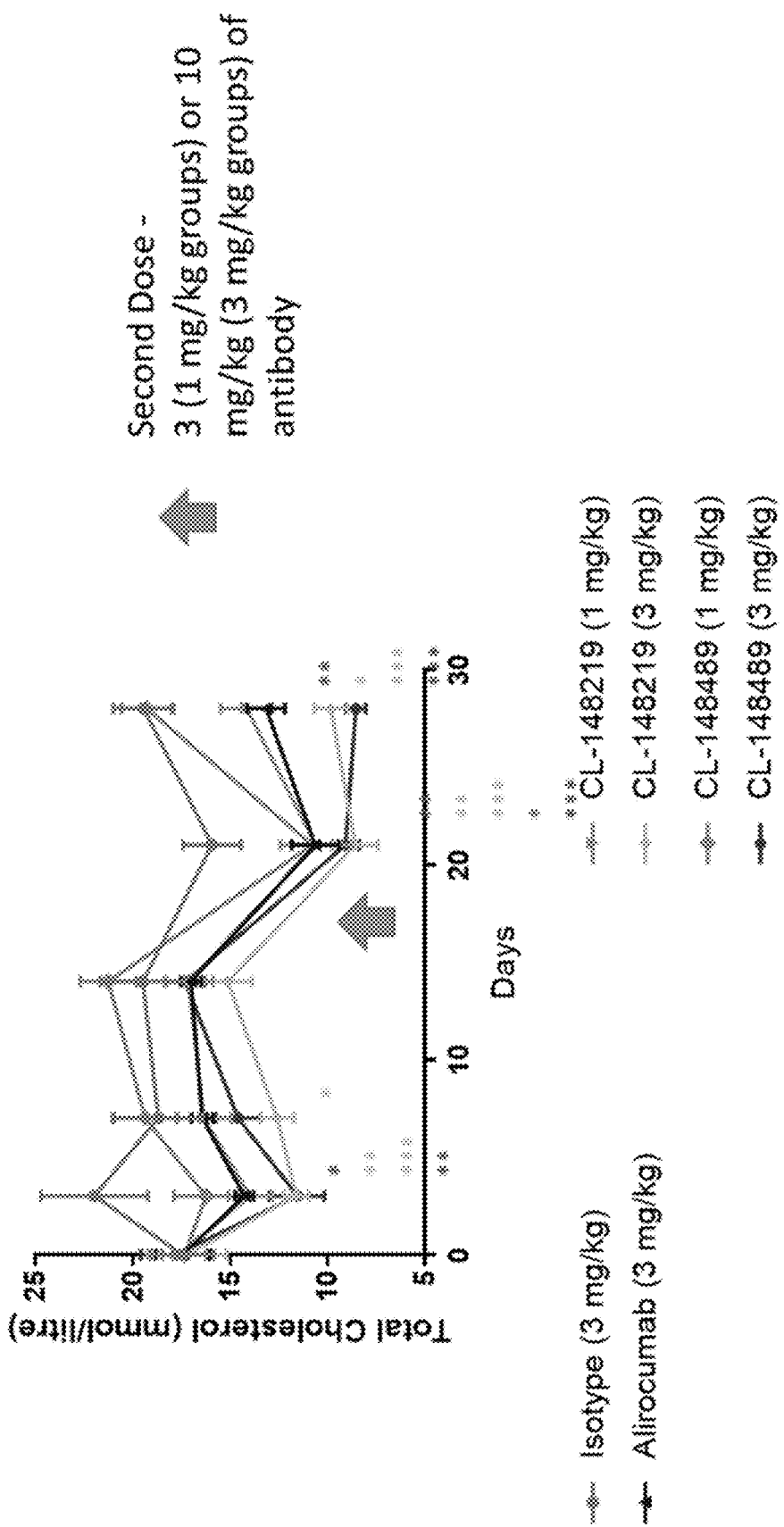
FIG. 10: Total cholesterol.

Total Cholesterol (FIG. 10)

The isotype control group showed plasma total cholesterol levels of 16-22 mmol/L during the study.

Alirocumab significantly reduced total cholesterol at day 3 in the 3 mg/kg dose (−34.9%), and day 21 and 28 (respectively 3 and 10 days after the second injection) in the 10 mg/kg dose (−33.2% and −32.3%, respectively) compared to the isotype control antibody.

CL-148219 significantly reduced total cholesterol at day 3 in both the 1 and 3 mg/kg dose (−36.4% and −47.0%, respectively) and at day 7 in the 3 mg/kg dose (−32.6%). Following the second dose CL-148219 significantly reduced total cholesterol at day 21 and day in both the 3 mg/kg dose (−33.4% and −27.1%, respectively) and 10 mg/kg dose (−46.3% and −49.6%, respectively).

CL-148489 significantly reduced total cholesterol at day 3 and day 21 (3 days after the second injection) in the 3 mg/kg dose (−47.3% and −32.3%, respectively) and following the second dose on day 21 and day 28 in the 10 mg/kg dose (−42.9% and −56.0%, respectively).

Figure 11:
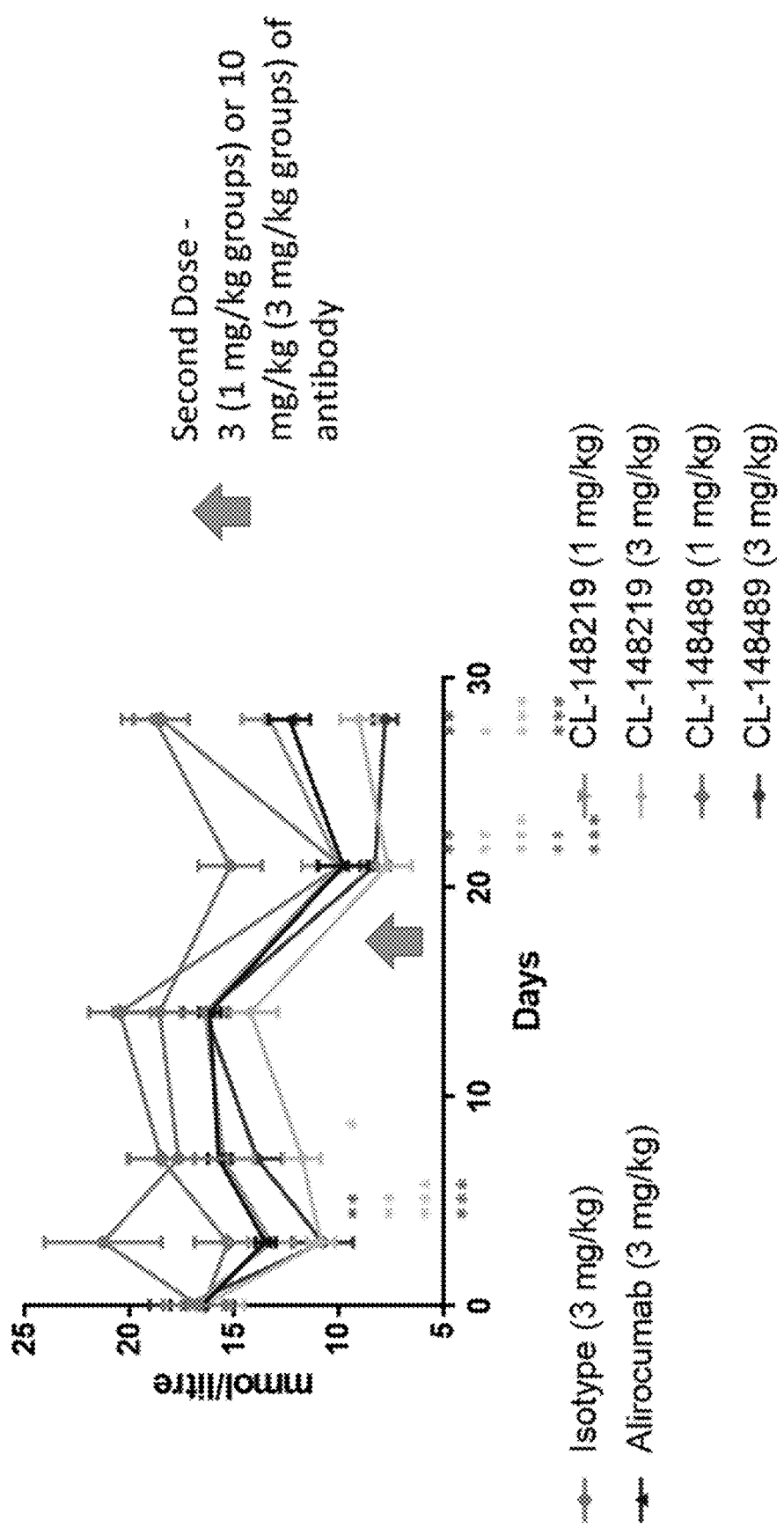
FIG. 11: Total Non-HDL Cholesterol.

Total Non-HDL Cholesterol (FIG. 11)

The isotype control group showed non-HDL-cholesterol levels of 15.2-21.3 mmol/L during the study.

Alirocumab significantly reduced non-HDL-cholesterol at day 3 in the 3 mg/kg dose (−36.5%), and day 21 and 28 (respectively 3 and 10 days after the second injection) in the 10 mg/kg dose (−35.5% and 34.3%, respectively) compared to the isotype control antibody.

CL-148219 significantly reduced non-HDL-cholesterol at day 3 in both the 1 and 3 mg/kg dose (−37.7% and −49.1%, respectively), and at day 7 in the 3 mg/kg dose (−33.5%). Following the second injection CL-148219 significantly reduced non-HDL-cholesterol at day 21 and day 28 in both the 3 mg/kg (−34.4% and −29.2%, respectively) and 10 mg/kg dose (−49.6% and −51.8%, respectively).

CL-148489 significantly reduced non-HDL-cholesterol at day 3 and day 21 (3 days after the second injection) in the 3 mg/kg dose (−49.4% and −35.0%, respectively) and at following the second injection at day 21 and day 28 in the 10 mg/kg dose (−45.5% and −58.5%, respectively).

Figure 12:
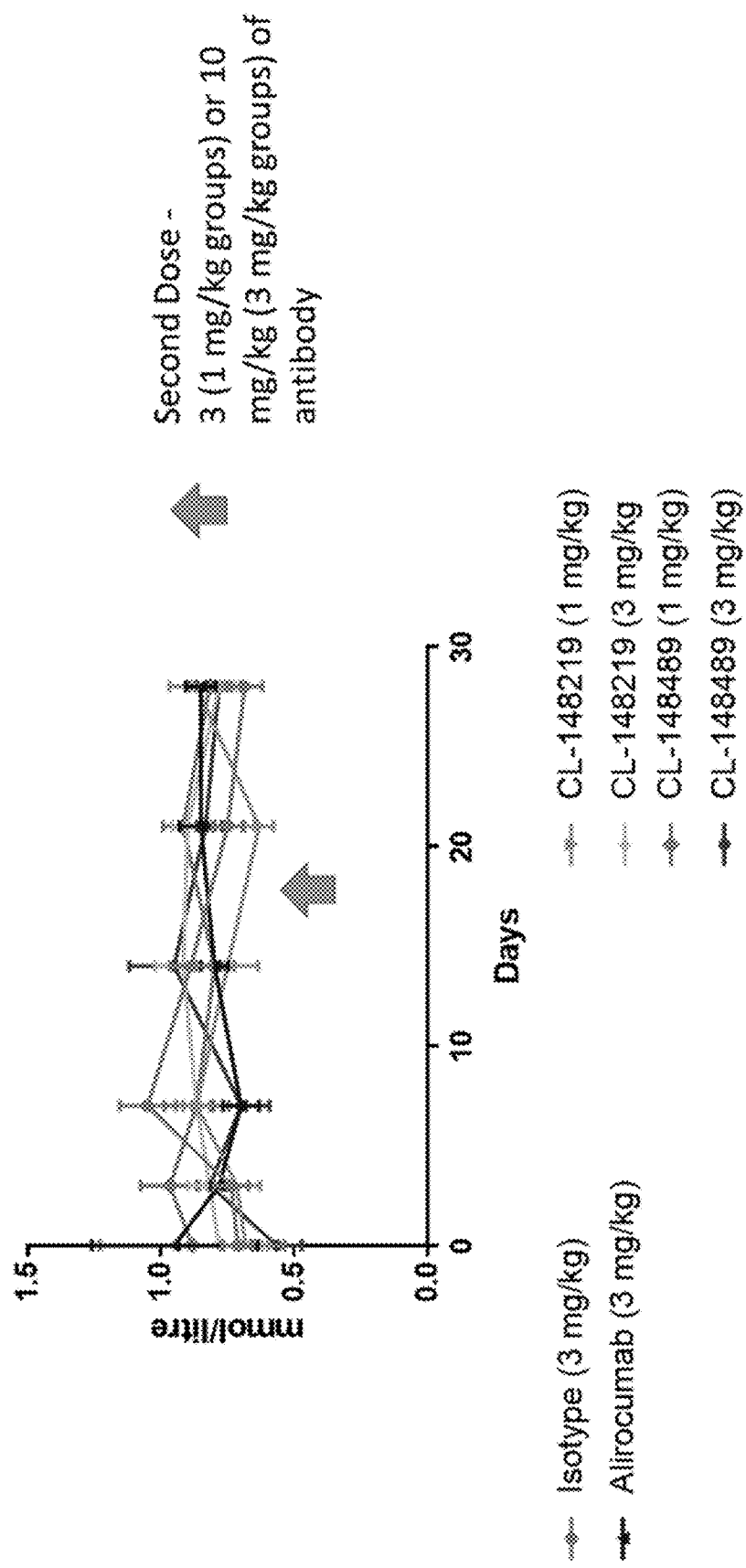
FIG. 12: HDL cholesterol.

HDL Cholesterol (FIG. 12)

None of the antibodies had an effect on HDL cholesterol.

Figure 13:
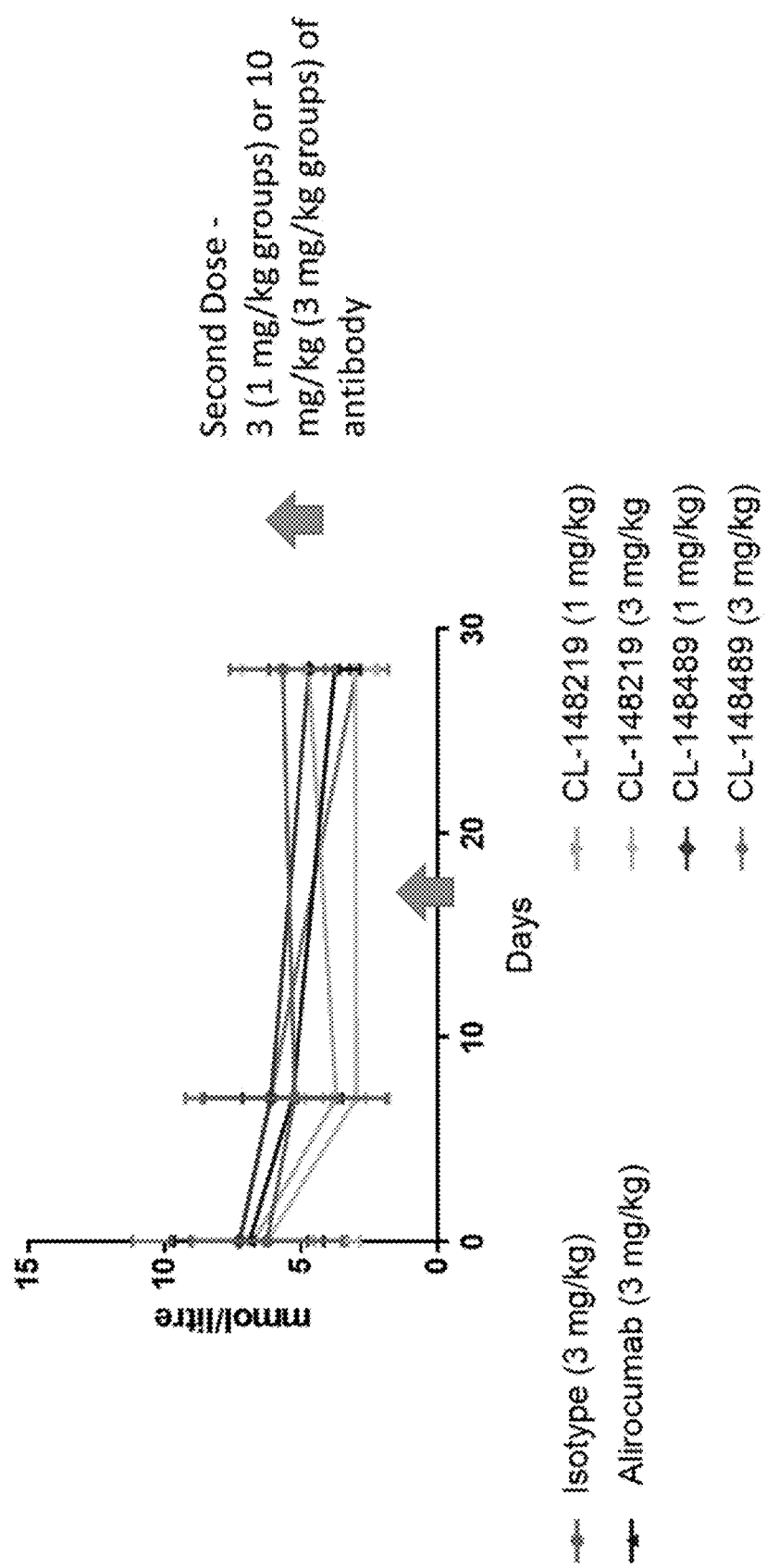
FIG. 13: Triglycerides.

Triglycerides (FIG. 13)

During the study, plasma triglyceride levels remained stable in the isotype control group. Whilst none of the antibodies significantly affected plasma triglycerides compared to the isotype control group CL-148219, CI-148489 and Alirocumab showed a trend towards lower triglyceride levels at day 28.

Figure 14A:
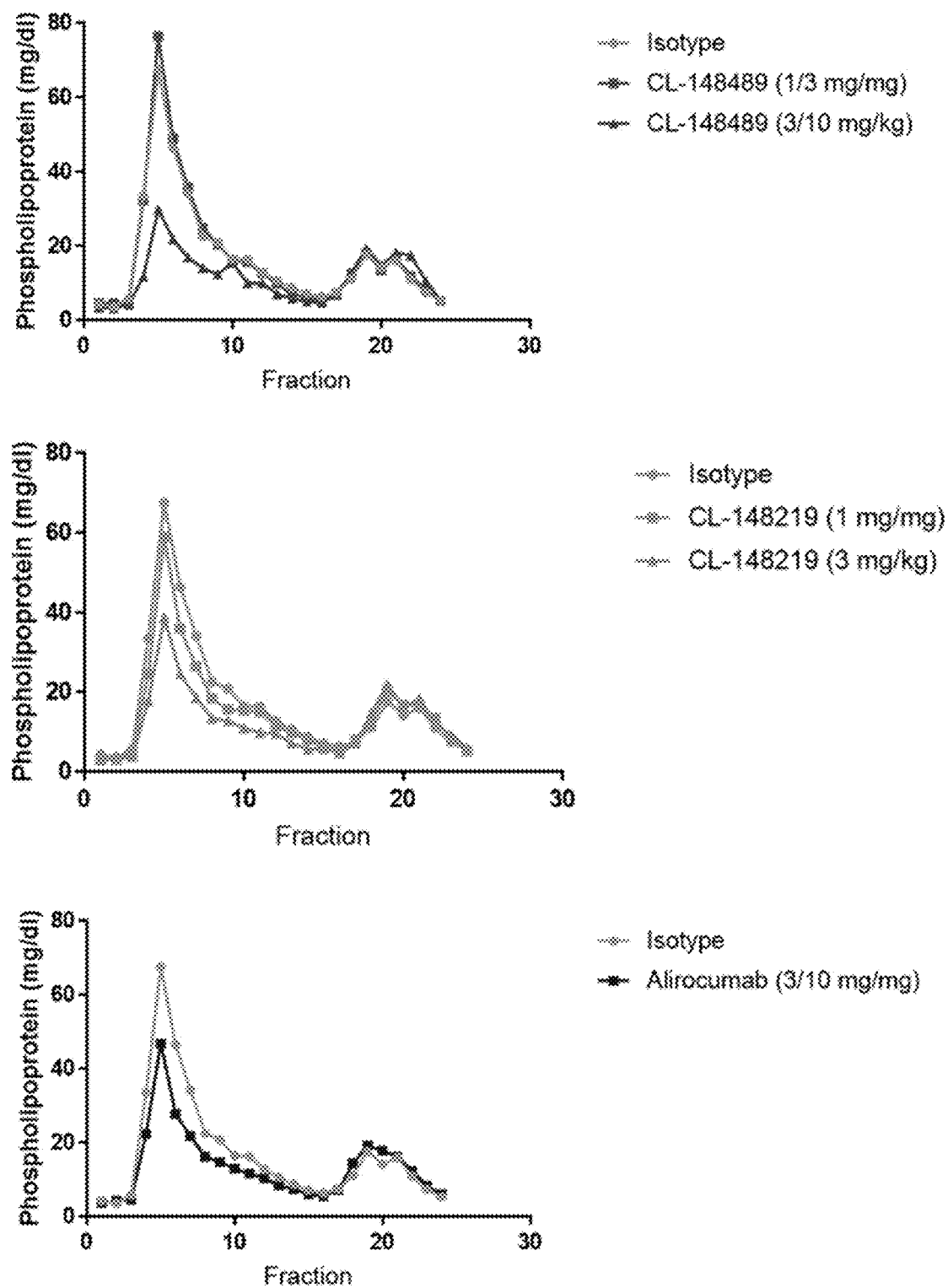
FIGS. 14a-14b.
Figure 14B:
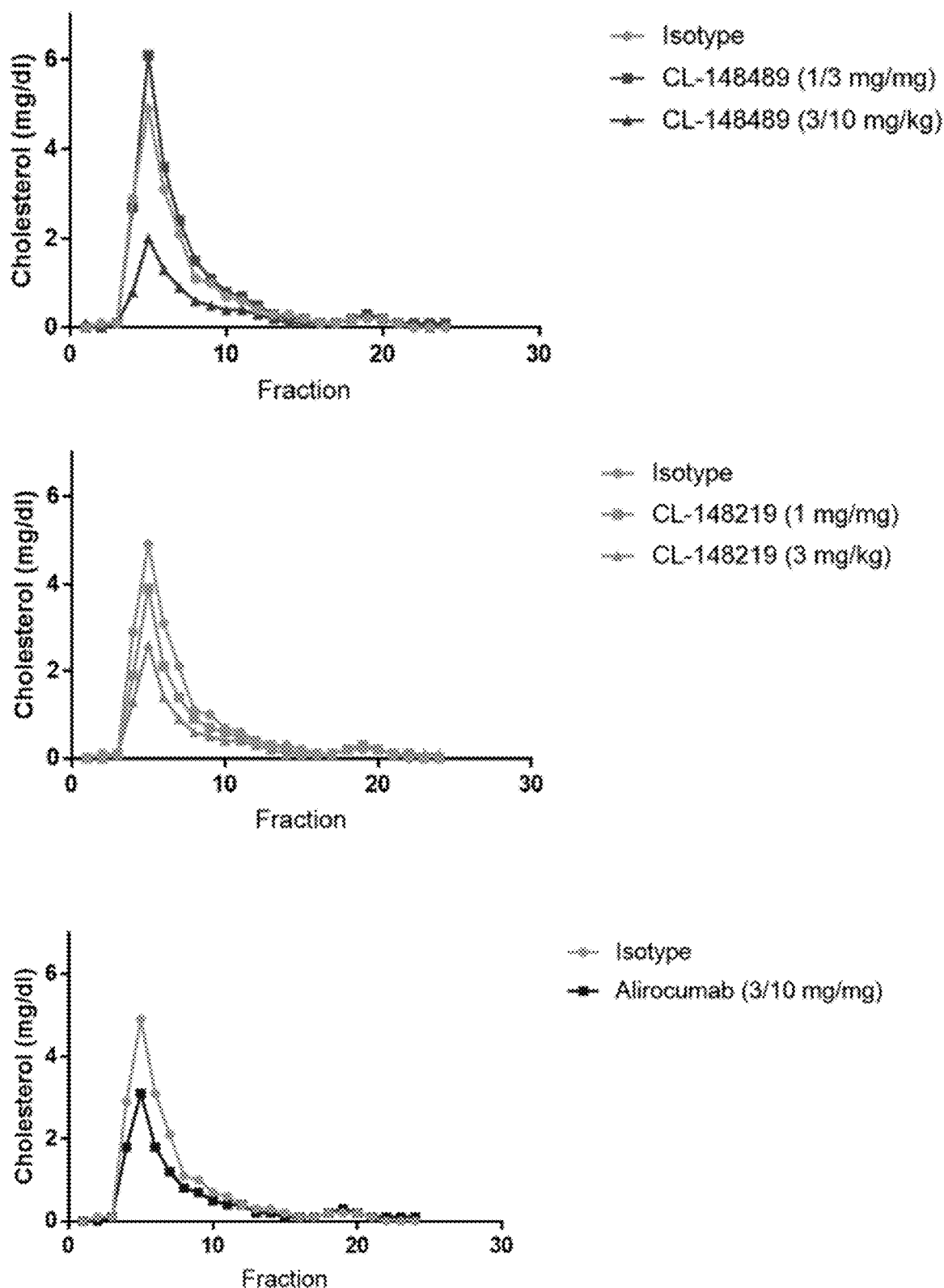

Phospholipid and Cholesterol Profile (FIG. 14)

Phospholipid (A) and Cholesterol (B) profiles for the pooled samples are shown below—fractions 4-8 are considered VLDL, 9-15 as LDL and 16-24 as HDL. No statistics were performed as the measurements are carried out on one pooled sample was used per group. The lipoprotein profiles confirm that alirocumab, CL-274711, CL-148219QLT, CL-274698, CL-148219 and CL-148489 (eg, CL-274711 or CL-148219QLT) reduced VLDL-cholesterol and LDL-cholesterol and had no effect on HDL-cholesterol.

CONCLUSIONS

Our antibodies were well tolerated with the animals showing normal behavior and no signs of discomfort during the study;

Sectioning of the tissues showed no gross pathology;

Body weight and food intake were not significantly affected by any of the antibodies;

Liver weight were not significantly affected by any of the antibodies;

CL-148219, and CL-148489 significantly decreased plasma total cholesterol and plasma non-HDL-cholesterol in a dose-dependent fashion compared to the isotype control group. Lipoprotein profiles showed decreased plasma VLDL-cholesterol in mice treated with these antibodies;

None of our antibodies significantly affected HDL-cholesterol compared to the isotype control group.

None of the antibodies significantly affected plasma triglyceride levels, although Alirocumab, CL-274711, CL-148219QLT, CL-274698, CL-148219 and CL-148489 (eg, CL-274711 or CL-148219QLT) showed a trend towards decreased plasma triglyceride levels compared to the isotype control group.

Examples 3 & 4

Mice

For Example 3, female APOE*3Leiden.CETP transgenic mice were bred. Mice were housed in macrolon cages (3 or 4 mice per cage) in animal rooms; relative humidity 40-70%, temperature 20-24° C., light cycle 7 am to 7 pm. Mice were supplied with a food and sterilized tap water ad libitum. For Example 4, C57BL/6 mice weighing 18-22 g on the day of the experiment were used. The animals were be housed in groups of 2-4 in polysulfone cages (floor area=1500 cm2) under standard conditions: room temperature (22±2° C.), hygrometry (55±10%), light/dark cycle (12 h/12 h), air replacement (15-20 volumes/hour), water and food ad libitum.

Plasma Cholesterol, Lipoprotein and Triglyceride Analysis

Total plasma cholesterol was determined using the Cholesterol CHOD-PAP kit (Roche, Mannheim, Germany) and triglycerides was determined using the Triglycerides GPO-PAP kit (Roche, Mannheim, Germany). To determine plasma HDL-cholesterol ApoB-containing lipids were precipitated using PEG-6000/glycine followed by quantification using the Cholesterol CHOD-PAP kit (Roche, Mannheim, Germany). Lipoprotein profiles were measured by FPLC analysis using an AKTA apparatus (GE Healthcare). Analysis was performed on pooled group samples pooled. Fractions were collected based on retention time and cholesterol and phospholipids measured in the fractions using the Cholesterol CHOD-PAP kit from (Roche, Mannheim, Germany) and Phospholipids kit (Instruchemie, Delfzijl, Netherlands).

Serum Antibody Concentration

Serum antibody concentration were determined using a capture ELISA. Plates were coated overnight at 2-8° C. with an Anti-Human IgG (Fc specific) antibody. The following day the assay plate was washed three times with 300 μL/well of PBS+0.1% Tween (PBS-T) using a plate washer. The plates were then blocked with 250 μL/well 2.5% Milk per well for at least 1 hr at room temperature.

Standards and QC's were prepared in Eppendorf tubes. The standards, samples and QCs were then diluted to the 1 in 20 MRD in assay buffer in Eppendorf tubes. The plates were washed three times with 300 μL/well of PBS-T using a plate washer. 100 μL per well of standard curve, sample and QC was added to the assay plate as per plate map. The plate was incubated for 1 hr at RT, shaking at 300 RPM. Plates were washed five times with 300 μL/well of PBS-T using a plate washer and 100 μL of Anti-Human IgG (Fc specific)-Peroxidase diluted 1 in 5000 in PBS added to each well and the plate then incubated for 1 hr at RT, shaking at 300 RPM. The plate was then washed five times with 300 μL of PBS-T using a plate washer. 100 μL of TMB substrate was added to each well and the plate incubated for 15 minutes at room temperature in the dark. 100 μL/well of stop solution (1M sulfuric acid) was then added to each well and the optical density determined using a microplate reader set to 450 nm with a reference read at 540 nm. The reference reading was then subtracted from the 450 nm reading using plate reader software. Softmax Pro was then used for analysis of the data using regression analysis and a 4PL curve fit. The concentrations were measured off the standard curve.

Example 3

Female, 8-14 weeks of age APOE*3Leiden.CETP transgenic mice were put on Western-type diet (WTD) containing 0.15% cholesterol and 15% saturated fat. After the 4 weeks run-in period low-responder mice were removed from the study. The remaining mice were matched for age, body weight, plasma cholesterol, and triglycerides. The animals were placed in groups of 6 (isotype control group) or 10.

Animals received a subcutaneous injection at day 0 (5 mL/kg). Antibodies (Isotype Control, Benchmark Antibody F, CL-148218 and CL-274711) were administered at 1, 3 or 10 mg/kg. On days 0, 3, 7, 14, 18, 21, and 28 post treatment blood samples were taken from the tail vein following a 4-hour fasting period, animals. Blood was collected using CB 300 K2E microvettes (Sarstedt, Nürnbrecht, Germany) containing EDTA-dipotassium salt for total cholesterol, triglycerides (day 0, 7 and 28), and HDL-cholesterol measurements. The tubes or capillaries were placed on ice immediately. EDTA plasma was obtained after centrifugation (10 min at 6000 rpm) at 4° C. Mice were sacrificed at day 28 by $CO_2$ asphyxiation, directly after the last tail vein blood sampling point. Group lipoprotein profiles were ascertained on the day 28 samples.

The aim of this experiment was to evaluate the pharmacodynamic effects on total/non-HDL cholesterol and lipoprotein profiles of a dose response of antibodies CL-274711, CL-148219 QLT and Benchmark Antibody F in APOE*3Leiden.CETP transgenic mice feed a Western-type diet containing 0.15% cholesterol and 15% saturated fat.

Figure 15:
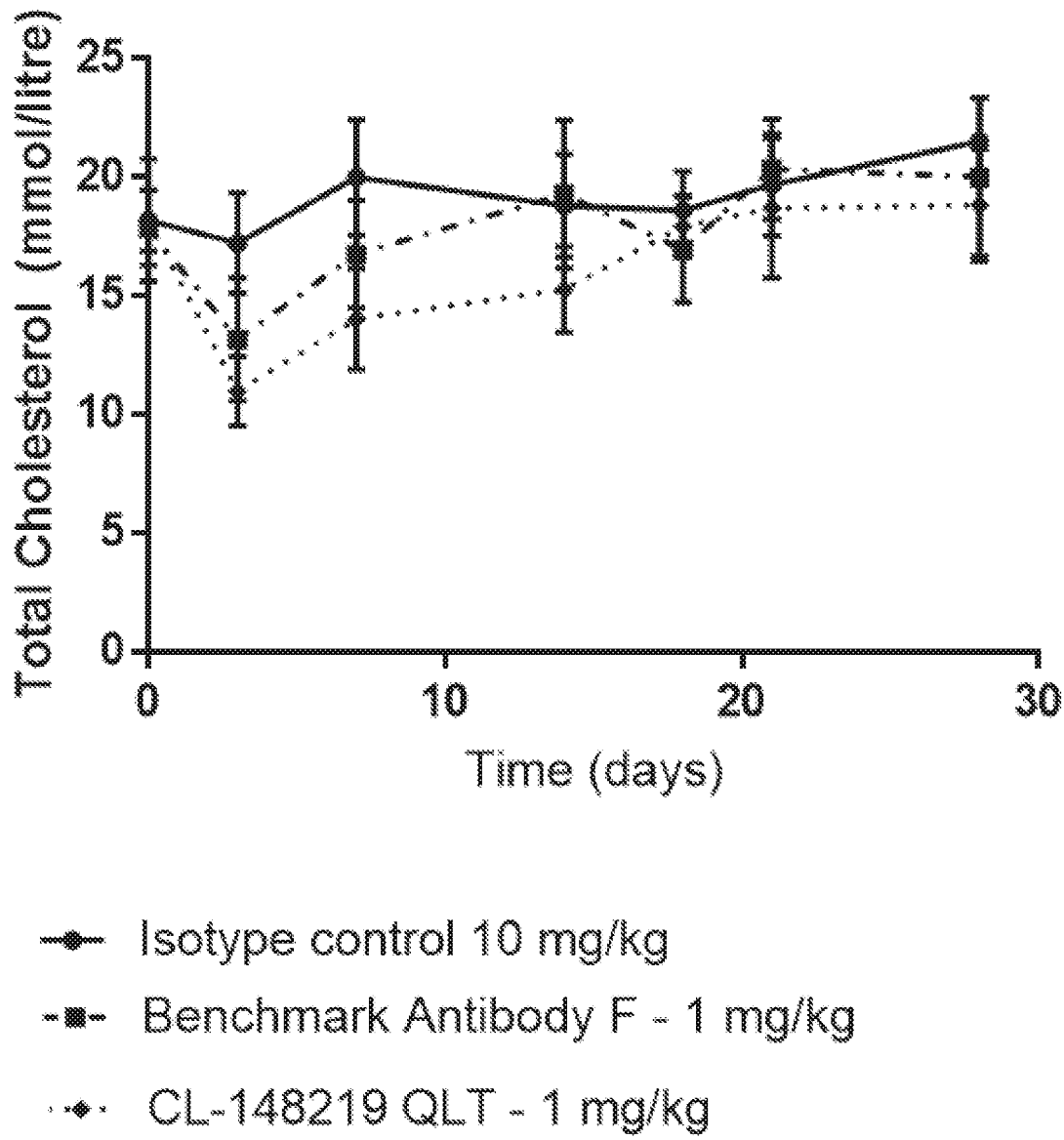
FIG. 15: Shows the effects of a single 1 mg/kg subcutaneous dose of CL-148219 QLT, Benchmark Antibody F (a commercially-marketed antibody) or a single dose of 10 mg/kg of Isotype Control subcutaneously on total cholesterol levels (±SEM) in APOE*3Leiden.CETP transgenic mice feed a Western-type diet containing 0.15% cholesterol and 15% saturated fat.
Figure 16:
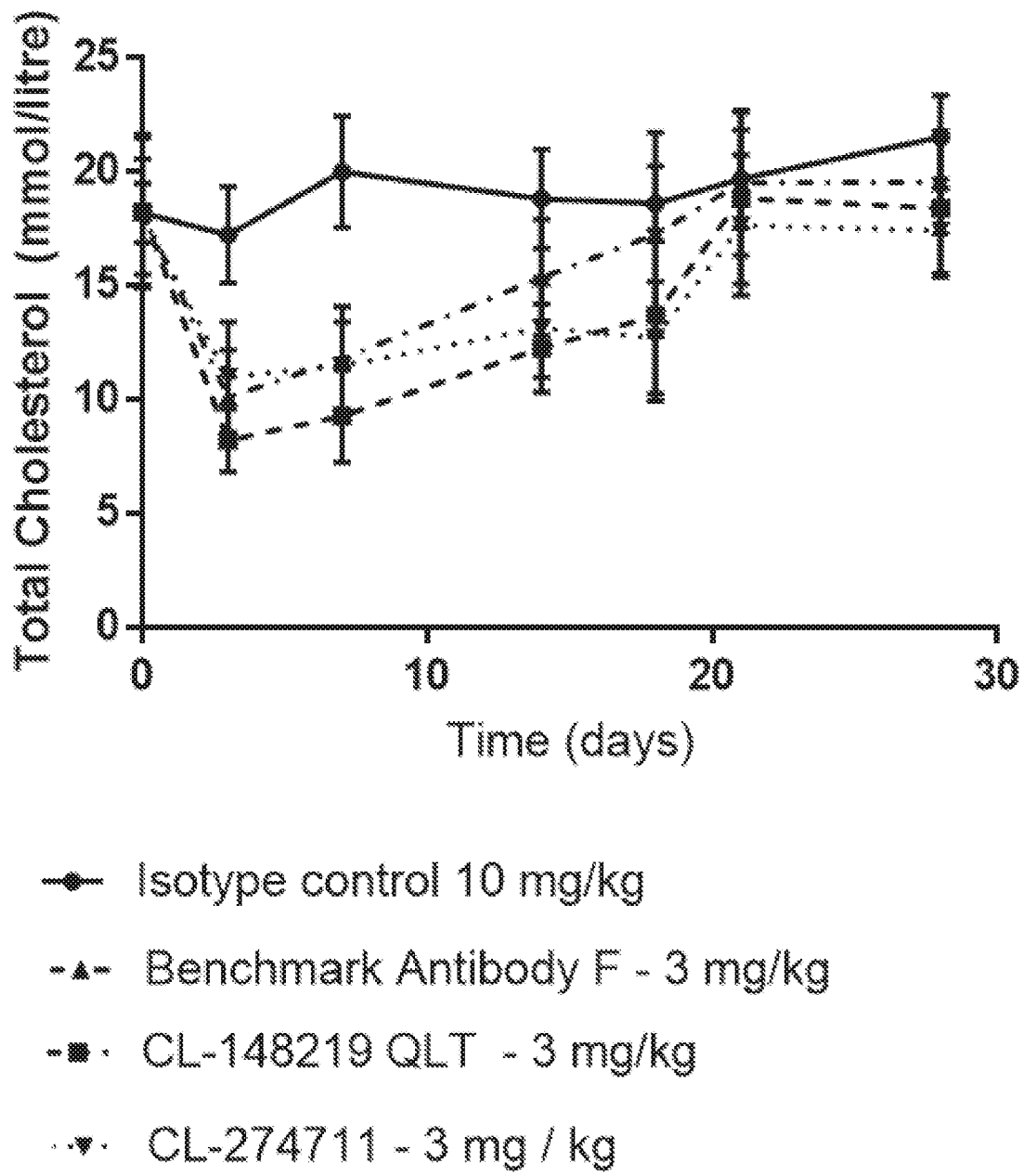
FIG. 16: Shows the effects of a single 3 mg/kg subcutaneous dose of CL-148219 QLT, Benchmark Antibody F or a single dose of 10 mg/kg of Isotype Control subcutaneously on total cholesterol levels (±SEM) in APOE*3Leiden.CETP transgenic mice feed a Western-type diet containing 0.15% cholesterol and 15% saturated fat.
Figure 17:
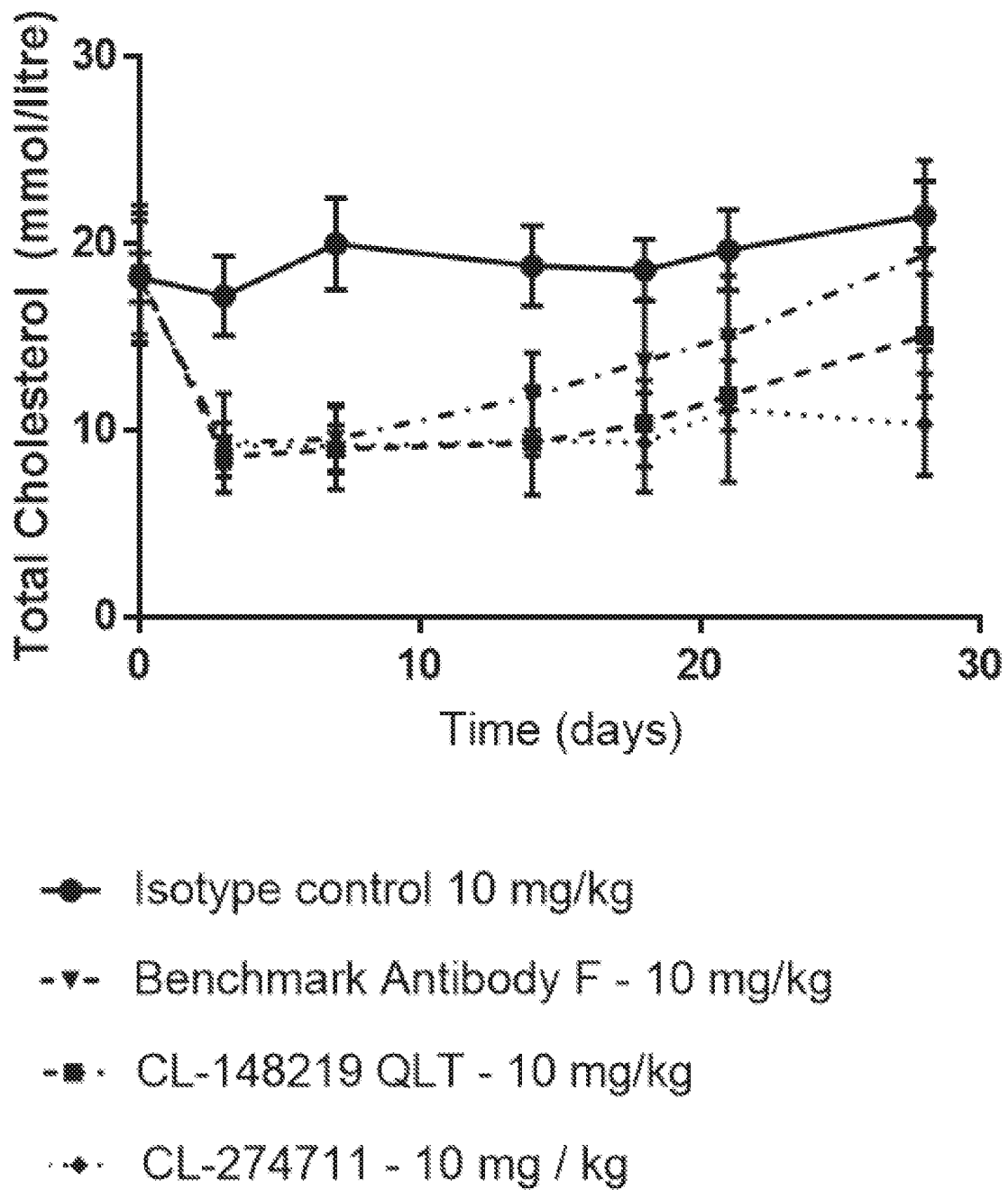
FIG. 17: Shows the effects of a single 10 mg/kg subcutaneous dose of CL-148219 QLT, Benchmark Antibody F or Isotype Control on total cholesterol levels (±SEM) in APOE*3Leiden.CETP transgenic mice feed a Western-type diet containing 0.15% cholesterol and 15% saturated fat.
Figure 18:
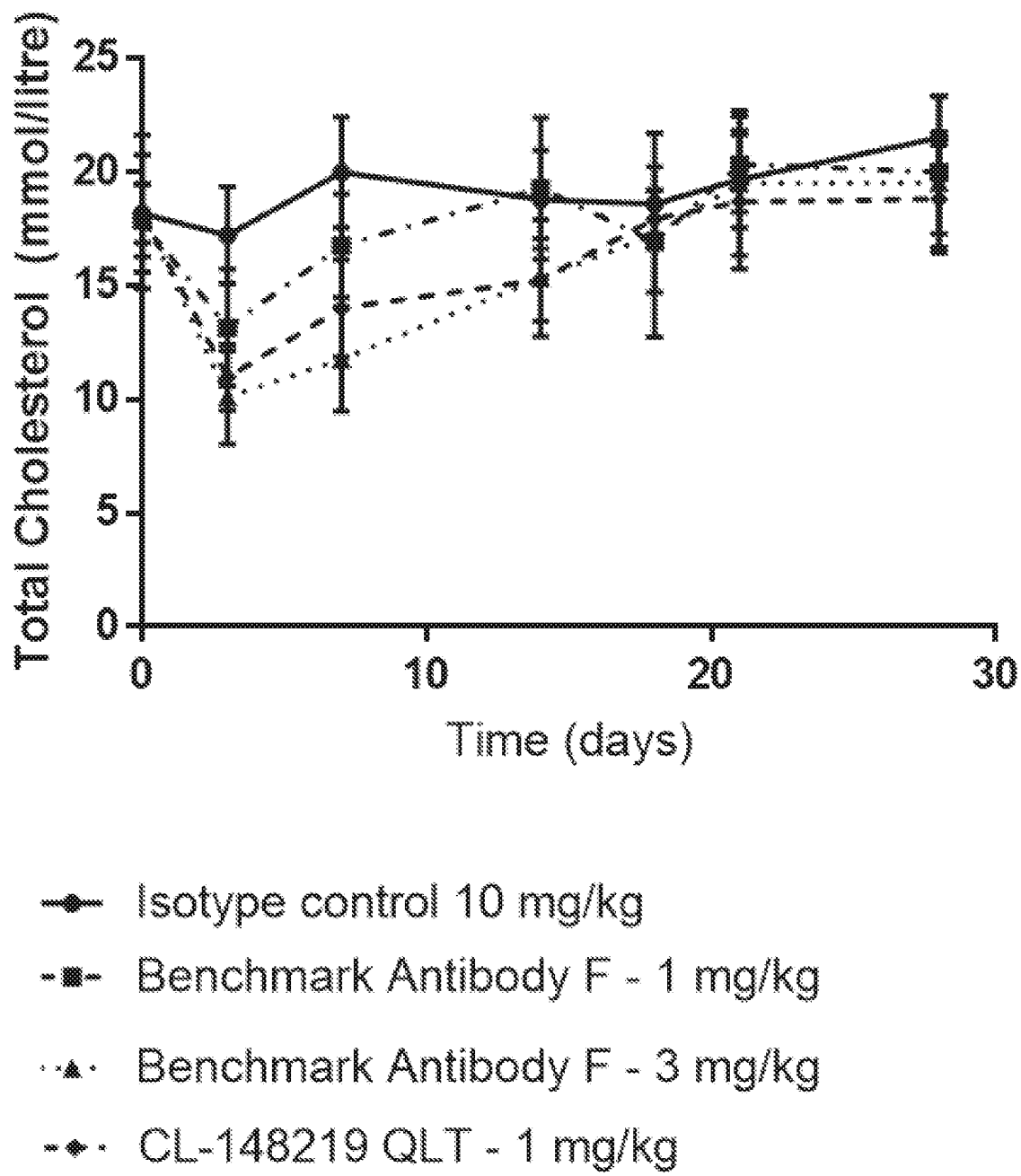
FIG. 18: Comparison of the effects of a single 1 mg/kg subcutaneous dose of CL-148219 QLT with a 1 and 3 mg/kg dose of Benchmark Antibody F on total cholesterol levels (±SEM) in APOE*3Leiden.CETP transgenic mice feed a Western-type diet containing 0.15% cholesterol and 15% saturated fat.
Figure 19:
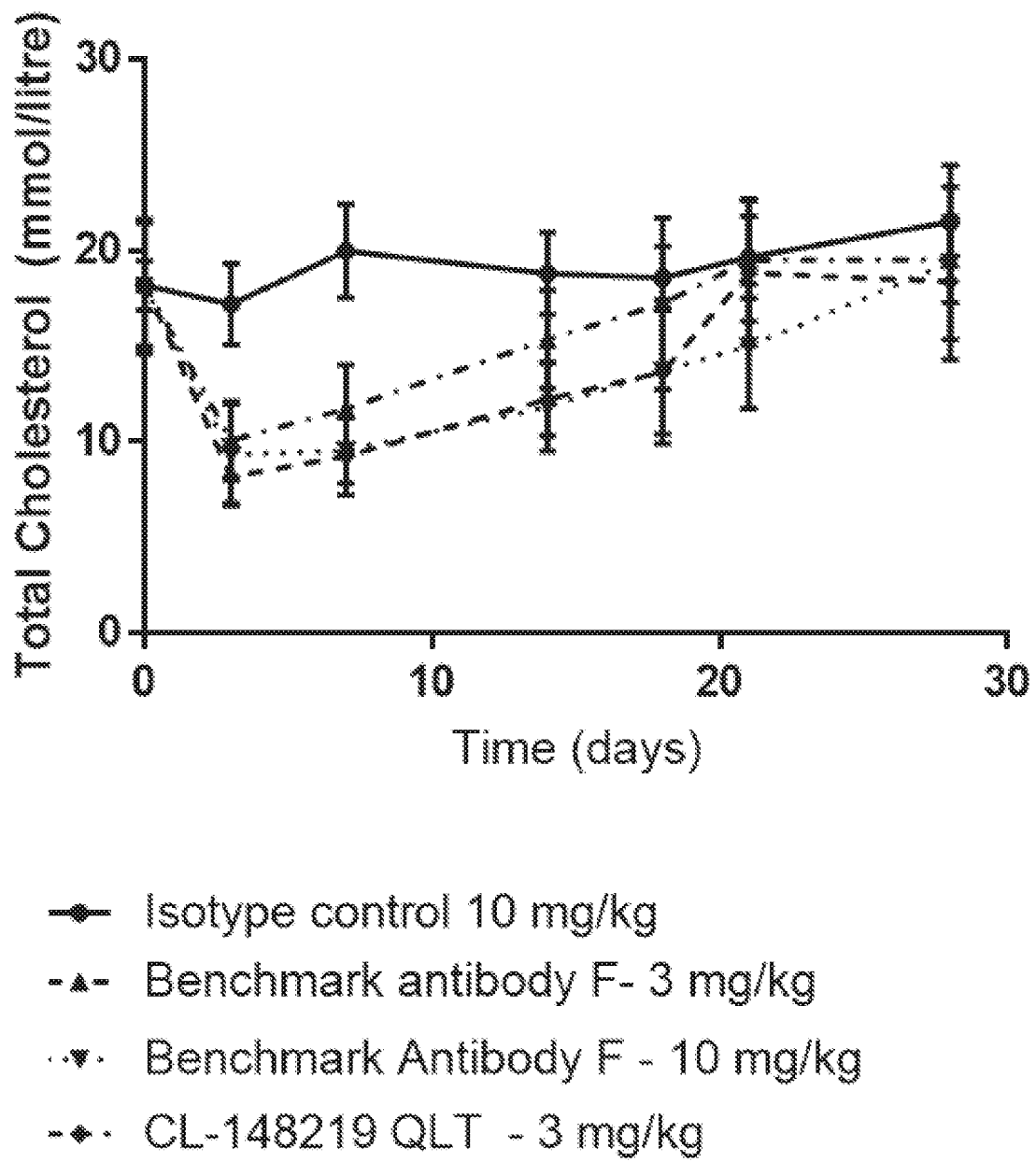
FIG. 19: Comparison of the effects of a single 3 mg/kg subcutaneous dose of CL-148219 QLT with a 3 and 10 mg/kg dose of Benchmark Antibody F on total cholesterol levels (±SEM) in APOE*3Leiden.CETP transgenic mice feed a Western-type diet containing 0.15% cholesterol and 15% saturated fat.

All three antibodies reduced cholesterol levels at all doses tested (see FIGS. 15-17) and increasing the dose increased the reduction in cholesterol seen and duration of the effect. At 1 and 3 mg/kg CL-148219 QLT was more effective than Benchmark Antibody F at reducing cholesterol levels and at all doses tested CL-148219 QLT had a longer duration of effect than Benchmark Antibody F (FIGS. 15-17). Further analysis showed that CL-148219 QLT was as effective as a 3 times higher dose of Benchmark Antibody F at reducing cholesterol levels and had the same duration of effect as that higher dose of Benchmark Antibody F (FIGS. 18-19). CL-274711 reduced cholesterol levels to the same levels as those seen with the same dose of Benchmark Antibody F but had a longer duration of effect (FIG. 16-17).

Figure 20A:
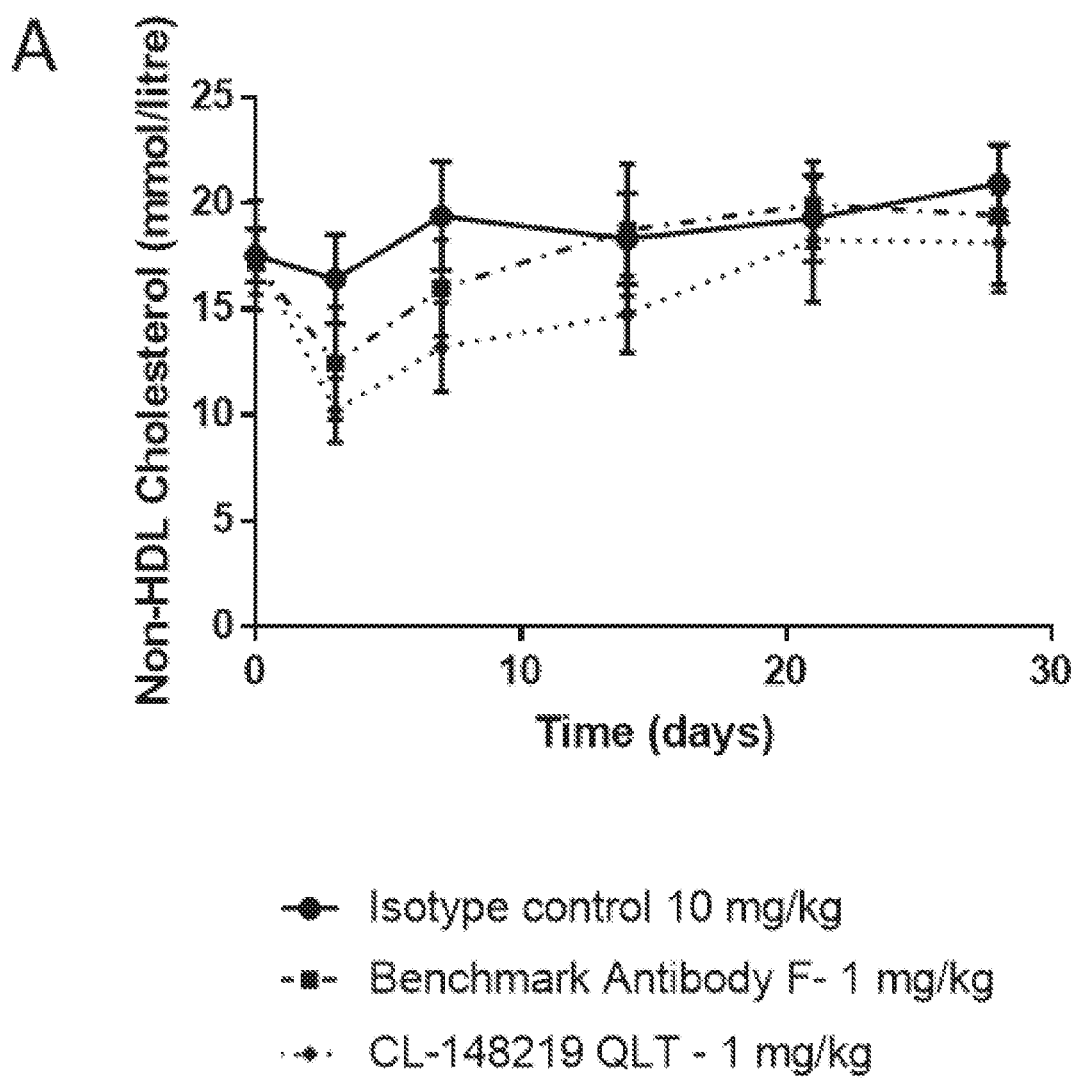
FIG. 20: Shows the effects of a single 1 (A), 3 (B) or 10 mg/kg (C) subcutaneous dose of CL-148219 QLT/Benchmark Antibody F, 1 and 3 mg/kg of CL-274711 (A,B) or 10 mg/kg of Isotype Control on non-HDL cholesterol levels (±SEM) in APOE*3Leiden.CETP transgenic mice feed a Western-type diet containing 0.15% cholesterol and 15% saturated fat.
Figure 20B:
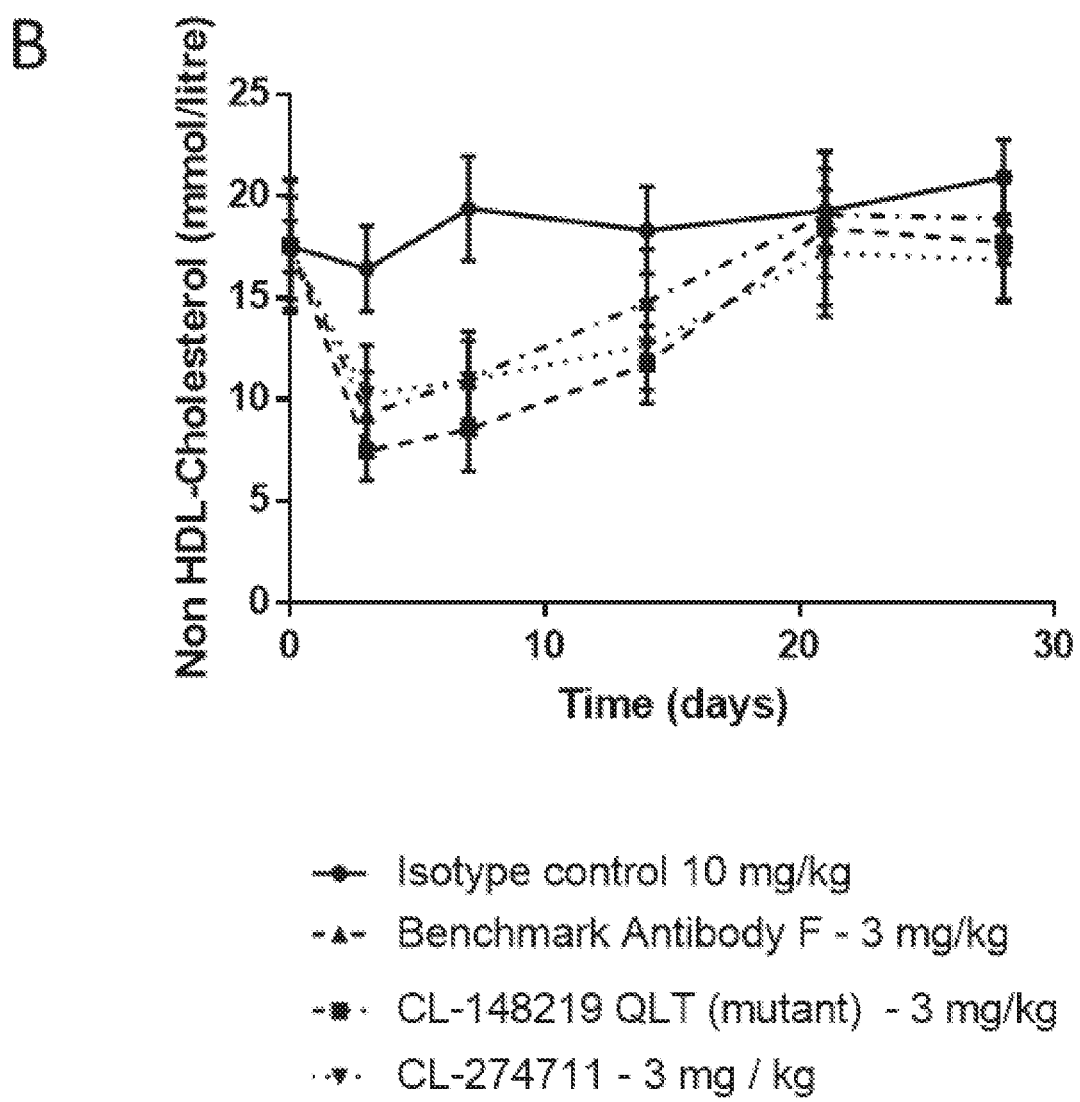
Figure 20C:
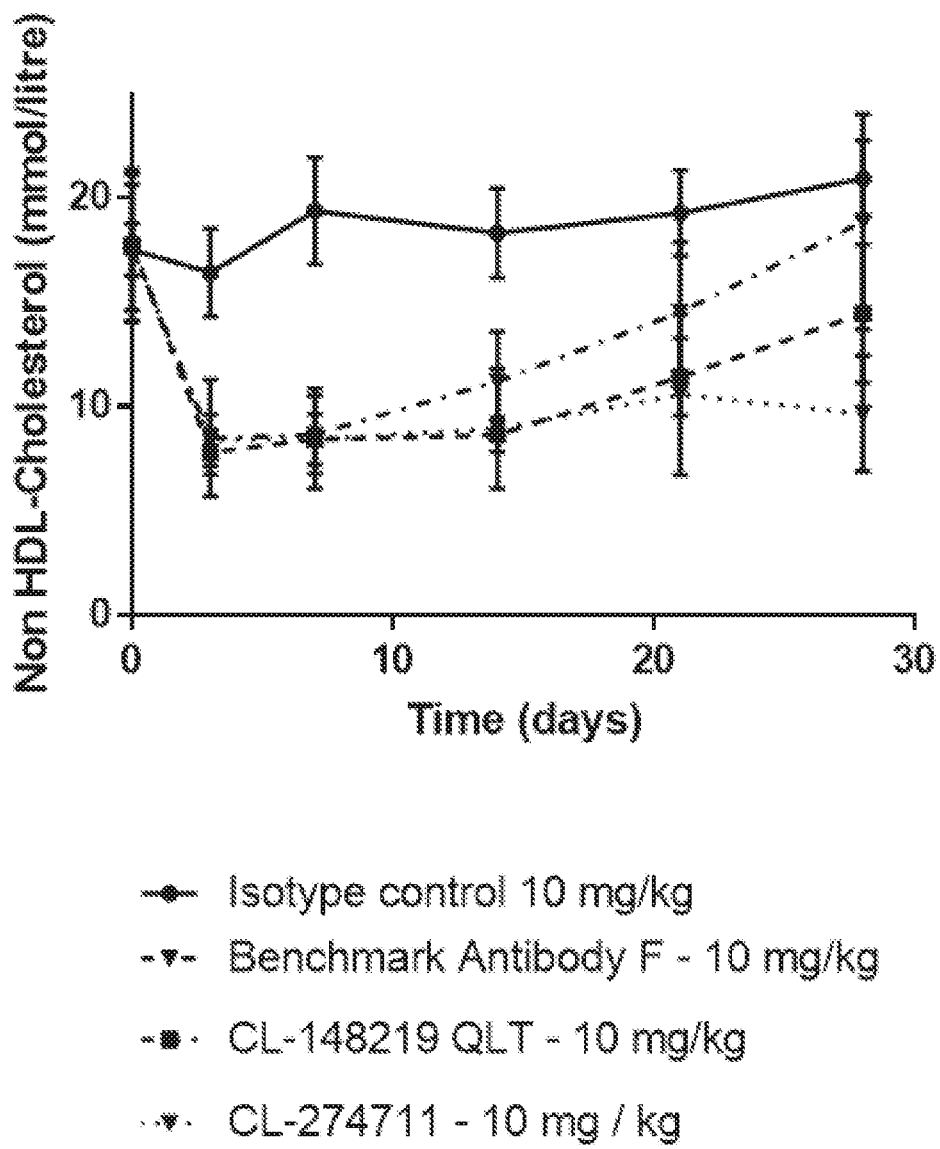
Figure 21A:
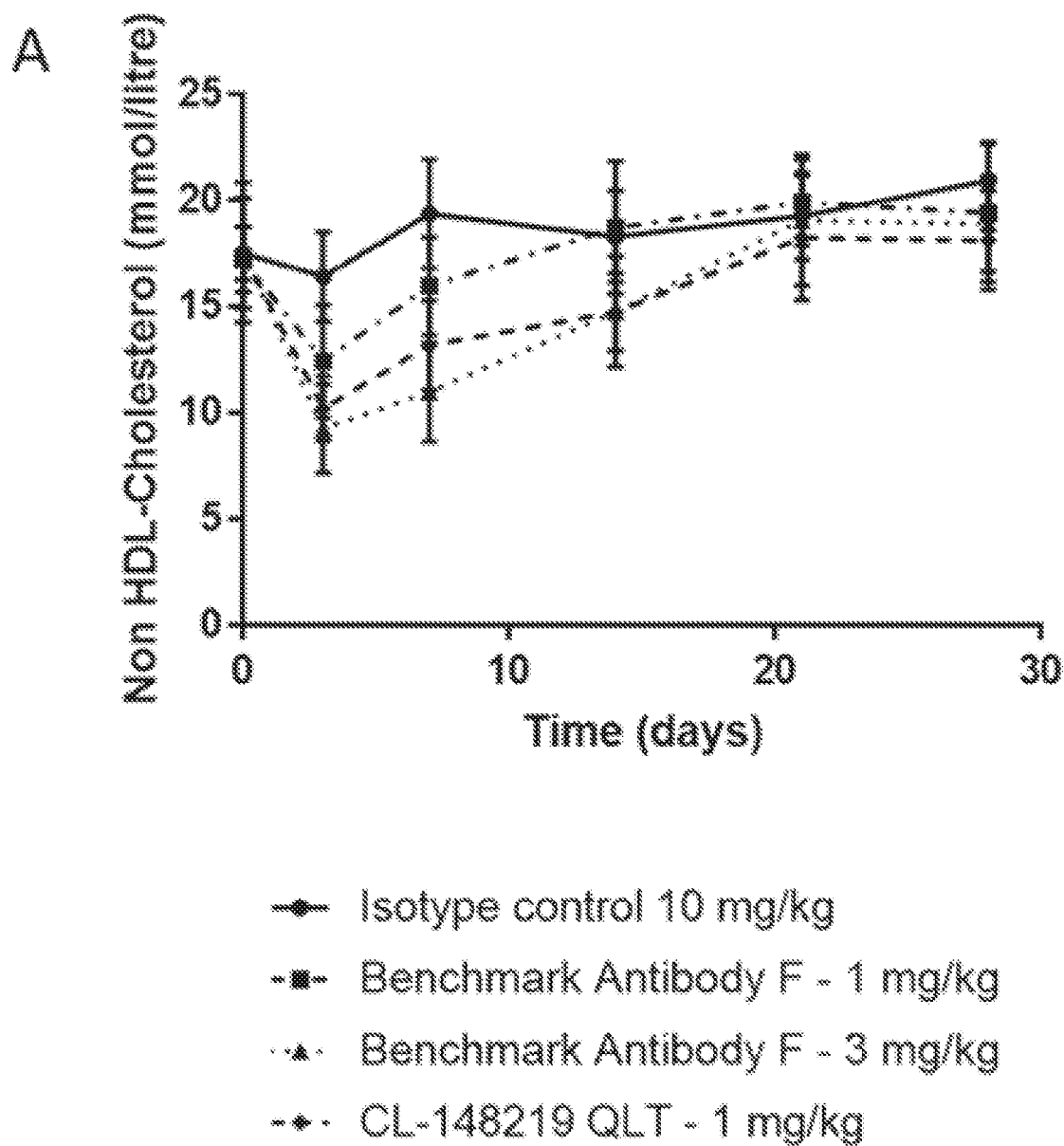
FIG. 21: Comparison of the effects of a single 1 (A) and 3 mg/kg (B) subcutaneous dose of CL-148219 QLT with 1 and 3 (A) or 3 and 10 mg/kg (B) doses of Benchmark Antibody F on non-HDL cholesterol levels(±SEM) in APOE*3Leiden.CETP transgenic mice feed a Western-type diet containing 0.15% cholesterol and 15% saturated fat.
Figure 21B:
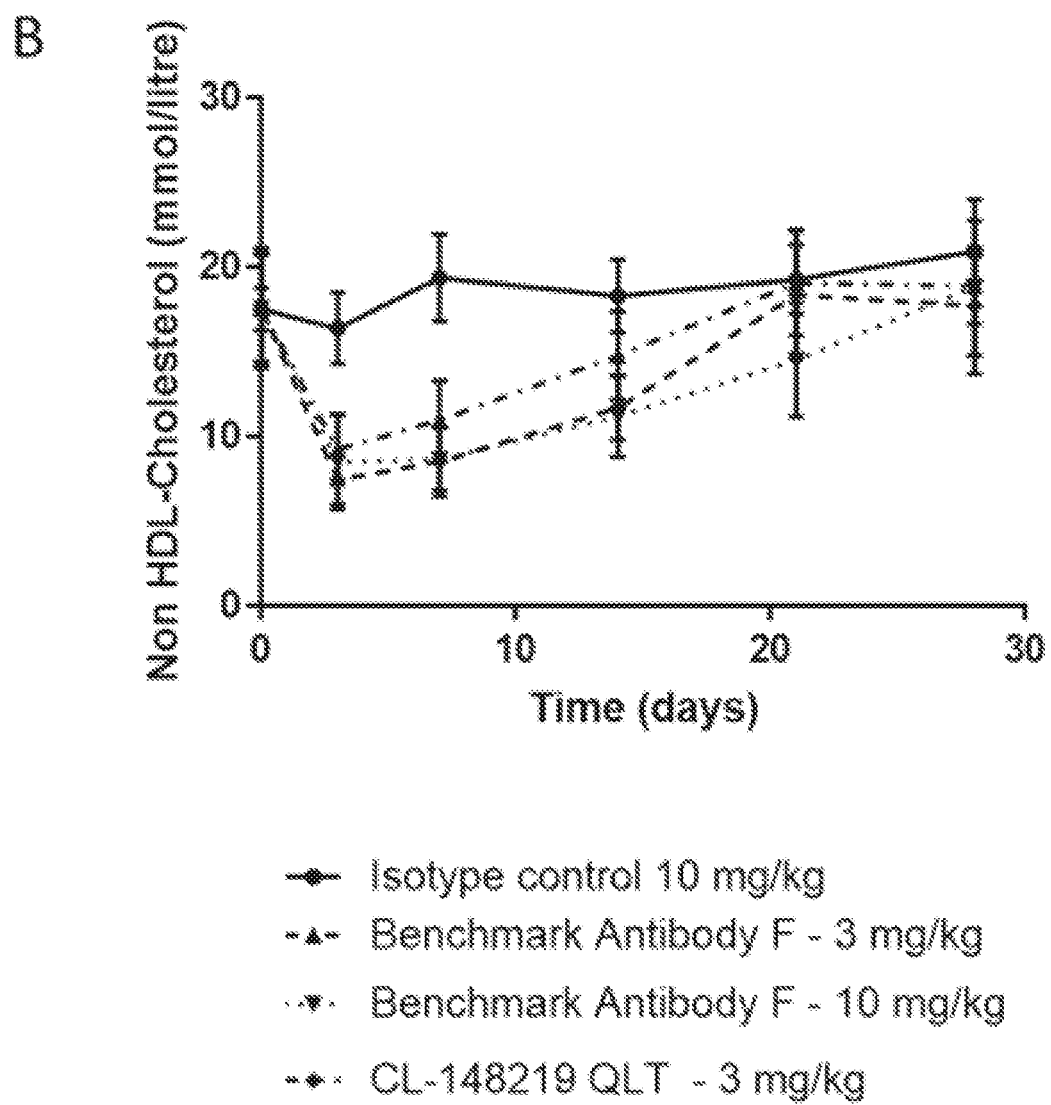

The antibodies showed an equivalent reduction in non-HDL cholesterol levels at all doses tested (see FIG. 20) with increasing doses resulting in incremental increases in the reduction in non-HDL cholesterol and the duration of the response. At 1 and 3 mg/kg CL-148219 QLT was more effective than Benchmark Antibody F at reducing non-HDL cholesterol levels and at all the doses tested CL-148219 QLT had a longer duration of effect than Benchmark Antibody F (FIG. 20). Further analysis also showed that CL-148219 QLT was as effective as a 3 times higher dose of Benchmark Antibody F at reducing non-HDL cholesterol levels and had the same duration of effect as that higher dose of Benchmark Antibody F (FIG. 21). CL-274711 reduced cholesterol levels to the same levels as those seen with the same dose of Benchmark Antibody F but had a longer duration of effect (FIG. 21). Evaluation of the phospholipid profiles at day 28 (FIG. 22) showed that both CL-274711 and CL-148219 QLT reduced VLDL/LDL cholesterol and phospholipids in a dose dependent manner. In comparison with Benchmark Antibody F both CL-274711 and CL-148219 QLT at 10 mg/kg were more effective at reducing VLDL/LDL cholesterol and phospholipids Example 4

Male C57BL/6 mice (JANVIER LABS, C.S. 4105, Saint-Berthevin F-53941, France), weighing 18-22 g on the day of the experiment were used for the study. Animals received a 3 mg/kg subcutaneous injection of CL-148219 QLT, CL-274711 or Benchmark F on day 0 (10 mL/kg). Blood sampling was performed on days 1, 3, 7, 14, 21 and 28 post-dose (n=3 per sampling point). Serum was then prepared from each blood sample which was then used to determine the antibody concentration at each time point.

Figure 23:
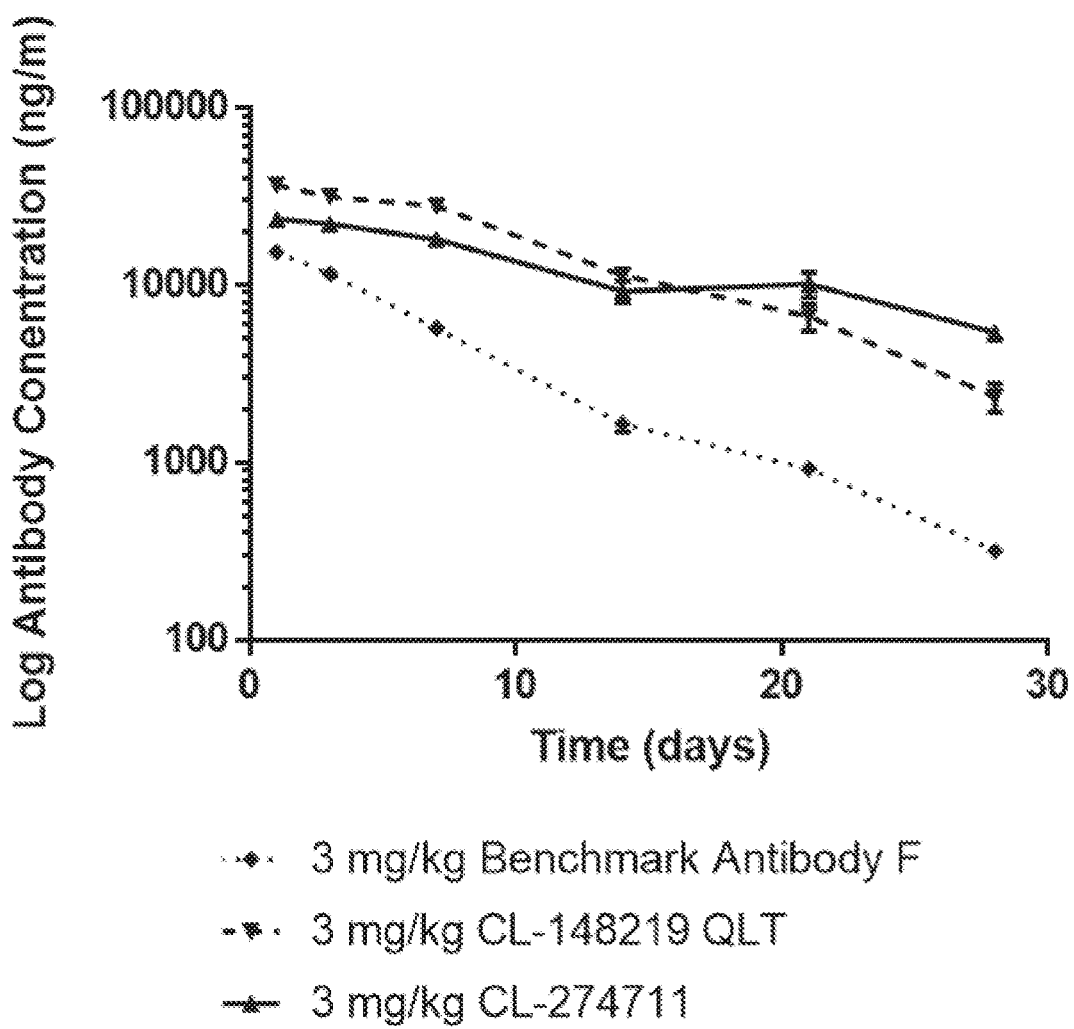
FIG. 23: Shows the antibody concentrations (±SEM) over time following a single 3 mg/kg subcutaneous dose of Benchmark Antibody F, CL-148219 QLT or CL-274711 in male, C57/B16 mice.

The aim of the experiment was to evaluate the pharmacokinetics of CL-148219 QLT, CL-274711 and Benchmark Antibody F over the course of 28 days. Evaluation of the PK profiles showed that both CL-274711 and CL-148218 had a higher initial serum antibody concentration than Benchmark Antibody F and this higher serum antibody concentration was retained for the 28 days of the study (FIG. 23). CL-148219 QLT initially had a higher serum antibody concentration than CL-274711 but CL-274711 had a slower clearance from the serum.

Figure 24:
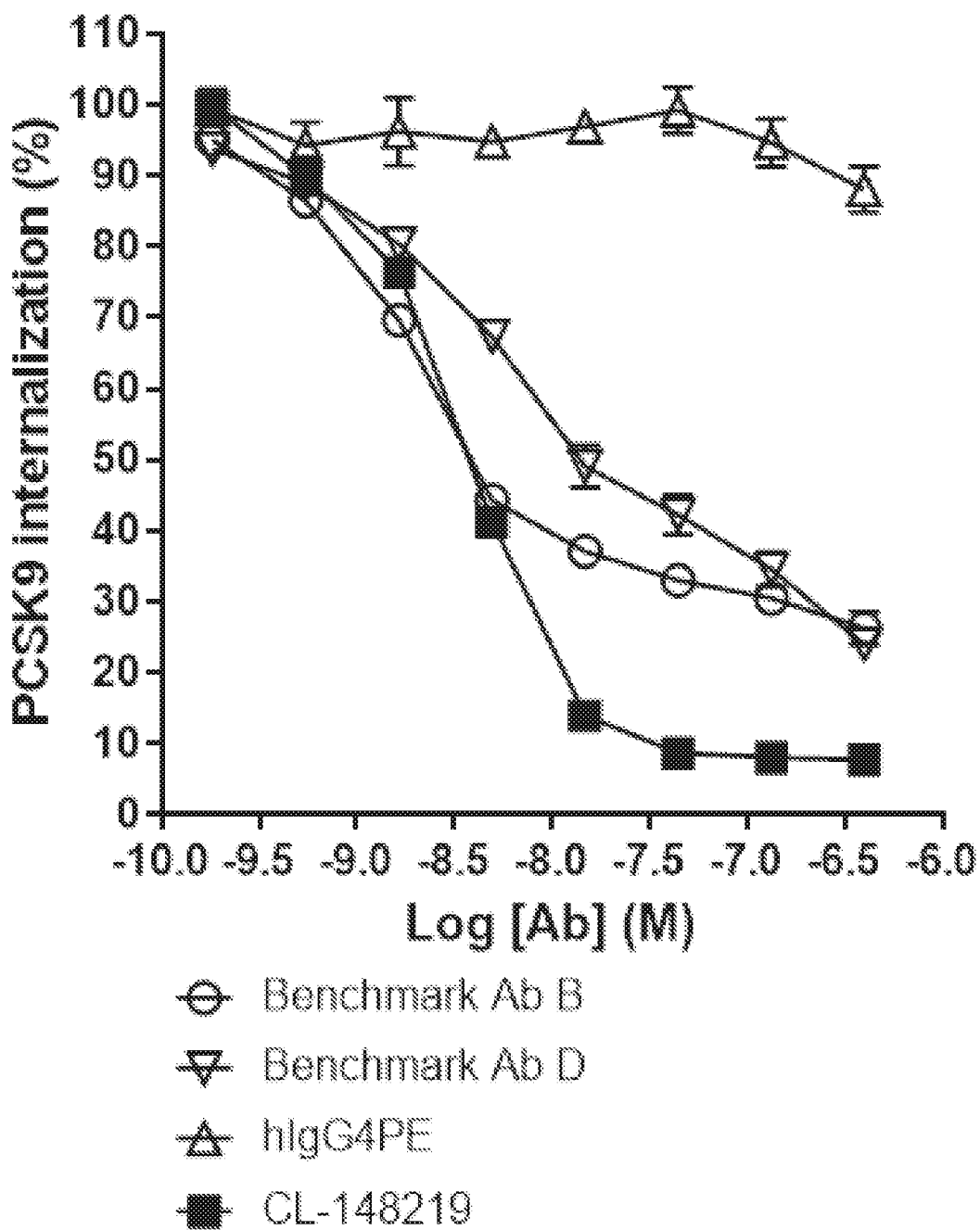
FIG. 24. CL-148219 neuralised human PCSK9 internalisation more than benchmarks in a cell-based assay in vitro. HepG2 cells were treated with AF647-labelled human PCSK9 gain-of-function mutant in the presence of isotype control, benchmarks, or CL-148219, followed by treatment with BODIPY LDL. Cells were then collected and the fluorescent signals of AF647 was detected by CytoFlex™ flow cytometer.
Figure 25:
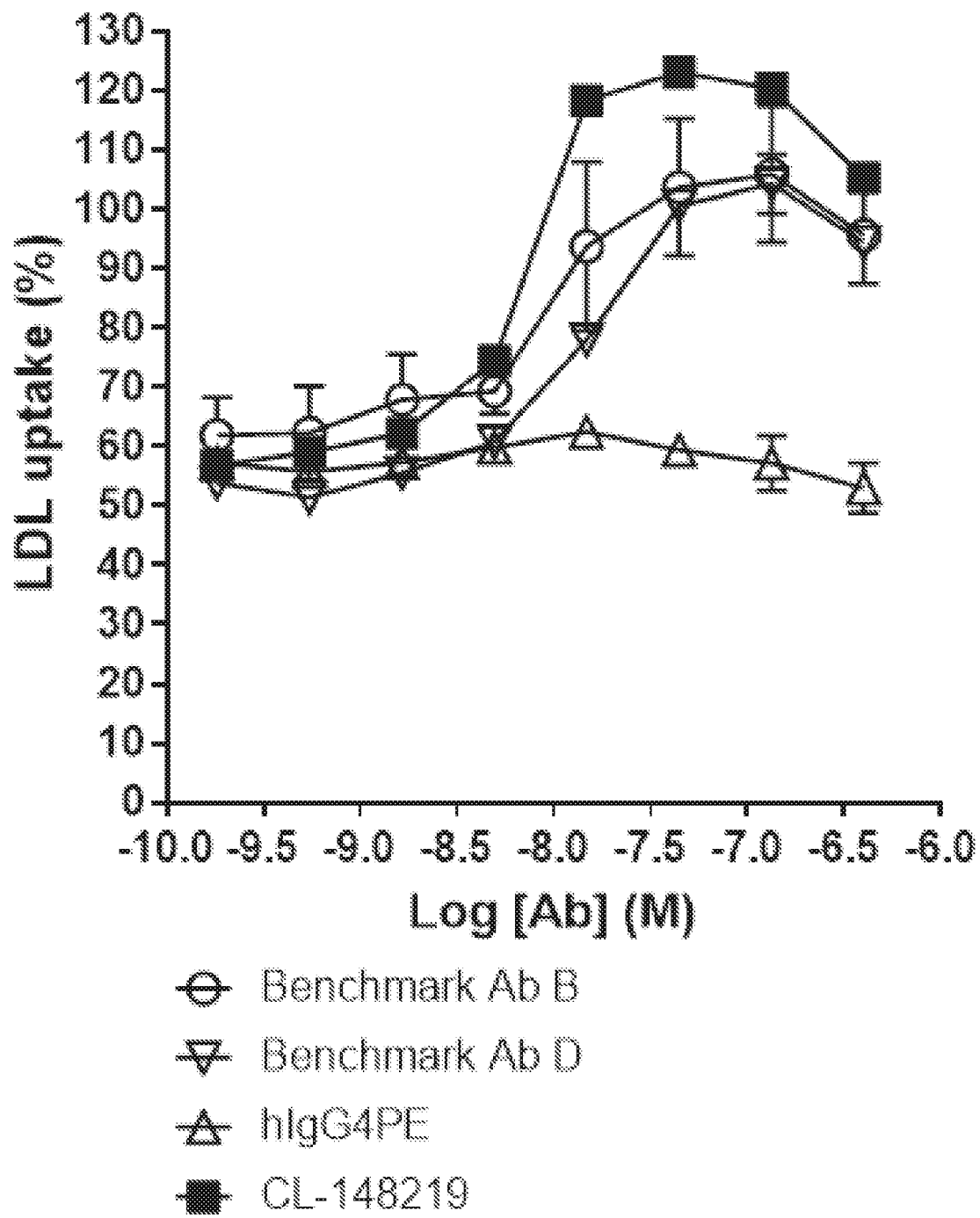
FIG. 25: CL-148219 increased LDL uptake better than benchmarks in a cell-based assay in vitro. HepG2 cells were treated with AF647-labelled human PCSK9 gain-of-function mutant in the presence of isotype control, benchmarks, or CL-148219, followed by treatment with BODIPY LDL. Cells were then collected and the fluorescent signals of BODIPY was detected by CytoFlex flow cytometer.
Figure 26:
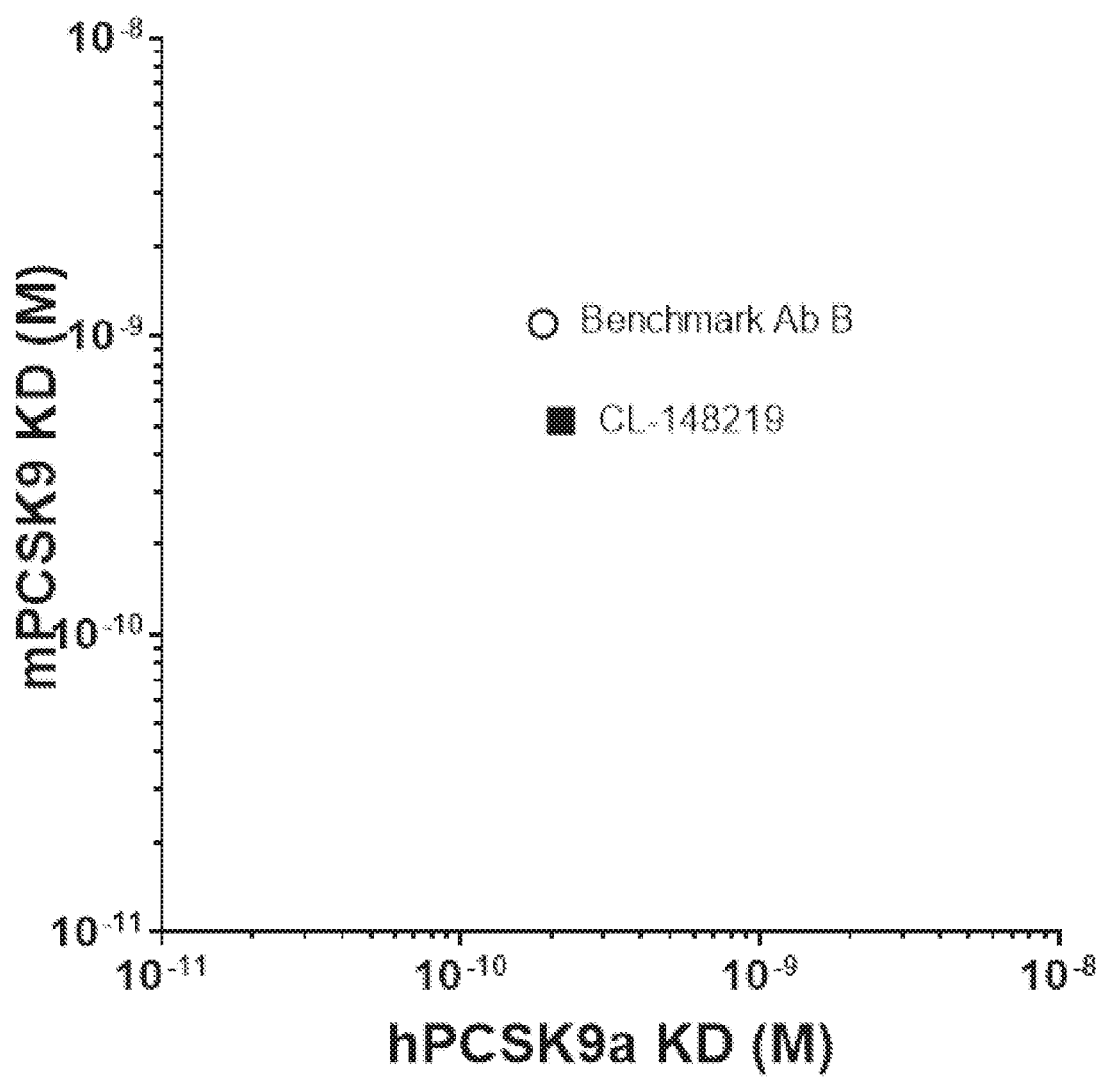
FIG. 26: Affinity of CL-148219. The affinity was determined by KD. The KD of CL-148219 was measured against human and mouse PCSK9 at pH7.6 by Proteon™ SPR analysis system.
Figure 27:
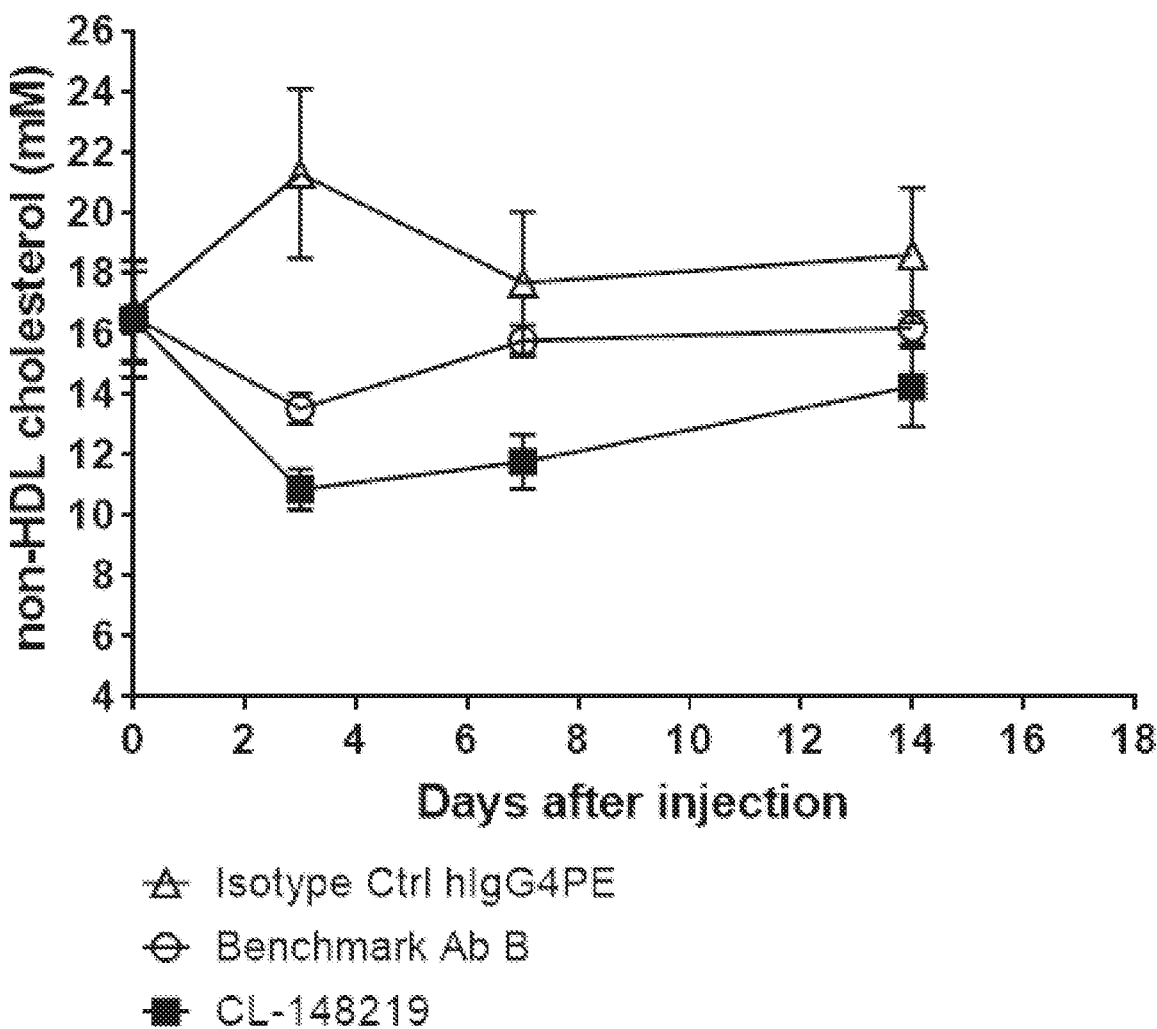
FIG. 27: CL-148219 showed superior function to reduce non-HDL cholesterol compared to benchmarks in a hyperlipidemia mouse model (E3L.CETP mice). E3L.CETP mice were treated with western diet for 4 weeks followed by antibody injection. At different time after Ab injection, blood was collected and the amount of plasma HDL and total cholesterol were measured. The amount of plasma non-HDL cholesterol was then calculated by subtracting HDL from total cholesterol.
Figure 28:
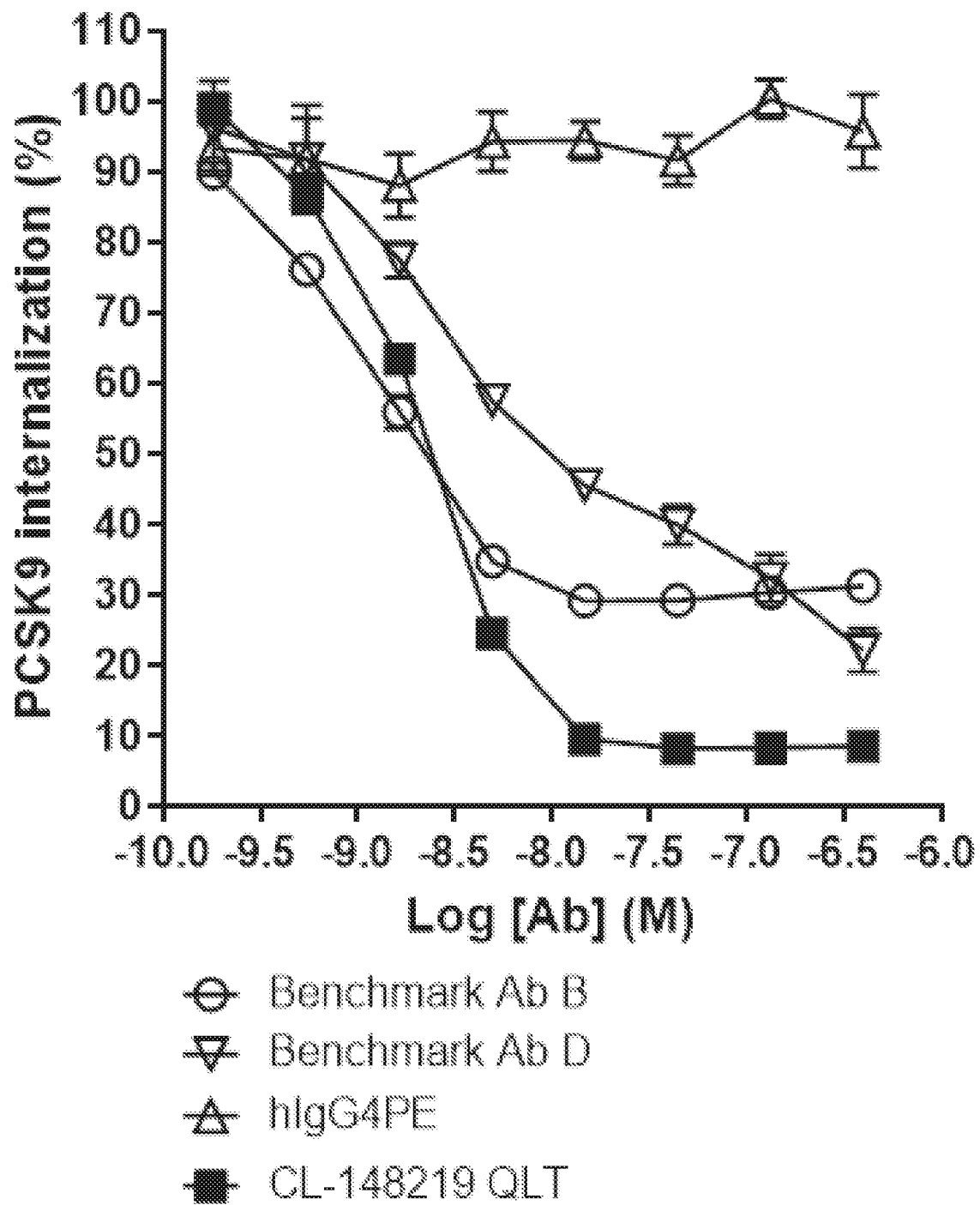
FIG. 28: CL-148219 QLT neuralised human PCSK9 internalisation more than benchmarks in a cell-based assay in vitro. HepG2 cells were treated with AF647-labelled human PCSK9 gain-of-function mutant in the presence of isotype control, benchmarks, or CL-148219 QLT, followed by treatment with BODIPY LDL. Cells were then collected and the fluorescent signals of AF647 was detected by CytoFlex flow cytometer.
Figure 29:
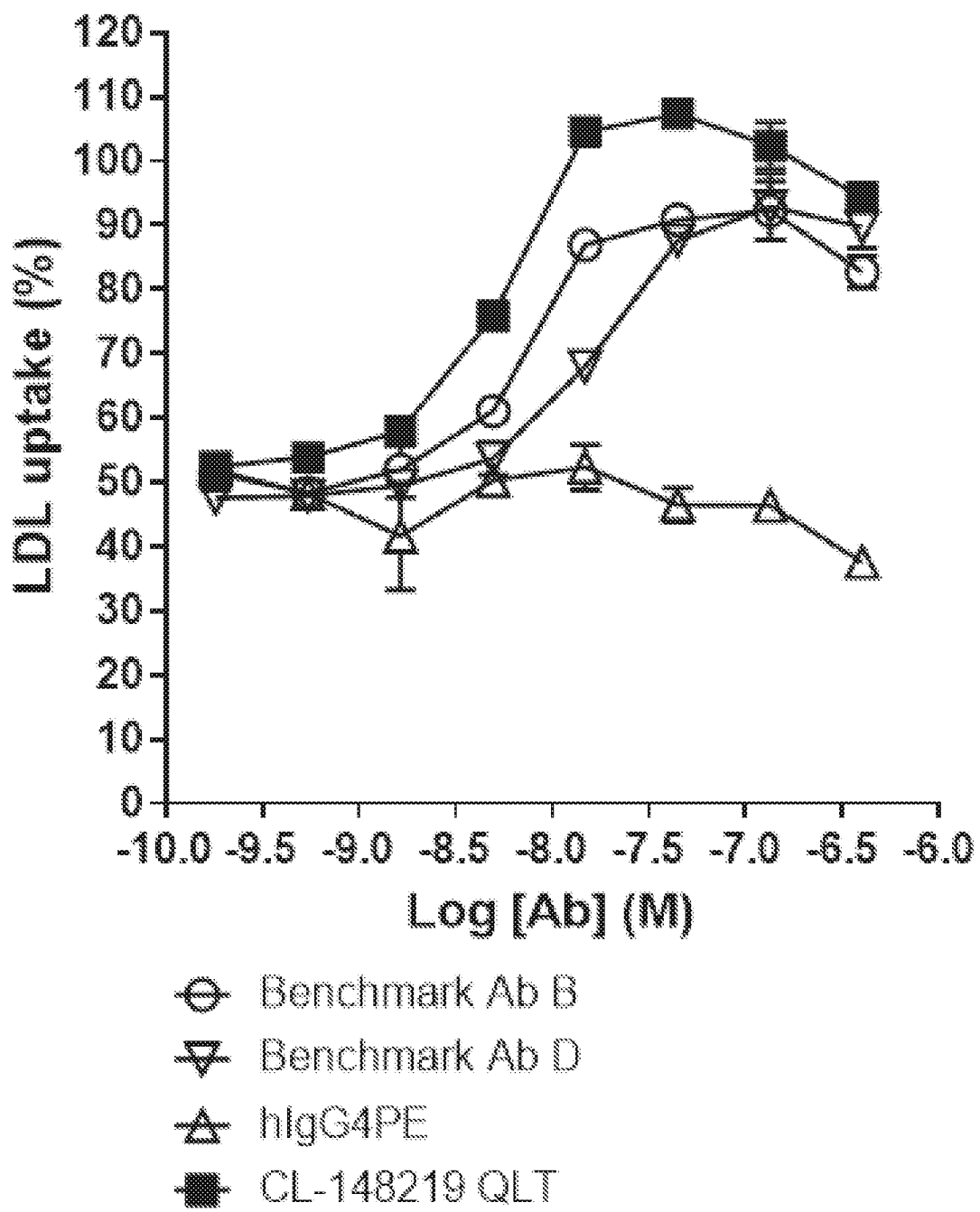
FIG. 29: CL-148219 QLT increased LDL uptake better than benchmarks in a cell-based assay in vitro. HepG2 cells were treated with AF647-labelled human PCSK9 gain-of-function mutant in the presence of isotype control, benchmarks, or CL-148219 QLT, followed by treatment with BODIPY LDL. Cells were then collected and the fluorescent signals of BODIPY was detected by CytoFlex flow cytometer.
Figure 30:
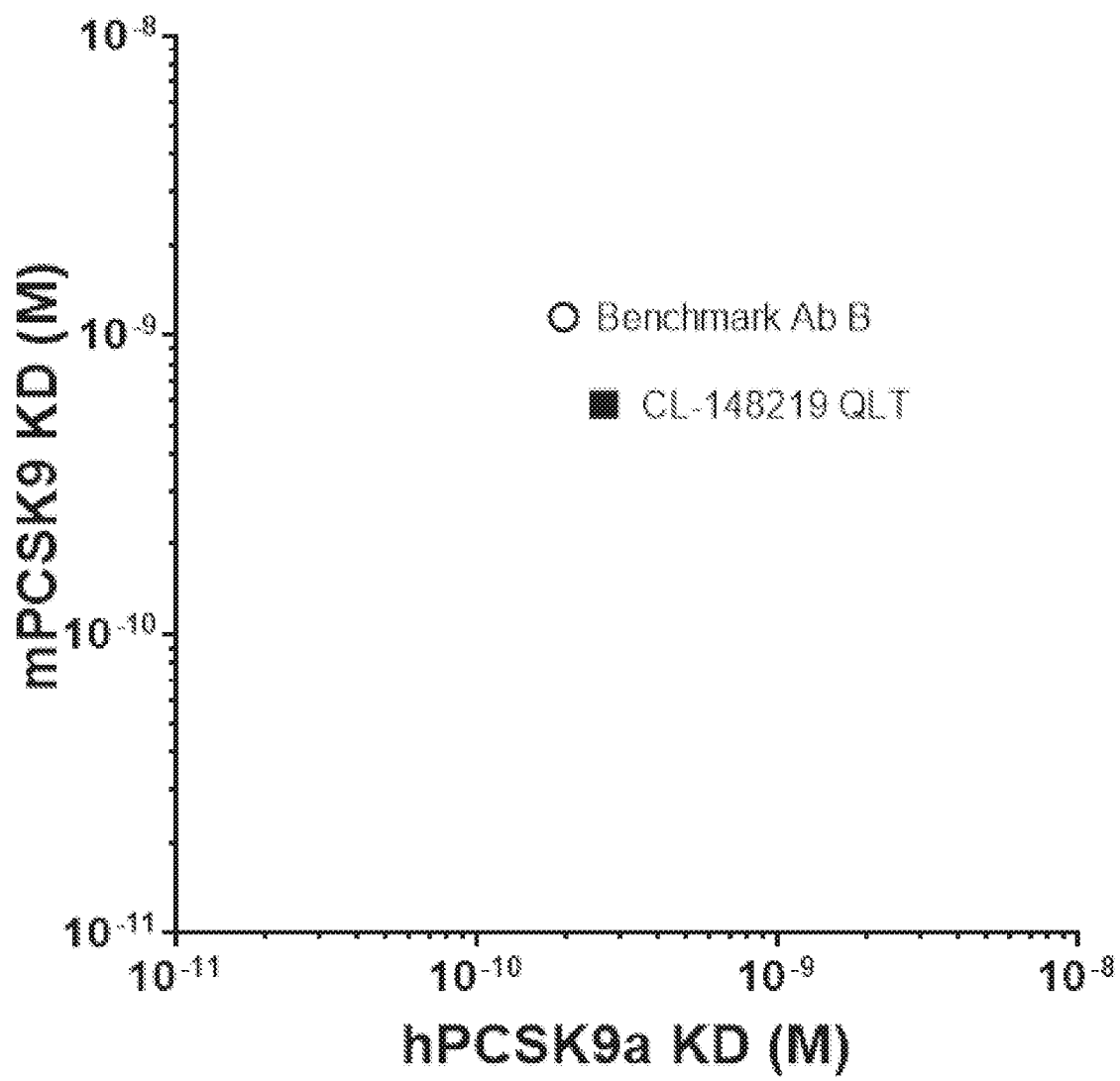
FIG. 30: Affinity of CL-148219 QLT. The affinity was determined by KD. The KD of CL-148219 QLT was measured against human and mouse PCSK9 at pH7.6 by Proteon SPR analysis system.
Figure 31:
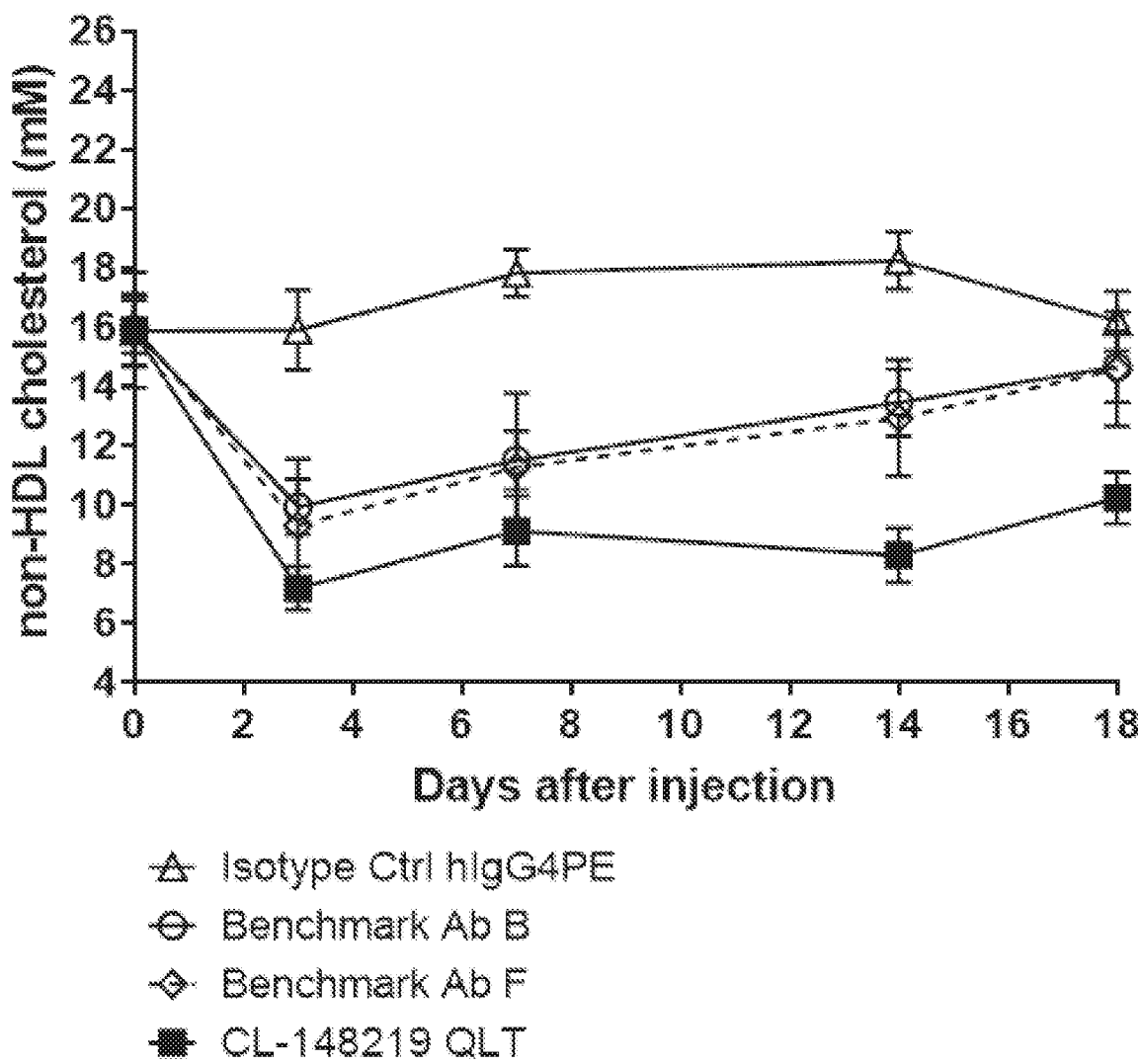
FIG. 31: CL-148219 QLT showed superior function to reduce non-HDL cholesterol compared to benchmarks in a hyperlipidemia mouse model (E3L.CETP mice). E3L.CETP mice were treated with western diet for 4 weeks followed by antibody injection. At different time after Ab injection, blood was collected and the amount of plasma HDL and total cholesterol were measured. The amount of plasma non-HDL cholesterol was then calculated by subtracting HDL from total cholesterol.
Figure 32:
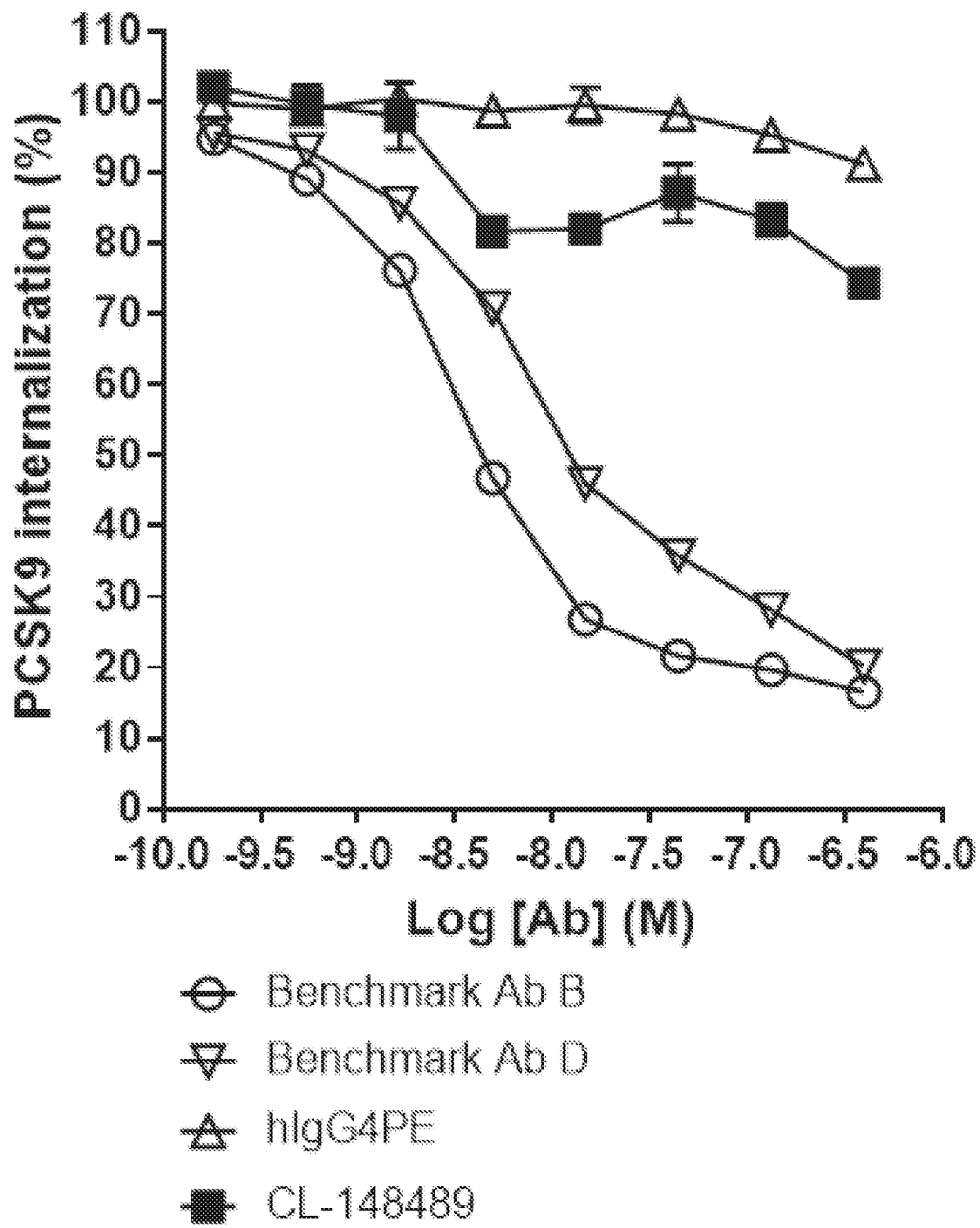
FIG. 32: CL-148489 moderately neuralised human PCSK9 internalisation in a cell-based assay in vitro. HepG2 cells were treated with AF647-labelled human PCSK9 gain-of-function mutant in the presence of isotype control, benchmarks, or CL-148489, followed by treatment with BODIPY LDL. Cells were then collected and the fluorescent signals of AF647 was detected by CytoFlex flow cytometer.
Figure 33:
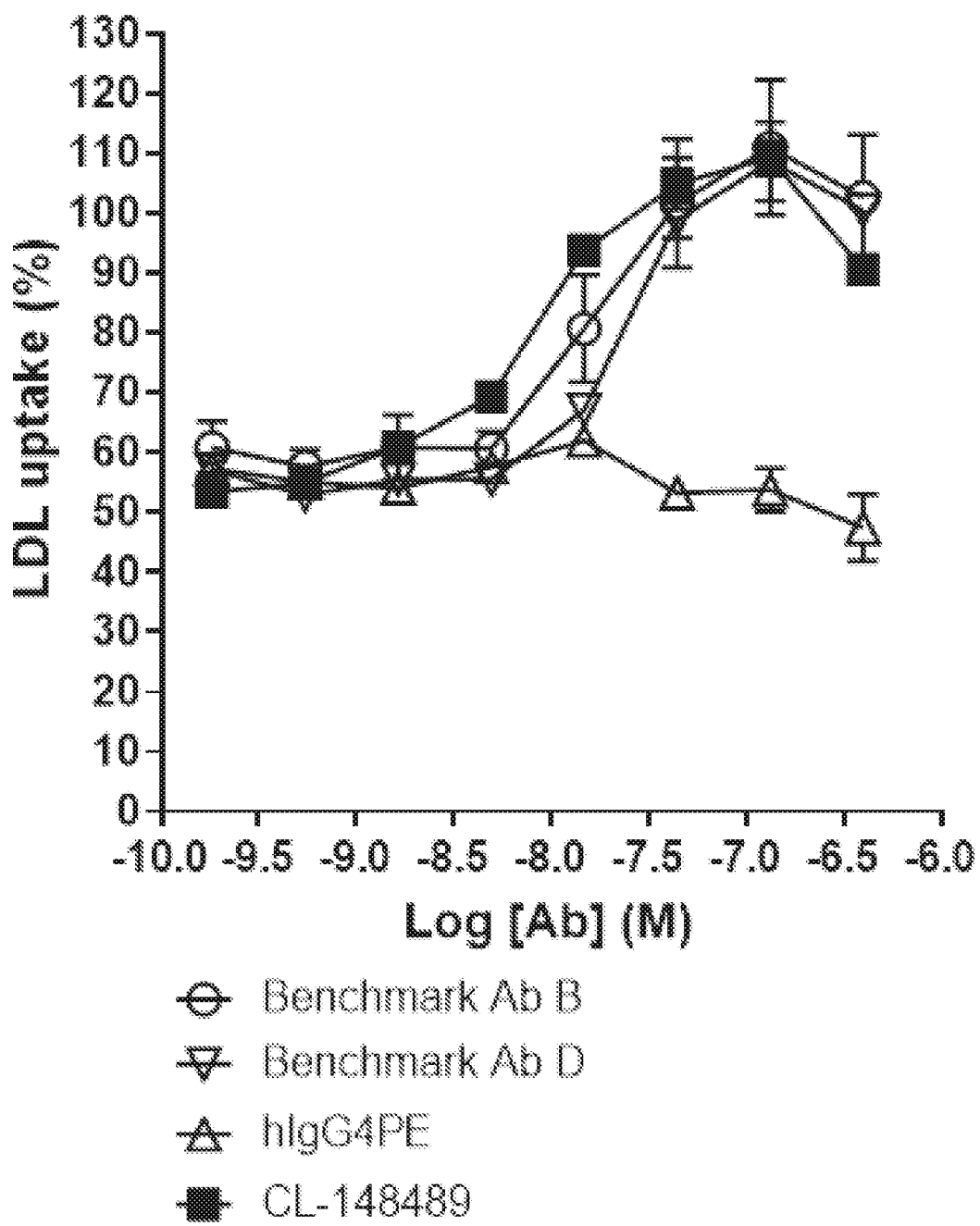
FIG. 33: CL-148489 increased LDL uptake better than benchmarks in a cell-based assay in vitro. HepG2 cells were treated with AF647-labelled human PCSK9 gain-of-function mutant in the presence of isotype control, benchmarks, or CL-148489, followed by treatment with BODIPY LDL. Cells were then collected and the fluorescent signals of BODIPY was detected by CytoFlex flow cytometer.
Figure 34:
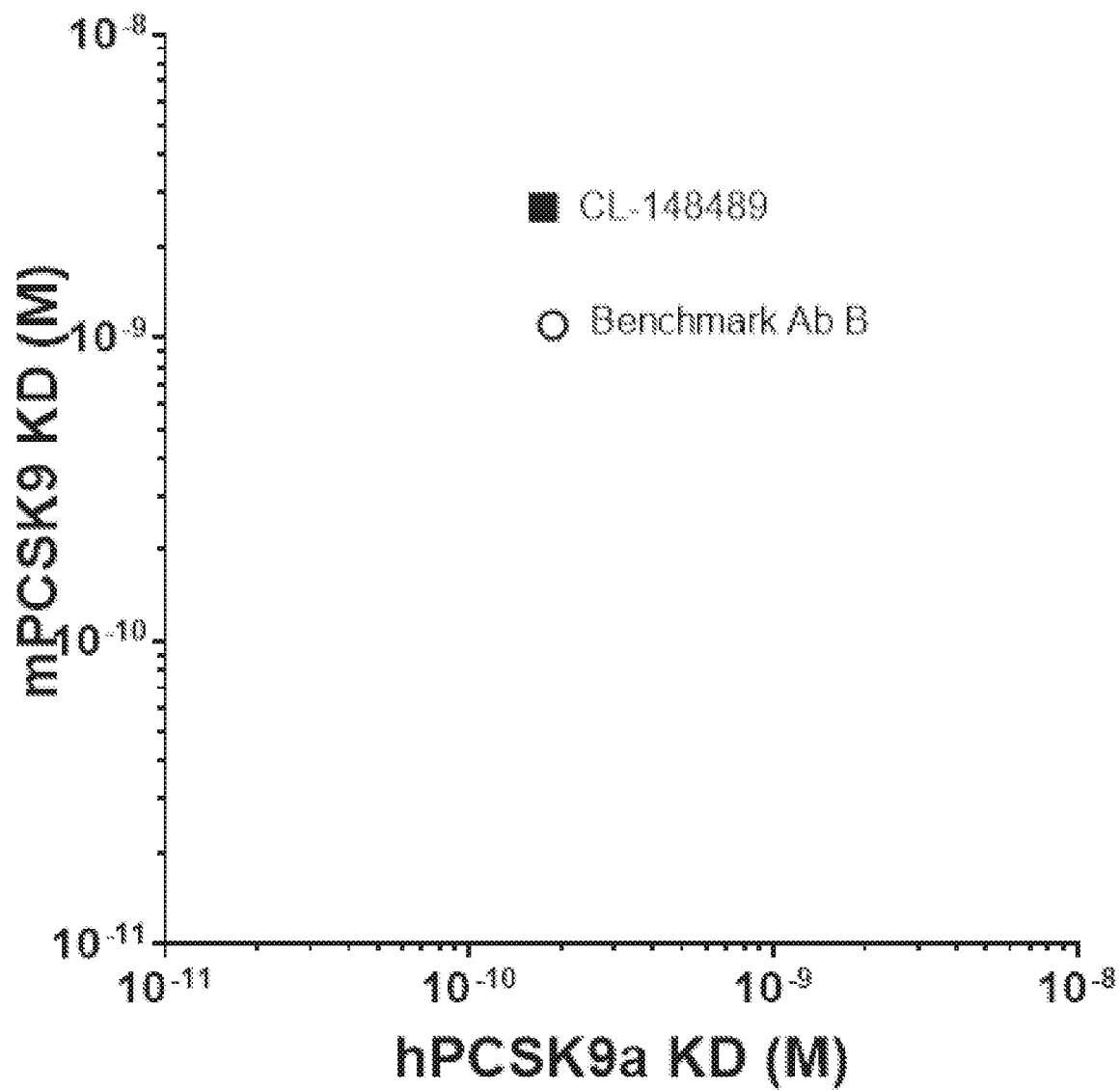
FIG. 34: Affinity of CL-148489. The affinity was determined by KD. The KD of CL-148489 was measured against human and mouse PCSK9 at pH7.6 by Proteon SPR analysis system.
Figure 35:
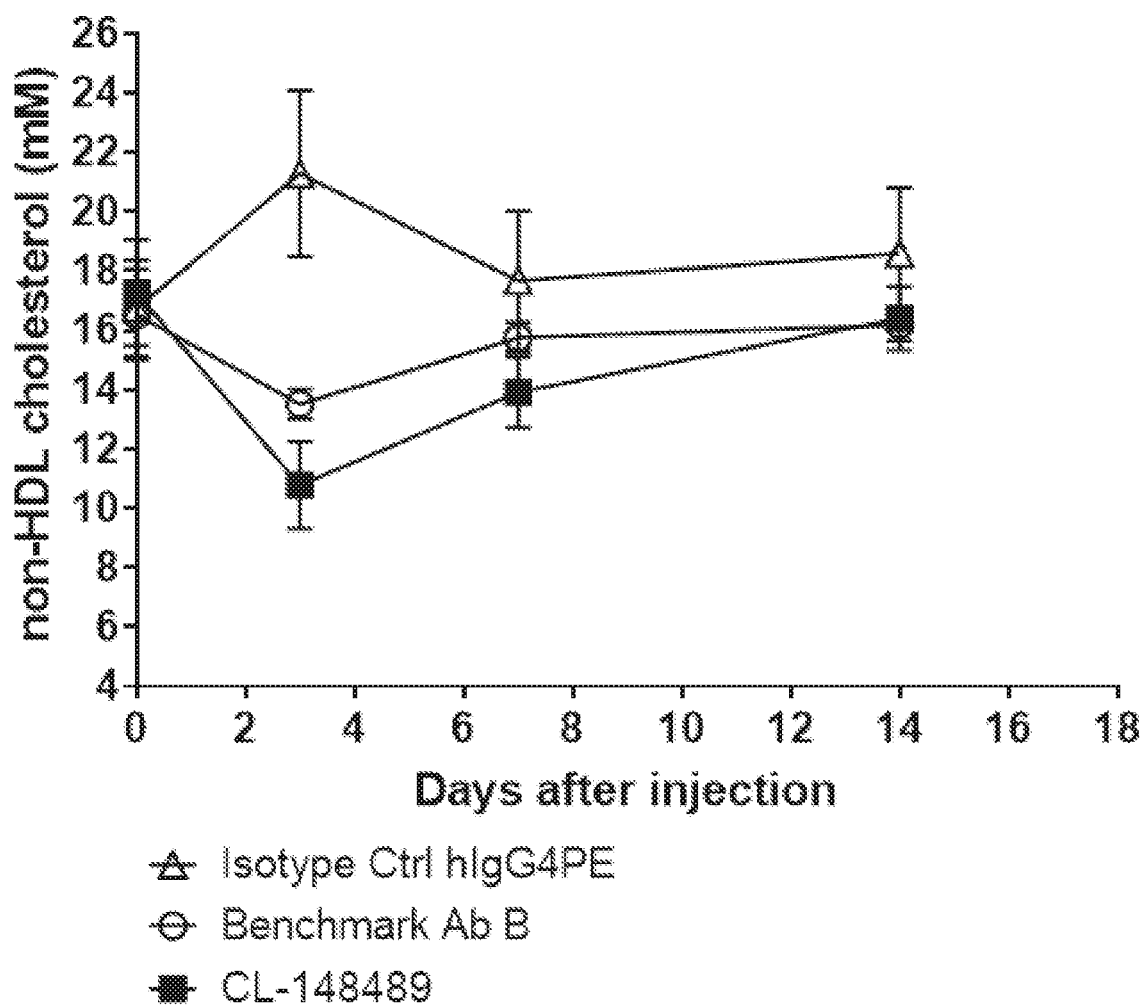
FIG. 35: CL-148489 showed superior function to reduce non-HDL cholesterol compared to benchmarks in a hyperlipidemia mouse model (E3L.CETP mice). E3L.CETP mice were treated with western diet for 4 weeks followed by antibody injection. At different time after Ab injection, blood was collected and the amount of plasma HDL and total cholesterol were measured. The amount of plasma non-HDL cholesterol was then calculated by subtracting HDL from total cholesterol.
Figure 36:
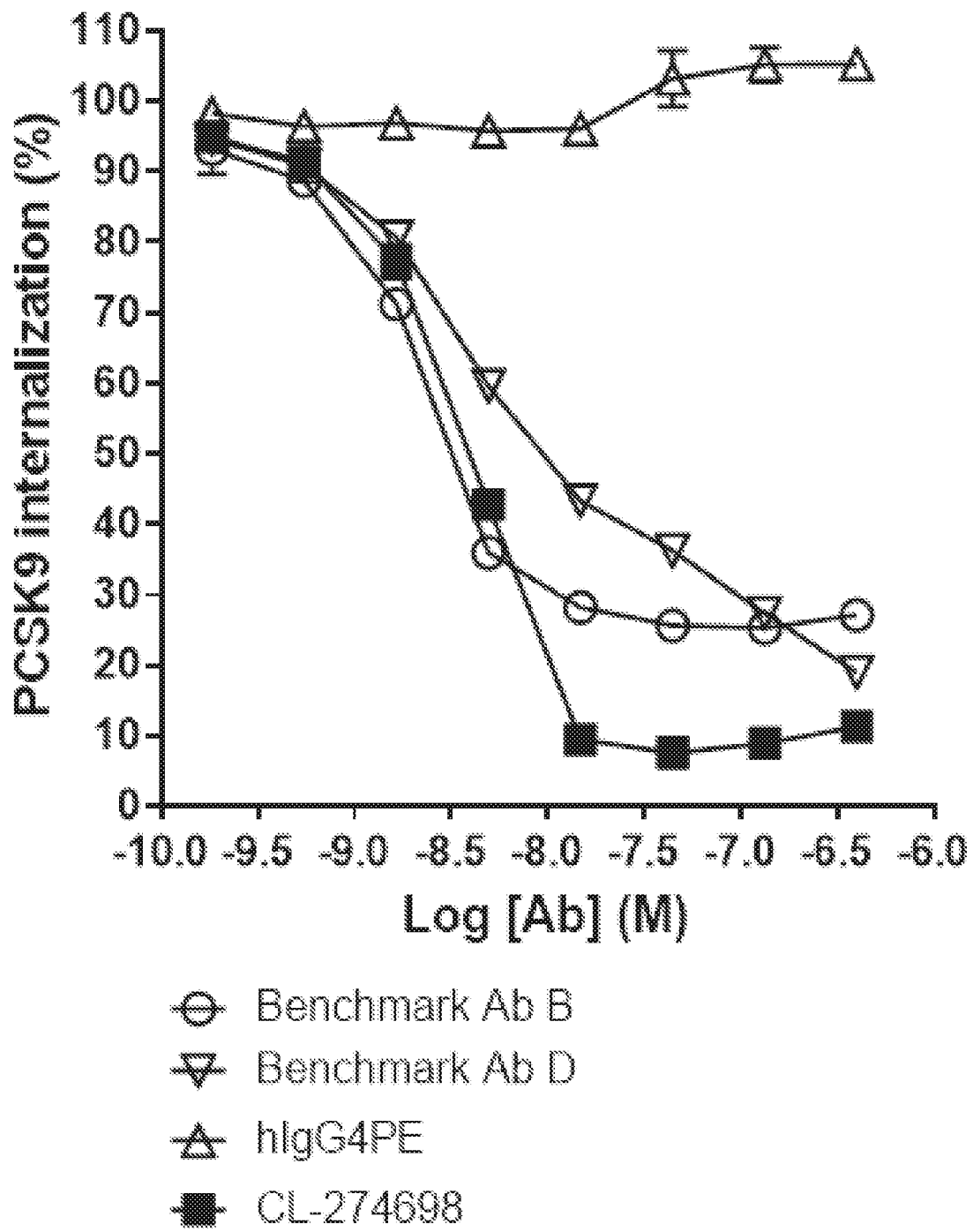
FIG. 36: CL-274698 neuralised human PCSK9 internalisation more than benchmarks in a cell-based assay in vitro. HepG2 cells were treated with AF647-labelled human PCSK9 gain-of-function mutant in the presence of isotype control, benchmarks, or CL-274698, followed by treatment with BODIPY LDL. Cells were then collected and the fluorescent signals of AF647 was detected by CytoFlex flow cytometer.
Figure 37:
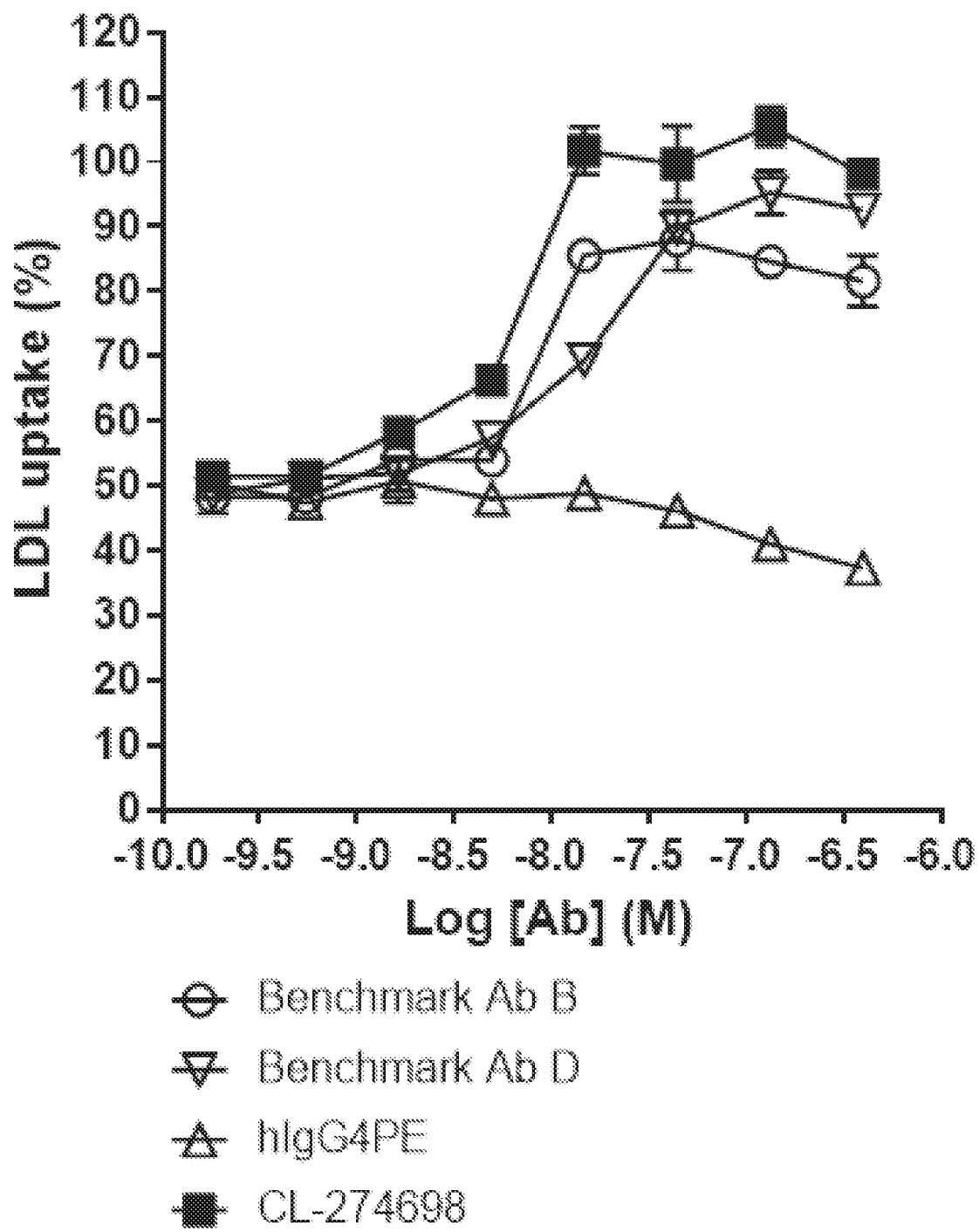
FIG. 37: CL-274698 increased LDL uptake better than benchmarks in a cell-based assay in vitro. HepG2 cells were treated with AF647-labelled human PCSK9 gain-of-function mutant in the presence of isotype control, benchmarks, or CL-274698, followed by treatment with BODIPY LDL. Cells were then collected and the fluorescent signals of BODIPY was detected by CytoFlex flow cytometer.
Figure 38:
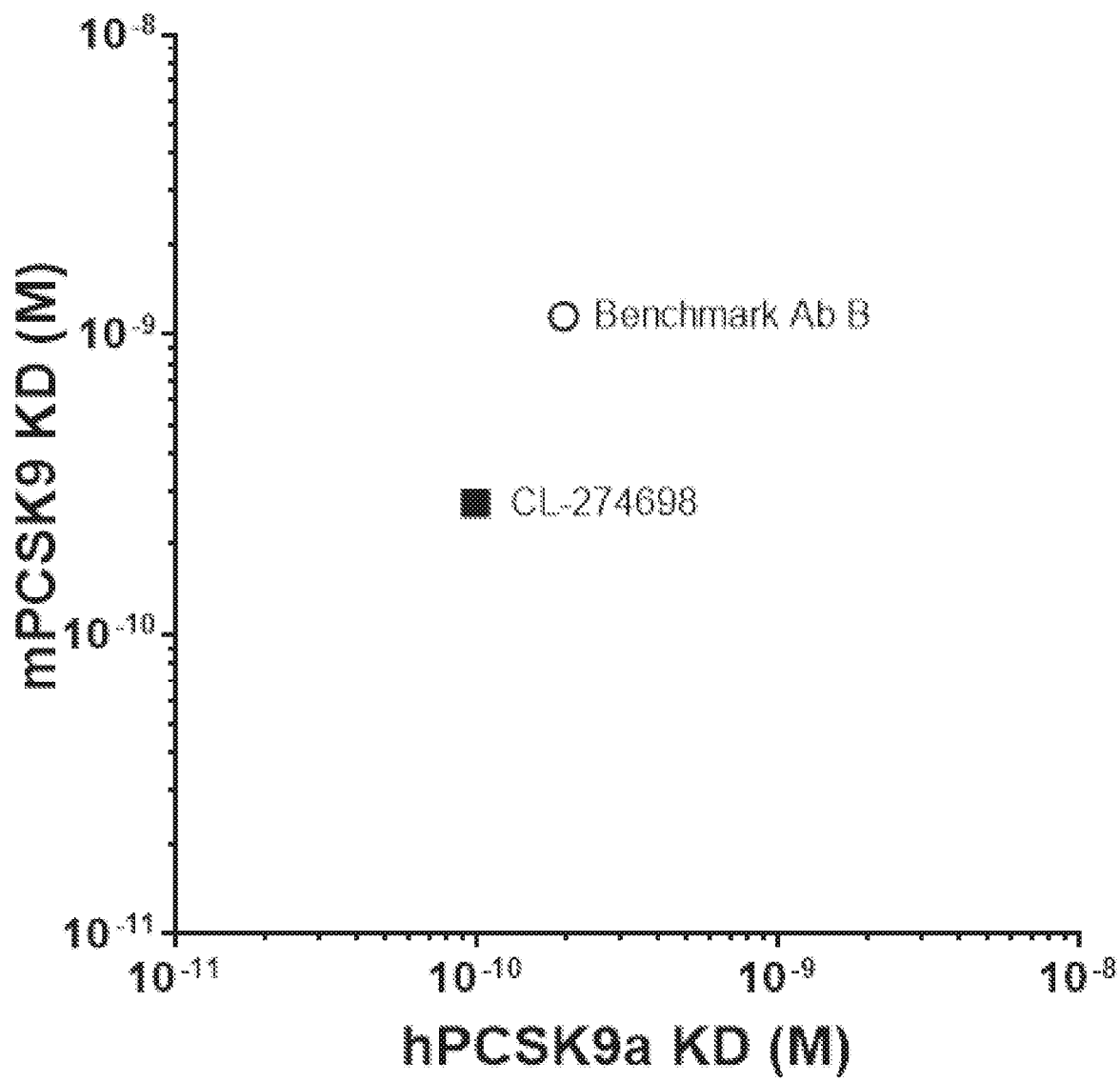
FIG. 38: Affinity of CL-274698. The affinity was determined by KD. The KD of CL-274698 was measured against human and mouse PCSK9 at pH7.6 by Proteon SPR analysis system.
Figure 39:
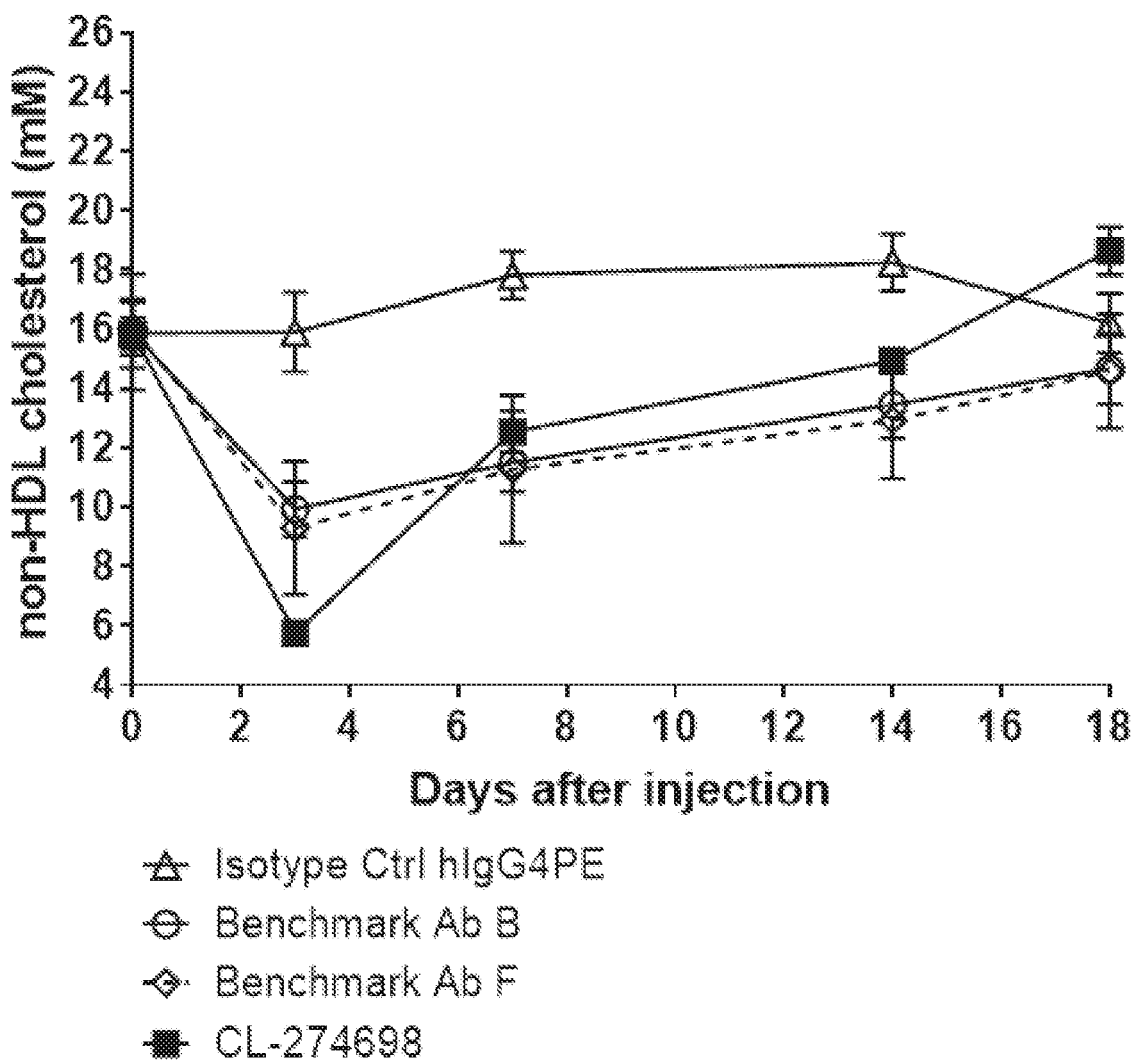
FIG. 39: CL-274698 showed superior function to reduce non-HDL cholesterol compared to benchmarks in a hyperlipidemia mouse model (E3L.CETP mice). E3L.CETP mice were treated with western diet for 4 weeks followed by antibody injection. At different time after Ab injection, blood was collected and the amount of plasma HDL and total cholesterol were measured. The amount of plasma non-HDL cholesterol was then calculated by subtracting HDL from total cholesterol.
Figure 40:
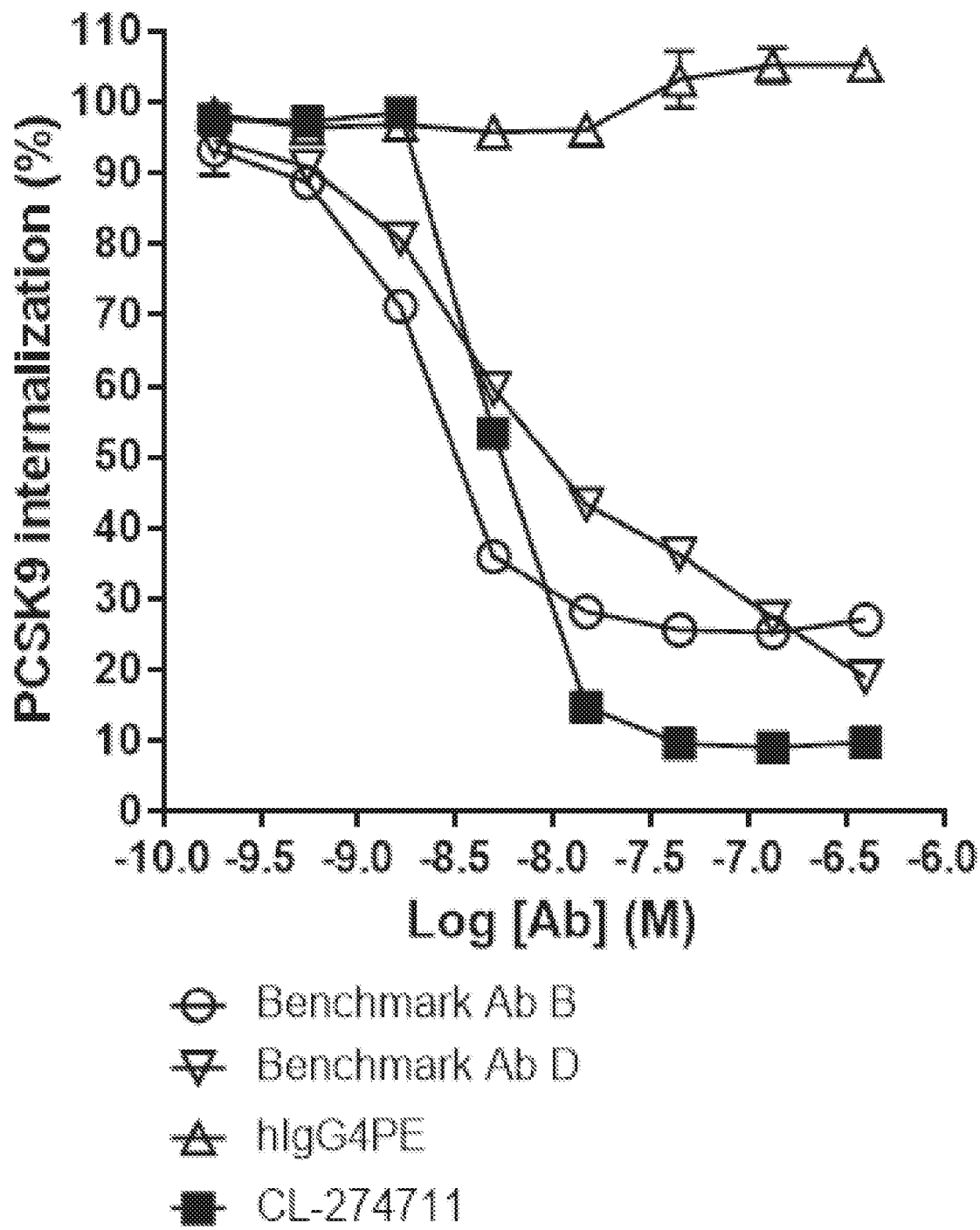
FIG. 40: CL-274711 neuralised human PCSK9 internalisation more than benchmarks in a cell-based assay in vitro. HepG2 cells were treated with AF647-labelled human PCSK9 gain-of-function mutant in the presence of isotype control, benchmarks, or CL-274711, followed by treatment with BODIPY LDL. Cells were then collected and the fluorescent signals of AF647 was detected by CytoFlex flow cytometer.
Figure 41:
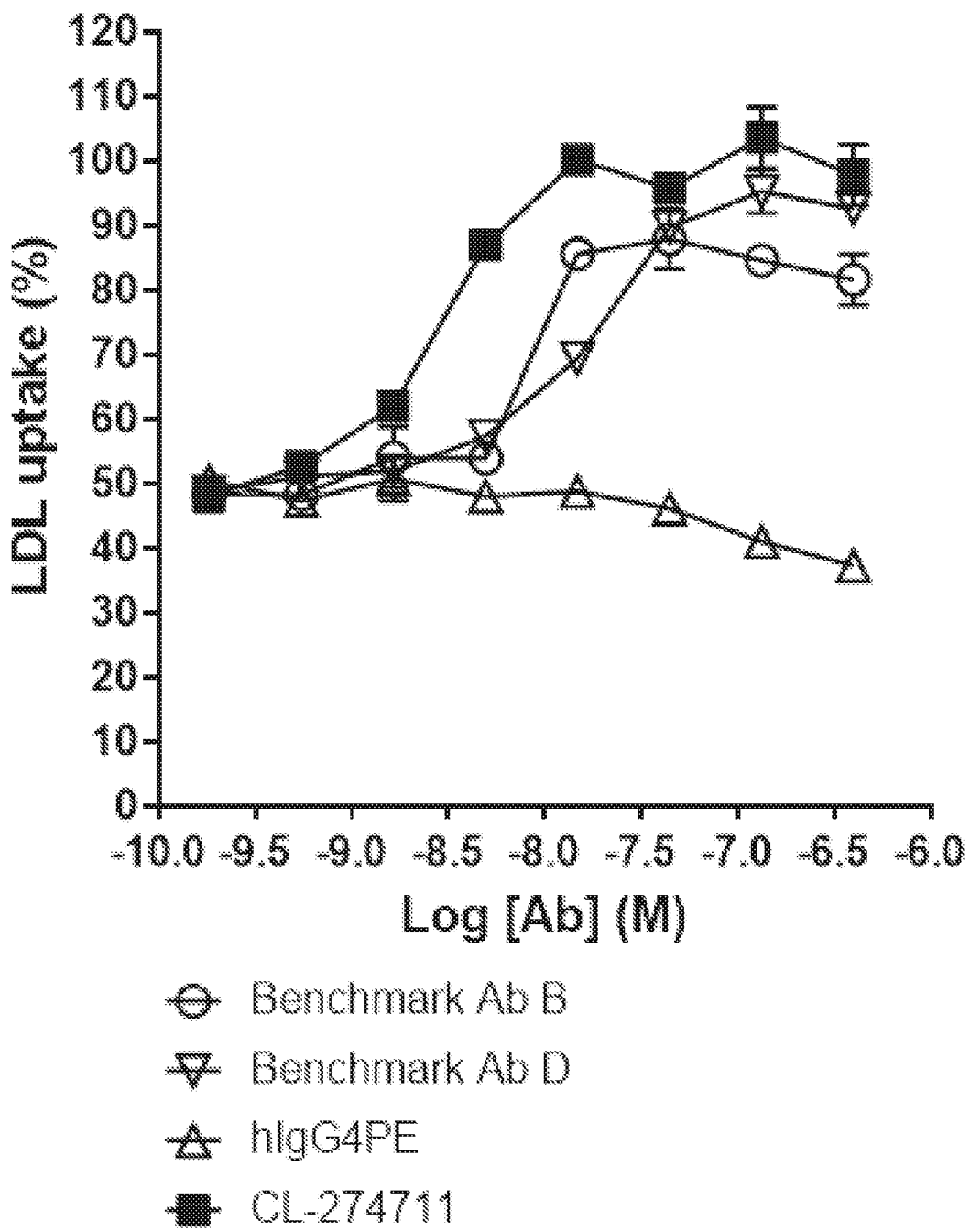
FIG. 41: CL-274711 increased LDL uptake better than benchmarks in a cell-based assay in vitro. HepG2 cells were treated with AF647-labelled human PCSK9 gain-of-function mutant in the presence of isotype control, benchmarks, or CL-274711, followed by treatment with BODIPY LDL. Cells were then collected and the fluorescent signals of BODIPY was detected by CytoFlex flow cytometer.
Figure 42:
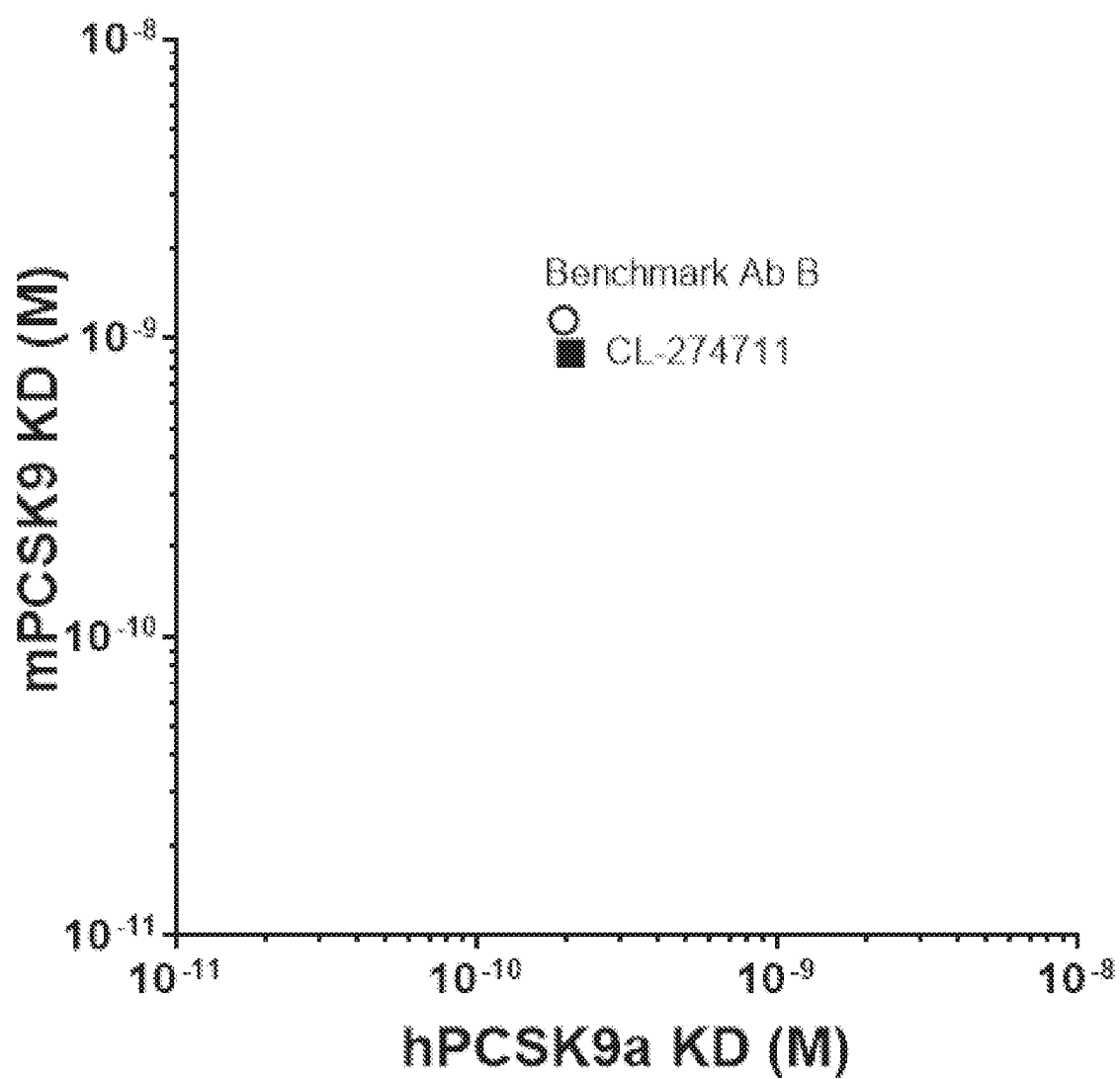
FIG. 42: Affinity of CL-274711. The affinity was determined by KD. The KD of CL-274711 was measured against human and mouse PCSK9 at pH7.6 by Proteon SPR analysis system.
Figure 43:
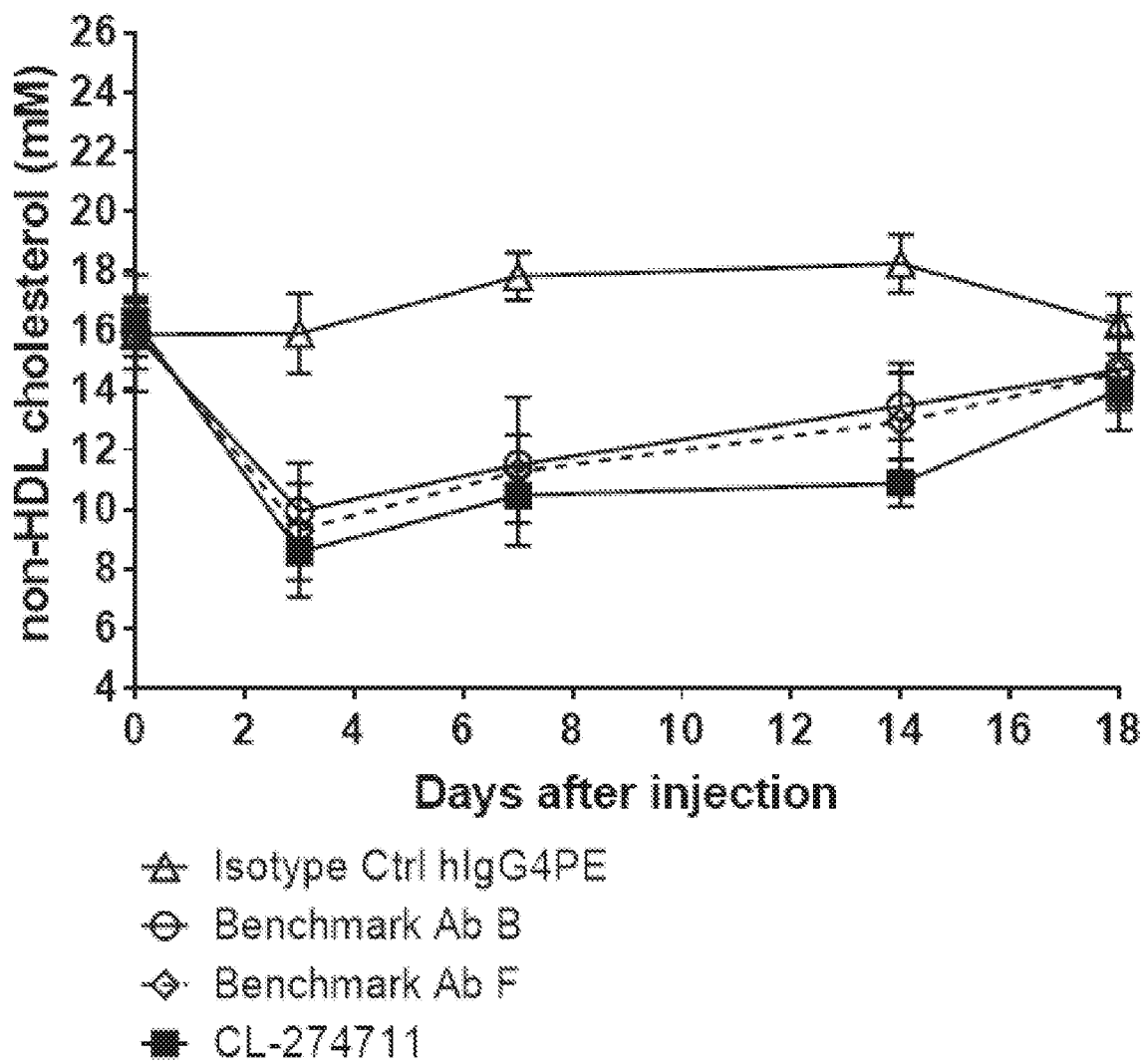
FIG. 43: CL-274711 showed superior function to reduce non-HDL cholesterol compared to benchmarks in a hyperlipidemia mouse model (E3L.CETP mice). E3L.CETP mice were treated with western diet for 4 weeks followed by antibody injection. At different time after Ab injection, blood was collected and the amount of plasma HDL and total cholesterol were measured. The amount of plasma non-HDL cholesterol was then calculated by subtracting HDL from total cholesterol.

Further Data:

Reference is made to FIG. 24 onwards showing efficacy of antibodies of the invention. Reference is also made to Table 1 showing antibody affinity against human PCSK9 variants, cynomolgus monkey PCSK9, and mouse PCSK9 at neutral pH (7.6) versus acidic pH (5.8). KD was measured by ProteOn™ SPR analysis system.

We included six PCSK9 benchmark antibodies as controls for comparison. Three benchmark antibodies were versions of marketed antibodies (benchmark antibody A, B, and F) and three were selected from antibodies in clinical trials (benchmark antibody C, D, and E). Benchmark antibody A, B, C, D, and E were made in human IgG4PE format. Benchmark antibody F was in human IgG1 format.

Antigens used for immunisation and/or screening included 4 human PCSK9 variants, cynomolgus monkey PCSK9, and mouse PCSK9. Here we called 4 human PCSK9 variants as following: human PCSK9 reference (hPCSK9 Ref), human PCSK9 variant a (hPCSK9a), human PCSK9 variant b (hPCSK9b), and human PCSK9 D374Y gain-of-function mutant (hPCSK9 GOF). Relative to the human PCSK9 reference sequence, human variant a has V474I and G670E amino acid substitution, and human variant b has A53V, V474I, and G670E amino acid substitution. We included these 4 human variants for assay screening in order to find an antibody with capability to neutralise all the 4 variants and the mutant in human population.

CL-148219

Compared to the benchmarks, CL-148219 showed stronger neutralisation activity with higher capacity to restore LDL uptake in vitro, suggesting CL-148219 may directly block the interaction between PCSK9 and LDLR. In a mouse model of hyperlipidemia (E3L.CETP mice; de Knijff, Westerterp, Ason, van den Hoek and Kühnast), CL-148219 reduced plasma non-HDL cholesterol superior to benchmark Ab with longer duration of effect. See FIGS. 24-27 and Table 1.

CL-148219 QLT Mutant

By sequence analysis in silicon, a N-glycosylation motif was found in the heavy chain of CL-148219. The NLT motif, located in the framework 3 region of the heavy chain, may be glycosylated and may have adverse effect in developability. It was later confirmed by Mass Spectrometry that the NLT motif in CL-148219 was indeed N-glycosylated. We thus introduced mutation to the NLT motif by replacing N with Q residue, generating CL-148219 QLT mutant to disrupt glycosylation. Removal of glycosylation was further confirmed by Mass Spectrometry. CL-148219 QLT mutant showed similar affinity and functionality in vitro when compared to the parental CL-148219. Like parental CL-148219, the QLT mutant reduced plasma non-HDL cholesterol superior to benchmarks with longer duration of effect in a hyperlipidemia mouse model (E3L.CETP mice). See FIGS. 27-31 and Table 1.

CL-148489

In the in vitro cell-based assay, CL-148489 neutralised hPCSK9 moderately but contained significant capacity to restore LDL uptake, suggesting this antibody may indirectly interfere the binding of PCSK9 to LDLR, possibly via blocking HSPG binding to PCSK9. This antibody also reduced plasma non-HDL cholesterol in a mouse model of hyperlipidemia (E3L.CETP mice) better than benchmarks with similar duration of effect. See FIGS. 32-35 and Table 1.

CL-274698

Unlike CL-148219 and CL-148489 that were derived from a mouse with humanized antibody loci and without knock-out of the PCSK9 gene, CL-274698 was derived from a PCSK9 knockout mouse. In the absence of PCSK9, mice produced high affinity antibodies against immunogens including both human and mouse PCSK9. CL-274698 was thus generated and screened. CL-274698 not only showed high affinity against PCSK9 with KD in a sub-nM range, but also exhibited superior function to neutralise hPCSK9 and restore LDL uptake in vitro. In the in vivo efficacy study by using E3L.CETP mice, CL-274698 reduced plasma non-HDL cholesterol more than benchmarks within 3 days after Ab injection, with the fact that the level of non-HDL cholesterol was similar to benchmarks after day 7. See FIGS. 36-39 and Table 1.

CL-274711

Similar to CL-274698, CL-274711 was generated by immunizing a PCSK9 knockout mouse. In the in vitro cell-based assays, CL-274711 neutralised hPCSK9 and restored LDL uptake better than benchmarks. In the in vivo efficacy assay by using E3L.CETP mice, CL-274711 showed slightly superior function in reducing plasma non-HDL cholesterol with longer duration of effect compared to benchmarks. See FIGS. 40-43 and Table 1.

Method

Cell-Based Functional Assay In Vitro

HepG2 cells were seeded at $6\times10^4$ cells/well into 96-well clear flat-bottom cell culture plates (Costar) in complete culture medium, containing 10% FBS, 1× Penicillin/Streptomycin and 1× NEAA in MEMα. To allow attachment, cells were incubated in 5% $CO_2$ incubator at 37° C. for 24 hours. The next day media were replaced by serum-free culture media (1× NEAA and 1× Penicillin/Streptomycin in MEMα), and cells were kept in incubator overnight (16-18 hours). On the following day, cells were treated with various concentrations of anti-PCSK9 monoclonal antibodies that were pre-incubated with 5 µg/ml AF647-labelled hPCSK9 GOF antigen. The antibodies were diluted from 60 µg/ml with 3 fold series dilutions. After 1 hour incubation with hPCSK9 GOF plus anti-PCSK9 antibodies, BODIPY LDL (Invitrogen) was added to cells at a final concentration of 10 µg/ml. LDL uptake was allowed by incubating cells for additional 3 hours. In the end of treatment, cells were detached by accutase (BD), and followed by fixation with 2% paraformaldehyde diluted in PBS (Alfa Aesar) overnight at 4° C. After washes, cells were resuspended in PBS containing 5 mM EDTA, and fluorescent cells were detected by CytoFlex flow cytometry.

ProteOn SPR Analysis

ProteOn™ XPR36 (Bio-Rad) was used to measure antibody binding affinity to antigen (human PCSK9 variants, cynomolgus monkey PCSK9 and mouse PCSK9) in neutral (HBS-EP+, pH7.6) and acidic buffer (30 mM sodium acetate, 150 mM NaCl, 0.05% P20, pH5.8) at 25° C. The SPR runs were performed using a GLC chip (Bio-Rad) immobilised with anti-human Fc antibodies. The analyte human antibodies were captured on the chip surface at 2 µg/ml. The PCSK9 proteins were injected at 100 nM, 25 nM, 6.25 nM, 1.56 nM, 0.39 nM for 180 seconds and dissociation was monitored for 600 seconds at a flow rate of 30 µL/min. The chip surface was regenerated using two injections of 10 mM Glycine pH 1.5 for 160 seconds at 30 µl/min. The sensorgrams were then fitted with a 1:1 model (Langmuir kinetic model) where ka and kd are fitted and KD was calculated by the ProteOn software.

TABLE 1

| | | pH 7.6 | | | pH 5.8 | | |
|---|---|---|---|---|---|---|---|
| | | ka (1/Ms) | kd (1/s) | KD (M) | ka (1/Ms) | kd (1/s) | KD (M) |
| Benchmark Ab B | Human PCSK9 var A | 1.53E+06 | 3.00E-04 | 1.96E-10 | 1.68E+06 | 1.20E-04 | 7.13E-11 |
| | Human PCSK9 var B | 1.57E+06 | 2.91E-04 | 1.86E-10 | 1.75E+06 | 1.10E-04 | 6.27E-11 |
| | Human PCSK9 Ref | 1.50E+06 | 2.93E-04 | 1.95E-10 | 1.77E+06 | 1.06E-04 | 5.99E-11 |
| | Human PCSK9 GOF | 1.32E+06 | 7.21E-04 | 5.48E-10 | 1.69E+06 | 3.27E-04 | 1.94E-10 |
| | Cyno PCSK9 | 1.21E+06 | 2.30E-04 | 1.90E-10 | 1.31E+06 | 6.95E-05 | 5.32E-11 |
| | Mouse PCSK9 | 1.16E+06 | 1.33E-03 | 1.15E-09 | 1.34E+06 | 4.96E-04 | 3.70E-10 |
| CL-148219 | Human PCSK9 var A | 1.08E+06 | 2.34E-04 | 2.16E-10 | 9.08E+05 | 3.87E-04 | 4.26E-10 |
| | Human PCSK9 var B | 1.05E+06 | 2.25E-04 | 2.15E-10 | 9.18E+05 | 3.78E-04 | 4.12E-10 |
| | Human PCSK9 Ref | 1.13E+06 | 2.30E-04 | 2.05E-10 | 1.02E+06 | 3.74E-04 | 3.68E-10 |
| | Human PCSK9 GOF | 9.49E+05 | 2.33E-04 | 2.45E-10 | 9.08E+05 | 3.91E-04 | 4.31E-10 |
| | Cyno PCSK9 | 9.58E+05 | 2.84E-04 | 2.96E-10 | 9.75E+05 | 3.36E-04 | 3.45E-10 |
| | Mouse PCSK9 | 7.91E+05 | 4.11E-04 | 5.20E-10 | 1.01E+06 | 7.01E-04 | 6.91E-10 |
| CL-148219 QLT | Human PCSK9 var A | 8.56E+05 | 2.29E-04 | 2.67E-10 | 6.02E+05 | 4.29E-04 | 7.12E-10 |
| | Human PCSK9 var B | 8.62E+05 | 2.21E-04 | 2.57E-10 | 6.07E+05 | 4.21E-04 | 6.94E-10 |
| | Human PCSK9 Ref | 8.33E+05 | 2.26E-04 | 2.72E-10 | 6.22E+05 | 4.15E-04 | 6.67E-10 |
| | Human PCSK9 GOF | 7.21E+05 | 2.19E-04 | 3.03E-10 | 6.06E+05 | 4.56E-04 | 7.53E-10 |
| | Cyno PCSK9 | 7.28E+05 | 2.56E-04 | 3.52E-10 | 5.84E+05 | 3.31E-04 | 5.68E-10 |
| | Mouse PCSK9 | 6.00E+05 | 3.52E-04 | 5.87E-10 | 4.72E+05 | 6.75E-04 | 1.43E-09 |
| CL-148489 | Human PCSK9 var A | 8.94E+05 | 1.57E-04 | 1.75E-10 | 1.25E+06 | 1.00E-5* | <8.0E-12** |
| | Human PCSK9 var B | 8.48E+05 | 1.64E-04 | 1.93E-10 | 1.54E+06 | 1.00E-5* | <6.49E-12** |
| | Human PCSK9 Ref | 9.24E+05 | 1.63E-04 | 1.76E-10 | 1.50E+06 | 1.00E-5* | <6.67E-12** |
| | Human PCSK9 GOF | 9.47E+05 | 1.29E-04 | 1.36E-10 | 1.37E+06 | 1.00E-5* | <7.30E-12** |
| | Cyno PCSK9 | 1.13E+06 | 5.73E-05 | 5.06E-11 | 1.31E+06 | 1.21E-04 | 9.24E-11 |
| | Mouse PCSK9 | 7.14E+05 | 1.92E-03 | 2.69E-09 | 1.38E+06 | 6.32E-04 | 4.60E-10 |
| CL-274698 | Human PCSK9 var A | 1.37E+06 | 1.36E-04 | 9.98E-11 | 1.56E+06 | 4.81E-05 | 3.09E-11 |
| | Human PCSK9 var B | 1.39E+06 | 1.27E-04 | 9.10E-11 | 1.60E+06 | 4.19E-05 | 2.62E-11 |
| | Human PCSK9 Ref | 1.35E+06 | 1.25E-04 | 9.29E-11 | 1.60E+06 | 4.60E-05 | 2.86E-11 |
| | Human PCSK9 GOF | 1.21E+06 | 8.36E-05 | 6.89E-11 | 1.53E+06 | 3.83E-05 | 2.50E-11 |
| | Cyno PCSK9 | 1.10E+06 | 1.08E-04 | 9.84E-11 | 1.26E+06 | 3.75E-05 | 2.97E-11 |
| | Mouse PCSK9 | 9.41E+05 | 2.57E-04 | 2.73E-10 | 1.33E+06 | 1.37E-04 | 1.03E-10 |

TABLE 1-continued

|  |  | pH 7.6 | | | pH 5.8 | | |
| --- | --- | --- | --- | --- | --- | --- | --- |
|  |  | ka (1/Ms) | kd (1/s) | KD (M) | ka (1/Ms) | kd (1/s) | KD (M) |
| CL-274711 | Human PCSK9 var A | 2.95E+05 | 6.11E−05 | 2.07E−10 | 4.46E+05 | 6.99E−05 | 1.57E−10 |
|  | Human PCSK9 var B | 3.04E+05 | 5.44E−05 | 1.79E−10 | 4.42E+05 | 7.15E−05 | 1.62E−10 |
|  | Human PCSK9 Ref | 2.94E+05 | 6.04E−05 | 2.05E−10 | 4.33E+05 | 6.58E−05 | 1.52E−10 |
|  | Human PCSK9 GOF | 2.99E+05 | 5.29E−05 | 1.77E−10 | 4.86E+05 | 9.60E−05 | 1.98E−10 |
|  | Cyno PCSK9 | 4.06E+05 | 5.87E−05 | 1.45E−10 | 5.45E+05 | 8.91E−05 | 1.64E−10 |
|  | Mouse PCSK9 | 2.85E+05 | 2.53E−04 | 8.89E−10 | 5.08E+05 | 6.39E−04 | 1.26E−09 |

*1e−5 is the lower detection limits
**KD cannot be accurately determined.

VARIABLE REGION SEQUENCE SUMMARY

| SEQ ID NO | CL-148219 | CL-148489 | DESCRIPTION | AMINO ACID | NUCLEOTIDE |
| --- | --- | --- | --- | --- | --- |
| 1 | X |   | VH REGION | X |   |
| 65 |   | X |   | X |   |
| 2 | X |   |   |   | X |
| 66 |   | X |   |   | X |
| 7 | X |   | HCDR1-IMGT | X |   |
| 69 |   | X |   | X |   |
| 8 | X |   |   |   | X |
| 70 |   | X |   |   | X |
| 11 | X |   | HCDR2-IMGT | X |   |
| 73 |   | X |   | X |   |
| 12 | X |   |   |   | X |
| 74 |   | X |   |   | X |
| 15 | X |   | HCDR3-IMGT | X |   |
| 77 |   | X |   | X |   |
| 16 | X |   |   |   | X |
| 78 |   | X |   |   | X |
| 21 | X |   | HCDR1-Kabat | X |   |
| 83 |   | X |   | X |   |
| 22 | X |   |   |   | X |
| 84 |   | X |   |   | X |
| 25 | X |   | HCDR2-Kabat | X |   |
| 87 |   | X |   | X |   |
| 26 | X |   |   |   | X |
| 88 |   | X |   |   | X |
| 29 | X |   | HCDR3-Kabat | X |   |
| 91 |   | X |   | X |   |
| 30 | X |   |   |   | X |
| 92 |   | X |   |   | X |
| 5 | X |   | VH FR1-IMGT | X |   |
| 67 |   | X |   | X |   |
| 6 | X |   |   |   | X |
| 68 |   | X |   |   | X |
| 9 | X |   | VH FR2-IMGT | X |   |
| 71 |   | X |   | X |   |
| 10 | X |   |   |   | X |
| 72 |   | X |   |   | X |
| 13 | X |   | VH FR3-IMGT | X |   |
| 75 |   | X |   | X |   |
| 14 | X |   |   |   | X |
| 76 |   | X |   |   | X |
| 17 | X |   | VH FR4-IMGT | X |   |
| 79 |   | X |   | X |   |
| 18 | X |   |   |   | X |
| 80 |   | X |   |   | X |
| 19 | X |   | VH FR1-Kabat | X |   |
| 81 |   | X |   | X |   |
| 20 | X |   |   |   | X |
| 82 |   | X |   |   | X |
| 23 | X |   | VH FR2-Kabat | X |   |
| 85 |   | X |   | X |   |
| 24 | X |   |   |   | X |
| 86 |   | X |   |   | X |
| 27 | X |   | VH FR3-Kabat | X |   |
| 89 |   | X |   | X |   |
| 28 | X |   |   |   | X |
| 90 |   | X |   |   | X |
| 31 | X |   | VH FR4-Kabat | X |   |
| 93 |   | X |   | X |   |
| 32 | X |   |   |   | X |
| 94 |   | X |   |   | X |
| 33 | X |   | VL REGION | X |   |
| 95 |   | X |   | X |   |
| 34 | X |   |   |   | X |
| 96 |   | X |   |   | X |
| 39 | X |   | LCDR1-IMGT | X |   |
| 99 |   | X |   | X |   |
| 40 | X |   |   |   | X |
| 100 |   | X |   |   | X |
| 43 | X |   | LCDR2-IMGT | X |   |
| 103 |   | X |   | X |   |
| 44 | X |   |   |   | X |
| 104 |   | X |   |   | X |
| 47 | X |   | LCDR3-IMGT | X |   |
| 107 |   | X |   | X |   |
| 48 | X |   |   |   | X |
| 108 |   | X |   |   | X |
| 53 | X |   | LCDR1-Kabat | X |   |
| 113 |   | X |   | X |   |
| 54 | X |   |   |   | X |
| 114 |   | X |   |   | X |
| 57 | X |   | LCDR2-Kabat | X |   |
| 117 |   | X |   | X |   |
| 58 | X |   |   |   | X |
| 118 |   | X |   |   | X |
| 61 | X |   | LCDR3-Kabat | X |   |
| 121 |   | X |   | X |   |
| 62 | X |   |   |   | X |
| 122 |   | X |   |   | X |
| 37 | X |   | VL FR1-IMGT | X |   |
| 97 |   | X |   | X |   |
| 38 | X |   |   |   | X |
| 98 |   | X |   |   | X |
| 41 | X |   | VL FR2-IMGT | X |   |
| 101 |   | X |   | X |   |
| 42 | X |   |   |   | X |
| 102 |   | X |   |   | X |
| 45 | X |   | VL FR3-IMGT | X |   |
| 105 |   | X |   | X |   |
| 46 | X |   |   |   | X |
| 106 |   | X |   |   | X |
| 49 | X |   | VL FR4-IMGT | X |   |
| 109 |   | X |   | X |   |
| 50 | X |   |   |   | X |
| 110 |   | X |   |   | X |
| 51 | X |   | VL FR1-Kabat | X |   |
| 111 |   | X |   | X |   |
| 52 | X |   |   |   | X |
| 112 |   | X |   |   | X |
| 55 | X |   | VL FR2-Kabat | X |   |

VARIABLE REGION SEQUENCE SUMMARY

| SEQ ID NO | CL-148219 | CL-148489 | DESCRIPTION | AMINO ACID | NUCLEOTIDE |
|---|---|---|---|---|---|
| 115 | | X | | X | |
| 56 | X | | | | X |
| 116 | | X | | | X |
| 59 | X | | VL FR3-Kabat | X | |
| 119 | | X | | X | |
| 60 | X | | | | X |
| 120 | | X | | | X |
| 63 | X | | VL FR4-Kabat | X | |
| 123 | | X | | X | |
| 64 | X | | | | X |
| 124 | | X | | | X |

CONSTANT REGION SEQUENCE SUMMARY

| SEQ ID NO: | | AMINO ACID | NUCLEOTIDE |
|---|---|---|---|
| 3 | IgG4-PE | X | |
| 4 | | | X |
| 125 | IGHG1*01 | | X |
| 126 | | X | |
| 127 | IGHG1*02 or | | X |
| 128 | IGHG1*05 | X | |
| 129 | IGHG1*03 | | X |
| 130 | | X | |
| 131 | IGHG1*04 | | X |
| 132 | | X | |
| 133 | Disabled human IGHG1*01 | | X |
| 134 | | X | |
| 135 | IGHG2*01 or | | X |
| 136 | IGHG2*04 or IGHG2*05 | X | |
| 137 | IGHG2*02 | | X |
| 138 | | X | |
| 139 | IGHG2*04 | | X |
| 140 | | X | |
| 141 | IGHG2*06 | | X |
| 142 | | X | |
| 143 | IGHG4*01 or | | X |
| 144 | IGHG4*04 | X | |
| 145 | IGHG4*02 | | X |
| 146 | | X | |
| 147 | IGHG4*03 | | X |
| 148 | | X | |
| 149 | IGHG4-PE | | X |
| 150 | | X | |
| 151 | | | X |
| 152 | | X | |
| 153 | Inactivated IGHG4 | | X |
| 154 | | X | |
| 155 | IGKC*01 | | X |
| 156 | | X | |
| 157 | IGKC*02 | | X |
| 158 | | X | |
| 159 | IGKC*03 | | X |
| 160 | | X | |
| 161 | IGKC*04 | | X |
| 162 | | X | |
| 163 | IGKC*05 | | X |
| 164 | | X | |
| 165 | IGLC1*01 | | X |
| 166 | | X | |
| 167 | IGLC1*02 | | X |
| 168 | | X | |
| 169 | | | X |
| 170 | IGLC2*01 | | X |
| 171 | | | X |
| 172 | | X | |
| 173 | IGLC2*02 or | | X |
| 174 | IGLC2*03 | X | |
| 175 | IGLC3*01 | | X |
| 176 | | X | |
| 177 | IGLC3*02 | | X |
| 178 | | X | |
| 179 | IGLC3*03 | | X |
| 180 | | X | |
| 181 | IGLC3*04 | | X |
| 182 | | X | |
| 183 | IGLC6*01 | | X |
| 184 | | X | |
| 185 | IGLC7*01 or | | X |
| 186 | IGLC7*02 | X | |
| 187 | IGLC7*03 | | X |
| 188 | | X | |

SEQUENCES

CL-148219

CL-148219 Heavy Chain
Variable region amino acid sequence
(SEQ ID NO: 1)
Q V H L Q E S G P G L V K P S E T L S L

T C T V S G G S I S S Y Y W S W I R Q Y

P G K G L E W I G Y I S Y S G S S N Y N

P S L K R R V T I S R D T S K N Q F S L

N L T S V I A A D T A V Y Y C A R N L M

I R G A Y G M D V W G Q G T T V T V S S

Variable region nucleotide sequence
(SEQ ID NO: 2)
caggtgcacctgcaggagtcgggcccaggactggtgaagccttcggagac cctgtccctcacgtgcactgtctctggtggctccatcagtagttactact ggagctggatccggcagtacccaggaaagggactggagtggattggatat atctcttacagtgggagcagcaattataatccccctcaagaggcgagtc accatatcacgagacacgtccaagaaccagttctccctgaatctgacctc tgtaatcgctgcggacacggccgtttattactgtgcgagaaatcttatga ttcggggagcctacggcatggacgtctggggccaagggaccacggtcacc gtctcctca FR1-IMGT amino acid sequence
(SEQ ID NO: 5)
Q V H L Q E S G P G L V K P S E T L S L T C T V S FR1-IMGT nucleotide sequence
(SEQ ID NO: 6)
CAGGTGCACCTGCAGGAGTCGGGCCCAGGACTGGTGAAGCCTTCGGAGAC

CCTGTCCCTCACGTGCACTGTCTCT

CDR1-IMGT amino acid sequence
(SEQ ID NO: 7)
G G S I S S Y Y

CDR1-IMGT nucleotide sequence
(SEQ ID NO: 8)
GGTGGCTCCATCAGTAGTTACTAC

FR2-IMGT amino acid sequence
(SEQ ID NO: 9)
W S W I R Q Y P G K G L E W I G Y

FR2-IMGT nucleotide sequence
(SEQ ID NO: 10)
TGGAGCTGGATCCGGCAGTACCCAGGAAAGGGACTGGAGTGGATTGGATA
T CDR2-IMGT amino acid sequence
(SEQ ID NO: 11)
I S Y S G S S CDR2-IMGT nucleotide sequence
(SEQ ID NO: 12)
ATCTCTTACAGTGGGAGCAGC FR3-IMGT amino acid sequence
(SEQ ID NO: 13)
N Y N P S L K R R V T I S R D T S K N Q F S L N L
T S V I A A D T A V Y Y C FR3-IMGT nucleotide sequence
(SEQ ID NO: 14)
AATTATAATCCCTCCCTCAAGAGGCGAGTCACCATATCACGAGACACGTC
CAAGAACCAGTTCTCCCTGAATCTGACCTCTGTAATCGCTGCGGACACGG
CCGTTTATTACTGT CDR3-IMGT amino acid sequence
(SEQ ID NO: 15)
A R N L M I R G A Y G M D V CDR3-IMGT nucleotide sequence
(SEQ ID NO: 16)
GCGAGAAATCTTATGATTCGGGGAGCCTACGGCATGGACGTC FR4-IMGT amino acid sequence
(SEQ ID NO: 17)
W G Q G T T V T V S S FR4-IMGT nucleotide sequence
(SEQ ID NO: 18)
TGGGGCCAAGGGACCACGGTCACCGTCTCCTCA FR1-KABAT amino acid sequence
(SEQ ID NO: 19)
Q V H L Q E S G P G L V K P S E T L S L T C T V S
G G S I S FR1-KABAT nucleotide sequence
(SEQ ID NO: 20)
CAGGTGCACCTGCAGGAGTCGGGCCCAGGACTGGTGAAGCCTTCGGAGAC
CCTGTCCCTCACGTGCACTGTCTCTGGTGGCTCCATCAGT CDR1-KABAT amino acid sequence
(SEQ ID NO: 21)
S Y Y W S CDR1-KABAT nucleotide sequence
(SEQ ID NO: 22)
AGTTACTACTGGAGC FR2-KABAT amino acid sequence
(SEQ ID NO: 23)
W I R Q Y P G K G L E W I G FR2-KABAT nucleotide sequence
(SEQ ID NO: 24)
TGGATCCGGCAGTACCCAGGAAAGGGACTGGAGTGGATTGGA CDR2-KABAT amino acid sequence
(SEQ ID NO: 25)
Y I S Y S G S S N Y N P S L K R CDR2-KABAT nucleotide sequence
(SEQ ID NO: 26)
TATATCTCTTACAGTGGGAGCAGCAATTATAATCCCTCCCTCAAGAGG FR3-KABAT amino acid sequence
(SEQ ID NO: 27)
R V T I S R D T S K N Q F S L N L T S V I A A D T
A V Y Y C A R FR3-KABAT nucleotide
(SEQ ID NO: 28)
CGAGTCACCATATCACGAGACACGTCCAAGAACCAGTTCTCCCTGAATCT
GACCTCTGTAATCGCTGCGGACACGGCCGTTTATTACTGTGCGAGA CDR3-KABAT amino acid sequence
(SEQ ID NO: 29)
N L M I R G A Y G M D V CDR3-KABAT nucleotide sequence
(SEQ ID NO: 30)
AATCTTATGATTCGGGGAGCCTACGGCATGGACGTC FR4-KABAT amino acid sequence
(SEQ ID NO: 31)
W G Q G T T V T V S S FR4-KABAT nucleotide sequence
(SEQ ID NO: 32)
TGGGGCCAAGGGACCACGGTCACCGTCTCCTCA CL-148219 Light Chain kappa
Variable region amino acid sequence
(SEQ ID NO: 33)
D T V M T Q S P L S L P V T P G E P A S
I S C R S S Q S L L H S N G Y N Y L D W
Y L Q K A G Q S P Q L L I Y L G S N R A
S G V P D R F S G S V S G T D F T L K I
S R V E A E D V G I Y Y C M Q A L Q T P
F T F G P G T K V D I K Variable region nucleotide sequence
(SEQ ID NO: 34)
gatactgtgatgactcagtctccactctccctgcccgtcacccctggaga
gccggcctccatctcctgcaggtctagtcagagcctcctgcatagtaatg
gatacaattatttggattggtacctgcagaaggcaggacagtctccacaa
ctcctgatctatttgggttctaatcgggcctccggggtccctgacaggtt
cagtggcagtgtatcaggcacagatttcacactgaaaatcagcagagtgg
aggctgaggatgttgggatttattactgcatgcaagctctacaaactcca
ttcactttcggccctgggaccaaagtggatatcaaa C-region amino acid sequence
(SEQ ID NO: 35)
R T V A A P S V F I F P P S D E Q L K S
G T A S V V C L L N N F Y P R E A K V Q
W K V D N A L Q S G N S Q E S V T E Q D
S K D S T Y S L S S T L T L S K A D Y E
K H K V Y A C E V T H Q G L S S P V T K
S F N R G E C C-region nucleotide sequence
(SEQ ID NO: 36)
cgtacggtggccgctccctccgtgttcatcttccaccttccgacgagca
gctgaagtccggcaccgcttctgtcgtgtgcctgctgaacaacttctacc
ccgcgaggccaaggtgcagtggaaggtggacaacgccctgcagtccggc
aactcccaggaatccgtgaccgagcaggactccaaggacagcacctactc
cctgtcctccaccctgaccctgtccaaggccgactacgagaagcacaagg
tgtacgcctgcgaagtgacccaccagggcctgtctagccccgtgaccaag
tctttcaaccggggcgagtgt FR1-IMGT amino acid sequence
(SEQ ID NO: 37)
D T V M T Q S P L S L P V T P G E P A S I S C R S S FR1-IMGT nucleotide sequence
(SEQ ID NO: 38)
GATACTGTGATGACTCAGTCTCCACTCTCCCTGCCCGTCACCCCTGGAGA
GCCGGCCTCCATCTCCTGCAGGTCTAGT CDR1-IMGT amino acid sequence
(SEQ ID NO: 39)
Q S L L H S N G Y N Y CDR1-IMGT nucleotide sequence
(SEQ ID NO: 40)
CAGAGCCTCCTGCATAGTAATGGATACAATTAT FR2-IMGT amino acid sequence
(SEQ ID NO: 41)
L D W Y L Q K A G Q S P Q L L I Y FR2-IMGT nucleotide sequence
(SEQ ID NO: 42)
TTGGATTGGTACCTGCAGAAGGCAGGACAGTCTCCACAACTCCTGATCTAT CDR2-IMGT amino acid sequence
(SEQ ID NO: 43)
L G S CDR2-IMGT nucleotide sequence
(SEQ ID NO: 44)
TTGGGTTCT FR3-IMGT amino acid sequence
(SEQ ID NO: 45)
N R A S G V P D R F S G S V S G T D F T L K I S R V E A E D V G I Y Y C FR3-IMGT nucleotide sequence
(SEQ ID NO: 46)
AATCGGGCCTCCGGGGTCCCTGACAGGTTCAGTGGCAGTGTATCAGGCAC
AGATTTCACACTGAAAATCAGCAGAGTGGAGGCTGAGGATGTTGGGATTT
ATTACTGC CDR3-IMGT amino acid sequence
(SEQ ID NO: 47)
M Q A L Q T P F T CDR3-IMGT nucleotide sequence
(SEQ ID NO: 48)
ATGCAAGCTCTACAAACTCCATTCACT FR4-IMGT amino acid sequence
(SEQ ID NO: 49)
F G P G T K V D I K FR4-IMGT nucleotide sequence
(SEQ ID NO: 50)
TTCGGCCCTGGGACCAAAGTGGATATCAAA FR1-KABAT amino acid sequence
(SEQ ID NO: 51)
D T V M T Q S P L S L P V T P G E P A S I S C FR1-KABAT nucleotide sequence
(SEQ ID NO: 52)
GATACTGTGATGACTCAGTCTCCACTCTCCCTGCCCGTCACCCCTGGAGA
GCCGGCCTCCATCTCCTGC CDR1-KABAT amino acid sequence
(SEQ ID NO: 53)
R S S Q S L L H S N G Y N Y L D CDR1-KABAT nucleotide sequence
(SEQ ID NO: 54)
AGGTCTAGTCAGAGCCTCCTGCATAGTAATGGATACAATTATTTGGAT FR2-KABAT amino acid sequence
(SEQ ID NO: 55)
W Y L Q K A G Q S P Q L L I Y FR2-KABAT nucleotide sequence
(SEQ ID NO: 56)
TGGTACCTGCAGAAGGCAGGACAGTCTCCACAACTCCTGATCTAT CDR2-KABAT amino acid sequence
(SEQ ID NO: 57)
L G S N R A S CDR2-KABAT nucleotide sequence
(SEQ ID NO: 58)
TTGGGTTCTAATCGGGCCTCC FR3-KABAT amino acid sequence
(SEQ ID NO: 59)
G V P D R F S G S V S G T D F T L K I S R V E A E D V G I Y Y C FR3-KABAT nucleotide sequence
(SEQ ID NO: 60)
GGGGTCCCTGACAGGTTCAGTGGCAGTGTATCAGGCACAGATTTCACACT
GAAAATCAGCAGAGTGGAGGCTGAGGATGTTGGGATTTATTACTGC CDR3-KABAT amino acid sequence
(SEQ ID NO: 61)
M Q A L Q T P F T CDR3-KABAT nucleotide sequence
(SEQ ID NO: 62)
ATGCAAGCTCTACAAACTCCATTCACT FR4-KABAT amino acid sequence
(SEQ ID NO: 63)
F G P G T K V D I K FR4-KABAT nucleotide sequence
(SEQ ID NO: 64)
TTCGGCCCTGGGACCAAAGTGGATATCAAA

CL-148489

CL-148489 Heavy Chain
Variable region amino acid sequence
(SEQ ID NO: 65)

E V Q L V E S G G G L V Q P G R S L R L

S C T A S G F T F A D Y V M H W V R Q T

P G K G L E W V S G I S W N S Y S I N Y

A D S V K G R F T I S R D N A Q N S L Y

L Q M N S L R A E D T A L Y F C A K D I

T Y D L L T G Y N Y N Y G L D V W G Q G

T T V T V S S

Variable region nucleotide sequence
(SEQ ID NO: 66)

gaagtgcagctggtagagtctgggggaggcttggtacagcctggcaggtccctgagactc tcctgtacagcctctggattcacctttgctgattatgtcatgcactgggtccggcaaact ccagggaagggcctggagtgggtctcaggtattagttggaatagttatagtataaattat gcggactctgtgaagggccgattcaccatctccagagacaacgcccagaactccctgtat ctgcaaatgaacagtctgagagctgaggacacggccttgtattttgtgcaaaagatata acttacgatcttttgactggttataactacaactacggtttagacgtctggggccaaggg accacggtcaccgtctcctca FR1-IMGT amino acid sequence
(SEQ ID NO: 67)
E V Q L V E S G G G L V Q P G R S L R L S C T A S FR1-IMGT nucleotide sequence
(SEQ ID NO: 68)
GAAGTGCAGCTGGTAGAGTCTGGGGGAGGCTTGGTACAGCCTGGCAGGTCCCTGAGACTCTCCTGTACAGCC

TCT

CDR1-IMGT amino acid sequence
(SEQ ID NO: 69)
G F T F A D Y V

CDR1-IMGT nucleotide sequence
(SEQ ID NO: 70)
GGATTCACCTTTGCTGATTATGTC

FR2-IMGT amino acid sequence
(SEQ ID NO: 71)
M H W V R Q T P G K G L E W V S G

FR2-IMGT nucleotide sequence
(SEQ ID NO: 72)
ATGCACTGGGTCCGGCAAACTCCAGGGAAGGGCCTGGAGTGGGTCTCAGGT CDR2-IMGT amino acid sequence
(SEQ ID NO: 73)
I S W N S Y S I CDR2-IMGT nucleotide sequence
(SEQ ID NO: 74)
ATTAGTTGGAATAGTTATAGTATA FR3-IMGT amino acid sequence
(SEQ ID NO: 75)
N Y A D S V K G R F T I S R D N A Q N S L Y L Q M N S L R A E D T A L Y F C FR3-IMGT nucleotide sequence
(SEQ ID NO: 76)
AATTATGCGGACTCTGTGAAGGGCCGATTCACCATCTCCAGAGACAACGCCCAGAACTCCCTGTATCTGCAAA

TGAACAGTCTGAGAGCTGAGGACACGGCCTTGTATTTTTGT

```
CDR3-IMGT amino acid sequence
                                                           (SEQ ID NO: 77)
A K D I T Y D L L T G Y N Y N Y G L D V
CDR3-IMGT nucleotide sequence
                                                           (SEQ ID NO: 78)
GCAAAAGATATAACTTACGATCTTTTGACTGGTTATAACTACAACTACGGTTTAGACGTC
FR4-IMGT amino acid sequence
                                                           (SEQ ID NO: 79)
W G Q G T T V T V S S
FR4-IMGT nucleotide sequence
                                                           (SEQ ID NO: 80)
TGGGGCCAAGGGACCACGGTCACCGTCTCCTCA FR1-KABAT amino acid sequence
                                                           (SEQ ID NO: 81)
E V Q L V E S G G G L V Q P G R S L R L S C T A S G F T F A
FR1-KABAT nucleotide sequence
                                                           (SEQ ID NO: 82)
GAAGTGCAGCTGGTAGAGTCTGGGGGAGGCTTGGTACAGCCTGGCAGGTCCCTGAGACTCTCCTGTACAGCC

TCTGGATTCACCTTTGCT

CDR1-KABAT amino acid sequence
                                                           (SEQ ID NO: 83)
D Y V M H CDR1-KABAT nucleotide sequence
                                                           (SEQ ID NO: 84)
GATTATGTCATGCAC FR2-KABAT amino acid sequence
                                                           (SEQ ID NO: 85)
W V R Q T P G K G L E W V S
FR2-KABAT nucleotide sequence
                                                           (SEQ ID NO: 86)
TGGGTCCGGCAAACTCCAGGGAAGGGCCTGGAGTGGGTCTCA CDR2-KABAT amino acid sequence
                                                           (SEQ ID NO: 87)
G I S W N S Y S I N Y A D S V K G
CDR2-KABAT nucleotide sequence
                                                           (SEQ ID NO: 88)
GGTATTAGTTGGAATAGTTATAGTATAAATTATGCGGACTCTGTGAAGGGC FR3-KABAT amino acid sequence
                                                           (SEQ ID NO: 89)
R F T I S R D N A Q N S L Y L Q M N S L R A E D T A L Y F C A K
FR3-KABAT nucleotide sequence
                                                           (SEQ ID NO: 90)
CGATTCACCATCTCCAGAGACAACGCCCAGAACTCCCTGTATCTGCAAATGAACAGTCTGAGAGCTGAGGACA

CGGCCTTGTATTTTTGTGCAAAA

CDR3-KABAT amino acid sequence
                                                           (SEQ ID NO: 91)
D I T Y D L L T G Y N Y N Y G L D V
CDR3-KABAT nucleotide sequence
                                                           (SEQ ID NO: 92)
GATATAACTTACGATCTTTTGACTGGTTATAACTACAACTACGGTTTAGACGTC FR4-KABAT amino acid sequence
                                                           (SEQ ID NO: 93)
W G Q G T T V T V S S
FR4-KABAT nucleotide sequence
                                                           (SEQ ID NO: 94)
TGGGGCCAAGGGACCACGGTCACCGTCTCCTCA CL-148489 Light Chain kappa
Variable region amino acid sequence
                                                           (SEQ ID NO: 95)
D I V M T Q T P L S L S V T P G Q P A S

I S C R S S Q S L L H S D G K T Y L Y W
```

-continued

```
Y L Q K P G Q P P Q L L I Y E V S N R F

S G V P D R F S G S G S G T D F T L K I

S R V E A E D V G L Y Y C M Q S I Q L P

L T F G G G T K V E I K
```

Variable region nucleotide sequence (SEQ ID NO: 96)

```
gatattgtgatgacccagactccactctctctgtccgtcacccctggacagccggcctcc atctcctgcaggtctagtcagagcctcctacatagtgatggaaagacctatttgtattgg tacctgcagaagcccggccagcctccacagctcctgatctatgaagtttccaaccgtttc tctggagtgccagataggttcagtggcagcgggtcagggacagatttcacactgaagatc agccgggtggaggctgaagatgttggcctttattactgcatgcaaagtatacagcttccg ctcactttcggcggagggaccaaggtagagatcaaa
```

FR1-IMGT amino acid sequence (SEQ ID NO: 97)

```
D I V M T Q T P L S L S V T P G Q P A S I S C R S S
```

FR1-IMGT nucleotide sequence (SEQ ID NO: 98)

```
GATATTGTGATGACCCAGACTCCACTCTCTCTGTCCGTCACCCCTGGACAGCCGGCCTCCATCTCCTGCAGGTC
TAGT
```

CDR1-IMGT amino acid sequence (SEQ ID NO: 99)

```
Q S L L H S D G K T Y
```

CDR1-IMGT nucleotide sequence (SEQ ID NO: 100)

```
CAGAGCCTCCTACATAGTGATGGAAAGACCTAT
```

FR2-IMGT amino acid sequence (SEQ ID NO: 101)

```
L Y W Y L Q K P G Q P P Q L L I Y
```

FR2-IMGT nucleotide sequence (SEQ ID NO: 102)

```
TTGTATTGGTACCTGCAGAAGCCCGGCCAGCCTCCACAGCTCCTGATCTAT
```

CDR2-IMGT amino acid sequence (SEQ ID NO: 103)

```
E V S
```

CDR2-IMGT nucleotide sequence (SEQ ID NO: 104)

```
GAAGTTTCC
```

FR3-IMGT amino acid sequence (SEQ ID NO: 105)

```
N R F S G V P D R F S G S G S G T D F T L K I S R V E A E D V G L Y Y C
```

FR3-IMGT nucleotide sequence (SEQ ID NO: 106)

```
AACCGTTTCTCTGGAGTGCCAGATAGGTTCAGTGGCAGCGGGTCAGGGACAGATTTCACACTGAAGATCAGC
CGGGTGGAGGCTGAAGATGTTGGCCTTTATTACTGC
```

CDR3-IMGT amino acid sequence (SEQ ID NO: 107)

```
M Q S I Q L P L T
```

CDR3-IMGT nucleotide sequence (SEQ ID NO: 108)

```
ATGCAAAGTATACAGCTTCCGCTCACT
```

FR4-IMGT amino acid sequence (SEQ ID NO: 109)

```
F G G G T K V E I K
```

FR4-IMGT nucleotide sequence (SEQ ID NO: 110)

```
TTCGGCGGAGGGACCAAGGTAGAGATCAAA
```

-continued

FR1-KABAT amino acid sequence
(SEQ ID NO: 111)
D I V M T Q T P L S L S V T P G Q P A S I S C FR1-KABAT nucleotide sequence
(SEQ ID NO: 112)
GATATTGTGATGACCCAGACTCCACTCTCTCTGTCCGTCACCCCTGGACAGCCGGCCTCCATCTCCTGC CDR1-KABAT amino acid sequence
(SEQ ID NO: 113)
R S S Q S L L H S D G K T Y L Y CDR1-KABAT nucleotide sequence
(SEQ ID NO: 114)
AGGTCTAGTCAGAGCCTCCTACATAGTGATGGAAAGACCTATTTGTAT FR2-KABAT amino acid sequence
(SEQ ID NO: 115)
W Y L Q K P G Q P P Q L L I Y FR2-KABAT nucleotide sequence
(SEQ ID NO: 116)
TGGTACCTGCAGAAGCCCGGCCAGCCTCCACAGCTCCTGATCTAT CDR2-KABAT amino acid sequence
(SEQ ID NO: 117)
E V S N R F S CDR2-KABAT nucleotide sequence
(SEQ ID NO: 118)
GAAGTTTCCAACCGTTTCTCT FR3-KABAT amino acid sequence
(SEQ ID NO: 119)
G V P D R F S G S G S G T D F T L K I S R V E A E D V G L Y Y C FR3-KABAT nucleotide sequence
(SEQ ID NO: 120)
GGAGTGCCAGATAGGTTCAGTGGCAGCGGGTCAGGGACAGATTTCACACTGAAGATCAGCCGGGTGGAGGC

TGAAGATGTTGGCCTTTATTACTGC

CDR3-KABAT amino acid sequence
(SEQ ID NO: 121)
M Q S I Q L P L T

CDR3-KABAT nucleotide sequence
(SEQ ID NO: 122)
ATGCAAAGTATACAGCTTCCGCTCACT

FR4-KABAT amino acid sequence
(SEQ ID NO: 123)
F G G G T K V E I K

FR4-KABAT nucleotide sequence
(SEQ ID NO: 124)
TTCGGCGGAGGGACCAAGGTAGAGATCAAA

CL-274698

CL-274698 Heavy Chain
Variable region amino acid sequence
(SEQ ID NO: 199)
QVQLQESGPG LVKPSGTLSL TCAVSGGSIS SSKWWSWVRQ PPGKGLEWIG ETHYSGSTNY NPSLKSRVTI

SVDKSKNQFS LKLRSVTAAD TAVYYCARVG ATENFWGQGT LVTVSS

Variable region nucleotide sequence
(SEQ ID NO: 200)
CAGGTGCAGC TGCAGGAGTC GGGCCCAGGA CTGGTGAAGC CTTCGGGGAC CCTGTCCCTC ACCTGCGCTG

TCTCTGGTGG CTCCATCAGC AGTAGTAAAT GGTGGAGTTG GGTCCGCCAG CCCCCAGGGA

AGGGGCTGGA GTGGATTGGG GAAACCCATT ATAGTGGGAG CACCAACTAC AACCCGTCCC

TCAAGAGTCG AGTCACCATA TCAGTAGACA AGTCCAAGAA CCAGTTCTCC CTGAAGCTGA GGTCTGTGAC

-continued

```
CGCCGCGGAC ACGGCCGTTT ATTACTGTGC GAGAGTGGGT GCTACTGAGA ACTTCTGGGG

CCAGGGAACC CTGGTCACCG TCTCCTCA

FR1-IMGT amino acid sequence
                                                          (SEQ ID NO: 201)
QVQLQESGPG LVKPSGTLSL TCAVS FR1-IMGT nucleotide sequence
                                                          (SEQ ID NO: 202)
CAGGTGCAGCTGCAGGAGTCGGGCCCAGGACTGGTGAAGCCTTCGGGGACCCTGTCCCTCACCTGCGCTGTC

TCT

CDR1-IMGT amino acid sequence
                                                          (SEQ ID NO: 203)
GGSIS SSKW CDR1-IMGT nucleotide sequence
                                                          (SEQ ID NO: 204)
GGTGGCTCCATCAGCAGTAGTAAATGG FR2-IMGT amino acid sequence
                                                          (SEQ ID NO: 205)
WSWVRQ PPGKGLEWIG E FR2-IMGT nucleotide sequence
                                                          (SEQ ID NO: 206)
TGGAGTTGGGTCCGCCAGCCCCCAGGGAAGGGGCTGGAGTGGATTGGGGAA CDR2-IMGT amino acid sequence
                                                          (SEQ ID NO: 207)
THYSGST CDR2-IMGT nucleotide sequence
                                                          (SEQ ID NO: 208)
ACCCATTATAGTGGGAGCACC FR3-IMGT amino acid sequence
                                                          (SEQ ID NO: 209)
NY NPSLKSRVTI SVDKSKNQFS LKLRSVTAAD TAVYYC FR3-IMGT nucleotide sequence
                                                          (SEQ ID NO: 210)
AACTACAACCCGTCCCTCAAGAGTCGAGTCACCATATCAGTAGACAAGTCCAAGAACCAGTTCTCCCTGAAGC

TGAGGTCTGTGACCGCCGCGGACACGGCCGTTTATTACTGT

CDR3-IMGT amino acid sequence
                                                          (SEQ ID NO: 211)
ARVG ATENF CDR3-IMGT nucleotide sequence
                                                          (SEQ ID NO: 212)
GCGAGAGTGGGTGCTACTGAGAACTTC FR4-IMGT amino acid sequence
                                                          (SEQ ID NO: 213)
WGQGT LVTVSS FR4-IMGT nucleotide sequence
                                                          (SEQ ID NO: 214)
TGGGGCCAGGGAACCCTGGTCACCGTCTCCTCAG FR1-KABAT amino acid sequence
                                                          (SEQ ID NO: 215)
QVQLQESGPG LVKPSGTLSL TCAVSGGSIS FR1-KABAT nucleotide sequence
                                                          (SEQ ID NO: 216)
CAGGTGCAGCTGCAGGAGTCGGGCCCAGGACTGGTGAAGCCTTCGGGGACCCTGTCCCTCACCTGCGCTGTC

TCTGGTGGCTCCATCAGC

CDR1-KABAT amino acid sequence
                                                          (SEQ ID NO: 217)
SSKWWS CDR1-KABAT nucleotide sequence
                                                          (SEQ ID NO: 218)
```

-continued

AGTAGTAAATGGTGGAGT

FR2-KABAT amino acid sequence
(SEQ ID NO: 219)
WVRQ PPGKGLEWIG

FR2-KABAT nucleotide sequence
(SEQ ID NO: 220)
TGGGTCCGCCAGCCCCCAGGGAAGGGGCTGGAGTGGATTGGG CDR2-KABAT amino acid sequence
(SEQ ID NO: 221)
ETHYSGSTNY NPSLKS CDR2-KABAT nucleotide sequence
(SEQ ID NO: 222)
GAAACCCATTATAGTGGGAGCACCAACTACAACCCGTCCCTCAAGAGT FR3-KABAT amino acid sequence
(SEQ ID NO: 223)
RVTI SVDKSKNQFS LKLRSVTAAD TAVYYCAR FR3-KABAT nucleotide sequence
(SEQ ID NO: 224)
CGAGTCACCATATCAGTAGACAAGTCCAAGAACCAGTTCTCCCTGAAGCTGAGGTCTGTGACCGCCGCGGACA

CGGCCGTTTATTACTGTGCGAGA

CDR3-KABAT amino acid sequence
(SEQ ID NO: 225)
VG ATENF

CDR3-KABAT nucleotide sequence
(SEQ ID NO: 226)
GTGGGTGCTACTGAGAACTTC

FR4-KABAT amino acid sequence
(SEQ ID NO: 227)
WGQGT LVTVSS

FR4-KABAT nucleotide sequence
(SEQ ID NO: 228)
TGGGGCCAGGGAACCCTGGTCACCGTCTCCTCAG CL-274698 Light Chain kappa
Variable region amino acid sequence
(SEQ ID NO: 229)
EIVLTQSPAT LSLSPGERAT LSCRASQSVF RYLAWYQQKP GQAPRLLIYD ASTRATDIPA RFSGSGSGTD

FTLTISSLEP EDFAVYYCQQ RSNWPPTFGQ GTKVEIK

Variable region nucleotide sequence
(SEQ ID NO: 230)
GAAATTGTGT TGACACAGTC TCCAGCCACC CTGTCTTTGT CTCCAGGGGA AAGAGCCACC CTCTCCTGCA

GGGCCAGTCA GAGTGTTTTC AGGTACTTAG CCTGGTACCA ACAGAAACCT GGCCAGGCTC CCAGGCTCCT

CATCTATGAT GCATCCACCA GGGCCACTGA CATCCCAGCC AGGTTCAGTG GCAGTGGGTC TGGGACAGAT

TTCACTCTCA CCATCAGCAG CCTAGAGCCT GAAGATTTTG CAGTTTATTA CTGTCAGCAA CGTAGCAACT

GGCCTCCGAC GTTCGGCCAA GGGACCAAGG TGGAAATCAA A

FR1-IMGT amino acid sequence
(SEQ ID NO: 231)
EIVLTQSPAT LSLSPGERAT LSCRAS

FR1-IMGT nucleotide sequence
(SEQ ID NO: 232)
GAAATTGTGTTGACACAGTCTCCAGCCACCCTGTCTTTGTCTCCAGGGGAAAGAGCCACCCTCTCCTGCAGGG

CCAGT

CDR1-IMGT amino acid sequence
(SEQ ID NO: 233)
QSVF RY

CDR1-IMGT nucleotide sequence
(SEQ ID NO: 234)
CAGAGTGTTTTCAGGTAC

```
FR2-IMGT amino acid sequence
                                                     (SEQ ID NO: 235)
LAWYQQKP GQAPRLLIY FR2-IMGT nucleotide sequence
                                                     (SEQ ID NO: 236)
TTAGCCTGGTACCAACAGAAACCTGGCCAGGCTCCCAGGCTCCTCATCTAT CDR2-IMGT amino acid sequence
                                                     (SEQ ID NO: 237)
D AS CDR2-IMGT nucleotide sequence
                                                     (SEQ ID NO: 238)
GATGCATCC FR3-IMGT amino acid sequence
                                                     (SEQ ID NO: 239)
TRATDIPA RFSGSGSGTD FTLTISSLEP EDFAVYYC FR3-IMGT nucleotide sequence
                                                     (SEQ ID NO: 240)
ACCAGGGCCACTGACATCCCAGCCAGGTTCAGTGGCAGTGGGTCTGGGACAGATTTCACTCTCACCATCAGCA
GCCTAGAGCCTGAAGATTTTGCAGTTTATTACTGT CDR3-IMGT amino acid sequence
                                                     (SEQ ID NO: 241)
QQ RSNWPPT CDR3-IMGT nucleotide sequence
                                                     (SEQ ID NO: 242)
CAGCAACGTAGCAACTGGCCTCCGACG FR4-IMGT amino acid sequence
                                                     (SEQ ID NO: 243)
FGQ GTKVEIK FR4-IMGT nucleotide sequence
                                                     (SEQ ID NO: 244)
TTCGGCCAAGGGACCAAGGTGGAAATCAAA FR1-KABAT amino acid sequence
                                                     (SEQ ID NO: 245)
EIVLTQSPAT LSLSPGERAT LSC FR1-KABAT nucleotide sequence
                                                     (SEQ ID NO: 246)
GAAATTGTGTTGACACAGTCTCCAGCCACCCTGTCTTTGTCTCCAGGGGAAAGAGCCACCCTCTCCTGC CDR1-KABAT amino acid sequence
                                                     (SEQ ID NO: 247)
RASQSVF RYLA CDR1-KABAT nucleotide sequence
                                                     (SEQ ID NO: 248)
AGGGCCAGTCAGAGTGTTTTCAGGTACTTAGCC FR2-KABAT amino acid sequence
                                                     (SEQ ID NO: 249)
WYQQKP GQAPRLLIY FR2-KABAT nucleotide sequence
                                                     (SEQ ID NO: 250)
TGGTACCAACAGAAACCTGGCCAGGCTCCCAGGCTCCTCATCTAT CDR2-KABAT amino acid sequence
                                                     (SEQ ID NO: 251)
D ASTRAT CDR2-KABAT nucleotide sequence
                                                     (SEQ ID NO: 252)
GATGCATCCACCAGGGCCACT FR3-KABAT amino acid sequence
                                                     (SEQ ID NO: 253)
DIPA RFSGSGSGTD FTLTISSLEP EDFAVYYC
```

-continued

FR3-KABAT nucleotide sequence
(SEQ ID NO: 254)
GACATCCCAGCCAGGTTCAGTGGCAGTGGGTCTGGGACAGATTTCACTCTCACCATCAGCAGCCTAGAGCCTG

AAGATTTTGCAGTTTATTACTGT

CDR3-KABAT amino acid sequence
(SEQ ID NO: 255)
QQ RSNWPPT

CDR3-KABAT nucleotide sequence
(SEQ ID NO: 256)
CAGCAACGTAGCAACTGGCCTCCGACG

FR4-KABAT amino acid sequence
(SEQ ID NO: 257)
FGQ GTKVEIK

FR4-KABAT nucleotide sequence
(SEQ ID NO: 258)
TTCGGCCAAGGGACCAAGGTGGAAATCAAA

CL-274711

CL-274711 Heavy Chain
Variable region amino acid sequence
(SEQ ID NO: 259)
QVQLQESGPG LVKPSQTLSL TCTVSGGSIS SGGYYWSWIR QHPGKGLEWI GHIFYSGSTY YNPSLKSRVT

ISVDTSKNQF SLKLNSVTAA DTAVYYCASE GGYYDIPDVW GQGTTVTVSS

Variable region nucleotide sequence
(SEQ ID NO: 260)
CAGGTGCAGC TGCAGGAGTC GGGCCCAGGA CTGGTGAAGC CTTCACAGAC CCTGTCCCTC ACCTGCACTG

TCTCTGGTGG CTCCATCAGC AGTGGTGGTT ACTACTGGAG CTGGATCCGC CAGCACCCAG GGAAGGGCCT

GGAGTGGATT GGGCACATCT TTTACAGTGG GAGCACCTAC TACAACCCGT CCCTCAAGAG TCGAGTTACC

ATATCAGTTG ACACGTCTAA GAACCAGTTC TCCCTGAAGC TGAACTCTGT GACTGCCGCG GACACGGCCG

TGTATTACTG TGCGAGCGAG GGAGGGTATT ACGATATTCC GGACGTCTGG GGCCAAGGGA

CCACGGTCAC CGTCTCCTCA

FR1-IMGT amino acid sequence
(SEQ ID NO: 261)
QVQLQESGPG LVKPSQTLSL TCTVS

FR1-IMGT nucleotide sequence
(SEQ ID NO: 262)
CAGGTGCAGCTGCAGGAGTCGGGCCCAGGACTGGTGAAGCCTTCACAGACCCTGTCCCTCACCTGCACTGTCT

CT

CDR1-IMGT amino acid sequence
(SEQ ID NO: 263)
GGSIS SGGYY

CDR1-IMGT nucleotide sequence
(SEQ ID NO: 264)
GGTGGCTCCATCAGCAGTGGTGGTTACTAC

FR2-IMGT amino acid sequence
(SEQ ID NO: 265)
WSWIR QHPGKGLEWI GH

FR2-IMGT nucleotide sequence
(SEQ ID NO: 266)
TGGAGCTGGATCCGCCAGCACCCAGGGAAGGGCCTGGAGTGGATTGGGCAC CDR2-IMGT amino acid sequence
(SEQ ID NO: 267)
IFYSGST CDR2-IMGT nucleotide sequence
(SEQ ID NO: 268)
ATCTTTTACAGTGGGAGCACC FR3-IMGT amino acid sequence
(SEQ ID NO: 269)
Y YNPSLKSRVT ISVDTSKNQF SLKLNSVTAA DTAVYYC FR3-IMGT nucleotide sequence
(SEQ ID NO: 270)
TACTACAACCCGTCCCTCAAGAGTCGAGTTACCATATCAGTTGACACGTCTAAGAACCAGTTCTCCCTGAAGCT

GAACTCTGTGACTGCCGCGGACACGGCCGTGTATTACTGT

CDR3-IMGT amino acid sequence
(SEQ ID NO: 271)
ASE GGYYDIPDV

CDR3-IMGT nucleotide sequence
(SEQ ID NO: 272)
GCGAGCGAGGGAGGGTATTACGATATTCCGGACGTC FR4-IMGT amino acid sequence
(SEQ ID NO: 273)
W GQGTTVTVSS FR4-IMGT nucleotide sequence
(SEQ ID NO: 274)
TGGGGCCAAGGGACCACGGTCACCGTCTCCTCA FR1-KABAT amino acid sequence
(SEQ ID NO: 275)
QVQLQESGPG LVKPSQTLSL TCTVSGGSIS FR1-KABAT nucleotide sequence
(SEQ ID NO: 276)
CAGGTGCAGCTGCAGGAGTCGGGCCCAGGACTGGTGAAGCCTTCACAGACCCTGTCCCTCACCTGCACTGTCT

CTGGTGGCTCCATCAGC

CDR1-KABAT amino acid sequence
(SEQ ID NO: 277)
SGGYYWS

CDR1-KABAT nucleotide sequence
(SEQ ID NO: 278)
AGTGGTGGTTACTACTGGAGC

FR2-KABAT amino acid sequence
(SEQ ID NO: 279)
WIR QHPGKGLEWI G

FR2-KABAT nucleotide sequence
(SEQ ID NO: 280)
TGGATCCGCCAGCACCCAGGGAAGGGCCTGGAGTGGATTGGG CDR2-KABAT amino acid sequence
(SEQ ID NO: 281)
HIFYSGSTY YNPSLKS CDR2-KABAT nucleotide sequence
(SEQ ID NO: 282)
CACATCTTTTACAGTGGGAGCACCTACTACAACCCGTCCCTCAAGAGT FR3-KABAT amino acid sequence
(SEQ ID NO: 283)
RVT ISVDTSKNQF SLKLNSVTAA DTAVYYCAS FR3-KABAT nucleotide sequence
(SEQ ID NO: 284)
CGAGTTACCATATCAGTTGACACGTCTAAGAACCAGTTCTCCCTGAAGCTGAACTCTGTGACTGCCGCGGACA

CGGCCGTGTATTACTGTGCGAGC

CDR3-KABAT amino acid sequence
(SEQ ID NO: 285)
E GGYYDIPDV

CDR3-KABAT nucleotide sequence
(SEQ ID NO: 286)
GAGGGAGGGTATTACGATATTCCGGACGTC

FR4-KABAT amino acid sequence
(SEQ ID NO: 287)
W GQGTTVTVSS

FR4-KABAT nucleotide sequence
(SEQ ID NO: 288)
TGGGGCCAAGGGACCACGGTCACCGTCTCCTCA CL-274711 Light Chain kappa
Variable region amino acid sequence
(SEQ ID NO: 289)
EIVLTQSPAT LSLSPGERAT LSCRASQSVS NYLAWYQQKP GQAPRLLISD ASNRATGIPA RFSGSGSGTD

FTLTISSLEP EDFAIYYCQQ RSNWPLTFGG GTKVEIK

Variable region nucleotide sequence
(SEQ ID NO: 290)
GAAATTGTGT TGACACAGTC TCCAGCCACC CTGTCTTTGT CTCCAGGGGA AAGAGCCACC CTCTCCTGCA

GGGCCAGTCA GAGTGTTAGC AACTACTTAG CCTGGTACCA ACAGAAACCT GGCCAGGCTC CCAGGCTCCT

CATCTCTGAT GCATCCAACA GGGCCACTGG CATCCCAGCC AGGTTCAGTG GCAGTGGGTC TGGGACAGAC

TTCACTCTCA CCATCAGCAG CCTAGAGCCT GAAGATTTTG CAATTTATTA CTGTCAGCAG CGTAGCAACT

GGCCGCTCAC TTTCGGCGGA GGGACCAAGG TGGAGATCAA A

FR1-IMGT amino acid sequence
(SEQ ID NO: 291)
EIVLTQSPAT LSLSPGERAT LSCRAS

FR1-IMGT nucleotide sequence
(SEQ ID NO: 292)
GAAATTGTGTTGACACAGTCTCCAGCCACCCTGTCTTTGTCTCCAGGGGAAAGAGCCACCCTCTCCTGCAGGG

CCAGT

CDR1-IMGT amino acid sequence
(SEQ ID NO: 293)
QSVS NY

CDR1-IMGT nucleotide sequence
(SEQ ID NO: 294)
CAGAGTGTTAGCAACTAC

FR2-IMGT amino acid sequence
(SEQ ID NO: 295)
LAWYQQKP GQAPRLLIS

FR2-IMGT nucleotide sequence
(SEQ ID NO: 236)
TTAGCCTGGTACCAACAGAAACCTGGCCAGGCTCCCAGGCTCCTCATCTCT CDR2-IMGT amino acid sequence
(SEQ ID NO: 297)
D AS CDR2-IMGT nucleotide sequence
(SEQ ID NO: 298)
GATGCATCC FR3-IMGT amino acid sequence
(SEQ ID NO: 299)
NRATGIPA RFSGSGSGTD FTLTISSLEP EDFAIYYC FR3-IMGT nucleotide sequence
(SEQ ID NO: 300)
AACAGGGCCACTGGCATCCCAGCCAGGTTCAGTGGCAGTGGGTCTGGGACAGACTTCACTCTCACCATCAGC

AGCCTAGAGCCTGAAGATTTTGCAATTTATTACTGT

CDR3-IMGT amino acid sequence
(SEQ ID NO: 301)
QQ RSNWPLT

CDR3-IMGT nucleotide sequence
(SEQ ID NO: 302)
CAGCAGCGTAGCAACTGGCCGCTCACT

-continued

FR4-IMGT amino acid sequence (SEQ ID NO: 303)

FGG GTKVEIK

FR4-IMGT nucleotide sequence (SEQ ID NO: 304)

TTCGGCGGAGGGACCAAGGTGGAGATCAAA

FR1-KABAT amino acid sequence (SEQ ID NO: 305)

EIVLTQSPAT LSLSPGERAT LSC

FR1-KABAT nucleotide sequence (SEQ ID NO: 306)

GAAATTGTGTTGACACAGTCTCCAGCCACCCTGTCTTTGTCTCCAGGGGAAAGAGCCACCCTCTCCTGC

CDR1-KABAT amino acid sequence (SEQ ID NO: 307)

RASQSVS NYLA

CDR1-KABAT nucleotide sequence (SEQ ID NO: 308)

AGGGCCAGTCAGAGTGTTAGCAACTACTTAGCC

FR2-KABAT amino acid sequence (SEQ ID NO: 309)

WYQQKP GQAPRLLIS

FR2-KABAT nucleotide sequence (SEQ ID NO: 310)

TGGTACCAACAGAAACCTGGCCAGGCTCCCAGGCTCCTCATCTCT

CDR2-KABAT amino acid sequence (SEQ ID NO: 311)

D ASNRAT

CDR2-KABAT nucleotide sequence (SEQ ID NO: 312)

GATGCATCCAACAGGGCCACT

FR3-KABAT amino acid sequence (SEQ ID NO: 313)

GIPA RFSGSGSGTD FTLTISSLEP EDFAIYYC

FR3-KABAT nucleotide sequence (SEQ ID NO: 314)

GGCATCCCAGCCAGGTTCAGTGGCAGTGGGTCTGGGACAGACTTCACTCTCACCATCAGCAGCCTAGAGCCTG

AAGATTTTGCAATTTATTACTGT

CDR3-KABAT amino acid sequence (SEQ ID NO: 315)

QQ RSNWPLT

CDR3-KABAT nucleotide sequence (SEQ ID NO: 316)

CAGCAGCGTAGCAACTGGCCGCTCACT

FR4-KABAT amino acid sequence (SEQ ID NO: 317)

FGG GTKVEIK

FR4-KABAT nucleotide sequence (SEQ ID NO: 318)

TTCGGCGGAGGGACCAAGGTGGAGATCAAA

55

CL-148219QLT

CL-148219QLT Heavy Chain
Variable region amino acid sequence (SEQ ID NO: 319)

QVHLQESGPG LVKPSETLSL TCTVSGGSIS SYYWSWIRQY PGKGLEWIGY ISYSGSSNYN PSLKRRVTIS

RDTSKNQFSL QLTSVIAADT AVYYCARNLM IRGAYGMDVW GQGTTVTVSS

Variable region nucleotide sequence
(SEQ ID NO: 320)
CAGGTGCACC TGCAGGAGTC GGGCCCAGGA CTGGTGAAGC CTTCGGAGAC CCTGTCCCTC ACGTGCACTG

TCTCTGGTGG CTCCATCAGT AGTTACTACT GGAGCTGGAT CCGGCAGTAC CCAGGAAAGG GACTGGAGTG

GATTGGATAT ATCTCTTACA GTGGGAGCAG CAATTATAAT CCCTCCCTCA AGAGGCGAGT CACCATATCA

CGAGACACGT CCAAGAACCA GTTCTCCCTG CAGCTGACCT CTGTAATCGC TGCGGACACG GCCGTTTATT

ACTGTGCGAG AAATCTTATG ATTCGGGGAG CCTACGGCAT GGACGTCTGG GGCCAAGGGA

CCACGGTCAC CGTCTCCTCA

FR1-IMGT amino acid sequence
(SEQ ID NO: 321)
QVHLQESGPG LVKPSETLSL TCTVS

FR1-IMGT nucleotide sequence
(SEQ ID NO: 322)
CAGGTGCACCTGCAGGAGTCGGGCCCAGGACTGGTGAAGCCTTCGGAGACCCTGTCCCTCACGTGCACTGTC

TCT

CDR1-IMGT amino acid sequence
(SEQ ID NO: 323)
GGSIS SYY

CDR1-IMGT nucleotide sequence
(SEQ ID NO: 324)
GGTGGCTCCATCAGTAGTTACTAC

FR2-IMGT amino acid sequence
(SEQ ID NO: 325)
WSWIRQY PGKGLEWIGY

FR2-IMGT nucleotide sequence
TGGAGCTGGATCCGGCAGTACCCAGGAAAGGGACTGGAGTGGATTGGATAT CDR2-IMGT amino acid sequence
(SEQ ID NO: 327)
ISYSGSS CDR2-IMGT nucleotide sequence
(SEQ ID NO: 328)
ATCTCTTACAGTGGGAGCAGC FR3-IMGT amino acid sequence
(SEQ ID NO: 329)
NYN PSLKRRVTIS RDTSKNQFSL QLTSVIAADT AVYYC FR3-IMGT nucleotide sequence
(SEQ ID NO: 330)
AATTATAATCCCTCCCTCAAGAGGCGAGTCACCATATCACGAGACACGTCCAAGAACCAGTTCTCCCTGCAGCT

GACCTCTGTAATCGCTGCGGACACGGCCGTTTATTACTGT

CDR3-IMGT amino acid sequence
(SEQ ID NO: 331)
ARNLM IRGAYGMDV

CDR3-IMGT nucleotide sequence
(SEQ ID NO: 332)
GCGAGAAATCTTATGATTCGGGGAGCCTACGGCATGGACGTC FR4-IMGT amino acid sequence
(SEQ ID NO: 333)
W GQGTTVTVSS FR4-IMGT nucleotide sequence
(SEQ ID NO: 334)
TGGGGCCAAGGGACCACGGTCACCGTCTCCTCA FR1-KABAT amino acid sequence
(SEQ ID NO: 335)
QVHLQESGPG LVKPSETLSL TCTVSGGSI FR1-KABAT nucleotide sequence
(SEQ ID NO: 336)
CAGGTGCACCTGCAGGAGTCGGGCCCAGGACTGGTGAAGCCTTCGGAGACCCTGTCCCTCACGTGCACTGTC

TCTGGTGGCTCCATC

CDR1-KABAT amino acid sequence
(SEQ ID NO: 337)
S SYYWS

CDR1-KABAT nucleotide sequence
(SEQ ID NO: 338)
AGTAGTTACTACTGGAGC

FR2-KABAT amino acid sequence
(SEQ ID NO: 339)
WIRQY PGKGLEWIG

FR2-KABAT nucleotide sequence
(SEQ ID NO: 340)
TGGATCCGGCAGTACCCAGGAAAGGGACTGGAGTGGATTGGA CDR2-KABAT amino acid sequence
(SEQ ID NO: 341)
Y ISYSGSSNYN PSLKR CDR2-KABAT nucleotide sequence
(SEQ ID NO: 342)
TATATCTCTTACAGTGGGAGCAGCAATTATAATCCCTCCCTCAAGAGG FR3-KABAT amino acid sequence
(SEQ ID NO: 343)
RVTIS RDTSKNQFSL QLTSVIAADT AVYYCAR FR3-KABAT nucleotide sequence
(SEQ ID NO: 344)
CGAGTCACCATATCACGAGACACGTCCAAGAACCAGTTCTCCCTGCAGCTGACCTCTGTAATCGCTGCGGACA

CGGCCGTTTATTACTGTGCGAGA

CDR3-KABAT amino acid sequence
(SEQ ID NO: 345)
NLM IRGAYGMDV

CDR3-KABAT nucleotide sequence
(SEQ ID NO: 346)
AATCTTATGATTCGGGGAGCCTACGGCATGGACGTC FR4-KABAT amino acid sequence
(SEQ ID NO: 347)
W GQGTTVTVSS FR4-KABAT nucleotide sequence
(SEQ ID NO: 348)
TGGGGCCAAGGGACCACGGTCACCGTCTCCTCA CL-148219QLT Light Chain kappa
Variable region amino acid sequence
(SEQ ID NO: 349)
DTVMTQSPLS LPVTPGEPAS ISCRSSQSLL HSNGYNYLDW YLQKAGQSPQ LLIYLGSNRA SGVPDRFSGS

VSGTDFTLKI SRVEAEDVGI YYCMQALQTP FTFGPGTKVD IK

Variable region nucleotide sequence
(SEQ ID NO: 350)
GATACTGTGA TGACTCAGTC TCCACTCTCC CTGCCCGTCA CCCCTGGAGA GCCGGCCTCC ATCTCCTGCA

GGTCTAGTCA GAGCCTCCTG CATAGTAATG GATACAATTA TTTGGATTGG TACCTGCAGA AGGCAGGACA

GTCTCCACAA CTCCTGATCT ATTTGGGTTC TAATCGGGCC TCCGGGGTCC CTGACAGGTT CAGTGGCAGT

GTATCAGGCA CAGATTTCAC ACTGAAAATC AGCAGAGTGG AGGCTGAGGA TGTTGGGATT TATTACTGCA

TGCAAGCTCT ACAAACTCCA TTCACTTTCG GCCCTGGGAC CAAAGTGGAT ATCAAA

FR1-IMGT amino acid sequence
(SEQ ID NO: 351)
DTVMTQSPLS LPVTPGEPAS ISCRSS

```
FR1-IMGT nucleotide sequence
                                                           (SEQ ID NO: 352)
GATACTGTGATGACTCAGTCTCCACTCTCCCTGCCCGTCACCCCTGGAGAGCCGGCCTCCATCTCCTGCAGGTC
TAGT CDR1-IMGT amino acid sequence
                                                           (SEQ ID NO: 353)
QSLL HSNGYNY CDR1-IMGT nucleotide sequence
                                                           (SEQ ID NO: 354)
CAGAGCCTCCTGCATAGTAATGGATACAATTAT FR2-IMGT amino acid sequence
                                                           (SEQ ID NO: 355)
LDW YLQKAGQSPQ LLIY FR2-IMGT nucleotide sequence
                                                           (SEQ ID NO: 356)
TTGGATTGGTACCTGCAGAAGGCAGGACAGTCTCCACAACTCCTGATCTAT CDR2-IMGT amino acid sequence
                                                           (SEQ ID NO: 357)
LGS CDR2-IMGT nucleotide sequence
                                                           (SEQ ID NO: 358)
TTGGGTTCT FR3-IMGT amino acid sequence
                                                           (SEQ ID NO: 359)
NRA SGVPDRFSGS VSGTDFTLKI SRVEAEDVGI YYC FR3-IMGT nucleotide sequence
                                                           (SEQ ID NO: 360)
AATCGGGCCTCCGGGGTCCCTGACAGGTTCAGTGGCAGTGTATCAGGCACAGATTTCACACTGAAAATCAGC
AGAGTGGAGGCTGAGGATGTTGGGATTTATTACTGC CDR3-IMGT amino acid sequence
                                                           (SEQ ID NO: 361)
MQALQTP FT CDR3-IMGT nucleotide sequence
                                                           (SEQ ID NO: 362)
ATGCAAGCTCTACAAACTCCATTCACT FR4-IMGT amino acid sequence
                                                           (SEQ ID NO: 363)
FGPGTKVD IK FR4-IMGT nucleotide sequence
                                                           (SEQ ID NO: 364)
TTCGGCCCTGGGACCAAAGTGGATATCAAA FR1-KABAT amino acid sequence
DTVMTQSPLS LPVTPGEPAS ISC FR1-KABAT nucleotide sequence
                                                           (SEQ ID NO: 366)
GATACTGTGATGACTCAGTCTCCACTCTCCCTGCCCGTCACCCCTGGAGAGCCGGCCTCCATCTCCTGC CDR1-KABAT amino acid sequence
                                                           (SEQ ID NO: 367)
RSSQSLL HSNGYNYLD CDR1-KABAT nucleotide sequence
                                                           (SEQ ID NO: 368)
AGGTCTAGTCAGAGCCTCCTGCATAGTAATGGATACAATTATTTGGAT FR2-KABAT amino acid sequence
                                                           (SEQ ID NO: 369)
W YLQKAGQSPQ LLIY FR2-KABAT nucleotide sequence
                                                           (SEQ ID NO: 370)
TGGTACCTGCAGAAGGCAGGACAGTCTCCACAACTCCTGATCTAT
```

```
CDR2-KABAT amino acid sequence
                                                            (SEQ ID NO: 371)
LGSNRA S CDR2-KABAT nucleotide sequence
                                                            (SEQ ID NO: 372)
TTGGGTTCTAATCGGGCCTCC FR3-KABAT amino acid sequence
                                                            (SEQ ID NO: 373)
GVPDRFSGS VSGTDFTLKI SRVEAEDVGI YYC FR3-KABAT nucleotide sequence
                                                            (SEQ ID NO: 374)
GGGGTCCCTGACAGGTTCAGTGGCAGTGTATCAGGCACAGATTTCACACTGAAAATCAGCAGAGTGGAGGCT

GAGGATGTTGGGATTTATTACTGC

CDR3-KABAT amino acid sequence
                                                            (SEQ ID NO: 375)
MQALQTP FT CDR3-KABAT nucleotide sequence
                                                            (SEQ ID NO: 376)
ATGCAAGCTCTACAAACTCCATTCACT
FR4-KABAT amino acid sequence
                                                            (SEQ ID NO: 377)
FGPGTKVD IK FR4-KABAT nucleotide sequence
                                                            (SEQ ID NO: 378)
TTCGGCCCTGGGACCAAAGTGGATATCAAA
```

Constant Regions for Antibodies & Fragments of the Invention

| | | SEQ ID NO: | |
|---|---|---|---|
| Human IgG1 constant region | IGHG1*01 | 125 | Human Heavy Chain Constant Region (IGHG1*01) Nucleotide Sequence | gcctccaccaagggcccatcggtcttccccctggcaccctcctccaagagcacctctgggggcacagcggcct gggctgcctggtcaaggactacttccccgaaccggtgacggtgtcgtggaactcaggcgccctgaccagcggc gtgcacaccttcccggctgtcctacagtcctcaggactctactccctcagcagcgtggtgaccgtgccctccagc agcttgggcacccagacctacatctgcaacgtgaatcacaagcccagcaacaccaaggtggacaagaaagtt gagcccaaatcttgtgacaaaactcacacatgcccaccgtgcccagcacctgaactcctggggggaccgtcag tcttcctcttccccccaaaacccaaggacaccctcatgatctcccggacccctgaggtcacatgcgtggtggtgg acgtgagccacgaagaccctgaggtcaagttcaactggtacgtggacggcgtggaggtgcataatgccaagac aaagccgcgggaggagcagtacaacagcacgtaccgtgtggtcagcgtcctcaccgtcctgcaccaggact ggctgaatggcaaggagtacaagtgcaaggtctccaacaaagccctcccagcccccatcgagaaaaccatct ccaaagccaaagggcagccccgagaaccacaggtgtacaccctgcccccatcccgggatgagctgaccaaga accaggtcagcctgacctgcctggtcaaaggcttctatcccagcgacatcgccgtggagtgggagagcaatgg gcagccggagaacaactacaagaccacgcctcccgtgctggactccgacggctccttcttcctctacagcaagc taccgtggacaagagcaggtggcagcaggggaacgtcttctcatgctccgtgatgcatgaggctctgcacaa ccactacacgcagaagagcctctccctgtctccgggtaaa |
| | | 126 | Human Heavy Chain Constant Region (IGHG1*01) Protein Sequence (P01857) | ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSRDE LTKNQVSLTCLVKGFYPSDIAVEWESNGQPENNYKTTPPVLDSDGSFFLYSKLTVDKSRW QQGNVFSCSVMHEALHNHYTQKSLSLSPGK |
| Human IgG1 constant region | IGHG1*02 or IGHG1*05 | 127 | Human Heavy Chain Constant Region (IGHG1*02 or IGHG1*05) Nucleotide Sequence | gcctccaccaagggcccatcggtcttccccctggcaccctcctccaagagcacctctgggggcacagcggcct gggctgcctggtcaaggactacttccccgaaccggtgacggtgtcgtggaactcaggcgccctgaccagcggc gtgcacaccttcccggctgtcctacagtcctcaggactctactccctcagcagcgtggtgaccgtgccctccagc agcttgggcacccagacctacatctgcaacgtgaatcacaagcccagcaacaccaaggtggacaagaaagtt gagcccaaatcttgtgacaaaactcacacatgcccaccgtgcccagcacctgaactcctggggggaccgtcag tcttcctcttccccccaaaacccaaggacaccctcatgatctcccggacccctgaggtcacatgcgtggtggtgg acgtgagccacgaagaccctgaggtcaagttcaactggtacgtggacggcgtggaggtgcataatgccaaga caaagccgcgggaggagcagtacaacagcacgtaccgtgtggtcagcgtcctcaccgtcctgcaccaggactg gctgaatggcaaggagtacaagtgcaaggtctccaacaaagccctcccagcccccatcgagaaaaccatctcc aaagccaaagggcagccccgagaaccacaggtgtacaccctgcccccatcccgggatgagctgaccaagaa ccaggtcagcctgacctgcctggtcaaaggcttctatcccagcgacatcgccgtggagtgggagagcaatggg cagccggagaacaactacaagaccacgcctcccgtgctggactccgacggctccttcttcctctacagcaagct caccgtggacaagagcaggtggcagcaggggaacgtcttctcatgctccgtgatgcatgaggctctgcacaac cactacacgcagaagagcctctccctgtctccgggtaaa |
| | | 128 | Human Heavy Chain Constant Region (IGHG1*02) Protein Sequence | ASTKGPSVFPLAPSSKSTSGGTAALGCLVKDYFPEPVTVSWNSG ALTSGVHTFPAVLQSSGLYSLSSVVTVPSSSLGTQTYICNVNHKP SNTKVDKKVEPKSCDKTHTCPPCPAPELLGGPSVFLFPPKPKDT LMISRTPEVTCVVVDVSHEDPEVKEMYVDGVEVHNAKTKPRE EQYNSTYRVVSVLTVLHQDWLNGKEYKCKVSNKALPAPIEKTIS KAKGQPREPQVYTLPPSRDELTKNQVSLTCLVKGFYPSDIAVEW ESNGQPENNYKTTPPVLDSDGSFFLYSKLTVDKSRWQQGNVFS CSVMHEALHNHYTQKSLSLSPGK |

Constant Regions for Antibodies & Fragments of the Invention

| | SEQ ID NO: | |
|---|---|---|
| Human IgG1 constant region | IGHG1*03 | Human Heavy Chain Constant Region (IGHG1*03) Nucleotide Sequence (Y14737) |
| | 129 | gcctcccaccaagggcccatcggtcttccccctggcaccctcctccaagagcacctctgggggcacagcggccct gggctgcctggtcaaggactacttccccgaaccggtgacggtgtcgtggaactcaggcgccctgaccagcggc gtgcacaccttcccggctgtcctacagtcctcaggactctactccctcagcagcgtggtgaccgtgccctccagc agcttgggcacccagacctacatctgcaacgtgaatcacaagcccagcaacaccaaggtggacaagagagtt gagcccaaatcttgtgacaaaactcacacatgcccaccgtgcccagcacctgaactcctggggggaccgtcag tcttcctcttccccccaaaacccaaggacaccctcatgatctcccggacccctgaggtcacatgcgtggtggtgg acgtgagccacgaagaccctgaggtcaagttcaactggtacgtggacggcgtggaggtgcataatgccaaga caaagccgcgggaggagcagtacaacagcacgtaccgtgtggtcagcgtcctcaccgtcctgcaccaggactg gctgaatggcaaggagtacaagtgcaaggtctccaacaaagccctcccagcccccatcgagaaaaccatctcc aaagccaaagggcagccccgagaaccacaggtgtacaccctgcccccatcccgggatgagctgaccaagaa ccaggtcagcctgacctgcctggtcaaaggcttctatcccagcgacatcgccgtggagtgggagagcaatggg cagccggagaacaactacaagaccacgcctcccgtgctggactccgacggctccttcttcctctatagcaagct caccgtggacaagagcaggtggcagcaggggaacgtcttctcatgctccgtgatgcatgaggctctgcacaac cactacacgcagaagagcctctccctgtctccgggtaaa |
| | 130 | Human Heavy Chain Constant Region (IGHG1*03) Protein Sequence<br>ASTKGPSVFPLAPSSKSTSGGTAALGCLVKDYFPEPVTVSWNSG ALTSGVHTFPAVLQSSGLYSLSSVVTVPSSSLGTQTYICNVNHKP SNTKVDKRVEPKSCDKTHTCPPCPAPELLGGPSVFLFPPKPKDT LMISRTPEVTCVVVDVSHEDPEVKFNWYVDGVEVHNAKTKPRE EQYNSTYRVVSVLTVLHQDWLNGKEYKCKVSNKALPAPIEKTIS KAKGQPREPQVYTLPPSREEMTKNQVSLTCLVKGFYPSDIAVE WESNGQPENNYKTTPPVLDSDGSFFLYSKLTVDKSRWQQGNVF SCSVMHEALHNHYTQKSLSLSPGK |
| | 131 | Human Heavy Chain Constant Region (IGHG1*04) Nucleotide Sequence | gcctcccaccaagggcccatcggtcttccccctggcaccctcctccaagagcacctctgggggcacagcggccct gggctgcctggtcaaggactacttccccgaaccggtgacggtgtcgtggaactcaggcgccctgaccagcggc gtgcacaccttcccggctgtcctacagtcctcaggactctactccctcagcagcgtggtgaccgtgccctccagc agcttgggcacccagacctacatctgcaacgtgaatcacaagcccagcaacaccaaggtggacaaagaagtt gagcccaaatcttgtgacaaaactcacacatgcccaccgtgcccagcacctgaactcctggggggaccgtcag tcttcctcttccccccaaaacccaaggacaccctcatgatctcccggacccctgaggtcacatgcgtggtggtgg acgtgagccacgaagaccctgaggtcaagttcaactggtacgtggacggcgtggaggtgcataatgccaaga caaagccgcgggaggagcagtacaacagcacgtaccgtgtggtcagcgtcctcaccgtcctgcaccaggactg gctgaatggcaaggagtacaagtgcaaggtctccaacaaagccctcccagcccccatcgagaaaaccatctcc aaagccaaagggcagccccgagaaccacaggtgtacaccctgcccccatcccgggatgagctgaccaagaa ccaggtcagcctgacctgcctggtcaaaggcttctatcccagcgacatcgccgtggagtgggagagcaatggg cagccggagaacaactacaagaccacacctcccgtgctggactccgacggctccttcttcctctacagcaagct cacagtggacaagagcaggtggcagcaggggaacgtcttctcatgctccgtgatgcatgaggctctgcacaac cactacacgcagaagagcctctccctgtctccgggtaaa |
| | 132 | Human Heavy Chain Constant Region (IGHG1*04) Protein Sequence | ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSRDE LTKNQVSLTCLVKGFYPSDIAVEWESNGQPENNYKTTPPVLDSDGSFFLYSKLTVDKSRW QQGNIFSCSVMHEALHNHYTQKSLSLSPGK |
| Disabled Human IgG1 heavy | Disabled human IGHG1*01 | Disabled Human IGHG1*01 Heavy Chain |
| | 133 | Gcctcccaccaagggcccatcggtcttccccctggcaccctcctccaagagcacctctgggggcacagcggccct gggctgcctggtcaaggactacttccccgaaccggtgacggtgtcgtggaactcaggcgccctgaccagcggc gtgcacaccttcccggctgtcctacagtcctcaggactctactccctcagcagcgtggtgaccgtgccctccagc agcttgggcacccagacctacatctgcaacgtgaatcacaagcccagcaacaccaaggtggacaagaaagtg |

Constant Regions for Antibodies & Fragments of the Invention

| | SEQ ID NO: | |
|---|---|---|
| chain constant region | | gagcccaaatctgtgacaaaactcacacatgccaccgtgcccagcacctgaactcgcggggcaccgtcag<br>tcttcctcttccccccaaaacccaaggacaccctcatgatctcccggacccctgaggtcacatgcgtggtgg<br>acgtgagccacgaagaccctgaggtcaagttcaactggtacgtggacggcgtggaggtgcataatgccaaga<br>caaagccgcgggaggagcagtacaacagcacgtaccgtgtggtcagcgtcctcaccgtcctgcaccaggact<br>ggctgaatggcaaggagtacaagtgcaaggtctccaacaaagccctcccagcccccatcgagaaaaccatctcc<br>aaagccaaagggcagccccgagaaccacaggtgtacaccctgcccccatcccgggatgagctgaccaagaa<br>ccaggtcagcctgacctgcctggtcaaaggcttctatcccagcgacatcgccgtggagtgggagagcaatggg<br>cagccggagaacaactacaagaccacgcctcccgtgctggactccgacggctccttcttcctctacagcaagct<br>caccgtggacaagagcaggtggcagcaggggaacgtcttctcatgctccgtgatgcatgaggctctgcacaac<br>cactacacgcagaagagcctctccctgtctccgggtaaa<br>ASTKGPSVFPLAPSSKSTSGGTAALGCLVKDYFPEPVTVSWNSGALTSGVHTFPAVLQSS<br>GLYSLSSVVTVPSSSLGTQTYICNVNHKPSNTKVDKKVEPKSCDKTHTCPPCPAPELAGA<br>PSVFLFPPKPKDTLMISRTPEVTCVVVDVSHEDPEVKFNWYVDGVEVHNAKTKPREEQY<br>NSTYRVVSVLTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLYSKLTVDKSR<br>WQQGNVFSCSVMHEALHNHYTQKSLSLSPGK |
| | 134 | |
| Disabled Human IGHG1*01 Heavy Chain Constant Region Amino Acid Sequence. Two residues that differ from the wild-type sequence are identified in bold. | | |
| Human IgG2 constant region | | gctccaccaaggccccatcggtcttcccccctggcgccctgctccaggagcacctccgagagcacagcgcct<br>gggcctgctggtcaaggactacttccccgaaccggtgacggtgtcgtggaactcaggcgctgtgaccagcggc<br>gtgcacaccttcccagctgtcctacagtcctcaggactctactccctcagcagcgtggtgaccgtgccctccagc<br>aacttcggcacccagacctacatctgcaacgtagatcacaagcccagcaacaccaaggtggacaagacagtt<br>gagcgcaaatgttgtgtcgagtgcccaccgtgcccagcaccacctgtggcaggaccgtcagtcttcctcttcccc<br>ccaaaacccaaggacaccctcatgatctcccggacccctgaggtcacgtgcgtggtggtggacgtgagccacg<br>aagaccccgaggtccagttcaactggtacgtggacggcgtggaggtgcataatgccaagacaaagccacgg<br>gaggagcagttcaacagcacgttccgtgtggtcagcgtcctcaccgtcgtgcaccaggactggctgaacggcaa<br>ggagtacaagtgcaaggtctccaacaaaggcctcccagcccccatcgagaaaaccatctccaaaaccaaagg<br>gcagccccgagaaccacaggtgtacaccctgcccccatcccgggaggagatgaccaagaaccaggtcagcct<br>gacctgcctggtcaaaggcttctaccccagcgacatcgccgtggagtgggagagcaatgggcagccggagaa<br>caactacaagaccacacctcccatgctggactccgacggctccttcttcctctacagcaagctcaccgtggaca<br>agagcaggtggcagcaggggaacgtcttctcatgctccgtgatgcatgaggctctgcacaaccactacacgca<br>gaagagcctctccctgtctccgggtaaa<br>ASTKGPSVFPLAPCSRSTSESTAALGCLVKDYFPEPVTVSWNSGALTSGVHTFPAVLQSS<br>GLYSLSSVVTVPSSNFGTQTYTCNVDHKPSNTKVDKTVERKCCVECPPCPAPPVAGPSVF<br>LFPPKPKDTLMISRTPEVTCVVVDVSHEDPEVQFNWYVDGVEVHNAKTKPREEQFNST<br>FRVVSVLTVVHQDWLNGKEYKCKVSNKGLPAPIEKTISKTKGQPREPQVYTLPPSREEMT<br>KNQVSLTCLVKGFYPSDIAVEWESNGQPENNYKTTPPMLDSDGSFFLYSKLTVDKSRW<br>QQGNVFSCSVMHEALHNHYTQKSLSLSPGK |
| IGHG2*01 or IGHG2*04 or IGHG2*05 | | |
| Human Heavy Chain Constant Region (IGHG2*01 or IGHG2*03 or IGHG2*05) Nucleotide Sequence | | |
| | 135 | |
| | 136 | |
| Human Heavy Chain Constant Region (IGHG2*01) Protein sequence | | |

Constant Regions for Antibodies & Fragments of the Invention

| | | SEQ ID NO: | |
|---|---|---|---|
| Human IgG2 constant Region | IGHG2*02 Human Heavy Chain Constant region (IGHG2*02) Nucleotide Sequence | 137 | GCTTCCACCAAGGGCCCATCGTCTTCCCCCTGGCGCCCTGCTCCAGGAGCACCTCC GAGAGCACAGCGGCCCTGGGCTGCCTGGTCAAGGACTACTTCCCCGAACCGGTGAC GGTGTCGTGGAACTCAGGCGCTCTGACCAGCGGCGTGCACACCTTCCCGGCTGTCCT ACAGTCCTCAGGACTCTACTCCCTCAGCAGCGTGGTGACCGTGACCTCCAGCAACTT CGGCACCCAGACCTACACCTGCAACGTAGATCACAAGCCCAGCAACACCAAGGTGG ACAAGACAGTTGAGCGCAAATGTTGTGTCGAGTGCCCACCGTGCCCAGCACCACCT GTGGCAGGACCGTCAGTCTTCCTCTTCCCCCCAAAACCCAAGGACACCCTCATGATCT CCCGGACCCCTGAGGTCACGTGCGTGGTGGTGGACGTGAGCCACGAAGACCCCGA GGTCCAGTTCAACTGGTACGTGGACGGCGTGGAGGTGCATAATGCCAAGACAAAGC CACGGGAGGAGCAGTTCAACAGCACGTTCCGTGTGGTCAGCGTCCTCACCGTCGTG CACCAGGACTGGCTGAACGGCAAGGAGTACAAGTGCAAGGTCTCCAACAAAGGCCT CCCAGCCCCCATCGAGAAAACCATCTCCAAAACCAAAGGGCAGCCCCGAGAACCAC AGGTGTACACCCTGCCCCCATCCCGGGAGGAGATGACCAAGAACCAGGTCAGCCTG ACCTGCCTGGTCAAAGGCTTCTACCCCAGCGACATCGCCGTGGAGTGGGAGAGCAA TGGGCAGCCGGAGAACAACTACAAGACCACACCTCCCATGCTGGACTCCGACGGCT CCTTCTTCCTCTACAGCAAGCTCACCGTGACAAGAGACAGGTGGCAGCAGGGGAAC GTCTTCTCATGCTCCGTGATGCATGAGGCTCTGCACAACCACTACACACAGAAGAGC CTCTCCCTGTCTCCGGGTAAA |
| | Human Heavy Chain Constant Region (IGHG2*02) Protein Sequence | 138 | ASTKGPSVFPLAPCSRSTSESTAALGCLVKDYFPEPVTVSWNSGALTSGVHTFPAVLQSS GLYSLSSVVTVTSSNFGTQTYTCNVDHKPSNTKVDKTVERKCCVECPPCPAPPVAGPSVF LFPPKPKDTLMISRTPEVTCVVVDVSHEDPEVQFNWYVDGMEVHNAKTKPREEQFNST FRVVSVLTVVHQDWLNGKEYKCKVSNKGLPAPIEKTISKTKGQPREPQVYTLPPSREEMT KNQVSLTCLVKGFYPSDIAVEWESNGQPENNYKTTPPMLDSDGSFFLYSKLTVDKSRW QQGNVFSCSVMHEALHNHYTQKSLSLSPGK |
| Human IgG2 constant region | IGHG2*04 Human Heavy Chain Constant Region (IGHG2*04) Nucleotide sequence | 139 | gcttccaccaagggcccatcgtcttccccctggcgccctgctccaggagcacctcc gggctgcctggtcaaggactacttcccccgaaccggtgacggtgtcgtggaactcaggcgc tgtcacacctttccccagctgtcctacagtcctcaggactctactccctcagcagcgttgtgaccgtgccctccagc agcttgggcacccagaccctacacctgcaacgtagatcacaaggccagcaacaccaaggtggacaagacagtt gagcgcaaatgttgtgtcgagtgcccaccgtgcccagcaccacctgtggcaggaccgtcagtcttcctcttcccc ccaaaacccaaggacaccctcatgatctcccggaccctgaggtcacgtgcgtggtggtggacgtgagccacg aagacccccgaggtccagttcaactggtacgtggacggcgtggaggtgcataatgccaagacaaagccacgg gaggagcagttcaacagcacgttccgtgtggtcagcgtcctcaccgtcgtgcaccaggactggctgaacggcaa ggagtacaagtgcaaggtctccaacaaaggcctcccagcccccatcgcccccagcaccccgagaaaaccatctccaaaaccaaagg gcagccccgagaaccacaggtgtacaccctgccccccatcccgggaggagatgaccaagaaccaggtcagcct gacctgcctggtcaaaggcttctaccccagcgacatcgccgtggagtgggagagcaatgggcagccggagaa caactacaagaccacacctcccatgctggactccgacggctccttcttcctctacagcaagctcaccgtggaca agagcaggtggcagcaggggaacgtcttctcatgctccgtgatgcatgaggctctgcacaaccactacacgca gaagagcctctccctgtctccgggtaaa |
| | Human Heavy Chain Constant Region (IGHG2*04) Protein Sequence | 140 | ASTKGPSVFPLAPCSRSTSESTAALGCLVKDYFPEPVTVSWNSGALTSGVHTFPAVLQSS GLYSLSSVVTVTPSSSLGTQTYTCNVDHKPSNTKVDKTVERKCCVECPPCPAPPVAGPSVF LFPPKPKDTLMISRTPEVTCVVVDVSHEDPEVQFNWYVDGVEVHNAKTKPREEQFNST FRVVSVLTVVHQDWLNGKEYKCKVSNKGLPAPIEKTISKTKGQPREPQVYTLPPSREEMT KNQVSLTCLVKGFYPSDIAVEWESNGQPENNYKTTPPMLDSDGSFFLYSKLTVDKSRW QQGNVFSCSVMHEALHNHYTQKSLSLSPGK |

Constant Regions for Antibodies & Fragments of the Invention

| | | SEQ ID NO: | |
|---|---|---|---|
| Human IgG2 constant region | Human Heavy Chain Constant Region (IGHG2*06) Nucleotide Sequence | 141 | GCTTCCACCAAGGGCCCATCCGTCTTCCCCCTGGCGCCCTGCTCCAGGAGCACCTCC GAGAGCACAGCGGCCCTGGGCTGCCTGGTCAAGGACTACTTCCCCGAACCGGTGAC GGTGTCGTGGAACTCAGGCGCTCTGACCAGCGGCGTGCACACCTTCCCGGCTGTCCT ACAGTCCTCAGGACTCTACTCCCTCAGCAGCGTGGTGACCGTGCCCTCCAGCAACTT CGGCACCCAGACCTACACCTGCAACGTAGATCACAAGCCCAGCAACACCAAGGTGG ACAAGACAGTTGAGCGCAAATGTTGTGTCGAGTGCCCACCGTGCCCAGCACCACCT GTGGCAGGACCGTCAGTCTTCCTCTTCCCCCCAAAACCCAAGGACACCCTCATGATCT CCCGGACCCCTGAGGTCACGTGCGTGGTGGTGGACGTGAGCCACGAAGACCCCGA GGTCCAGTTCAACTGGTACGTGGACGGCGTGGAGGTGCATAATGCCAAGACAAAGC CACGGGAGGAGCAGTTCAACAGCACGTTCCGTGTGGTCAGCGTCCTCACCGTCGTG CACCAGGACTGGCTGAACGGCAAGGAGTACAAGTGCAAGGTCTCCAACAAAGGCCT CCCAGCCCCCATCGAGAAAACCATCTCCAAAACCAAAGGGCAGCCCCGAGAACCAC AGGTGTACACCCTGCCCCCATCCCGGGAGGAGATGACCAAGAACCAGGTCAGCCTG ACCTGCCTGGTCAAAGGCTTCTACCCCAGCGACATCGCCGTGGAGTGGGAGAGCAA TGGGCAGCCGGAGAACAACTACAAGACCACACCTCCCATGCTGGACTCCGACGGCT CCTTCTTCCTCTACAGCAAGCTCACCGTGGACAAGAGCAGGTGGCAGCAGGGGAAC GTCTTCTCATGCTCCGTGATGCATGAGGCTCTGCACAACCACTACACACAGAAGAGC CTCTCCCTGTCTCCGGGTAAA |
| | Human Heavy Chain Constant Region (IGHG2*06) Protein Sequence | 142 | ASTKGPSVFPLAPCSRSTSESTAALGCLVKDYFPEPVTVSWNSGALTSGVHTFPAVLQSS GLYSLSSVVTVPSSNFGTQTYTCNVDHKPSNTKVDKTVERKCCVECPPCPAPPVAGPSVF LFPPKPKDTLMISRTPEVTCVVVDVSHEDPEVQFNWYVDGVEVHNAKTKPREQFNST FRVVSVLTVLHQDWLNGKEYKCKVSNKGLPAPIEKTISKTKGQPREPQVYTLPPSREEMT KNQVSLTCLVKGFYPSDIAVEWESNGQPENNYKTTPPMLDSDGSFFLYSKLTVDKSRWQ QGNVFSCSVMHEALHNHYTQKSLSLSPGK |
| Human IgG4 constant region | Human Heavy Chain Constant Region (IGHG4*01 or IGHG4*04) Nucleotide Sequence | 143 | gcttccaccaagggcccatccgtcttccccctggcgccctgctccaggagcacctct gggctgcctggtcaaggactacttccccgaaccggtgacggtgtcgtggaactcaggcgcc ctgaccagcggcgtgcacaccttcccggctgtcctacagtcctcaggactctactccctcagc agcgtggtgaccgtgccctccagcagcttgggcacgaagacctacacctgcaacgtagatc acaagcccagcaacaccaaggtggacaagagagttgagtccaaatatggtcccccatgccc accatgcccagcacctgagttcctggggggaccatcagtcttcctgttccccccaaaacccaag gacactctcatgatctccggacccctgaggtcacgtgcgtggtggtggacgtgagccaggaa gaccccgaggtccagttcaactggtacgtggatggcgtggaggtgcataatgccaagacaaa gccgcgggaggagcagttcaacagcacgtaccgtgtggtcagcgtcctcaccgtcctgcac caggactggctgaacggcaaggagtacaagtgcaaggtctccaacaaaggcctcccgtcctc catcgagaaaaccatctccaaagccaaagggcagccccgagagccacaggtgtacaccctg cccccatcccaggaggagatgaccaagaaccaggtcagcctgacctgcctggtcaaaggcttc taccccagcgacatcgccgtggagtgggagagcaatgggcagccggagaacaactacaag accacgcctcccgtgctggactccgacggctccttcttcctctacagcaggctaaccgtggac aagagcaggtggcaggaggggaatgtcttctcatgctccgtgatgcatgaggctctgcacaac cactacacacagaagagcctctccctgtctctgggtaaa |
| | Human Heavy Chain Constant Region (IGHG4*01) Protein Sequence (P01861) | 144 | ASTKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPSCPAPEFLGGPSVF LFPPKPKDTLMISRTPEVTCVVVDVSQEDPEVQFNWYVDGVEVHNAKTKPREQFNST YRVVSVLTVLHQDWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLYSRLTVDKSRWQ EGNVFSCSVMHEALHNHYTQKSLSLSLGK |

Constant Regions for Antibodies & Fragments of the Invention

| | | SEQ ID NO: | |
|---|---|---|---|
| Human IgG4 constant region | IGHG4*02 Human Heavy Chain Constant Region (IGHG4*02) Nucleotide Sequence | 145 | gcttcccaccaagggcccatccgtcttccccctggcgccctgctcccaggagcacctccgagagcacagccgccct gggctgcctggtcaaggactacttccccgaaccggtgacggtgtcgtggaactcaggcgccctgaccagcggc gtgcacaccttcccggctgtcctacagtcctcaggactctactccctcagcagcgtggtgaccgtgccctccagc agcttgggcacgaagacctacacctgcaacgtagatcacaagcccagcaacaccaaggtggacaagagagtt gagtcccaaatatgttgcccatcatgcccaccacctgagttcctgggggaccatcagtcttcctgttc ccccaaaacccaaggacactctcatgatctccggaccctgaggtcacgtgcgtggtggtggacgtgagcc aggaagaccccgaggtccagttcaactggtacgtggatggcgtggaggtgcataatgccaagacaaagccg cgggaggagcagttcaacagcacgtaccgtgtggtcagcgtcctcaccgtcctgcaccaggactggctgaacgg caaggagtacaagtgcaaggtctccaacaaaggcctcccgtcctccatcgagaaaaccatctccaaagccaa agggcagccccgagagccacaggtgtacaccctgcccccatcccaggaggagatgaccaagaaccaggtca gcctgacctgcctggtcaaaggcttctaccccagcgacatcgccgtggagtgggagagcaatgggcagccgga gaacaactacaagaccacgcctcccgtgctggactccgacggctccttcttcctctacagcaggctaaccgtgg acaagagcaggtggcaggagggaatgtcttctcatgctccgtgatgcatgaggctctgcacaaccactacac gcagaagagcctctccctgtctctgggtaaa |
| | Human Heavy Chain Constant Region (IGHG4*02) Protein Sequence | 146 | ASTKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPSCPAPEFLGGPSVF LFPPKPKDTLMISRTPEVTCVVVDVSQEDPEVQFNWYVDGVEVHNAKTKPREEQFNST YRVVSVLTVVHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSRLTVDKSRW QEGNVFSCSVMHEALHNHYTQKSLSLSLGK |
| | IGHG4*03 Human Heavy Chain Constant Region (IGHG4*03) Nucleotide sequence | 147 | gcttcccaccaagggcccatccgtcttccccctggcgccctgctcccaggagcacctccgagagcacagccgccct gggctgcctggtcaaggactacttccccgaaccggtgacggtgtcgtggaactcaggcgccctgaccagcggc gtgcacaccttcccggctgtcctacagtcctcaggactctactccctcagcagcgtggtgaccgtgccctccagc agcttgggcacgaagacctacacctgcaacgtagatcacaagcccagcaacaccaaggtggacaagagagtt gagtcccaaatatgttgcccatcatgcccaccacctgagttcctgggggaccatcagtcttcctgttc ccccaaaacccaaggacactctcatgatctccggaccctgaggtcacgtgcgtggtggtggacgtgagcc aggaagaccccgaggtccagttcaactggtacgtggatggcgtggaggtgcataatgccaagacaaagccg cgggaggagcagttcaacagcacgtaccgtgtggtcagcgtcctcaccgtcctgcaccaggactggctgaacgg caaggagtacaagtgcaaggtctccaacaaaggcctcccgtcctccatcgagaaaaccatctccaaagccaa agggcagccccgagagccacaggtgtacaccctgcccccatcccaggaggagatgaccaagaaccaggtca gcctgacctgcctggtcaaaggcttctaccccagcgacatcgccgtggagtgggagagcaatgggcagccgga gaacaactacaagaccacgcctcccgtgctggactccgacggctccttcttcctctacagcaagctcaccgtgg acaagagcaggtggcaggagggaatgtcttctcatgctccgtgatgcatgaggctctgcacaaccactacac gcagaagagcctctccctgtctctgggtaaa |
| | Human Heavy Chain Constant Region (IGHG4*03) Protein | 148 | ASTKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPSCPAPEFLGGPSVF LFPPKPKDTLMISRTPEVTCVVVDVSQEDPEVQFNWYVDGVEVHNAKTKPREEQFNST YRVVSVLTVLHQDWLNGKEYKCKVSNKGLPSSIEKTISKAKGQPREPQVYTLPPSQEMT KNQVSLTCLVKGFYPSDIAVEWESNGQPENNYKTTPPVLDSDGSFFLYSKLTVDKSRMQ EGNVFSCSVMHEALHNHYTQKSLSLSLGK |

Constant Regions for Antibodies & Fragments of the Invention

| | | SEQ ID NO: | Sequence |
|---|---|---|---|
| Human IgG4PE constant region | IGHG4-PE | | |
| | Human Heavy Chain Constant Region (IGHG4-PE) Nucleotide Sequence Version A | 149 | gctcccaccaaggcccatcctgtcttccccctggcctgctgtcctcaggagcacctccgagagcacggcccct gggctgcctggtcaaggactactccccggaaccagtgacgtcgtggaactcaggcgccctgaccagcggc gtgcacaccttccggctgtcctacagcctcaggactcctactcctcagcctcagcagtggtgaccgtgccctccagc agcttgggcacgaagaccntacacctgcaacgtagatcacaagcccagcaacaccaaggtggacaagagagtt gagtcccaaatatgtccccatgcccaccatgcccagcacctgagttcctgggggaccatcagtcttcctgttc cccccaaaacccaaggacactctcatgatctccggaccccctgaggtcacgtgcgtggtggtggacgtgagc caggaagaccccgaggtccagttcaactggtacgtggacggcgtggaggtgcataatgccaagacaaagccg cgggaggagcagttcaacagcacgtaccgtgtggtcagcgtcctcaccgtcctgcaccaggactggctgaacgg caaggagtacaagtgcaaggtctccaacaaaggcctcccgtcctccatcgagaaaaccatctccaaagccaaa gggcagccccgagaaccacaggtgtacaccctgcccccatcccgggaggagatgaccaagaaccaggtca gcctgacctgcctggtcaaaggcttctaccccagcgacatcgccgtggagtgggagagcaatgggcagccgga gaacaactacaagaccacgcctcccgtgctggactccgacggctccttcttcctctacagcaggctaaccgtgg acaagagcaggtggcaggaggggaatgtcttctcatgctccgtgatgcatgaggctctgcacaaccactacac acagaagagcctctccctgtctctgggtaaa |
| | Human Heavy Chain Constant Region (IGHG4-PE) Nucleotide Sequence Version B | 150 | gctcccaccaaggacccctcagcgtgttccctcgagcctccacaaagagtccaccgtgccctgc ggctgtctggtgaaagactactccgccgctgtcagagacgggctggctcctggaagccgagagcccgagctcgt gcacacatcccggccgtgctctacagcctcagcagcgtgacctgtgtgaccgtgtcccagctcca gcctcggccaccaaaaactacacctgcaacgtcgaccacaagccctccaacaccaaggtggacaagacagtt gagagcaagtacggcccccccaatgcccaccttgcccctgcccggtctcagagttccagcccgagggcc ccaaaaccccaaggacaccctcatgatctccgggcaccctgaggtcacatgcgtggtggtggacgtgacgga ggagtacgttcaatggcgtggaggtgcataatgccaagacaaagccgagggagcagttcaactggtatgtggatggca tggccagcgagggtctacaaaggtcctccaaaggccccaagcgaagacccacagccaaaaccaaggtgtcc aatacaaggtgtaccaggtggagcagcctcagcccaccagcgtggagaccccaccatctctgacagcactc ctgcggatgctcaaggtccagcatcttggcacacctccgtacaccacccgtctgatgatgcaatggcagccagccgagacc gagggccaggtccagcgtcgatacccatcaaaaacccaccgtcctctctcattctgtctctgcccggtgatgga aaggatgaaggggggaacgtctctctcgagccctgaatcaatactccaccgag aagaagaagctctcctggtaaggaa |
| | Human Heavy Chain Constant Region (IGHG4-PE) Nucleotide Sequence Version C | 151 | gccagtcaccaaggccccaaggccccatcaggtctccctctggcctcagcagaggccaccttaccctcacagcgctcct gggctgtcgtgaaaagactacttccccaagctcgatgacctccagcgcgtcctggtgagacagtccgcg tccacacctcctgccaactaccctagcgggactcaggcaagccacgtgacccctggtgcctgttcctgc ctcgccacaagtccaagaccctcttgtgacacagccccccctccccccttacggcagggggccgcttccttc aggctacagaggaccctctccccaaggtagacccacggggacgtgttcatctgctcccccccgctgagaccagg cctaaggacaagggggaccacgtgcccggccacctcaggagccagcaagtcacttcccatcagcctacctatgac tgtgcccagttaatccggcaggggtcgggagccccacagctcaccccggggaggagagggggcagacggcccccggg aagagcagtaccaaagaccagcccccgatgaacctccctctcccagggacccgcatcgcgaagctgcaggacgca ggagtcaaggccgaaggccccagtgctgcagggctcaggggagcggcatgccacggtagccaagacctccaagctgagc tgacctccggagggatctccacaccctccccgacacgacgatctcttctgtactccagggctccgagctcagaa acattaagacccaccctccacacgacggtgcagaagagccggatccttcagagcgacgcagctgacctggacgga gtccagtggcagaaggcaacgtgttcagctctgctgatgatgccacggaggcctccaccagggcagaatcactacacccag agtcctgtgagcctgtctgggtaaag |
| | Human Heavy Chain Constant Region (IGHG4-PE) | 152 | ASTKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPPCPAPEFEGGPSVF LFPPKPKDTLMISRTPEVTCVVVDVSQEDPEVQFNWYVDGVEVHNAKTKPREEQFNST |

Constant Regions for Antibodies & Fragments of the Invention

| | SEQ ID NO: | |
|---|---|---|
| Inactivated Human IgG4 constant region | | PE) Protein Sequence (Amino acid substitution shown in BOLD) |
| | | YRVVSVLTVLHQDWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLYSRLTVDKSRMQ EGNVFSCSVMHEALHNHYTQKSLSLGK |
| Inactivated Inactivated IGHG4 Human Heavy Chain Constant Region Nucleotide Sequence | 153 | gcctcccaccaagggcccatccgtcttccccctggcgccctgctccaggagcacctccgagagcacccggccct gggtgcctggtcaaggactacttcccgaaccagtgacggtgtcgtggaactcaggcgccctgaccagcggc gtgcacacctccggcgtccagctctctctactctctccactccagcagcgtggtgaccgtgccctccagc agcttgggcacgaagaccctacacctgcaacgtagatcccagcgcccagcaacaccaaggtggacaagagagt gagtccaaatatggtccccatgctcccccagcacactctatgatctccggaccccctgaggtcacgtgcgtggtggtggacgtgagc aggaagaccccgaggtccagttcaactgtacgtggatgcggagtgcataatgccaagacaaagccgc gggaggagcagttcaacagcacgtaccgtgtgtcagcgcctcaccgtcctgcaccaggactggctgaacgg caaggagtacaagtgcaaggtctccaacaaagcctccgtctccaacaaaggcctcccgtccccatcccaggaggagatgaccaagaaccaggtca gctgacctgcctggtcaaaggcttctaccccagcgacatcgccgtggagtgggagagcaatgggcagccgga gaacaactacaagaccacgcctcccgtgctgactccgacggcttcttcttctctctacagcaggctaaccgtgg acaagagcaggtggcaggaggagaatgctcttcatgctcctgtgatcatgaggctctgcacaaccactacac acagaagagcctctcctgtctccgggtaaa |
| Inactivated Human Heavy Chain Constant Region (IGHG4) Protein Sequence (inactivating mutations from human IgG4 shown in bold) | 154 | ASTKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPPCPAPPVAGGPSV FLFPPKPKDTLMISRTPEVTCVVVDVSQEDPEVQFNWYVDGVEVHNAKTKPREEQFNS TYRVVSVLTVLHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSRLTVDKSRW QEGNVFSCSVMHEALHNHYTQKSLSLGK |
| Human Cκ constant region | IGKC*01 | Human Cκ Light Chain Constant Region (IGKC*01) Nucleotide Sequence |
| | 155 | cgtacggtggccgctcctccgtgttcatcttcccgacgagcagctgaagtccggcaccgcttctgtcg tgcctgctgaacaacttctaccccggaggccaaggtgcagtggaaggtggacaacgcctgcagtccgg caactcccaggaatccgtgaccgagcaggactccaaggacagcacctactcctgtcctccaaccctgt ccaaggccgactacgagaaacagcaaggtgtacgcctgcgaagtgacccaccaggggctgtcagcccctgtga ccaagtcttcaacggggcgagtgt |
| | 156 | Cκ Light Chain Constant Region (IGKC*01) Amino Acid Sequence |
| | | RTVAAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC |

-continued

Constant Regions for Antibodies & Fragments of the Invention

| | | SEQ ID NO: | |
|---|---|---|---|
| Human Cκ constant region | IGKC*02 | | |
| | Cκ Light Chain Constant Region (IGKC*02) Nucleotide Sequence | 157 | cgaactgtggctgcaccatctgtcttcatcttcccgccattctgatgagcagttgaaatctgaactgcctctgttg tgtgcctgctgaataacttctatcccagaggccaaagtacagtggaaggtggataacgcctccaatcgggt aactcccaggagagtgtcacagacaggagagacaaagtctacagcctcagcagcctacagcctcagcactctgacgct gagcaaagcagactacgagaaacacaaagtctacgcctgcgaagtcacccatcagggcctgagctcgcccgt cacaaagagcttcaacaggggagagtgt |
| | Cκ Light Chain Constant Region (IGKC*02) Amino Acid Sequence | 158 | RTVAAPSVFIFPPSDEQLKSGTASVVCLLNNFYPREAKVQWKVDNALQSGNSQESVTEQ ESKDSTYSLSSTLTLSKADYEKHKVYAGEVTHQGLSSPVTKSFNRGEC |
| Human Cκ constant region | IGKC*03 | | |
| | Cκ Light Chain Constant Region (IGKC*03) Nucleotide Sequence | 159 | cgaactgtggctgcaccatctgtcttcatcttcccgccattctgatgagcagttgaaatctgaactgcctctgttg tgtgcctgctgaataacttctatcccagaggccaaagtacagcggaaggtggataacgccctccaatcggg taactcccaggagtgtcacagacagcaaagtctacagcctcagcagcctacagcctcagcactctgacgct gagcaaagcagactacgagaaacacaaagtctacgcctgcgaagtcacccatcagggcctgagctcgcccgt cacaaagagcttcaacaggggagagtgt |
| | Cκ Light Chain Constant Region (IGKC*03) Amino Acid Sequence | 160 | RTVAAPSVFIFPPSDEQLKSGTASVVCLLNNFYPREAKVQRKVDNALQSGNSQESVTEQ ESKDSTYSLSSTLTLSKADYEKHKVYACEVTHQGLSSPVTKSFNRGEC |
| Human Cκ constant region | IGKC*04 | | |
| | Cκ Light Chain Constant Region (IGKC*04) Nucleotide Sequence | 161 | cgaactgtggctgcaccatctgtcttcatcttcccgccattctgatgagcagttgaaatctgaactgcctctgttg tgtgcctgctgaataacttctatcccagaggccaaagtacagtggaaggtggataacgccctccaatcggct aactcccaggagtgtcacagacaggcagcaaagtctacagcctcagcagcctcagcctcagcacactgacgtc agcaaagcagactacgagaaacacaactctacgcctgcgaagtcacccatcagggcctgagctcgcccgtc acaaagagcttcaacaggggagagtgt |
| | Cκ Light Chain Constant Region (IGKC*04) Amino Acid Sequence | 162 | RTVAAPSVFIFPPSDEQLKSGTASVVCLLNNFYPREAKVQWKVDNALQSGNSQESVTEQ DSKDSTYSLSSTLTLSKADYEKHKLYACEVTHQGLSSPVTKSFNRGEC |
| Human Cκ constant region | IGKC*05 | | |
| | Cκ Light Chain Constant Region (IGKC*05) Nucleotide Sequence | 163 | cgaactgtggctgcaccatctgtcttcatcttcccgccattctgatgagcagttgaaatctgaactgcctctgttg tgtgcctgctgaataacttctatcccagaggccaaagtacagtggaaggtggataacgcctccaatcgggtg aactcccaggagtgtcacagacagcaaagacacaccctcagcaacccctcagcctcagcctcagcctcagcctgacgctg agcaaagcagactacgagaaacacaaagtctacgcctgcgaagtcacccatcagggcctgagctcgcccgtc acaaagagcttcagttgtctcaacaggggagagtgc |
| | Cκ Light Chain | 164 | RTVAAPSVFIFPPSDEQLKSGTASVVCLLNNFYPREAKVQWKVDNALQSGNSQESVTEQ DSKDSTYSLSNTLTLSKADYEKHKVYACEVTHQGLSSPVTKSFNRGEC |

-continued

Constant Regions for Antibodies & Fragments of the Invention

| | | SEQ ID NO: | |
|---|---|---|---|
| Human Cλ constant region | IGLC1*01 | | |
| | Cλ Light Chain Constant Region (IGKC*05) Amino Acid Sequence | | |
| | Cλ Light Chain Constant Region (IGLC1*01) Nucleotide Sequence (ENST00000390321.2) | 165 | cccaaggcccaacccactgtcactctgttcccgccctcctgaggagctccaagccaacaaggccacactagt gtgtctgatcagtgacttctaccgggagctgtgacagtggcctgaaggcagatggcagcccgtcaaggcg ggagtggagacgaccaacccctccaaacagagcaacaacaagtacgccagctgcagctacctgagcctgac gcccgacagtgaagtcccacagaagctacagctgcagctgcaggtcacgcatgagggagcacgtggagaaga cagtggccctacagaatgttca |
| | Cλ Light Chain Constant Region (IGLC1*01) Amino Acid Sequence (A0A075B6K8) | 166 | PKANPTVTLFPPSSEELQANKATLVCLISDFYPGAVTVAWKADGSPVKAGVETTKPSKQS NNKYAASSYLSLTPEQWKSHRSYSCQVTHEGSTVEKTVAPTECS |
| Human Cλ constant region | IGLC1*02 | | |
| | Cλ Light Chain Constant Region (IGLC1*02) Nucleotide Sequence Version A | 167 | ggtcagcccaaggccaaccccactgtcactcttgttcccgccctctctgaggagctcaagccaacaaggccac actagtgtgtctgatcagtgacttctaccgggagctgtgacagtgcctgaaggcagatggcagcccgtca aggcgggagtggagacgaccaacccctccaaacagagcaacaacaagtacgccagctgcagctacctgagc ctgacgcccgagcagtggaagtcccacagaagctacagctgccaggtcacgcatgaaggggagcaccgtggag aagacagtggccctacagaatgttca |
| | Cλ Light Chain Constant Region (IGLC1*02) Nucleotide Sequence Version B | 168 | ggtcagcccaaggccaaccccactgtcactcttgttcccgccctctctgaggagctcaagccaacaaggccac actagtgtgtctgatcagtgacttctaccgggagctgtgacagtgcctgaaggcagatggcagcccgtca agcggagtggagacgaccaacccctccaaacagagcaacaacaagtacgccagctgcagctacctgagc ctgacgcccgagcagtggaagtcccacagaagctacagctgccaggtcacgcatgaaggggagcaccgtggag aagacagtggccctacagaatgttca |
| | Cλ Light Chain Constant Region (IGLC1*02) Amino Acid Sequence | 169 | GQPKANPTVTLFPPSSEELQANKATLVCLISDFYPGAVTVAWKADGSPVKAGVETTKPS KQSNNKYAASSYLSLTPEQWKSHRSYSCQVTHEGSTVEKTVAPTECS |

Constant Regions for Antibodies & Fragments of the Invention

| | | SEQ ID NO: | |
|---|---|---|---|
| Human Cλ constant region | IGLC2*01 | Cλ Light Chain Constant Region (IGLC2*01) Nucleotide Sequence Version A | 170 | ggccagctaagccgtccttctgtgaccctgttccccatcctccgagaactgcaggctaacaaggccac cctcgtgtgcctgatcagcgacttctacccgggcgtgaccgtgaagggcgtggaggtgatagctcctgtgaa ggccggggtgaaaccaccacccccttccaagcagtcccaagcaacaaatacgccgcctctcctctactgcctga ccctgagcgagtgaagtccccaccggtcctacgagcgccaagtgaccacgaggctccaccgtgaaaga ccgtggcctcctaccgagtgctcc |
| | | Cλ Light Chain Constant Region (IGLC2*01) Nucleotide Sequence Version B | 171 | ggccagctaaagctgccccagctgcaccctgtttcctcctccagcgaggagtccagggccaacaaggcca ccctcgtgtgcctgatctcgacttctatcccgggcgtgtgaccgtgaagcgactccagccctgtca agccgggtgagaccaacaccccaagcgactgccaacaacaagtacgcgcctccagctatctctcctct gaccctgagcaagtggaagtccccaccagtcctactcctgtcagtgaccctcaggtgaccaccagctccaccgtgaaag accgctcgcccccaccgagtgctcc |
| | | Cλ Light Chain Constant Region (IGLC1*02) Amino Acid Sequence | 172 | GQPKAAPSVTLFPPSSEELQANKATLVCLISDFYPGAVTVAWKADSSPVKAGVETTTPSK QSNNKYAASSYLSLTPEQWKSHRSYSCQVTHEGSTVEKTVAPTECS |
| Human Cλ constant region | IGLC2*02 or IGLC2*03 | Cλ Light Chain Constant Region (IGLC2*02 or IGLC2*03) Nucleotide Sequence | 173 | ggtcagcccaaggctgcccccctcggtcactctgttccgcccctcctgaggagctcaagcaacaggccac actggtgtgtctcataagtgactgactctacccgggagccgtgaccagtgccctgaaagcagatgcagcagccgtca aggcggagtggagaccaacaacgcccaaacaacgacacaacaagtacgggccagcagctattgagc ctgacgcctgagcgctgaaagtggaagtccaacagctacagcgtgccagtgcagcgtcaccgtgaagggagcaccgtggag aagacagtggccccctacagaatgttca |
| | | Cλ Light Chain Constant Region (IGLC2*02) Amino Acid Sequence | 174 | GQPKAAPSVTLFPPSSEELQANKATLVCLISDFYPGAVTVAWKADSSPVKAGVETTTPSK QSNNKYAASSYLSLTPEQWKSHRSYSCQVTHEGSTVEKTVAPTECS |

-continued

Constant Regions for Antibodies & Fragments of the Invention

| | | SEQ ID NO: | |
|---|---|---|---|
| Human Cλ constant region | IGLC3*01 Cλ Light Chain Constant Region (IGLC3*01) Nucleotide Sequence | 175 | cccaaggctgcccctcggtcactctgttcccaccctcctgaggagcttcaagccaacaaggccacactggt gtgtctcataagtgacttctaccgggagcctgacagttgctgaaggcagatagcagcccgtcaagcg gggtggagaccaccacccctccaaacaaagcaacagcaagcaagtacagcgcagtcagcagctacctgagcctgac gctgagcagtgaagtccacaaagctacagctgccaggtcacgtgcaggtcacatgaaggagcaccgtggagaaga cagttgccctacgaatgtca |
| | Cλ Light Chain Constant Region (IGLC3*01) Amino Acid Sequence | 176 | PKAAPSVTLFPPSSEELQANKATLVCLISDFYPGAVTVAWKADSSPVKAGVETTTPSKQS NNKYAASSYLSLTPEQWKSHKSYSCQVTHEGSTVEKTVAPTECS |
| Human Cλ constant region | IGLC3*02 Cλ Light Chain Constant Region (IGLC3*02) Nucleotide Sequence | 177 | ggtcagcccaaggctgcccctcggtcactctgttcccaccctctgaggagcttcaagccaacaaggccac actggtgtgtctcataagtgacttctaccgggccagtgacagttgctgaaggccagtagcagcccgtca aggcgggggtggagaccaccacccctccaaacaaagcaacagcaagctacagcgcgccagcagctacctgagc ctgacgctgagcagtgaagtccacaaagctacagctgccaggtcacgtgcaggtcacatgaaggagcaccgtggag aagacagtggccctacgaatgtca |
| | Cλ Light Chain Constant Region (IGLC1*02) Amino Acid Sequence | 178 | GQPKAAPSVTLFPPSSEELQANKATLVCLISDFYPGPVTVAWKADSSPVKAGVETTTPSK QSNNKYAASSYLSLTPEQWKSHKSYSCQVTHEGSTVEKTVAPTECS |
| Human Cλ constant region | IGLC3*03 Cλ Light Chain Constant Region (IGLC3*03) Nucleotide Sequence | 179 | ggtcagcccaaggctgcccctcggtcactctgttcccaccctctgaggagcttcaagccaacaaggccac actggtgtgtctcataagtgacttctaccgggagccgtgacagtgcctgaaggccagatagcagcccgtca aggcgggggtggagaccaccacccctccaaacaaagcaacagcaagccgggccagcagctacctgagc ctgacgctgagcagtgaagtccacaaagctacagctgccaggtcacgtgccaggtcacatgaaggagcaccgtggag aagacagtggccctacagaatgtca |
| | Cλ Light Chain Constant Region (IGLC3*03) Amino Acid Sequence | 180 | GQPKAAPSVTLFPPSSEELQANKATLVCLISDFYPGAVTVAWKADSSPVKAGVETTTPSK QSNNKYAASSYLSLTPEQWKSHKSYSCQVTHEGSTVEKTVAPTECS |

-continued

Constant Regions for Antibodies & Fragments of the Invention

| | | SEQ ID NO: | |
|---|---|---|---|
| Human Cλ constant region | Cλ Light Chain Constant Region (IGLC3*04) Nucleotide Sequence IGLC3*04 | 181 | ggtcagcccaaggctgccccctcggtcactcttgttcccgccctcctctgaggagcttcaagccaacaaggccac actggtgtgtctcataagtgacttctcaccggagcgtgacagtgcctgaaggcagatgcagccccgtca agcgggagtggagaaccaccacccctccaaacaaagctacaacaagtacgcggcagctacctgagc ctgacgcctgagcagtggaagtccacagactacagctgccaggtcacgcatgaaggggagcaccgtggag aagacagtggcccctacagaatgttca |
| | Cλ Light Chain Constant Region (IGLC3*04) Amino Acid Sequence | 182 | GQPKAAPSVTLFPPSSEELQANKATLVCLISDFYPGAVTVAWKADSSPVKAGVETTTPSK QSNNKYAASSYLSLTPEQWKSHRSYSCQVTHEGSTVEKTVAPTECS |
| Human Cλ constant region | Cλ Light Chain Constant Region (IGLC6*01) Nucleotide Sequence IGLC6*01 | 183 | ggtcagcccaaggctgccccatcggtcactcttgttcccgccctcctctgaggagcttcaagccaacaaggccgtc actggtgcctgatcagtggaccaccaccccctccaaacagagcaacaacaagtacgctggcagctactgag aacacggagtggagaaccaccacccctccaaagaacaacaaagtacgccaggtcacgcatgaaggggagcaccgtgga gaagacagtggcccctgcagaatgttca |
| | Cλ Light Chain Constant Region (IGLC6*01) Amino Acid Sequence | 184 | GQPKAAPSVTLFPPSSEELQANKATLVCLISDFYPGAVKVAWKADGSPVNTGVETTTPSK QSNNKYAASSYLSLTPEQWKSHRSYSCQVTHEGSTVEKTVAPAECS |
| Human Cλ constant region | Cλ Light Chain Constant Region (IGLC7*01 or IGLC7*02) Nucleotide Sequence IGLC7*01 or IGLC7*02 | 185 | ggtcagcccaaggctgccccatcggtcactctgttccaccctcctctgaggagcttcaagccaacaaggccac actggtgtctcgtaagtgacttctcaccggagcgtgacagtgcctgaaggcagatggcagccccgtca agtgggagtggagaaccaccacccctccaaacaaagctacaacaagtacgccggccagctacctgagc ctgacgcccgagcagtggaagtccacagaagctacagctgccggtcacgcgtggggtcacgcatgaagggagcaccgtggag aagacagtggcccctgcagaatgtctct |
| | Cλ Light Chain Constant Region (IGLC7*01) Amino Acid Sequence | 186 | GQPKAAPSVTLFPPSSEELQANKATLVCLVSDFYPGAVTVAWKADGSPVKVGVETTKPS KQSNNKYAASSYLSLTPEQWKSHRSYSCRVTHEGSTVEKTVAPAECS |

Constant Regions for Antibodies & Fragments of the Invention

| | | SEQ ID NO: | |
|---|---|---|---|
| Human Cλ constant region | IGLC7*03 | | |
| | Cλ Light Chain Constant Region (IGLC7*03) Nucleotide Sequence | 187 | GGTCAGCCCAAGGCTGCCCCCTCGGTCACTCTGTTCCCACCCTCTCTGAGGAGCTTC AAGCCAACAAGGCCACACTGGTCTGTCTCGTAAGTGACTTCAACCCGGGAGCCGTG ACAGTGGCCTGGAAGGCAGATGGCAGCCCGTCAAGGTGGGAGTGGAGACCACCA AACCCTCCAAACAAAGCAACAACAAGTATGCGGCCAGCAGTTACCTGAGCCTGACG CCCGAGCAGTGGAAGTCCCACAGAAGTACAGAGTGCCGGGTCACGCATGAAGGGA GCACCGTGGAGAAGACAGTGGCCCCTGCAGAATGCTCT |
| | Cλ Light Chain Constant Region (IGLC7*03) Amino Acid Sequence | 188 | GQPKAAPSVTLFPPSSEELQANKATLVCLVSDFNPGAVTVAWKADGSPVKVGVETTKPS KQSNNKYAASSYLSLTPEQWKSHRSYSCRVTHEGSTVEKTVAPAECS |

C region amino acid sequence (SEQ ID NO: 3)

ASTKGPSVFPLAPCSRSTSE
STAALGCLVKDYFPEPVTVS
WNSGALTSGVHTFPAVLQSS
GLYSLSSVVTVPSSSLGTKT
YTCNVDHKPSNTKVDKRVES
KYGPPCPPCPAPEFEGGPSV
FLFPPKPKDTLMISRTPEVT
CVVVDVSQEDPEVQFNWYVD
GVEVHNAKTKPREEQFNSTY
RVVSVLTVLHQDWLNGKEYK
CKVSNKGLPSSIEKTISKAK
GQPREPQVYTLPPSQEEMTK
NQVSLTCLVKGFYPSDIAVE
WESNGQPENNYKTTPPVLDS
DGSFFLYSRLTVDKSRWQEG
NVFSCSVMHEALHNHYTQKS
LSLSLGK

C region nucleotide sequence (SEQ ID NO: 4)

gccagcaccaagggcccttccgtgttccccctggccccttgcagcaggagcacctccgaa
tccacagctgccctgggctgtctggtgaaggactactttcccgagcccgtgaccgtgagc
tggaacagcggcgctctgacatccggcgtccacacctttcctgccgtcctgcagtcctcc
ggcctctactcctgtcctccgtggtgaccgtgcctagctcctccctcggcaccaagacc
tacacctgtaacgtggaccacaaaccctccaacaccaaggtggacaaacgggtcgagagc
aagtacggcccccctgccctccttgtcctgcccccgagttcgaaggcggacccagcgtg
ttcctgttccctcctaagcccaaggacaccctcatgatcagccggacacccgaggtgacc
tgcgtggtggtggatgtgagccaggaggaccctgaggtccagttcaactggtatgtggat
ggcgtggaggtgcacaacgccaagacaaagcccgggaagagcagttcaactccacctac
agggtggtcagcgtgctgaccgtgctgcatcaggactggctgaacggcaaggagtacaag
tgcaaggtcagcaataagggactgcccagcagcatcgagaagaccatctccaaggctaaa
ggccagccccgggaacctcaggtgtacaccctgcctcccagccaggaggagatgaccaag
aaccaggtgagcctgacctgcctggtgaagggattctaccttccgacatcgccgtggag
tgggagtccaacggccagcccgagaacaattataagaccaccccctcccgtcctcgacagc
gacggatccttctttctgtactccaggctgaccgtggataagtccaggtggcaggaaggc
aacgtgttcagctgctccgtgatgcacgaggccctgcacaatcactacacccagaagtcc
ctgagcctgtccctgggaaag >PCSK9 reference sequence (SEQ ID NO: 189)

QEDEDGDYEELVLALRSEEDGLAEAPEHGT

TATFHRCAKDPWRLPGTYVVVLKEETHLSQSERTARRLQAQAARRGYLTKILHVFHGLLP

GFLVKMSGDLLELALKLPHVDYIEEDSSVFAQSIPWNLERITPPRYRADEYQPPDGGSLV

EVYLLDTSIQSDHREIEGRVMVTDFENVPEEDGTRFHRQASKCDSHGTHLAGVVSGRDAG

```
VAKGASMRSLRVLNCQGKGTVSGTLIGLEFIRKSQLVQPVGPLVVLLPLAGGYSRVLNAA

CQRLARAGVVLVTAAGNFRDDACLYSPASAPEVITVGATNAQDQPVTLGTLGTNFGRCVD

LFAPGEDIIGASSDCSTCFVSQSGTSQAAAHVAGIAAMMLSAEPELTLAELRQRLIHFSA

KDVINEAWFPEDQRVLTPNLVAALPPSTHGAGWQLFCRTVWSAHSGPTRMATAVARCAPD

EELLSCSSFSRSGKRRGERMEAQGGKLVCRAHNAFGGEGVYAIARCCLLPQANCSVHTAP

PAEASMGTRVHCHQQGHVLTGCSSHWEVEDLGTHKPPVLRPRGQPNQCVGHREASIHASC

CHAPGLECKVKEHGIPAPQEQVTVACEEGWTLTGCSALPGTSHVLGAYAVDNTCVVRSRD

VSTTGSTSEGAVTAVAICCRSRHLAQASQELQ

>PCSK9 variant a                                    (SEQ ID NO: 190)
QEDEDGDYEELVLALRSEEDGLAEAPEHGT

TATFHRCAKDPWRLPGTYVVVLKEETHLSQSERTARRLQAQAARRGYLTKILHVFHGLLP

GFLVKMSGDLLELALKLPHVDYIEEDSSVFAQSIPWNLERITPPRYRADEYQPPDGGSLV

EVYLLDTSIQSDHREIEGRVMVTDFENVPEEDGTRFHRQASKCDSHGTHLAGVVSGRDAG

VAKGASMRSLRVLNCQGKGTVSGTLIGLEFIRKSQLVQPVGPLVVLLPLAGGYSRVLNAA

CQRLARAGVVLVTAAGNFRDDACLYSPASAPEVITVGATNAQDQPVTLGTLGTNFGRCVD

LFAPGEDIIGASSDCSTCFVSQSGTSQAAAHVAGIAAMMLSAEPELTLAELRQRLIHFSA

KDVINEAWFPEDQRVLTPNLVAALPPSTHGAGWQLFCRTVWSAHSGPTRMATAIARCAPD

EELLSCSSFSRSGKRRGERMEAQGGKLVCRAHNAFGGEGVYAIARCCLLPQANCSVHTAP

PAEASMGTRVHCHQQGHVLTGCSSHWEVEDLGTHKPPVLRPRGQPNQCVGHREASIHASC

CHAPGLECKVKEHGIPAPQEQVTVACEEGWTLTGCSALPGTSHVLGAYAVDNTCVVRSRD

VSTTGSTSEEAVTAVAICCRSRHLAQASQELQ

>PCSK9 variant b                                    (SEQ ID NO: 191)
QEDEDGDYEELVLA

LRSEEDGLVEAPEHGTTATFHRCAKDPWRLPGTYVVVLKEETHLSQSERTARRLQAQA

ARRGYLTKILHVFHGLLPGFLVKMSGDLLELALKLPHVDYIEEDSSVFAQSIPWNLER

ITPPRYRADEYQPPDGGSLVEVYLLDTSIQSDHREIEGRVMVTDFENVPEEDGTRFHR

QASKCDSHGTHLAGVVSGRDAGVAKGASMRSLRVLNCQGKGTVSGTLIGLEFIRKSQL

VQPVGPLVVLLPLAGGYSRVLNAACQRLARAGVVLVTAAGNFRDDACLYSPASAPEVI

TVGATNAQDQPVTLGTLGTNFGRCVDLFAPGEDIIGASSDCSTCFVSQSGTSQAAAHV

AGIAAMMLSAEPELTLAELRQRLIHFSAKDVINEAWFPEDQRVLTPNLVAALPPSTHG

AGWQLFCRTVWSAHSGPTRMATAIARCAPDEELLSCSSFSRSGKRRGERMEAQGGKLV

CRAHNAFGGEGVYAIARCCLLPQANCSVHTAPPAEASMGTRVHCHQQGHVLTGCSSHW

EVEDLGTHKPPVLRPRGQPNQCVGHREASIHASCCHAPGLECKVKEHGIPAPQEQVTV

ACEEGWTLTGCSALPGTSHVLGAYAVDNTCVVRSRDVSTTGSTSEEAVTAVAICCRSR

HLAQASQELQ

>PCSK9 GOF mutant                                   (SEQ ID NO: 192)
QEDEDGDYEELVLA

LRSEEDGLAEAPEHGTTATFHRCAKDPWRLPGTYVVVLKEETHLSQSERTARRLQAQA

ARRGYLTKILHVFHGLLPGFLVKMSGDLLELALKLPHVDYIEEDSSVFAQSIPWNLER

ITPPRYRADEYQPPDGGSLVEVYLLDTSIQSDHREIEGRVMVTDFENVPEEDGTRFHR
```

```
QASKCDSHGTHLAGVVSGRDAGVAKGASMRSLRVLNCQGKGTVSGTLIGLEFIRKSQL

VQPVGPLVVLLPLAGGYSRVLNAACQRLARAGVVLVTAAGNFRDDACLYSPASAPEVI

TVGATNAQDQPVTLGTLGTNFGRCVDLFAPGEDIIGASSYCSTCFVSQSGTSQAAAHV

AGIAAMMLSAEPELTLAELRQRLIHFSAKDVINEAWFPEDQRVLTPNLVAALPPSTHG

AGWQLFCRTVWSAHSGPTRMATAVARCAPDEELLSCSSFSRSGKRRGERMEAQGGKLV

CRAHNAFGGEGVYAIARCCLLPQANCSVHTAPPAEASMGTRVHCHQQGHVLTGCSSHW

EVEDLGTHKPPVLRPRGQPNQCVGHREASIHASCCHAPGLECKVKEHGIPAPQEQVTV

ACEEGWTLTGCSALPGTSHVLGAYAVDNTCVVRSRDVSTTGSTSEGAVTAVAICCRSR

HLAQASQELQ

>PCSK9 cyno monkey
                                                    (SEQ ID NO: 193)
QEDEDGDYEELVLALRSEEDGLADAPEHGA

TATFHRCAKDPWRLPGTYVVVLKEETHRSQSERTARRLQAQAARRGYLTKILHVFHHLLP

GFLVKMSGDLLELALKLPHVDYIEEDSSVFAQSIPWNLERITPARYRADEYQPPKGGSLV

EVYLLDTSIQSDHREIEGRVMVTDFESVPEEDGTRFHRQASKCDSHGTHLAGVVSGRDAG

VAKGAGLRSLRVLNCQGKGTVSGTLIGLEFIRKSQLVQPVGPLVVLLPLAGGYSRVFNAA

CQRLARAGVVLVTAAGNFRDDACLYSPASAPEVITVGATNAQDQPVTLGTLGTNFGRCVD

LFAPGEDIIGASSDCSTCFVSRSGTSQAAAHVAGIAAMMLSAEPELTLAELRQRLIHFSA

KDVINEAWFPEDQRVLTPNLVAALPPSTHRAGWQLFCRTVWSAHSGPTRMATAVARCAQD

EELLSCSSFSRSGKRRGERIEAQGGKRVCRAHNAFGGEGVYAIARCCLLPQVNCSVHTAP

PAGASMGTRVHCHQQGHVLTGCSSHWEVEDLGTHKPPVLRPRGQPNQCVGHREASIHASC

CHAPGLECKVKEHGIPAPQEQVIVACEDGWTLTGCSALPGTSHVLGAYAVDNTCVVRSRD

VSTTGSTSEEAVAAVAICCRSRHLVQASQELQ

>PCSK9 mouse
                                                    (SEQ ID NO: 194)
QDEDGDYEELMLALPSQEDGLADEAA

HVATATFRRCSKEAWRLPGTYIVVLMEETQRLQIEQTAHRLQTRAARRGYVIKVLHIFYD

LFPGFLVKMSSDLLGLALKLPHVEYIEEDSFVFAQSIPWNLERIIPAWHQTEEDRSPDGS

SQVEVYLLDTSIQGAHREIEGRVTITDFNSVPEEDGTRFHRQASKCDSHGTHLAGVVSGR

DAGVAKGTSLHSLRVLNCQGKGTVSGTLIGLEFIRKSQLIQPSGPLVVLLPLAGGYSRIL

NAACRHLARTGVVLVAAAGNFRDDACLYSPASAPEVITVGATNAQDQPVTLGTLGTNFGR

CVDLFAPGKDIIGASSDCSTCFMSQSGTSQAAAHVAGIVARMLSREPTLTLAELRQRLIH

FSTKDVINMAWFPEDQQVLTPNLVATLPPSTHETGGQLLCRTVWSAHSGPTRTATATARC

APEEELLSCSSFSRSGRRRGDWIEAIGGQQVCKALNAFGGEGVYAVARCCLVPRANCSIH

NTPAARAGLETHVHCHQKDHVLTGCSFHWEVEDLSVRRQPALRSRRQPGQCVGHQAASVY

ASCCHAPGLECKIKEHGISGPSEQVTACEAGWTLTGCNVLPGASLTLGAYSVDNLCVAR

VHDTARADRTSGEATVAAAICCRSRPSAKASWVQ

Alirocumab HC (human IgG4)
                                                    (SEQ ID NO: 195)
EVQLVESGGGLVQPGGSLRLSCAASGFTFNNYAMNWVRQ

APGKGLDWVSTISGSGGTTNYADSVKGRFIISRDSSKHTLYLQMNSLRAEDTAVYYCAKD

SNWGNFDLWGRGTLVTVSSASTKGPSVFPLAPCSRSTSESTAALGCLVKDYFPEPVTVSW

NSGALTSGVHTFPAVLQSSGLYSLSSVVTVPSSSLGTKTYTCNVDHKPSNTKVDKRVESKYG

PPCPPCPAPEFEGGPSVFLFPPKPKDTLMISRTPEVTCVVVDVSQEDPEVQFNWYVDGVE
```

-continued

VHNAKTKPREEQFNSTYRVVSVLTVLHQDWLNGKEYKCKVSNKGLPSSIEKTISKAKGQPR

EPQVYTLPPSQEEMTKNQVSLTCLVKGFYPSDIAVEWESNGQPENNYKTTPPVLDSDGSFF

LYSRLTVDKSRWQEGNVFSCSVMHEALHNHYTQKSLSLSLGK

Alirocumab LC (human kappa) (SEQ ID NO: 196)
DIVMTQSPDSLAVSLGERATINCKSSQSVLYRSNNRNFLGWY

QQKPGQPPNLLIYWASTRESGVPDRFSGSGSGTDFTLTISSLQAEDVAVYYCQQYYTTPYTF

GQGTKLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC pH-Dependent Antibody HC (human IgG4) (SEQ ID NO: 197)
EMQLVESGGGLVQPGGSLRLSCAASGFTFSSHWMKWV

RQAPGKGLEWVANINQDGSEKYYVDSVKGRFTISRDNAKNSLFLQMNSLRAEDTAVYYCA

RDIVLMVYHMDYYYYGMDVWGQGTTVTVSSASTKGPSVFPLAPCSRSTSESTAALGCLVK

DYFPEPVTVSWNSGALTSGVHTFPAVLQSSGLYSLSSVVTVPSSSLGTKTYTCNVDHKPS

NTKVDKRVESKYGPPCPPCPAPEFEGGPSVFLFPPKPKDTLMISRTPEVTCVVVDVSQED

PEVQFNWYVDGVEVHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQKSLSLSLGK pH-dependent Antibody LC (human kappa) (SEQ ID NO: 198)
DIVMTQSPLSLPVTPGEPASISCRSSQSLHHSNGNNY

LDWYLQKPGQSPQLLIYLGSNRASGVPDRFSGSGSGTDFTLKISRVEAEDVGVYYCMQTL

QTPLTFGGGTKVEIKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLSSPVTKSFNRG

EC

---

The invention claimed is:

1. An antibody or a fragment thereof comprising a binding site which specifically binds to Proprotein Convertase Subtilisin Kexin type 9 (PCSK9), wherein the binding site of the antibody or the fragment thereof comprises:
   (i) a VH domain comprising a CDRH1 comprising SEQ ID NO: 263 or 277, a CDRH2 comprising SEQ ID NO: 267 or 281, and a CDRH3 comprising SEQ ID NO: 271 or 285, respectively; and
   a VL domain comprising a CDRL1 comprising SEQ ID NO: 293 or 307, a CDRL2 comprising SEQ ID NO: 297 or 311, and a CDRL3 comprising SEQ ID NO: 301 or 315, respectively; or
   (ii) a VH domain comprising a CDRH1 comprising SEQ ID NO: 323 or 337, a CDRH2 comprising SEQ ID NO: 327 or 341, and a CDRH3 comprising SEQ ID NO: 331 or 345, respectively; and
   a VL domain comprising a CDRL1 comprising SEQ ID NO: 353 or 367, a CDRL2 comprising SEQ ID NO: 357 or 371, and a CDRL3 comprising SEQ ID NO: 361 or 375, respectively; or
   (iii) a VH domain comprising a CDRH1 comprising SEQ ID NO: 7 or 21, a CDRH2 comprising SEQ ID NO: 11 or 25, and a CDRH3 comprising SEQ ID NO: 15 or 29, respectively; and
   a VL domain comprising a CDRL1 comprising SEQ ID NO: 39 or 53, a CDRL2 comprising SEQ ID NO: 43 or 57, and a CDRL3 comprising SEQ ID NO: 47 or 61, respectively; or
   (iv) a VH domain comprising a CDRH1 comprising SEQ ID NO: 69 or 83, a CDRH2 comprising SEQ ID NO: 73 or 87, and a CDRH3 comprising SEQ ID NO: 77 or 91, respectively; and
   a VL domain comprising a CDRL1 comprising SEQ ID NO: 99 or 113, a CDRL2 comprising SEQ ID NO: 103 or 117, and a CDRL3 comprising SEQ ID NO: 107 or 121, respectively, or
   (v) a VH domain comprising a CDRH1 comprising SEQ ID NO: 203 or 217, a CDRH2 comprising SEQ ID NO: 207 or 221, and a CDRH3 comprising SEQ ID NO: 211 or 225, respectively; and
   a VL domain comprising a CDRL1 comprising SEQ ID NO: 233 or 247, a CDRL2 comprising SEQ ID NO: 237 or 251, and a CDRL3 comprising SEQ ID NO: 241 or 255, respectively.

2. The antibody or the fragment thereof according to claim 1, wherein the binding site comprises:
   (i) a VH domain comprising SEQ ID NO: 259 or an amino acid sequence that is at least 70% identical thereto; and
   a VL domain comprising SEQ ID NO: 289, or an amino acid sequence that is at least 70% identical thereto; or
   (ii) a VH domain comprising SEQ ID NO: 319, or an amino acid sequence that is at least 70% identical thereto; and
   a VL domain comprising SEQ ID NO: 349, or an amino acid sequence that is at least 70% identical thereto; or
   (iii) a VH domain comprising SEQ ID NO: 1, or an amino acid sequence that is at least 70% identical thereto; and
   a VL domain comprising SEQ ID NO: 33, or an amino acid sequence that is at least 70% identical thereto; or
   (iv) a VH domain comprising SEQ ID NO: 65, or an amino acid sequence that is at least 70% identical thereto; and
   a VL domain comprising SEQ ID NO: 95, or an amino acid sequence that is at least 70% identical thereto; or
   (v) a VH domain comprising SEQ ID NO: 199, or an amino acid sequence that is at least 70% identical thereto; and
   a VL domain comprising SEQ ID NO: 229, or an amino acid sequence that is at least 70% identical thereto.

3. The antibody or the fragment thereof according claim 1, wherein the binding site comprises a VH domain comprising SEQ ID NO: 319 and a VL domain comprising SEQ ID NO: 349.

4. A method of treating hypercholesterolemia or hyperlipidemia in a subject, the method comprising:
   administering a therapeutically effective amount of the antibody or the fragment thereof according to claim 1 to the subject.

5. A nucleic acid that encodes the antibody or the fragment thereof according to claim 1.

6. A nucleic acid that encodes the antibody or the fragment thereof according to claim 3.

7. A vector comprising the nucleic acid of claim 5.

8. An isolated host cell comprising the nucleic acid of claim 5.

9. The antibody or the fragment thereof according to claim 1, wherein the binding site comprises a VH domain comprising SEQ ID NO: 259 and a VL domain comprising SEQ ID NO: 289.

* * * * *

SEQUENCE LISTING

<160> NUMBER OF SEQ ID NOS: 378

<210> SEQ ID NO 1
<211> LENGTH: 120
<212> TYPE: PRT
<213> ORGANISM: Homo Sapien

<400> SEQUENCE: 1

Gln Val His Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Tyr Pro Gly Lys Gly Leu Glu Trp Ile
        35                  40                  45

Gly Tyr Ile Ser Tyr Ser Gly Ser Ser Asn Tyr Asn Pro Ser Leu Lys
    50                  55                  60

Arg Arg Val Thr Ile Ser Arg Asp Thr Ser Lys Asn Gln Phe Ser Leu
65                  70                  75                  80

Asn Leu Thr Ser Val Ile Ala Ala Asp Thr Ala Val Tyr Tyr Cys Ala
                85                  90                  95

Arg Asn Leu Met Ile Arg Gly Ala Tyr Gly Met Asp Val Trp Gly Gln

```
                   100                105                110
Gly Thr Thr Val Thr Val Ser Ser
        115                120

<210> SEQ ID NO 2
<211> LENGTH: 360
<212> TYPE: DNA
<213> ORGANISM: Homo Sapien

<400> SEQUENCE: 2
caggtgcacc tgcaggagtc gggcccagga ctggtgaagc cttcggagac cctgtccctc    60
acgtgcactg tctctggtgg ctccatcagt agttactact ggagctggat ccggcagtac   120
ccaggaaagg gactggagtg gattggatat atctcttaca gtgggagcag caattataat   180
ccctccctca gaggcgagt caccatatca cgagacacgt ccaagaacca gttctccctg   240
aatctgacct ctgtaatcgc tgcggacacg gccgtttatt actgtgcgag aaatcttatg   300
attcggggag cctacggcat ggacgtctgg ggccaaggga ccacggtcac cgtctcctca   360

<210> SEQ ID NO 3
<211> LENGTH: 327
<212> TYPE: PRT
<213> ORGANISM: Homo Sapien

<400> SEQUENCE: 3

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
```

```
                    245                 250                 255
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 4
<211> LENGTH: 981
<212> TYPE: DNA
<213> ORGANISM: Homo Sapien

<400> SEQUENCE: 4
gccagcacca agggcccttc cgtgttcccc ctggccccct tgcagcagga cacctccgaa      60
tccacagctg ccctgggctg tctggtgaag gactactttc ccgagcccgt gaccgtgagc     120
tggaacagcg gcgctctgac atccggcgtc cacacctttc ctgccgtcct gcagtcctcc     180
ggcctctact ccctgtcctc cgtggtgacc gtgcctagct cctccctcgg caccaagacc     240
tacacctgta acgtggacca caaaccctcc aacaccaagg tggacaaacg ggtcgagagc     300
aagtacggcc ctccctgccc tcttgtcct gcccccgagt cgaaggcgg acccagcgtg      360 ttcctgttcc ctcctaagcc caaggacacc ctcatgatca gccggacacc cgaggtgacc     420
tgcgtggtgg tggatgtgag ccaggaggac cctgaggtcc agttcaactg gtatgtggat     480
ggcgtggagg tgcacaacgc caagacaaag ccccgggaag agcagttcaa ctccacctac     540
agggtggtca gcgtgctgac cgtgctgcat caggactggc tgaacggcaa ggagtacaag     600
tgcaaggtca gcaataaggg actgcccagc agcatcgaga agaccatctc caaggctaaa     660
ggccagcccc gggaacctca ggtgtacacc ctgcctccca gccaggagga gatgaccaag     720
aaccaggtga gcctgacctg cctggtgaag ggattctacc cttccgacat cgccgtggag     780
tgggagtcca acggccagcc cgagaacaat tataagacca cccctcccgt cctcgacagc     840
gacggatcct tctttctgta ctccaggctg accgtggata gtccaggtg gcaggaaggc     900 aacgtgttca gctgctccgt gatgcacgag gccctgcaca atcactacac ccagaagtcc     960
ctgagcctgt ccctgggaaa g                                               981

<210> SEQ ID NO 5
<211> LENGTH: 25
<212> TYPE: PRT
<213> ORGANISM: Homo Sapien

<400> SEQUENCE: 5

Gln Val His Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 6
<211> LENGTH: 75
<212> TYPE: DNA
<213> ORGANISM: Homo Sapien
```

```
<400> SEQUENCE: 6
caggtgcacc tgcaggagtc gggcccagga ctggtgaagc cttcggagac cctgtccctc    60
acgtgcactg tctct                                                     75

<210> SEQ ID NO 7
<211> LENGTH: 8
<212> TYPE: PRT
<213> ORGANISM: Homo Sapien

<400> SEQUENCE: 7

Gly Gly Ser Ile Ser Ser Tyr Tyr
1               5

<210> SEQ ID NO 8
<211> LENGTH: 24
<212> TYPE: DNA
<213> ORGANISM: Homo Sapien

<400> SEQUENCE: 8
ggtggctcca tcagtagtta ctac                                           24

<210> SEQ ID NO 9
<211> LENGTH: 17
<212> TYPE: PRT
<213> ORGANISM: Homo Sapien

<400> SEQUENCE: 9

Trp Ser Trp Ile Arg Gln Tyr Pro Gly Lys Gly Leu Glu Trp Ile Gly
1               5                   10                  15

Tyr

<210> SEQ ID NO 10
<211> LENGTH: 51
<212> TYPE: DNA
<213> ORGANISM: Homo Sapien

<400> SEQUENCE: 10
tggagctgga tccggcagta cccaggaaag ggactggagt ggattggata t              51

<210> SEQ ID NO 11
<211> LENGTH: 7
<212> TYPE: PRT
<213> ORGANISM: Homo Sapien

<400> SEQUENCE: 11

Ile Ser Tyr Ser Gly Ser Ser
1               5

<210> SEQ ID NO 12
<211> LENGTH: 21
<212> TYPE: DNA
<213> ORGANISM: Homo Sapien

<400> SEQUENCE: 12
atctcttaca gtgggagcag c                                              21

<210> SEQ ID NO 13
<211> LENGTH: 38
<212> TYPE: PRT
<213> ORGANISM: Homo Sapien

<400> SEQUENCE: 13
```

```
Asn Tyr Asn Pro Ser Leu Lys Arg Arg Val Thr Ile Ser Arg Asp Thr
1               5                   10                  15

Ser Lys Asn Gln Phe Ser Leu Asn Leu Thr Ser Val Ile Ala Ala Asp
                20                  25                  30

Thr Ala Val Tyr Tyr Cys
                35

<210> SEQ ID NO 14
<211> LENGTH: 114
<212> TYPE: DNA
<213> ORGANISM: Homo Sapien

<400> SEQUENCE: 14
aattataatc cctccctcaa gaggcgagtc accatatcac gagacacgtc caagaaccag      60
ttctccctga atctgacctc tgtaatcgct gcggacacgg ccgtttatta ctgt          114

<210> SEQ ID NO 15
<211> LENGTH: 14
<212> TYPE: PRT
<213> ORGANISM: Homo Sapien

<400> SEQUENCE: 15

Ala Arg Asn Leu Met Ile Arg Gly Ala Tyr Gly Met Asp Val
1               5                   10

<210> SEQ ID NO 16
<211> LENGTH: 42
<212> TYPE: DNA
<213> ORGANISM: Homo Sapien

<400> SEQUENCE: 16
gcgagaaatc ttatgattcg gggagcctac ggcatggacg tc                        42

<210> SEQ ID NO 17
<211> LENGTH: 11
<212> TYPE: PRT
<213> ORGANISM: Homo Sapien

<400> SEQUENCE: 17

Trp Gly Gln Gly Thr Thr Val Thr Val Ser Ser
1               5                   10

<210> SEQ ID NO 18
<211> LENGTH: 33
<212> TYPE: DNA
<213> ORGANISM: Homo Sapien

<400> SEQUENCE: 18
tggggccaag ggaccacggt caccgtctcc tca                                  33

<210> SEQ ID NO 19
<211> LENGTH: 30
<212> TYPE: PRT
<213> ORGANISM: Homo Sapien

<400> SEQUENCE: 19

Gln Val His Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
                20                  25                  30

<210> SEQ ID NO 20
```

```
<211> LENGTH: 90
<212> TYPE: DNA
<213> ORGANISM: Homo Sapien

<400> SEQUENCE: 20
caggtgcacc tgcaggagtc gggcccagga ctggtgaagc cttcggagac cctgtccctc    60
acgtgcactg tctctggtgg ctccatcagt                                     90

<210> SEQ ID NO 21
<211> LENGTH: 5
<212> TYPE: PRT
<213> ORGANISM: Homo Sapien

<400> SEQUENCE: 21

Ser Tyr Tyr Trp Ser
1               5

<210> SEQ ID NO 22
<211> LENGTH: 15
<212> TYPE: DNA
<213> ORGANISM: Homo Sapien

<400> SEQUENCE: 22
agttactact ggagc                                                     15

<210> SEQ ID NO 23
<211> LENGTH: 14
<212> TYPE: PRT
<213> ORGANISM: Homo Sapien

<400> SEQUENCE: 23

Trp Ile Arg Gln Tyr Pro Gly Lys Gly Leu Glu Trp Ile Gly
1               5                   10

<210> SEQ ID NO 24
<211> LENGTH: 42
<212> TYPE: DNA
<213> ORGANISM: Homo Sapien

<400> SEQUENCE: 24
tggatccggc agtacccagg aaagggactg gagtggattg ga                       42

<210> SEQ ID NO 25
<211> LENGTH: 16
<212> TYPE: PRT
<213> ORGANISM: Homo Sapien

<400> SEQUENCE: 25

Tyr Ile Ser Tyr Ser Gly Ser Ser Asn Tyr Asn Pro Ser Leu Lys Arg
1               5                   10                  15

<210> SEQ ID NO 26
<211> LENGTH: 48
<212> TYPE: DNA
<213> ORGANISM: Homo Sapien

<400> SEQUENCE: 26
tatatctctt acagtgggag cagcaattat aatccctccc tcaagagg                 48

<210> SEQ ID NO 27
<211> LENGTH: 32
<212> TYPE: PRT
<213> ORGANISM: Homo Sapien
```

```
<400> SEQUENCE: 27

Arg Val Thr Ile Ser Arg Asp Thr Ser Lys Asn Gln Phe Ser Leu Asn
1               5                   10                  15

Leu Thr Ser Val Ile Ala Ala Asp Thr Ala Val Tyr Tyr Cys Ala Arg
                20                  25                  30

<210> SEQ ID NO 28
<211> LENGTH: 96
<212> TYPE: DNA
<213> ORGANISM: Homo Sapien

<400> SEQUENCE: 28
cgagtcacca tatcacgaga cacgtccaag aaccagttct ccctgaatct gacctctgta      60
atcgctgcgg acacggccgt ttattactgt gcgaga                               96

<210> SEQ ID NO 29
<211> LENGTH: 12
<212> TYPE: PRT
<213> ORGANISM: Homo Sapien

<400> SEQUENCE: 29

Asn Leu Met Ile Arg Gly Ala Tyr Gly Met Asp Val
1               5                   10

<210> SEQ ID NO 30
<211> LENGTH: 36
<212> TYPE: DNA
<213> ORGANISM: Homo Sapien

<400> SEQUENCE: 30
aatcttatga ttcggggagc ctacggcatg gacgtc                               36

<210> SEQ ID NO 31
<211> LENGTH: 11
<212> TYPE: PRT
<213> ORGANISM: Homo Sapien

<400> SEQUENCE: 31

Trp Gly Gln Gly Thr Thr Val Thr Val Ser Ser
1               5                   10

<210> SEQ ID NO 32
<211> LENGTH: 33
<212> TYPE: DNA
<213> ORGANISM: Homo Sapien

<400> SEQUENCE: 32
tggggccaag ggaccacggt caccgtctcc tca                                  33

<210> SEQ ID NO 33
<211> LENGTH: 112
<212> TYPE: PRT
<213> ORGANISM: Homo Sapien

<400> SEQUENCE: 33

Asp Thr Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Ala Gly Gln Ser
            35                  40                  45
```

```
Pro Gln Leu Leu Ile Tyr Leu Gly Ser Asn Arg Ala Ser Gly Val Pro
    50                  55                  60
Asp Arg Phe Ser Gly Ser Val Ser Gly Thr Asp Phe Thr Leu Lys Ile
65                  70                  75                  80
Ser Arg Val Glu Ala Glu Asp Val Gly Ile Tyr Tyr Cys Met Gln Ala
                85                  90                  95
Leu Gln Thr Pro Phe Thr Phe Gly Pro Gly Thr Lys Val Asp Ile Lys
            100                 105                 110
```

<210> SEQ ID NO 34
<211> LENGTH: 336
<212> TYPE: DNA
<213> ORGANISM: Homo Sapien

<400> SEQUENCE: 34

```
gatactgtga tgactcagtc tccactctcc ctgcccgtca cccctggaga gccggcctcc     60
atctcctgca ggtctagtca gagcctcctg catagtaatg gatacaatta tttggattgg    120
tacctgcaga aggcaggaca gtctccacaa ctcctgatct atttgggttc taatcgggcc    180
tccggggtcc ctgacaggtt cagtggcagt gtatcaggca cagatttcac actgaaaatc    240
agcagagtgg aggctgagga tgttggaatt tattactgca tgcaagctct acaaactcca    300
ttcactttcg gccctgggac caaagtggat atcaaa                              336
```

<210> SEQ ID NO 35
<211> LENGTH: 107
<212> TYPE: PRT
<213> ORGANISM: Homo Sapien

<400> SEQUENCE: 35

```
Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

<210> SEQ ID NO 36
<211> LENGTH: 321
<212> TYPE: DNA
<213> ORGANISM: Homo Sapien

<400> SEQUENCE: 36

```
cgtacggtgg ccgctccctc cgtgttcatc ttcccacctt ccgacgagca gctgaagtcc     60
ggcaccgctt ctgtcgtgtg cctgctgaac aacttctacc ccgcgaggc caaggtgcag    120
tggaaggtgg acaacgccct gcagtccggc aactcccagg aatccgtgac cgagcaggac    180
tccaaggaca gcacctactc cctgtcctcc accctgaccc tgtccaaggc cgactacgag    240
aagcacaagg tgtacgcctg cgaagtgacc caccagggcc tgtctagccc cgtgaccaag    300
```

```
tctttcaacc ggggcgagtg t                                              321
```

<210> SEQ ID NO 37
<211> LENGTH: 26
<212> TYPE: PRT
<213> ORGANISM: Homo Sapien

<400> SEQUENCE: 37

```
Asp Thr Val Met Thr Gln Ser Pro Leu Ser Leu Pro Val Thr Pro Gly
1               5                   10                  15

Glu Pro Ala Ser Ile Ser Cys Arg Ser Ser
            20                  25
```

<210> SEQ ID NO 38
<211> LENGTH: 78
<212> TYPE: DNA
<213> ORGANISM: Homo Sapien

<400> SEQUENCE: 38

```
gatactgtga tgactcagtc tccactctcc ctgcccgtca cccctggaga gccggcctcc   60
atctcctgca ggtctagt                                                 78
```

<210> SEQ ID NO 39
<211> LENGTH: 11
<212> TYPE: PRT
<213> ORGANISM: Homo Sapien

<400> SEQUENCE: 39

```
Gln Ser Leu Leu His Ser Asn Gly Tyr Asn Tyr
1               5                   10
```

<210> SEQ ID NO 40
<211> LENGTH: 33
<212> TYPE: DNA
<213> ORGANISM: Homo Sapien

<400> SEQUENCE: 40

```
cagagcctcc tgcatagtaa tggatacaat tat                                33
```

<210> SEQ ID NO 41
<211> LENGTH: 17
<212> TYPE: PRT
<213> ORGANISM: Homo Sapien

<400> SEQUENCE: 41

```
Leu Asp Trp Tyr Leu Gln Lys Ala Gly Gln Ser Pro Gln Leu Leu Ile
1               5                   10                  15

Tyr
```

<210> SEQ ID NO 42
<211> LENGTH: 51
<212> TYPE: DNA
<213> ORGANISM: Homo Sapien

<400> SEQUENCE: 42

```
ttggattggt acctgcagaa ggcaggacag tctccacaac tcctgatcta t             51
```

<210> SEQ ID NO 43
<211> LENGTH: 3
<212> TYPE: PRT
<213> ORGANISM: Homo Sapien

<400> SEQUENCE: 43

Leu Gly Ser
1

<210> SEQ ID NO 44
<211> LENGTH: 9
<212> TYPE: DNA
<213> ORGANISM: Homo Sapien

<400> SEQUENCE: 44 ttgggttct                                                                   9

<210> SEQ ID NO 45
<211> LENGTH: 36
<212> TYPE: PRT
<213> ORGANISM: Homo Sapien

<400> SEQUENCE: 45

Asn Arg Ala Ser Gly Val Pro Asp Arg Phe Ser Gly Ser Val Ser Gly
1               5                   10                  15

Thr Asp Phe Thr Leu Lys Ile Ser Arg Val Glu Ala Glu Asp Val Gly
            20                  25                  30

Ile Tyr Tyr Cys
        35

<210> SEQ ID NO 46
<211> LENGTH: 108
<212> TYPE: DNA
<213> ORGANISM: Homo Sapien

<400> SEQUENCE: 46
aatcgggcct ccggggtccc tgacaggttc agtggcagtg tatcaggcac agatttcaca    60
ctgaaaatca gcagagtgga ggctgaggat gttgggattt attactgc               108

<210> SEQ ID NO 47
<211> LENGTH: 9
<212> TYPE: PRT
<213> ORGANISM: Homo Sapien

<400> SEQUENCE: 47

Met Gln Ala Leu Gln Thr Pro Phe Thr
1               5

<210> SEQ ID NO 48
<211> LENGTH: 27
<212> TYPE: DNA
<213> ORGANISM: Homo Sapien

<400> SEQUENCE: 48
atgcaagctc tacaaactcc attcact                                       27

<210> SEQ ID NO 49
<211> LENGTH: 10
<212> TYPE: PRT
<213> ORGANISM: Homo Sapien

<400> SEQUENCE: 49

Phe Gly Pro Gly Thr Lys Val Asp Ile Lys
1               5                   10

<210> SEQ ID NO 50
<211> LENGTH: 30
<212> TYPE: DNA

-continued

```
<213> ORGANISM: Homo Sapien

<400> SEQUENCE: 50
ttcggccctg ggaccaaagt ggatatcaaa                                      30

<210> SEQ ID NO 51
<211> LENGTH: 23
<212> TYPE: PRT
<213> ORGANISM: Homo Sapien

<400> SEQUENCE: 51

Asp Thr Val Met Thr Gln Ser Pro Leu Ser Leu Pro Val Thr Pro Gly
1               5                   10                  15

Glu Pro Ala Ser Ile Ser Cys
            20

<210> SEQ ID NO 52
<211> LENGTH: 69
<212> TYPE: DNA
<213> ORGANISM: Homo Sapien

<400> SEQUENCE: 52
gatactgtga tgactcagtc tccactctcc ctgcccgtca cccctggaga gccggcctcc     60
atctcctgc                                                             69

<210> SEQ ID NO 53
<211> LENGTH: 16
<212> TYPE: PRT
<213> ORGANISM: Homo Sapien

<400> SEQUENCE: 53

Arg Ser Ser Gln Ser Leu Leu His Ser Asn Gly Tyr Asn Tyr Leu Asp
1               5                   10                  15

<210> SEQ ID NO 54
<211> LENGTH: 48
<212> TYPE: DNA
<213> ORGANISM: Homo Sapien

<400> SEQUENCE: 54
aggtctagtc agagcctcct gcatagtaat ggatacaatt atttggat                  48

<210> SEQ ID NO 55
<211> LENGTH: 15
<212> TYPE: PRT
<213> ORGANISM: Homo Sapien

<400> SEQUENCE: 55

Trp Tyr Leu Gln Lys Ala Gly Gln Ser Pro Gln Leu Leu Ile Tyr
1               5                   10                  15

<210> SEQ ID NO 56
<211> LENGTH: 45
<212> TYPE: DNA
<213> ORGANISM: Homo Sapien

<400> SEQUENCE: 56
tggtacctgc agaaggcagg acagtctcca caactcctga tctat                     45

<210> SEQ ID NO 57
<211> LENGTH: 7
<212> TYPE: PRT
<213> ORGANISM: Homo Sapien
```

<400> SEQUENCE: 57

Leu Gly Ser Asn Arg Ala Ser
1               5

<210> SEQ ID NO 58
<211> LENGTH: 21
<212> TYPE: DNA
<213> ORGANISM: Homo Sapien

<400> SEQUENCE: 58
ttgggttcta atcgggcctc c                                              21

<210> SEQ ID NO 59
<211> LENGTH: 32
<212> TYPE: PRT
<213> ORGANISM: Homo Sapien

<400> SEQUENCE: 59

Gly Val Pro Asp Arg Phe Ser Gly Ser Val Ser Gly Thr Asp Phe Thr
1               5                   10                  15

Leu Lys Ile Ser Arg Val Glu Ala Glu Asp Val Gly Ile Tyr Tyr Cys
            20                  25                  30

<210> SEQ ID NO 60
<211> LENGTH: 96
<212> TYPE: DNA
<213> ORGANISM: Homo Sapien

<400> SEQUENCE: 60
ggggtccctg acaggttcag tggcagtgta tcaggcacag atttcacact gaaaatcagc    60
agagtggagg ctgaggatgt tgggatttat tactgc                              96

<210> SEQ ID NO 61
<211> LENGTH: 9
<212> TYPE: PRT
<213> ORGANISM: Homo Sapien

<400> SEQUENCE: 61

Met Gln Ala Leu Gln Thr Pro Phe Thr
1               5

<210> SEQ ID NO 62
<211> LENGTH: 27
<212> TYPE: DNA
<213> ORGANISM: Homo Sapien

<400> SEQUENCE: 62
atgcaagctc tacaaactcc attcact                                        27

<210> SEQ ID NO 63
<211> LENGTH: 10
<212> TYPE: PRT
<213> ORGANISM: Homo Sapien

<400> SEQUENCE: 63

Phe Gly Pro Gly Thr Lys Val Asp Ile Lys
1               5                   10

<210> SEQ ID NO 64
<211> LENGTH: 30
<212> TYPE: DNA
<213> ORGANISM: Homo Sapien

<400> SEQUENCE: 64
ttcggccctg ggaccaaagt ggatatcaaa                                          30

<210> SEQ ID NO 65
<211> LENGTH: 127
<212> TYPE: PRT
<213> ORGANISM: Homo Sapien

<400> SEQUENCE: 65

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ala Asp Tyr
            20                  25                  30

Val Met His Trp Val Arg Gln Thr Pro Gly Lys Gly Leu Glu Trp Val
        35                  40                  45

Ser Gly Ile Ser Trp Asn Ser Tyr Ser Ile Asn Tyr Ala Asp Ser Val
    50                  55                  60

Lys Gly Arg Phe Thr Ile Ser Arg Asp Asn Ala Gln Asn Ser Leu Tyr
65                  70                  75                  80

Leu Gln Met Asn Ser Leu Arg Ala Glu Asp Thr Ala Leu Tyr Phe Cys
                85                  90                  95

Ala Lys Asp Ile Thr Tyr Asp Leu Leu Thr Gly Tyr Asn Tyr Asn Tyr
            100                 105                 110

Gly Leu Asp Val Trp Gly Gln Gly Thr Thr Val Thr Val Ser Ser
        115                 120                 125

<210> SEQ ID NO 66
<211> LENGTH: 381
<212> TYPE: DNA
<213> ORGANISM: Homo Sapien

<400> SEQUENCE: 66
gaagtgcagc tggtagagtc tgggggaggc ttggtacagc ctggcaggtc cctgagactc      60
tcctgtacag cctctggatt cacctttgct gattatgtca tgcactgggt ccggcaaact     120
ccagggaagg gcctggagtg gtctcaggt attagttgga atagttatag tataaattat      180
gcggactctg tgaagggccg attcaccatc tccagagaca acgcccagaa ctccctgtat     240
ctgcaaatga acagtctgag agctgaggac acggccttgt attttgtgc aaaagatata     300 acttacgatc ttttgactgg ttataactac aactacggtt tagacgtctg ggggccaaggg     360 accacggtca ccgtctcctc a                                                381

<210> SEQ ID NO 67
<211> LENGTH: 25
<212> TYPE: PRT
<213> ORGANISM: Homo Sapien

<400> SEQUENCE: 67

Glu Val Gln Leu Val Glu Ser Gly Gly Gly Leu Val Gln Pro Gly Arg
1               5                   10                  15

Ser Leu Arg Leu Ser Cys Thr Ala Ser
            20                  25

<210> SEQ ID NO 68
<211> LENGTH: 75
<212> TYPE: DNA
<213> ORGANISM: Homo Sapien

<400> SEQUENCE: 68
gaagtgcagc tggtagagtc tgggggaggc ttggtacagc ctggcaggtc cctgagactc    60
tcctgtacag cctct                                                     75

<210> SEQ ID NO 69
<211> LENGTH: 8
<212> TYPE: PRT
<213> ORGANISM: Homo Sapien

<400> SEQUENCE: 69

Gly Phe Thr Phe Ala Asp Tyr Val
1               5

<210> SEQ ID NO 70
<211> LENGTH: 24
<212> TYPE: DNA
<213> ORGANISM: Homo Sapien

<400> SEQUENCE: 70
ggattcacct ttgctgatta tgtc                                           24

<210> SEQ ID NO 71
<211> LENGTH: 17
<212> TYPE: PRT
<213> ORGANISM: Homo Sapien

<400> SEQUENCE: 71

Met His Trp Val Arg Gln Thr Pro Gly Lys Gly Leu Glu Trp Val Ser
1               5                   10                  15

Gly

<210> SEQ ID NO 72
<211> LENGTH: 51
<212> TYPE: DNA
<213> ORGANISM: Homo Sapien

<400> SEQUENCE: 72
atgcactggg tccggcaaac tccagggaag ggcctggagt gggtctcagg t             51

<210> SEQ ID NO 73
<211> LENGTH: 8
<212> TYPE: PRT
<213> ORGANISM: Homo Sapien

<400> SEQUENCE: 73

Ile Ser Trp Asn Ser Tyr Ser Ile
1               5

<210> SEQ ID NO 74
<211> LENGTH: 24
<212> TYPE: DNA
<213> ORGANISM: Homo Sapien

<400> SEQUENCE: 74
attagttgga atagttatag tata                                           24

<210> SEQ ID NO 75
<211> LENGTH: 38
<212> TYPE: PRT
<213> ORGANISM: Homo Sapien

<400> SEQUENCE: 75

Asn Tyr Ala Asp Ser Val Lys Gly Arg Phe Thr Ile Ser Arg Asp Asn
1               5                   10                  15

Ala Gln Asn Ser Leu Tyr Leu Gln Met Asn Ser Leu Arg Ala Glu Asp
            20                  25                  30

Thr Ala Leu Tyr Phe Cys
            35

<210> SEQ ID NO 76
<211> LENGTH: 114
<212> TYPE: DNA
<213> ORGANISM: Homo Sapien

<400> SEQUENCE: 76
aattatgcgg actctgtgaa gggccgattc accatctcca gagacaacgc ccagaactcc    60
ctgtatctgc aaatgaacag tctgagagct gaggacacgg ccttgtattt ttgt         114

<210> SEQ ID NO 77
<211> LENGTH: 20
<212> TYPE: PRT
<213> ORGANISM: Homo Sapien

<400> SEQUENCE: 77

Ala Lys Asp Ile Thr Tyr Asp Leu Leu Thr Gly Tyr Asn Tyr Asn Tyr
1               5                   10                  15

Gly Leu Asp Val
            20

<210> SEQ ID NO 78
<211> LENGTH: 60
<212> TYPE: DNA
<213> ORGANISM: Homo Sapien

<400> SEQUENCE: 78
gcaaaagata taacttacga tcttttgact ggttataact acaactacgg tttagacgtc    60

<210> SEQ ID NO 79
<211> LENGTH: 11
<212> TYPE: PRT
<213> ORGANISM: Homo Sapien

<400> SEQUENCE: 79

Trp Gly Gln Gly Thr Thr Val Thr Val Ser Ser
1               5                   10

<210> SEQ ID NO 80
<211> LENGTH: 33
<212> TYPE: DNA
<213> ORGANISM: Homo Sapien

<400> SEQUENCE: 80
tggggccaag ggaccacggt caccgtctcc tca                                 33

<210> SEQ ID NO 81
<211> LENGTH: 30
<212> TYPE: PRT
<213> ORGANISM: Homo Sapien

<400> SEQUENCE: 81

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ala
            20                  25                  30

<210> SEQ ID NO 82
<211> LENGTH: 90
<212> TYPE: DNA
<213> ORGANISM: Homo Sapien

<400> SEQUENCE: 82
gaagtgcagc tggtagagtc tgggggaggc ttggtacagc ctggcaggtc cctgagactc    60
tcctgtacag cctctggatt cacctttgct                                    90

<210> SEQ ID NO 83
<211> LENGTH: 5
<212> TYPE: PRT
<213> ORGANISM: Homo Sapien

<400> SEQUENCE: 83

Asp Tyr Val Met His
1               5

<210> SEQ ID NO 84
<211> LENGTH: 15
<212> TYPE: DNA
<213> ORGANISM: Homo Sapien

<400> SEQUENCE: 84
gattatgtca tgcac                                                    15

<210> SEQ ID NO 85
<211> LENGTH: 14
<212> TYPE: PRT
<213> ORGANISM: Homo Sapien

<400> SEQUENCE: 85

Trp Val Arg Gln Thr Pro Gly Lys Gly Leu Glu Trp Val Ser
1               5                   10

<210> SEQ ID NO 86
<211> LENGTH: 42
<212> TYPE: DNA
<213> ORGANISM: Homo Sapien

<400> SEQUENCE: 86
tgggtccggc aaactccagg gaagggcctg gagtgggtct ca                      42

<210> SEQ ID NO 87
<211> LENGTH: 17
<212> TYPE: PRT
<213> ORGANISM: Homo Sapien

<400> SEQUENCE: 87

Gly Ile Ser Trp Asn Ser Tyr Ser Ile Asn Tyr Ala Asp Ser Val Lys
1               5                   10                  15

Gly

<210> SEQ ID NO 88
<211> LENGTH: 51
<212> TYPE: DNA
<213> ORGANISM: Homo Sapien

<400> SEQUENCE: 88
ggtattagtt ggaatagtta tagtataaat tatgcggact ctgtgaaggg c             51

```
<210> SEQ ID NO 89
<211> LENGTH: 32
<212> TYPE: PRT
<213> ORGANISM: Homo Sapien

<400> SEQUENCE: 89

Arg Phe Thr Ile Ser Arg Asp Asn Ala Gln Asn Ser Leu Tyr Leu Gln
1               5                   10                  15

Met Asn Ser Leu Arg Ala Glu Asp Thr Ala Leu Tyr Phe Cys Ala Lys
            20                  25                  30

<210> SEQ ID NO 90
<211> LENGTH: 96
<212> TYPE: DNA
<213> ORGANISM: Homo Sapien

<400> SEQUENCE: 90
cgattcacca tctccagaga caacgcccag aactccctgt atctgcaaat gaacagtctg      60
agagctgagg acacggcctt gtattttgt gcaaaa                                 96

<210> SEQ ID NO 91
<211> LENGTH: 18
<212> TYPE: PRT
<213> ORGANISM: Homo Sapien

<400> SEQUENCE: 91

Asp Ile Thr Tyr Asp Leu Leu Thr Gly Tyr Asn Tyr Asn Tyr Gly Leu
1               5                   10                  15

Asp Val

<210> SEQ ID NO 92
<211> LENGTH: 54
<212> TYPE: DNA
<213> ORGANISM: Homo Sapien

<400> SEQUENCE: 92
gatataactt acgatctttt gactggttat aactacaact acggtttaga cgtc            54

<210> SEQ ID NO 93
<211> LENGTH: 11
<212> TYPE: PRT
<213> ORGANISM: Homo Sapien

<400> SEQUENCE: 93

Trp Gly Gln Gly Thr Thr Val Thr Val Ser Ser
1               5                   10

<210> SEQ ID NO 94
<211> LENGTH: 33
<212> TYPE: DNA
<213> ORGANISM: Homo Sapien

<400> SEQUENCE: 94
tggggccaag ggaccacggt caccgtctcc tca                                   33

<210> SEQ ID NO 95
<211> LENGTH: 112
<212> TYPE: PRT
<213> ORGANISM: Homo Sapien

<400> SEQUENCE: 95

Asp Ile Val Met Thr Gln Thr Pro Leu Ser Leu Ser Val Thr Pro Gly
1               5                   10                  15
```

```
Gln Pro Ala Ser Ile Ser Cys Arg Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Ser
                85                  90                  95

Ile Gln Leu Pro Leu Thr Phe Gly Gly Gly Thr Lys Val Glu Ile Lys
            100                 105                 110

<210> SEQ ID NO 96
<211> LENGTH: 336
<212> TYPE: DNA
<213> ORGANISM: Homo Sapien

<400> SEQUENCE: 96
gatattgtga tgacccagac tccactctct ctgtccgtca cccctggaca gccggcctcc      60
atctcctgca ggtctagtca gagcctccta catagtgatg gaaagaccta tttgtattgg     120
tacctgcaga agcccggcca gcctccacag ctcctgatct atgaagtttc caaccgtttc     180
tctggagtgc cagataggtt cagtggcagc gggtcaggga cagatttcac actgaagatc     240
agccgggtgg aggctgaaga tgttggcctt tattactgca tgcaaagtat acagcttccg     300
ctcactttcg gcggagggac caaggtagag atcaaa                               336

<210> SEQ ID NO 97
<211> LENGTH: 26
<212> TYPE: PRT
<213> ORGANISM: Homo Sapien

<400> SEQUENCE: 97

Asp Ile Val Met Thr Gln Thr Pro Leu Ser Leu Ser Val Thr Pro Gly
1               5                   10                  15

Gln Pro Ala Ser Ile Ser Cys Arg Ser Ser
            20                  25

<210> SEQ ID NO 98
<211> LENGTH: 78
<212> TYPE: DNA
<213> ORGANISM: Homo Sapien

<400> SEQUENCE: 98
gatattgtga tgacccagac tccactctct ctgtccgtca cccctggaca gccggcctcc      60
atctcctgca ggtctagt                                                    78

<210> SEQ ID NO 99
<211> LENGTH: 11
<212> TYPE: PRT
<213> ORGANISM: Homo Sapien

<400> SEQUENCE: 99

Gln Ser Leu Leu His Ser Asp Gly Lys Thr Tyr
1               5                   10

<210> SEQ ID NO 100
<211> LENGTH: 33
```

<212> TYPE: DNA
<213> ORGANISM: Homo Sapien

<400> SEQUENCE: 100
cagagcctcc tacatagtga tggaaagacc tat                              33

<210> SEQ ID NO 101
<211> LENGTH: 17
<212> TYPE: PRT
<213> ORGANISM: Homo Sapien

<400> SEQUENCE: 101

Leu Tyr Trp Tyr Leu Gln Lys Pro Gly Gln Pro Pro Gln Leu Leu Ile
1               5                   10                  15

Tyr

<210> SEQ ID NO 102
<211> LENGTH: 51
<212> TYPE: DNA
<213> ORGANISM: Homo Sapien

<400> SEQUENCE: 102
ttgtattggt acctgcagaa gcccggccag cctccacagc tcctgatcta t           51

<210> SEQ ID NO 103
<211> LENGTH: 3
<212> TYPE: PRT
<213> ORGANISM: Homo Sapien

<400> SEQUENCE: 103

Glu Val Ser
1

<210> SEQ ID NO 104
<211> LENGTH: 9
<212> TYPE: DNA
<213> ORGANISM: Homo Sapien

<400> SEQUENCE: 104 gaagtttcc                                                          9

<210> SEQ ID NO 105
<211> LENGTH: 36
<212> TYPE: PRT
<213> ORGANISM: Homo Sapien

<400> SEQUENCE: 105

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Leu Tyr Tyr Cys
            35

<210> SEQ ID NO 106
<211> LENGTH: 108
<212> TYPE: DNA
<213> ORGANISM: Homo Sapien

<400> SEQUENCE: 106
aaccgtttct ctggagtgcc agataggttc agtggcagcg ggtcagggac agatttcaca    60
ctgaagatca gccgggtgga ggctgaagat gttggccttt attactgc                108

-continued

<210> SEQ ID NO 107
<211> LENGTH: 9
<212> TYPE: PRT
<213> ORGANISM: Homo Sapien

<400> SEQUENCE: 107

Met Gln Ser Ile Gln Leu Pro Leu Thr
1               5

<210> SEQ ID NO 108
<211> LENGTH: 27
<212> TYPE: DNA
<213> ORGANISM: Homo Sapien

<400> SEQUENCE: 108
atgcaaagta tacagcttcc gctcact                                           27

<210> SEQ ID NO 109
<211> LENGTH: 10
<212> TYPE: PRT
<213> ORGANISM: Homo Sapien

<400> SEQUENCE: 109

Phe Gly Gly Gly Thr Lys Val Glu Ile Lys
1               5                   10

<210> SEQ ID NO 110
<211> LENGTH: 30
<212> TYPE: DNA
<213> ORGANISM: Homo Sapien

<400> SEQUENCE: 110
ttcggcggag ggaccaaggt agagatcaaa                                        30

<210> SEQ ID NO 111
<211> LENGTH: 23
<212> TYPE: PRT
<213> ORGANISM: Homo Sapien

<400> SEQUENCE: 111

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 112
<211> LENGTH: 69
<212> TYPE: DNA
<213> ORGANISM: Homo Sapien

<400> SEQUENCE: 112
gatattgtga tgacccagac tccactctct ctgtccgtca cccctggaca gccggcctcc      60
atctcctgc                                                              69

<210> SEQ ID NO 113
<211> LENGTH: 16
<212> TYPE: PRT
<213> ORGANISM: Homo Sapien

<400> SEQUENCE: 113

Arg Ser Ser Gln Ser Leu Leu His Ser Asp Gly Lys Thr Tyr Leu Tyr
1               5                   10                  15

<210> SEQ ID NO 114
<211> LENGTH: 48
<212> TYPE: DNA
<213> ORGANISM: Homo Sapien

<400> SEQUENCE: 114
aggtctagtc agagcctcct acatagtgat ggaaagacct atttgtat            48

<210> SEQ ID NO 115
<211> LENGTH: 15
<212> TYPE: PRT
<213> ORGANISM: Homo Sapien

<400> SEQUENCE: 115

Trp Tyr Leu Gln Lys Pro Gly Gln Pro Pro Gln Leu Leu Ile Tyr
1               5                   10                  15

<210> SEQ ID NO 116
<211> LENGTH: 45
<212> TYPE: DNA
<213> ORGANISM: Homo Sapien

<400> SEQUENCE: 116
tggtacctgc agaagcccgg ccagcctcca cagctcctga tctat                45

<210> SEQ ID NO 117
<211> LENGTH: 7
<212> TYPE: PRT
<213> ORGANISM: Homo Sapien

<400> SEQUENCE: 117

Glu Val Ser Asn Arg Phe Ser
1               5

<210> SEQ ID NO 118
<211> LENGTH: 21
<212> TYPE: DNA
<213> ORGANISM: Homo Sapien

<400> SEQUENCE: 118
gaagtttcca accgtttctc t                                          21

<210> SEQ ID NO 119
<211> LENGTH: 32
<212> TYPE: PRT
<213> ORGANISM: Homo Sapien

<400> SEQUENCE: 119

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Leu Tyr Tyr Cys
            20                  25                  30

<210> SEQ ID NO 120
<211> LENGTH: 96
<212> TYPE: DNA
<213> ORGANISM: Homo Sapien

<400> SEQUENCE: 120
ggagtgccag ataggttcag tggcagcggg tcagggacag atttcacact gaagatcagc    60
cgggtggagg ctgaagatgt tggcctttat tactgc                              96

```
<210> SEQ ID NO 121
<211> LENGTH: 9
<212> TYPE: PRT
<213> ORGANISM: Homo Sapien

<400> SEQUENCE: 121

Met Gln Ser Ile Gln Leu Pro Leu Thr
1               5

<210> SEQ ID NO 122
<211> LENGTH: 27
<212> TYPE: DNA
<213> ORGANISM: Homo Sapien

<400> SEQUENCE: 122
atgcaaagta tacagcttcc gctcact                                          27

<210> SEQ ID NO 123
<211> LENGTH: 10
<212> TYPE: PRT
<213> ORGANISM: Homo Sapien

<400> SEQUENCE: 123

Phe Gly Gly Gly Thr Lys Val Glu Ile Lys
1               5                   10

<210> SEQ ID NO 124
<211> LENGTH: 30
<212> TYPE: DNA
<213> ORGANISM: Homo Sapien

<400> SEQUENCE: 124
ttcggcggag ggaccaaggt agagatcaaa                                       30

<210> SEQ ID NO 125
<211> LENGTH: 990
<212> TYPE: DNA
<213> ORGANISM: Homo Sapien

<400> SEQUENCE: 125
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcggggagga gcagtacaac    540 agcacgtacc gggtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
```

```
cagcagggga acgtcttctc atgctccgtg atgcatgagg ctctgcacaa ccactacacg        960
cagaagagcc tctccctgtc tccgggtaaa                                         990
```

<210> SEQ ID NO 126
<211> LENGTH: 330
<212> TYPE: PRT
<213> ORGANISM: Homo Sapien

<400> SEQUENCE: 126

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 127
<211> LENGTH: 990

```
<212> TYPE: DNA
<213> ORGANISM: Homo Sapien

<400> SEQUENCE: 127
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggggga    360
ccgtcagtct tcctcttccc cccaaaaccc aaggacaccc tcatgatctc ccggaccccct   420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                    990

<210> SEQ ID NO 128
<211> LENGTH: 330
<212> TYPE: PRT
<213> ORGANISM: Homo Sapien

<400> SEQUENCE: 128

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 129
<211> LENGTH: 990
<212> TYPE: DNA
<213> ORGANISM: Homo Sapien

<400> SEQUENCE: 129
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctggggggga    360 ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc cccgggtaaa                                      990

<210> SEQ ID NO 130
<211> LENGTH: 330
<212> TYPE: PRT
<213> ORGANISM: Homo Sapien
```

<400> SEQUENCE: 130

| Ala | Ser | Thr | Lys | Gly | Pro | Ser | Val | Phe | Pro | Leu | Ala | Pro | Ser | Ser | Lys |
|---|---|---|---|---|---|---|---|---|---|---|---|---|---|---|---|
| 1 | | | | 5 | | | | | 10 | | | | | 15 | |

| Ser | Thr | Ser | Gly | Gly | Thr | Ala | Ala | Leu | Gly | Cys | Leu | Val | Lys | Asp | Tyr |
|---|---|---|---|---|---|---|---|---|---|---|---|---|---|---|---|
| | | | 20 | | | | | 25 | | | | | 30 | | |

| Phe | Pro | Glu | Pro | Val | Thr | Val | Ser | Trp | Asn | Ser | Gly | Ala | Leu | Thr | Ser |
|---|---|---|---|---|---|---|---|---|---|---|---|---|---|---|---|
| | | 35 | | | | | 40 | | | | | 45 | | | |

| Gly | Val | His | Thr | Phe | Pro | Ala | Val | Leu | Gln | Ser | Ser | Gly | Leu | Tyr | Ser |
|---|---|---|---|---|---|---|---|---|---|---|---|---|---|---|---|
| | 50 | | | | | 55 | | | | | 60 | | | | |

| Leu | Ser | Ser | Val | Val | Thr | Val | Pro | Ser | Ser | Leu | Gly | Thr | Gln | Thr |
|---|---|---|---|---|---|---|---|---|---|---|---|---|---|---|
| 65 | | | | | 70 | | | | | 75 | | | | 80 |

| Tyr | Ile | Cys | Asn | Val | Asn | His | Lys | Pro | Ser | Asn | Thr | Lys | Val | Asp | Lys |
|---|---|---|---|---|---|---|---|---|---|---|---|---|---|---|---|
| | | | | 85 | | | | | 90 | | | | | 95 | |

| Arg | Val | Glu | Pro | Lys | Ser | Cys | Asp | Lys | Thr | His | Thr | Cys | Pro | Pro | Cys |
|---|---|---|---|---|---|---|---|---|---|---|---|---|---|---|---|
| | | | 100 | | | | | 105 | | | | | 110 | | |

| Pro | Ala | Pro | Glu | Leu | Leu | Gly | Gly | Pro | Ser | Val | Phe | Leu | Phe | Pro | Pro |
|---|---|---|---|---|---|---|---|---|---|---|---|---|---|---|---|
| | | 115 | | | | | 120 | | | | | 125 | | | |

| Lys | Pro | Lys | Asp | Thr | Leu | Met | Ile | Ser | Arg | Thr | Pro | Glu | Val | Thr | Cys |
|---|---|---|---|---|---|---|---|---|---|---|---|---|---|---|---|
| 130 | | | | | 135 | | | | | 140 | | | | | |

| Val | Val | Val | Asp | Val | Ser | His | Glu | Asp | Pro | Glu | Val | Lys | Phe | Asn | Trp |
|---|---|---|---|---|---|---|---|---|---|---|---|---|---|---|---|
| 145 | | | | | 150 | | | | | 155 | | | | | 160 |

| Tyr | Val | Asp | Gly | Val | Glu | Val | His | Asn | Ala | Lys | Thr | Lys | Pro | Arg | Glu |
|---|---|---|---|---|---|---|---|---|---|---|---|---|---|---|---|
| | | | 165 | | | | | 170 | | | | | 175 | | |

| Glu | Gln | Tyr | Asn | Ser | Thr | Tyr | Arg | Val | Val | Ser | Val | Leu | Thr | Val | Leu |
|---|---|---|---|---|---|---|---|---|---|---|---|---|---|---|---|
| | | | 180 | | | | | 185 | | | | | 190 | | |

| His | Gln | Asp | Trp | Leu | Asn | Gly | Lys | Glu | Tyr | Lys | Cys | Lys | Val | Ser | Asn |
|---|---|---|---|---|---|---|---|---|---|---|---|---|---|---|---|
| | | | 195 | | | | | 200 | | | | | 205 | | |

| Lys | Ala | Leu | Pro | Ala | Pro | Ile | Glu | Lys | Thr | Ile | Ser | Lys | Ala | Lys | Gly |
|---|---|---|---|---|---|---|---|---|---|---|---|---|---|---|---|
| | 210 | | | | | 215 | | | | | 220 | | | | |

| Gln | Pro | Arg | Glu | Pro | Gln | Val | Tyr | Thr | Leu | Pro | Pro | Ser | Arg | Glu | Glu |
|---|---|---|---|---|---|---|---|---|---|---|---|---|---|---|---|
| 225 | | | | | 230 | | | | | 235 | | | | | 240 |

| Met | Thr | Lys | Asn | Gln | Val | Ser | Leu | Thr | Cys | Leu | Val | Lys | Gly | Phe | Tyr |
|---|---|---|---|---|---|---|---|---|---|---|---|---|---|---|---|
| | | | 245 | | | | | 250 | | | | | 255 | | |

| Pro | Ser | Asp | Ile | Ala | Val | Glu | Trp | Glu | Ser | Asn | Gly | Gln | Pro | Glu | Asn |
|---|---|---|---|---|---|---|---|---|---|---|---|---|---|---|---|
| | | | 260 | | | | | 265 | | | | | 270 | | |

| Asn | Tyr | Lys | Thr | Thr | Pro | Pro | Val | Leu | Asp | Ser | Asp | Gly | Ser | Phe | Phe |
|---|---|---|---|---|---|---|---|---|---|---|---|---|---|---|---|
| | | 275 | | | | | 280 | | | | | 285 | | | |

| Leu | Tyr | Ser | Lys | Leu | Thr | Val | Asp | Lys | Ser | Arg | Trp | Gln | Gln | Gly | Asn |
|---|---|---|---|---|---|---|---|---|---|---|---|---|---|---|---|
| | 290 | | | | | 295 | | | | | 300 | | | | |

| Val | Phe | Ser | Cys | Ser | Val | Met | His | Glu | Ala | Leu | His | Asn | His | Tyr | Thr |
|---|---|---|---|---|---|---|---|---|---|---|---|---|---|---|---|
| 305 | | | | | 310 | | | | | 315 | | | | | 320 |

| Gln | Lys | Ser | Leu | Ser | Leu | Ser | Pro | Gly | Lys |
|---|---|---|---|---|---|---|---|---|---|
| | | | | 325 | | | | | 330 |

<210> SEQ ID NO 131
<211> LENGTH: 990
<212> TYPE: DNA
<213> ORGANISM: Homo Sapien

<400> SEQUENCE: 131
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180

```
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggaccccct   420 gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acatcttctc atgctccgtg atgcatgagg ctctgcacaa ccactacacg    960
cagaagagcc tctccctgtc tccgggtaaa                                     990
```

```
<210> SEQ ID NO 132
<211> LENGTH: 330
<212> TYPE: PRT
<213> ORGANISM: Homo Sapien

<400> SEQUENCE: 132

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
                225                 230                 235                 240
Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Ile Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 133
<211> LENGTH: 990
<212> TYPE: DNA
<213> ORGANISM: Homo Sapien

<400> SEQUENCE: 133
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agtggagccc   300
aaatcttgtg acaaaactca cacatgccca ccgtgcccag cacctgaact cgcggggggca   360 ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcggaggga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa                                    990

<210> SEQ ID NO 134
<211> LENGTH: 330
<212> TYPE: PRT
<213> ORGANISM: Homo Sapien

<400> SEQUENCE: 134

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 135
<211> LENGTH: 978
<212> TYPE: DNA
<213> ORGANISM: Homo Sapien

<400> SEQUENCE: 135
gcctccacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
```

-continued

```
gtggtcagcg tcctcaccgt tgtgcaccag gactggctga acggcaagga gtacaagtgc      600
aaggtctcca acaaaggcct cccagccccc atcgagaaaa ccatctccaa aaccaaaggg      660
cagccccgag aaccacaggt gtacaccctg cccccatccc gggaggagat gaccaagaac      720
caggtcagcc tgacctgcct ggtcaaaggc ttctacccca gcgacatcgc cgtggagtgg      780
gagagcaatg ggcagccgga gaacaactac aagaccacac ctcccatgct ggactccgac      840
ggctccttct tcctctacag caagctcacc gtggacaaga gcaggtggca gcaggggaac      900
gtcttctcat gctccgtgat gcatgaggct ctgcacaacc actacacgca gaagagcctc      960
tccctgtctc cgggtaaa                                                    978
```

<210> SEQ ID NO 136
<211> LENGTH: 326
<212> TYPE: PRT
<213> ORGANISM: Homo Sapien

<400> SEQUENCE: 136

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

Leu Thr Val Asp Lys Ser Arg Trp Gln Gln Gly Asn Val Phe Ser Cys
            290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 137
<211> LENGTH: 978
<212> TYPE: DNA
<213> ORGANISM: Homo Sapien

<400> SEQUENCE: 137

```
gcctccacca agggcccatc ggtcttcccc ctggcgccct gctccaggag cacctccgag    60
agcacagcgg ccctgggctg cctggtcaag gactacttcc ccgaaccggt gacggtgtcg   120
tggaactcag gcgctctgac cagcggcgtg cacaccttcc cggctgtcct acagtcctca   180
ggactctact ccctcagcag cgtggtgacc gtgacctcca gcaacttcgg cacccagacc   240
tacacctgca acgtagatca caagcccagc aacaccaagg tggacaagac agttgagcgc   300
aaatgttgtg tcgagtgccc accgtgccca gcaccacctg tggcaggacc gtcagtcttc   360
ctcttccccc caaaacccaa ggacaccctc atgatctccc ggacccctga ggtcacgtgc   420
gtggtggtgg acgtgagcca cgaagacccc gaggtccagt tcaactggta cgtggacggc   480
atggaggtgc ataatgccaa gacaaagcca cgggaggagc agttcaacag cacgttccgt   540
gtggtcagcg tcctcaccgt cgtgcaccag gactggctga acggcaagga gtacaagtgc   600
aaggtctcca acaaaggcct cccagccccc atcgagaaaa ccatctccaa aaccaaaggg   660
cagccccgag aaccacaggt gtacaccctg cccccatccc gggaggagat gaccaagaac   720
caggtcagcc tgacctgcct ggtcaaaggc ttctacccca gcgacatcgc cgtggagtgg   780
gagagcaatg ggcagccgga gaacaactac aagaccacac ctcccatgct ggactccgac   840
ggctccttct tcctctacag caagctcacc gtggacaaga gcaggtggca gcaggggaac   900
gtcttctcat gctccgtgat gcatgaggct ctgcacaacc actacacaca gaagagcctc   960
tccctgtctc cgggtaaa                                                 978
```

<210> SEQ ID NO 138
<211> LENGTH: 326
<212> TYPE: PRT
<213> ORGANISM: Homo Sapien

<400> SEQUENCE: 138

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Thr Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
    115         120        125

Thr Leu Met Ile Ser Arg Thr Pro Glu Val Thr Cys Val Val Val Asp
130         135        140

Val Ser His Glu Asp Pro Glu Val Gln Phe Asn Trp Tyr Val Asp Gly
145         150        155        160

Met Glu Val His Asn Ala Lys Thr Lys Pro Arg Glu Glu Gln Phe Asn
    165         170        175

Ser Thr Phe Arg Val Val Ser Val Leu Thr Val His Gln Asp Trp
    180         185        190

Leu Asn Gly Lys Glu Tyr Lys Cys Lys Val Ser Asn Lys Gly Leu Pro
    195         200        205

Ala Pro Ile Glu Lys Thr Ile Ser Lys Thr Lys Gly Gln Pro Arg Glu
    210         215        220

Pro Gln Val Tyr Thr Leu Pro Pro Ser Arg Glu Glu Met Thr Lys Asn
225         230        235        240

Gln Val Ser Leu Thr Cys Leu Val Lys Gly Phe Tyr Pro Ser Asp Ile
        245        250        255

Ala Val Glu Trp Glu Ser Asn Gly Gln Pro Glu Asn Asn Tyr Lys Thr
    260         265        270

Thr Pro Pro Met Leu Asp Ser Asp Gly Ser Phe Phe Leu Tyr Ser Lys
    275         280        285

Leu Thr Val Asp Lys Ser Arg Trp Gln Gln Gly Asn Val Phe Ser Cys
    290         295        300

Ser Val Met His Glu Ala Leu His Asn His Tyr Thr Gln Lys Ser Leu
305         310        315        320

Ser Leu Ser Pro Gly Lys
    325

<210> SEQ ID NO 139
<211> LENGTH: 978
<212> TYPE: DNA
<213> ORGANISM: Homo Sapien

<400> SEQUENCE: 139

```
gcctccacca agggcccatc ggtcttcccc ctggcgccct gctccaggag cacctccgag     60
agcacagcgg ccctgggctg cctggtcaag gactacttcc ccgaaccggt gacggtgtcg    120
tggaactcag gcgctctgac cagcggcgtg cacaccttcc cagctgtcct acagtcctca    180
ggactctact ccctcagcag cgtggtgacc gtgccctcca gcagcttggg cacccagacc    240
tacacctgca acgtagatca caagcccagc aacaccaagg tggacaagac agttgagcgc    300
aaatgttgtg tcgagtgccc accgtgccca gcaccacctg tggcaggacc gtcagtcttc    360
ctcttccccc caaaacccaa ggacaccctc atgatctccc ggacccctga ggtcacgtgc    420
gtggtggtgg acgtgagcca cgaagacccc gaggtccagt tcaactggta cgtggacggc    480
gtggaggtgc ataatgccaa gacaaagcca cgggaggagc agttcaacag cacgttccgt    540
gtggtcagcg tcctcaccgt tgtgcaccag gactggctga acggcaagga gtacaagtgc    600
aaggtctcca acaaaggcct cccagccccc atcgagaaaa ccatctccaa aaccaagggg    660
cagccccgag aaccacaggt gtacaccctg cccccatccc gggaggagat gaccaagaac    720
caggtcagcc tgacctgcct ggtcaaaggc ttctacccca gcgacatcgc cgtggagtgg    780
gagagcaatg ggcagccgga gaacaactac aagaccacac ctcccatgct ggactccgac    840
```

```
ggctccttct tcctctacag caagctcacc gtggacaaga gcaggtggca gcagggaac      900 gtcttctcat gctccgtgat gcatgaggct ctgcacaacc actacacgca gaagagcctc      960
tccctgtctc cgggtaaa                                                    978
```

<210> SEQ ID NO 140
<211> LENGTH: 326
<212> TYPE: PRT
<213> ORGANISM: Homo Sapien

<400> SEQUENCE: 140

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 141

<211> LENGTH: 978
<212> TYPE: DNA
<213> ORGANISM: Homo Sapien

<400> SEQUENCE: 141

```
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cggctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggaccctga  ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt cgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatctc cgtggagtgg     780
gagagcaatg ggcagccgga gaacaactac aagaccacac tcccatgctg gactccgac      840
ggctccttct tcctctacag caagctcacc gtggacaaga gcaggtggca gcaggggaac     900
gtcttctcat gctccgtgat gcatgaggct ctgcacaacc actacacaca gaagagcctc     960
tccctgtctc cgggtaaa                                                  978
```

<210> SEQ ID NO 142
<211> LENGTH: 326
<212> TYPE: PRT
<213> ORGANISM: Homo Sapien

<400> SEQUENCE: 142

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
```

```
                165                 170                 175
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 143
<211> LENGTH: 981
<212> TYPE: DNA
<213> ORGANISM: Homo Sapien

<400> SEQUENCE: 143
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc atcatgccca gcacctgagt tcctgggggg accatcagtc     360
ttcctgttcc cccaaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtggaca agagcaggtg gcaggagggg     900
aatgtcttct catgctccgt gatgcatgag gctctgcaca accactacac acagaagagc     960
ctctccctgt ctctgggtaa a                                              981

<210> SEQ ID NO 144
<211> LENGTH: 327
<212> TYPE: PRT
<213> ORGANISM: Homo Sapien
```

<400> SEQUENCE: 144

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 145
<211> LENGTH: 981
<212> TYPE: DNA
<213> ORGANISM: Homo Sapien

<400> SEQUENCE: 145
gcttccacca agggcccatc cgtcttcccc ctggcgccct gctccaggag cacctccgag    60
agcacagccg ccctgggctg cctggtcaag gactacttcc ccgaaccggt gacggtgtcg   120
tggaactcag gcgccctgac cagcggcgtg cacaccttcc cggctgtcct acagtcctca   180

```
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc ccccgtgccc atcatgccca gcacctgagt tcctgggggg accatcagtc    360
ttcctgttcc ccccaaaacc caaggacact ctcatgatct cccggacccc tgaggtcacg    420
tgcgtggtgg tggacgtgag ccaggaagac cccgaggtcc agttcaactg gtacgtggat    480
ggcgtggagg tgcataatgc caagacaaag ccgcgggagg agcagttcaa cagcacgtac    540
cgtgtggtca gcgtcctcac cgtcgtgcac caggactggc tgaacggcaa ggagtacaag    600
tgcaaggtct ccaacaaagg cctcccgtcc tccatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaggcta accgtggaca agagcaggtg gcaggagggg    900
aatgtcttct catgctccgt gatgcatgag gctctgcaca accactacac gcagaagagc    960
ctctccctgt ctctgggtaa a                                              981
```

<210> SEQ ID NO 146
<211> LENGTH: 327
<212> TYPE: PRT
<213> ORGANISM: Homo Sapien

<400> SEQUENCE: 146

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 147
<211> LENGTH: 981
<212> TYPE: DNA
<213> ORGANISM: Homo Sapien

<400> SEQUENCE: 147
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc atcatgccca gcacctgagt tcctgggggg accatcagtc     360
ttcctgttcc cccaaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaagctc accgtggaca agagcaggtg gcaggagggg     900
aacgtcttct catgctccgt gatgcatgag gctctgcaca accactacac gcagaagagc     960
ctctccctgt ctctgggtaa a                                               981

<210> SEQ ID NO 148
<211> LENGTH: 327
<212> TYPE: PRT
<213> ORGANISM: Homo Sapien

<400> SEQUENCE: 148

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 149
<211> LENGTH: 981
<212> TYPE: DNA
<213> ORGANISM: Homo Sapien

<400> SEQUENCE: 149
gcctccacca agggcccatc cgtcttcccc ctggcgccct gctccaggag cacctccgag     60
agcacggccg ccctgggctg cctggtcaag gactacttcc ccgaaccagt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc cccatgccca accatgccca gcgcctgaat tgaggggggg accatcagtc    360
ttcctgttcc cccaaaaacc caaggacact ctcatgatct cccggacccc tgaggtcacg    420
tgcgtggtgg tggacgtgag ccaggaagac cccgaggtcc agttcaactg gtacgtggat    480

-continued

```
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtca tcgatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggatcct tcttcctcta cagcaggcta accgtggaca agagcaggtg gcaggagggg    900
aatgtcttct catgctccgt gatgcatgag gctctgcaca accactacac acagaagagc    960 ctctcccctgt ctctgggtaa a    981
```

<210> SEQ ID NO 150
<211> LENGTH: 981
<212> TYPE: DNA
<213> ORGANISM: Homo Sapien

<400> SEQUENCE: 150

```
gcctccacca agggacctag cgtgttccct ctcgccccct gttccaggtc cacaagcgag    60
tccaccgctg ccctcggctg tctggtgaaa gactactttc ccgagcccgt gaccgtctcc    120
tggaatagcg gagccctgac ctccggcgtg cacacatttc ccgccgtgct gcagagcagc    180
ggactgtata gcctgagcag cgtggtgacc gtgcccagct ccagcctcgg caccaaaacc    240
tacacctgca acgtggacca caagccctcc aacaccaagg tggacaagcg ggtggagagc    300
aagtacggcc ccccttgccc tccttgtcct gcccctgagt tcgagggagg accctccgtg    360
ttcctgtttc cccccaaacc caaggacacc ctgatgatct cccggacacc cgaggtgacc    420
tgtgtggtcg tggacgtcag ccaggaggac cccgaggtgc agttcaactg gtatgtggac    480
ggcgtggagg tgcacaatgc caaaaccaag cccagggagg agcagttcaa ttccacctac    540
agggtggtga gcgtgctgac cgtcctgcat caggattggc tgaacggcaa ggagtacaag    600
tgcaaggtgt ccaacaaggg actgcccagc tccatcgaga agaccatcag caaggctaag    660
ggccagccga gggagcccca ggtgtatacc ctgcctccta gccaggaaga gatgaccaag    720
aaccaagtgt ccctgacctg cctggtgaag ggattctacc cctccgacat cgccgtggag    780
tgggagagca atggccagcc cgagaacaac tacaaaacaa cccctcccgt gctcgatagc    840
gacggcagct tctttctcta cagccggctg acagtggaca agagcaggtg gcaggagggc    900
aacgtgttct cctgttccgt gatgcacgag gccctgcaca atcactacac ccagaagagc    960 ctctcccctgt ccctgggcaa g    981
```

<210> SEQ ID NO 151
<211> LENGTH: 981
<212> TYPE: DNA
<213> ORGANISM: Homo Sapien

<400> SEQUENCE: 151

```
gccagcacca agggcccttc cgtgttcccc ctggcccctt gcagcaggag cacctccgaa    60
tccacagctg ccctgggctg tctggtgaag gactactttc ccgagcccgt gaccgtgagc    120
tggaacagcg gcgctctgac atccggcgtc cacacctttc ctgccgtcct gcagtcctcc    180
ggcctctact ccctgtcctc cgtggtgacc gtgcctagct cctccctcgg caccaagacc    240
tacacctgta acgtggacca caaaccctcc aacaccaagg tggacaaacg ggtcgagagc    300
aagtacggcc ctccctgccc tccttgtcct gccccgagt tcgaaggcgg acccagcgtg    360
```

```
ttcctgttcc ctcctaagcc caaggacacc ctcatgatca gccggacacc cgaggtgacc    420
tgcgtggtgg tggatgtgag ccaggaggac cctgaggtcc agttcaactg gtatgtggat    480
ggcgtggagg tgcacaacgc caagacaaag ccccgggaag agcagttcaa ctccacctac    540
agggtggtca gcgtgctgac cgtgctgcat caggactggc tgaacggcaa ggagtacaag    600
tgcaaggtca gcaataaggg actgcccagc agcatcgaga agaccatctc caaggctaaa    660
ggccagcccc gggaacctca ggtgtacacc ctgcctccca gccaggagga gatgaccaag    720
aaccaggtga gcctgacctg cctggtgaag ggattctacc cttccgacat cgccgtggag    780
tgggagtcca acggccagcc cgagaacaat tataagacca cccctcccgt cctcgacagc    840
gacggatcct tctttctgta ctccaggctg accgtggata agtccaggtg gcaggaaggc    900
aacgtgttca gctgctccgt gatgcacgag gccctgcaca tcactacac ccagaagtcc    960 ctgagcctgt ccctgggaaa g    981
```

<210> SEQ ID NO 152
<211> LENGTH: 327
<212> TYPE: PRT
<213> ORGANISM: Homo Sapien

<400> SEQUENCE: 152

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 153
<211> LENGTH: 981
<212> TYPE: DNA
<213> ORGANISM: Homo Sapien

<400> SEQUENCE: 153
gcctccacca agggcccatc cgtcttcccc ctggcgccct gctccaggag cacctccgag      60
agcacggccg ccctgggctg cctggtcaag gactacttcc ccgaaccagt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accatgccca gcgcctccag ttgcgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtca tcgatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggatcct tcttcctcta cagcaggcta accgtggaca agagcaggtg gcaggagggg     900
aatgtcttct catgctccgt gatgcatgag gctctgcaca accactacac acagaagagc     960
ctctccctgt ctctgggtaa a                                              981

<210> SEQ ID NO 154
<211> LENGTH: 327
<212> TYPE: PRT
<213> ORGANISM: Homo Sapien

<400> SEQUENCE: 154

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 155
<211> LENGTH: 321
<212> TYPE: DNA
<213> ORGANISM: Homo Sapien

<400> SEQUENCE: 155
cgtacggtgg ccgctccctc cgtgttcatc ttcccacctt ccgacgagca gctgaagtcc    60
ggcaccgctt ctgtcgtgtg cctgctgaac aacttctacc ccgcgaggc caaggtgcag   120 tggaaggtgg acaacgccct gcagtccggc aactcccagg aatccgtgac cgagcaggac   180
tccaaggaca gcacctactc cctgtcctcc accctgaccc tgtccaaggc cgactacgag   240
aagcacaagg tgtacgcctg cgaagtgacc caccagggcc tgtctagccc cgtgaccaag   300
tctttcaacc ggggcgagtg t                                            321

<210> SEQ ID NO 156
<211> LENGTH: 107
<212> TYPE: PRT
<213> ORGANISM: Homo Sapien

<400> SEQUENCE: 156

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 157
<211> LENGTH: 321
<212> TYPE: DNA
<213> ORGANISM: Homo Sapien

<400> SEQUENCE: 157
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggag   180
agcaaggaca gcacctacag cctcagcagc accctgacgc tgagcaaagc agactacgag   240
aaacacaaag tctacgccgg cgaagtcacc catcagggcc tgagctcgcc cgtcacaaag   300
agcttcaaca ggggagagtg t                                              321

<210> SEQ ID NO 158
<211> LENGTH: 107
<212> TYPE: PRT
<213> ORGANISM: Homo Sapien

<400> SEQUENCE: 158

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro Val Thr Lys Ser Phe Asn Arg Gly Glu Cys
            100                 105

<210> SEQ ID NO 159
<211> LENGTH: 321
<212> TYPE: DNA
<213> ORGANISM: Homo Sapien

<400> SEQUENCE: 159
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
cggaaggtgg ataacgccct ccaatcgggt aactcccagg agagtgtcac agagcaggag    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg t                                              321

<210> SEQ ID NO 160
<211> LENGTH: 107
<212> TYPE: PRT
<213> ORGANISM: Homo Sapien

<400> SEQUENCE: 160

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Arg Lys Val Asp Asn Ala Leu Gln
        35                  40                  45

Ser Gly Asn Ser Gln Glu Ser Val Thr Glu Gln Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 161
<211> LENGTH: 321
<212> TYPE: DNA
<213> ORGANISM: Homo Sapien

<400> SEQUENCE: 161
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaac tctacgcctg cgaagtcacc catcagggcc tgagctcgcc cgtcacaaag    300
agcttcaaca ggggagagtg t                                              321

<210> SEQ ID NO 162
<211> LENGTH: 107
<212> TYPE: PRT
<213> ORGANISM: Homo Sapien

<400> SEQUENCE: 162

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu

```
                65                   70                  75                  80
Lys His Lys Leu Tyr Ala Cys Glu Val Thr His Gln Gly Leu Ser Ser
                    85                  90                  95

Pro Val Thr Lys Ser Phe Asn Arg Gly Glu Cys
                100                 105

<210> SEQ ID NO 163
<211> LENGTH: 321
<212> TYPE: DNA
<213> ORGANISM: Homo Sapien

<400> SEQUENCE: 163
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct caatcgggt aactcccagg agagtgtcac agagcaggac      180
agcaaggaca gcacctacag cctcagcaac accctgacgc tgagcaaagc agactacgag     240
aaacacaaag tctacgcctg cgaagtcacc catcagggcc tgagctcgcc cgtcacaaag     300
agcttcaaca ggggagagtg c                                               321

<210> SEQ ID NO 164
<211> LENGTH: 107
<212> TYPE: PRT
<213> ORGANISM: Homo Sapien

<400> SEQUENCE: 164

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Asn Thr Leu Thr Leu Ser Lys Ala Asp Tyr Glu
65                  70                  75                  80

Lys His Lys Val Tyr Ala Cys Glu Val Thr His Gln Gly Leu Ser Ser
                    85                  90                  95

Pro Val Thr Lys Ser Phe Asn Arg Gly Glu Cys
                100                 105

<210> SEQ ID NO 165
<211> LENGTH: 312
<212> TYPE: DNA
<213> ORGANISM: Homo Sapien

<400> SEQUENCE: 165
cccaaggcca acccacggt cactctgttc ccgccctcct ctgaggagct ccaagccaac       60
aaggccacac tagtgtgtct gatcagtgac ttctacccgg gagctgtgac agtggcttgg    120
aaggcagatg cagcccccgt caaggcggga gtggagacga ccaaaccctc caaacagagc    180
aacaacaagt acgcggccag cagctacctg agcctgacgc cgagcagtg gaagtcccac     240 agaagctaca gctgccaggt cacgcatgaa gggagcaccg tggagaagac agtggcccct    300
acagaatgtt ca                                                        312

<210> SEQ ID NO 166
```

<211> LENGTH: 104
<212> TYPE: PRT
<213> ORGANISM: Homo Sapien

<400> SEQUENCE: 166

```
Pro Lys Ala Asn Pro Thr Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Gly Ser Pro Val Lys
        35                  40                  45

Ala Gly Val Glu Thr Thr Lys Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100
```

<210> SEQ ID NO 167
<211> LENGTH: 318
<212> TYPE: DNA
<213> ORGANISM: Homo Sapien

<400> SEQUENCE: 167

| ggtcagccca aggccaaccc cactgtcact ctgttcccgc cctcctctga ggagctccaa | 60 |
| gccaacaagg ccacactagt gtgtctgatc agtgacttct acccgggagc tgtgacagtg | 120 |
| gcctggaagg cagatggcag ccccgtcaag gcgggagtgg agaccaccaa accctccaaa | 180 |
| cagagcaaca acaagtacgc ggccagcagc tacctgagcc tgacgcccga gcagtggaag | 240 |
| tcccacagaa gctacagctg ccaggtcacg catgaaggga gcaccgtgga agacagtg | 300 |
| gcccctacag aatgttca | 318 |

<210> SEQ ID NO 168
<211> LENGTH: 318
<212> TYPE: DNA
<213> ORGANISM: Homo Sapien

<400> SEQUENCE: 168

| ggtcagccca aggccaaccc cactgtcact ctgttcccgc cctcctctga ggagctccaa | 60 |
| gccaacaagg ccacactagt gtgtctgatc agtgacttct acccgggagc tgtgacagtg | 120 |
| gcctggaagg cagatggcag ccccgtcaag gcgggagtgg agaccaccaa accctccaaa | 180 |
| cagagcaaca acaagtacgc ggccagcagc tacctgagcc tgacgcccga gcagtggaag | 240 |
| tcccacagaa gctacagctg ccaggtcacg catgaaggga gcaccgtgga agacagtg | 300 |
| gcccctacag aatgttca | 318 |

<210> SEQ ID NO 169
<211> LENGTH: 106
<212> TYPE: PRT
<213> ORGANISM: Homo Sapien

<400> SEQUENCE: 169

```
Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
```

```
                20                  25                  30
Phe Tyr Pro Gly Ala Val Thr Val Ala Trp Lys Ala Asp Gly Ser Pro
            35                  40                  45

Val Lys Ala Gly Val Glu Thr Thr Lys Pro Ser Lys Gln Ser Asn Asn
        50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

```
<210> SEQ ID NO 170
<211> LENGTH: 318
<212> TYPE: DNA
<213> ORGANISM: Homo Sapien

<400> SEQUENCE: 170
ggccagccta aggccgctcc ttctgtgacc ctgttccccc catcctccga ggaactgcag      60
gctaacaagg ccaccctcgt gtgcctgatc agcgacttct accctggcgc cgtgaccgtg     120
gcctggaagg ctgatagctc tcctgtgaag gccggcgtgg aaaccaccac cccttccaag     180
cagtccaaca acaaatacgc cgcctcctcc tacctgtccc tgaccctga gcagtggaag      240 tcccaccggt cctacagctg ccaagtgacc cacgagggct ccaccgtgga aaagaccgtg     300
gctcctaccg agtgctcc                                                   318
```

```
<210> SEQ ID NO 171
<211> LENGTH: 318
<212> TYPE: DNA
<213> ORGANISM: Homo Sapien

<400> SEQUENCE: 171
ggccagccta agctgccccc cagcgtcacc ctgtttcctc cctccagcga ggagctccag      60
gccaacaagg ccaccctcgt gtgcctgatc tccgacttct atcccggcgc tgtgaccgtg     120
gcttggaaag ccgactccag ccctgtcaaa gccggcgtgg agaccaccac accctccaag     180
cagtccaaca acaagtacgc cgcctccagc tatctctccc tgaccctga gcagtggaag      240 tcccaccggt cctactcctg tcaggtgacc cacgagggct ccaccgtgga aaagaccgtc     300
gcccccaccg agtgctcc                                                   318
```

```
<210> SEQ ID NO 172
<211> LENGTH: 106
<212> TYPE: PRT
<213> ORGANISM: Homo Sapien

<400> SEQUENCE: 172

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
 65                  70                  75                  80
```

Ser His Arg Ser Tyr Ser Cys Gln Val Thr His Glu Gly Ser Thr Val
            85                  90                  95

Glu Lys Thr Val Ala Pro Thr Glu Cys Ser
        100                 105

<210> SEQ ID NO 173
<211> LENGTH: 318
<212> TYPE: DNA
<213> ORGANISM: Homo Sapien

<400> SEQUENCE: 173
ggtcagccca aggctgcccc ctcggtcact ctgttcccgc cctcctctga ggagcttcaa      60
gccaacaagg ccacactggt gtgtctcata agtgacttct acccgggagc cgtgacagtg    120
gcctggaagg cagatagcag ccccgtcaag gcgggagtgg agaccaccac accctccaaa    180
caaagcaaca acaagtacgc ggccagcagc tatctgagcc tgacgcctga gcagtggaag    240
tcccacagaa gctacagctg ccaggtcacg catgaaggga gcaccgtgga agacagtg     300 gcccctacag aatgttca                                                  318

<210> SEQ ID NO 174
<211> LENGTH: 106
<212> TYPE: PRT
<213> ORGANISM: Homo Sapien

<400> SEQUENCE: 174

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
            85                  90                  95

Glu Lys Thr Val Ala Pro Thr Glu Cys Ser
        100                 105

<210> SEQ ID NO 175
<211> LENGTH: 312
<212> TYPE: DNA
<213> ORGANISM: Homo Sapien

<400> SEQUENCE: 175
cccaaggctg cccctcggt cactctgttc ccaccctcct ctgaggagct tcaagccaac      60
aaggccacac tggtgtgtct cataagtgac ttctacccgg agccgtgac agttgcctgg    120 aaggcagata gcagccccgt caaggcgggg gtggagacca ccacaccctc caaacaaagc    180
aacaacaagt acgcggccag cagctacctg agcctgacgc tgagcagtg gaagtcccac    240 aaaagctaca gctgccaggt cacgcatgaa gggagcaccg tggagaagac agttgcccct    300
acggaatgtt ca                                                        312

<210> SEQ ID NO 176
<211> LENGTH: 104

```
<212> TYPE: PRT
<213> ORGANISM: Homo Sapien

<400> SEQUENCE: 176

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Lys Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 177
<211> LENGTH: 318
<212> TYPE: DNA
<213> ORGANISM: Homo Sapien

<400> SEQUENCE: 177
ggtcagccca aggctgcccc ctcggtcact ctgttcccac cctcctctga ggagcttcaa        60
gccaacaagg ccacactggt gtgtctcata agtgacttct acccgggggcc agtgacagtt      120 gcctggaagg cagatagcag ccccgtcaag gcggggggtgg agaccaccac accctccaaa      180
caaagcaaca caagtacgc ggccagcagc tacctgagcc tgacgcctga gcagtggaag        240
tcccacaaaa gctacagctg ccaggtcacg catgaaggga gcaccgtgga agacagtg         300 gcccctacgg aatgttca                                                     318

<210> SEQ ID NO 178
<211> LENGTH: 106
<212> TYPE: PRT
<213> ORGANISM: Homo Sapien

<400> SEQUENCE: 178

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 179
<211> LENGTH: 318
<212> TYPE: DNA
```

<213> ORGANISM: Homo Sapien

<400> SEQUENCE: 179

```
ggtcagccca aggctgcccc ctcggtcact ctgttcccac cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca caagtacgc ggccagcagc tacctgagcc tgacgcctga gcagtggaag      240
tcccacaaaa gctacagctg ccaggtcacg catgaaggga gcaccgtgga aagacagtg      300
gcccctacag aatgttca                                                   318
```

<210> SEQ ID NO 180
<211> LENGTH: 106
<212> TYPE: PRT
<213> ORGANISM: Homo Sapien

<400> SEQUENCE: 180

Gly Gln Pro Lys Ala Ala Pro Ser Val Thr Leu Phe Pro Pro Ser Ser
1               5                   10                  15
Glu Glu Leu Gln Ala Asn Lys Ala Thr Leu Val Cys Leu Ile Ser Asp
            20                  25                  30
Phe Tyr Pro Gly Ala Val Thr Val Ala Trp Lys Ala Asp Ser Ser Pro
        35                  40                  45
Val Lys Ala Gly Val Glu Thr Thr Pro Ser Lys Gln Ser Asn Asn
    50                  55                  60
Lys Tyr Ala Ala Ser Ser Tyr Leu Ser Leu Thr Pro Glu Gln Trp Lys
65                  70                  75                  80
Ser His Lys Ser Tyr Ser Cys Gln Val Thr His Glu Gly Ser Thr Val
                85                  90                  95
Glu Lys Thr Val Ala Pro Thr Glu Cys Ser
            100                 105

<210> SEQ ID NO 181
<211> LENGTH: 318
<212> TYPE: DNA
<213> ORGANISM: Homo Sapien

<400> SEQUENCE: 181

```
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca caagtacgc ggccagcagc tacctgagcc tgacgcctga gcagtggaag      240
tcccacagaa gctacagctg ccaggtcacg catgaaggga gcaccgtgga aagacagtg      300
gcccctacag aatgttca                                                   318
```

<210> SEQ ID NO 182
<211> LENGTH: 106
<212> TYPE: PRT
<213> ORGANISM: Homo Sapien

<400> SEQUENCE: 182

Gly Gln Pro Lys Ala Ala Pro Ser Val Thr Leu Phe Pro Pro Ser Ser
1               5                   10                  15
Glu Glu Leu Gln Ala Asn Lys Ala Thr Leu Val Cys Leu Ile Ser Asp
            20                  25                  30

-continued

```
Phe Tyr Pro Gly Ala Val Thr Val Ala Trp Lys Ala Asp Ser Ser Pro
         35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105
```

<210> SEQ ID NO 183
<211> LENGTH: 318
<212> TYPE: DNA
<213> ORGANISM: Homo Sapien

<400> SEQUENCE: 183

```
ggtcagccca aggctgcccc atcggtcact ctgttcccgc cctcctctga ggagcttcaa      60
gccaacaagg ccacactggt gtgcctgatc agtgacttct acccgggagc tgtgaaagtg     120
gcctggaagg cagatggcag ccccgtcaac acgggagtgg agaccaccac accctccaaa     180
cagagcaaca caagtacgc  ggccagcagc tacctgagcc tgacgcctga gcagtggaag     240
tcccacagaa gctacagctg ccaggtcacg catgaaggga gcaccgtgga agacagtg      300
gccccctgcag aatgttca                                                  318
```

<210> SEQ ID NO 184
<211> LENGTH: 106
<212> TYPE: PRT
<213> ORGANISM: Homo Sapien

<400> SEQUENCE: 184

```
Gly Gln Pro Lys Ala Ala Pro Ser Val Thr Leu Phe Pro Pro Ser Ser
 1                5                  10                  15

Glu Glu Leu Gln Ala Asn Lys Ala Thr Leu Val Cys Leu Ile Ser Asp
             20                  25                  30

Phe Tyr Pro Gly Ala Val Lys Val Ala Trp Lys Ala Asp Gly Ser Pro
         35                  40                  45

Val Asn Thr Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Ala Glu Cys Ser
            100                 105
```

<210> SEQ ID NO 185
<211> LENGTH: 318
<212> TYPE: DNA
<213> ORGANISM: Homo Sapien

<400> SEQUENCE: 185

```
ggtcagccca aggctgcccc atcggtcact ctgttcccac cctcctctga ggagcttcaa      60
gccaacaagg ccacactggt gtgtctcgta agtgacttct acccgggagc cgtgacagtg     120
gcctggaagg cagatggcag ccccgtcaag gtggagtgg  agaccaccaa accctccaaa     180
caaagcaaca caagtatgc  ggccagcagc tacctgagcc tgacgcccga gcagtggaag     240
```
tcccacagaa gctacagctg ccgggtcacg catgaaggga gcaccgtgga aagacagtg    300 gccccctgcag aatgctct                                               318

<210> SEQ ID NO 186
<211> LENGTH: 106
<212> TYPE: PRT
<213> ORGANISM: Homo Sapien

<400> SEQUENCE: 186

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 187
<211> LENGTH: 318
<212> TYPE: DNA
<213> ORGANISM: Homo Sapien

<400> SEQUENCE: 187
ggtcagccca aggctgcccc ctcggtcact ctgttcccac cctcctctga ggagcttcaa    60
gccaacaagg ccacactggt gtgtctcgta agtgacttca acccgggagc cgtgacagtg   120
gcctggaagg cagatggcag ccccgtcaag gtgggagtgg agaccaccaa accctccaaa   180
caaagcaaca caagtatgc ggccagcagc tacctgagcc tgacgcccga gcagtggaag   240
tcccacagaa gctacagctg ccgggtcacg catgaaggga gcaccgtgga aagacagtg    300 gccccctgcag aatgctct                                               318

<210> SEQ ID NO 188
<211> LENGTH: 106
<212> TYPE: PRT
<213> ORGANISM: Homo Sapien

<400> SEQUENCE: 188

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Asn Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

-continued

Glu Lys Thr Val Ala Pro Ala Glu Cys Ser
            100                 105

<210> SEQ ID NO 189
<211> LENGTH: 662
<212> TYPE: PRT
<213> ORGANISM: Homo Sapien

<400> SEQUENCE: 189

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
    290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
            340                 345                 350

Ser Gly Thr Ser Gln Ala Ala Ala His Val Ala Gly Ile Ala Ala Met

```
                355                 360                 365
Met Leu Ser Ala Glu Pro Glu Leu Thr Leu Ala Glu Leu Arg Gln Arg
370                 375                 380
Leu Ile His Phe Ser Ala Lys Asp Val Ile Asn Glu Ala Trp Phe Pro
385                 390                 395                 400
Glu Asp Gln Arg Val Leu Thr Pro Asn Leu Val Ala Ala Leu Pro Pro
                405                 410                 415
Ser Thr His Gly Ala Gly Trp Gln Leu Phe Cys Arg Thr Val Trp Ser
            420                 425                 430
Ala His Ser Gly Pro Thr Arg Met Ala Thr Ala Val Ala Arg Cys Ala
                435                 440                 445
Pro Asp Glu Glu Leu Leu Ser Cys Ser Ser Phe Ser Arg Ser Gly Lys
450                 455                 460
Arg Arg Gly Glu Arg Met Glu Ala Gln Gly Gly Lys Leu Val Cys Arg
465                 470                 475                 480
Ala His Asn Ala Phe Gly Gly Glu Gly Val Tyr Ala Ile Ala Arg Cys
                485                 490                 495
Cys Leu Leu Pro Gln Ala Asn Cys Ser Val His Thr Ala Pro Pro Ala
            500                 505                 510
Glu Ala Ser Met Gly Thr Arg Val His Cys His Gln Gly His Val
                515                 520                 525
Leu Thr Gly Cys Ser Ser His Trp Glu Val Asp Leu Gly Thr His
            530                 535                 540
Lys Pro Pro Val Leu Arg Pro Arg Gly Gln Pro Asn Gln Cys Val Gly
545                 550                 555                 560
His Arg Glu Ala Ser Ile His Ala Ser Cys Cys His Ala Pro Gly Leu
                565                 570                 575
Glu Cys Lys Val Lys Glu His Gly Ile Pro Ala Pro Gln Glu Gln Val
            580                 585                 590
Thr Val Ala Cys Glu Glu Gly Trp Thr Leu Thr Gly Cys Ser Ala Leu
                595                 600                 605
Pro Gly Thr Ser His Val Leu Gly Ala Tyr Ala Val Asp Asn Thr Cys
            610                 615                 620
Val Val Arg Ser Arg Asp Val Ser Thr Thr Gly Ser Thr Ser Glu Gly
625                 630                 635                 640
Ala Val Thr Ala Val Ala Ile Cys Cys Arg Ser Arg His Leu Ala Gln
                645                 650                 655
Ala Ser Gln Glu Leu Gln
            660

<210> SEQ ID NO 190
<211> LENGTH: 662
<212> TYPE: PRT
<213> ORGANISM: Homo Sapien

<400> SEQUENCE: 190

Gln Glu Asp Glu Asp Gly Asp Tyr Glu Glu Leu Val Leu Ala Leu Arg
1               5                   10                  15
Ser Glu Glu Asp Gly Leu Ala Glu Ala Pro Glu His Gly Thr Thr Ala
                20                  25                  30
Thr Phe His Arg Cys Ala Lys Asp Pro Trp Arg Leu Pro Gly Thr Tyr
            35                  40                  45
Val Val Val Leu Lys Glu Glu Thr His Leu Ser Gln Ser Glu Arg Thr
50                  55                  60
```

```
Ala Arg Arg Leu Gln Ala Gln Ala Ala Arg Arg Gly Tyr Leu Thr Lys
 65                  70                  75                  80

Ile Leu His Val Phe His Gly Leu Leu Pro Gly Phe Leu Val Lys Met
                 85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
            195                 200                 205

Ala Gly Val Ala Lys Gly Ala Ser Met Arg Ser Leu Arg Val Leu Asn
210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
        290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
            340                 345                 350

Ser Gly Thr Ser Gln Ala Ala Ala His Val Ala Gly Ile Ala Ala Met
            355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Ile Ala Arg Cys Ala
            435                 440                 445

Pro Asp Glu Glu Leu Leu Ser Cys Ser Ser Phe Ser Arg Ser Gly Lys
450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
```

```
                    485             490             495
Cys Leu Leu Pro Gln Ala Asn Cys Ser Val His Thr Ala Pro Pro Ala
                500             505             510
Glu Ala Ser Met Gly Thr Arg Val His Cys His Gln Gln Gly His Val
                515             520             525
Leu Thr Gly Cys Ser Ser His Trp Glu Val Glu Asp Leu Gly Thr His
                530             535             540
Lys Pro Pro Val Leu Arg Pro Arg Gly Gln Pro Asn Gln Cys Val Gly
545             550             555             560
His Arg Glu Ala Ser Ile His Ala Ser Cys Cys His Ala Pro Gly Leu
                565             570             575
Glu Cys Lys Val Lys Glu His Gly Ile Pro Ala Pro Gln Glu Gln Val
                580             585             590
Thr Val Ala Cys Glu Gly Trp Thr Leu Thr Gly Cys Ser Ala Leu
                595             600             605
Pro Gly Thr Ser His Val Leu Gly Ala Tyr Ala Val Asp Asn Thr Cys
                610             615             620
Val Val Arg Ser Arg Asp Val Ser Thr Thr Gly Ser Thr Ser Glu Glu
625             630             635             640
Ala Val Thr Ala Val Ala Ile Cys Cys Arg Ser Arg His Leu Ala Gln
                        645             650             655
Ala Ser Gln Glu Leu Gln
            660

<210> SEQ ID NO 191
<211> LENGTH: 662
<212> TYPE: PRT
<213> ORGANISM: Homo Sapien

<400> SEQUENCE: 191

Gln Glu Asp Glu Asp Gly Asp Tyr Glu Glu Leu Val Leu Ala Leu Arg
1               5                   10                  15
Ser Glu Glu Asp Gly Leu Val Glu Ala Pro Glu His Gly Thr Thr Ala
                20                  25                  30
Thr Phe His Arg Cys Ala Lys Asp Pro Trp Arg Leu Pro Gly Thr Tyr
            35                  40                  45
Val Val Val Leu Lys Glu Glu Thr His Leu Ser Gln Ser Glu Arg Thr
        50                  55                  60
Ala Arg Arg Leu Gln Ala Gln Ala Ala Arg Arg Gly Tyr Leu Thr Lys
65                  70                  75                  80
Ile Leu His Val Phe His Gly Leu Leu Pro Gly Phe Leu Val Lys Met
                85                  90                  95
Ser Gly Asp Leu Leu Glu Leu Ala Leu Lys Leu Pro His Val Asp Tyr
                100                 105                 110
Ile Glu Glu Asp Ser Ser Val Phe Ala Gln Ser Ile Pro Trp Asn Leu
            115                 120                 125
Glu Arg Ile Thr Pro Pro Arg Tyr Arg Ala Asp Glu Tyr Gln Pro Pro
        130                 135                 140
Asp Gly Gly Ser Leu Val Glu Val Tyr Leu Leu Asp Thr Ser Ile Gln
145                 150                 155                 160
Ser Asp His Arg Glu Ile Glu Gly Arg Val Met Val Thr Asp Phe Glu
                165                 170                 175
Asn Val Pro Glu Glu Asp Gly Thr Arg Phe His Arg Gln Ala Ser Lys
            180                 185                 190
```

-continued

Cys Asp Ser His Gly Thr His Leu Ala Gly Val Val Ser Gly Arg Asp
    195                 200                 205

Ala Gly Val Ala Lys Gly Ala Ser Met Arg Ser Leu Arg Val Leu Asn
210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
                260                 265                 270

Arg Leu Ala Arg Ala Gly Val Val Leu Val Thr Ala Ala Gly Asn Phe
            275                 280                 285

Arg Asp Asp Ala Cys Leu Tyr Ser Pro Ala Ser Ala Pro Glu Val Ile
        290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
                340                 345                 350

Ser Gly Thr Ser Gln Ala Ala Ala His Val Ala Gly Ile Ala Ala Met
            355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
                420                 425                 430

Ala His Ser Gly Pro Thr Arg Met Ala Thr Ala Ile Ala Arg Cys Ala
            435                 440                 445

Pro Asp Glu Glu Leu Leu Ser Cys Ser Ser Phe Ser Arg Ser Gly Lys
450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
                500                 505                 510

Glu Ala Ser Met Gly Thr Arg Val His Cys His Gln Gln Gly His Val
            515                 520                 525

Leu Thr Gly Cys Ser Ser His Trp Glu Val Glu Asp Leu Gly Thr His
530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
                580                 585                 590

Thr Val Ala Cys Glu Glu Gly Trp Thr Leu Thr Gly Cys Ser Ala Leu
            595                 600                 605

Pro Gly Thr Ser His Val Leu Gly Ala Tyr Ala Val Asp Asn Thr Cys

```
              610                 615                 620
Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln
            660

<210> SEQ ID NO 192
<211> LENGTH: 662
<212> TYPE: PRT
<213> ORGANISM: Homo Sapien

<400> SEQUENCE: 192

Gln Glu Asp Glu Asp Gly Asp Tyr Glu Leu Val Leu Ala Leu Arg
1               5                   10                  15

Ser Glu Glu Asp Gly Leu Ala Glu Ala Pro Glu His Gly Thr Thr Ala
                20                  25                  30

Thr Phe His Arg Cys Ala Lys Asp Pro Trp Arg Leu Pro Gly Thr Tyr
            35                  40                  45

Val Val Val Leu Lys Glu Thr His Leu Ser Gln Ser Glu Arg Thr
50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
                100                 105                 110

Ile Glu Glu Asp Ser Ser Val Phe Ala Gln Ser Ile Pro Trp Asn Leu
            115                 120                 125

Glu Arg Ile Thr Pro Pro Arg Tyr Arg Ala Asp Glu Tyr Gln Pro Pro
130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
                180                 185                 190

Cys Asp Ser His Gly Thr His Leu Ala Gly Val Val Ser Gly Arg Asp
            195                 200                 205

Ala Gly Val Ala Lys Gly Ala Ser Met Arg Ser Leu Arg Val Leu Asn
210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
                260                 265                 270

Arg Leu Ala Arg Ala Gly Val Val Leu Val Thr Ala Ala Gly Asn Phe
            275                 280                 285

Arg Asp Asp Ala Cys Leu Tyr Ser Pro Ala Ser Ala Pro Glu Val Ile
            290                 295                 300

Thr Val Gly Ala Thr Asn Ala Gln Asp Gln Pro Val Thr Leu Gly Thr
305                 310                 315                 320
```

```
Leu Gly Thr Asn Phe Gly Arg Cys Val Asp Leu Phe Ala Pro Gly Glu
                325                 330                 335

Asp Ile Ile Gly Ala Ser Ser Tyr Cys Ser Thr Cys Phe Val Ser Gln
            340                 345                 350

Ser Gly Thr Ser Gln Ala Ala His Val Ala Gly Ile Ala Ala Met
        355                 360                 365

Met Leu Ser Ala Glu Pro Glu Leu Thr Leu Ala Glu Leu Arg Gln Arg
    370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Val Ala Arg Cys Ala
        435                 440                 445

Pro Asp Glu Glu Leu Leu Ser Cys Ser Ser Phe Ser Arg Ser Gly Lys
    450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gln Gly His Val
        515                 520                 525

Leu Thr Gly Cys Ser Ser His Trp Glu Val Glu Asp Leu Gly Thr His
    530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
            580                 585                 590

Thr Val Ala Cys Glu Glu Gly Trp Thr Leu Thr Gly Cys Ser Ala Leu
        595                 600                 605

Pro Gly Thr Ser His Val Leu Gly Ala Tyr Ala Val Asp Asn Thr Cys
    610                 615                 620

Val Val Arg Ser Arg Asp Val Ser Thr Thr Gly Ser Thr Ser Glu Gly
625                 630                 635                 640

Ala Val Thr Ala Val Ala Ile Cys Cys Arg Ser Arg His Leu Ala Gln
                645                 650                 655

Ala Ser Gln Glu Leu Gln
        660

<210> SEQ ID NO 193
<211> LENGTH: 662
<212> TYPE: PRT
<213> ORGANISM: Homo Sapien

<400> SEQUENCE: 193

Gln Glu Asp Glu Asp Gly Asp Tyr Glu Glu Leu Val Leu Ala Leu Arg
1               5                   10                  15

Ser Glu Glu Asp Gly Leu Ala Asp Ala Pro Glu His Gly Ala Thr Ala
            20                  25                  30
```

```
Thr Phe His Arg Cys Ala Lys Asp Pro Trp Arg Leu Pro Gly Thr Tyr
         35                  40                  45

Val Val Val Leu Lys Glu Glu Thr His Arg Ser Gln Ser Glu Arg Thr
 50                  55                  60

Ala Arg Arg Leu Gln Ala Gln Ala Ala Arg Arg Gly Tyr Leu Thr Lys
 65                  70                  75                  80

Ile Leu His Val Phe His His Leu Leu Pro Gly Phe Leu Val Lys Met
                     85                  90                  95

Ser Gly Asp Leu Leu Glu Leu Ala Leu Lys Leu Pro His Val Asp Tyr
                100                 105                 110

Ile Glu Glu Asp Ser Ser Val Phe Ala Gln Ser Ile Pro Trp Asn Leu
                115                 120                 125

Glu Arg Ile Thr Pro Ala Arg Tyr Arg Ala Asp Glu Tyr Gln Pro Pro
            130                 135                 140

Lys Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                    165                 170                 175

Ser Val Pro Glu Glu Asp Gly Thr Arg Phe His Arg Gln Ala Ser Lys
                180                 185                 190

Cys Asp Ser His Gly Thr His Leu Ala Gly Val Val Ser Gly Arg Asp
            195                 200                 205

Ala Gly Val Ala Lys Gly Ala Gly Leu Arg Ser Leu Arg Val Leu Asn
            210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                    245                 250                 255

Leu Pro Leu Ala Gly Gly Tyr Ser Arg Val Phe Asn Ala Ala Cys Gln
                260                 265                 270

Arg Leu Ala Arg Ala Gly Val Val Leu Val Thr Ala Ala Gly Asn Phe
            275                 280                 285

Arg Asp Asp Ala Cys Leu Tyr Ser Pro Ala Ser Ala Pro Glu Val Ile
            290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                    325                 330                 335

Asp Ile Ile Gly Ala Ser Ser Asp Cys Ser Thr Cys Phe Val Ser Arg
                340                 345                 350

Ser Gly Thr Ser Gln Ala Ala Ala His Val Ala Gly Ile Ala Ala Met
            355                 360                 365

Met Leu Ser Ala Glu Pro Glu Leu Thr Leu Ala Glu Leu Arg Gln Arg
            370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                    405                 410                 415

Ser Thr His Arg Ala Gly Trp Gln Leu Phe Cys Arg Thr Val Trp Ser
                420                 425                 430

Ala His Ser Gly Pro Thr Arg Met Ala Thr Ala Val Ala Arg Cys Ala
            435                 440                 445
```

```
Gln Asp Glu Leu Leu Ser Cys Ser Ser Phe Ser Arg Ser Gly Lys
    450                 455                 460

Arg Arg Gly Glu Arg Ile Glu Ala Gln Gly Gly Lys Arg Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Val Asn Cys Ser Val His Thr Ala Pro Pro Ala
                500                 505                 510

Gly Ala Ser Met Gly Thr Arg Val His Cys His Gln Gly His Val
                515                 520                 525

Leu Thr Gly Cys Ser Ser His Trp Glu Val Glu Asp Leu Gly Thr His
    530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys His Ala Pro Gly Leu
                565                 570                 575

Glu Cys Lys Val Lys Glu His Gly Ile Pro Ala Pro Gln Glu Gln Val
                580                 585                 590

Ile Val Ala Cys Glu Asp Gly Trp Thr Leu Thr Gly Cys Ser Ala Leu
    595                 600                 605

Pro Gly Thr Ser His Val Leu Gly Ala Tyr Ala Val Asp Asn Thr Cys
    610                 615                 620

Val Val Arg Ser Arg Asp Val Ser Thr Thr Gly Ser Thr Ser Glu Glu
625                 630                 635                 640

Ala Val Ala Ala Val Ala Ile Cys Cys Arg Ser Arg His Leu Val Gln
                645                 650                 655

Ala Ser Gln Glu Leu Gln
        660

<210> SEQ ID NO 194
<211> LENGTH: 660
<212> TYPE: PRT
<213> ORGANISM: Mus Musculus

<400> SEQUENCE: 194

Gln Asp Glu Asp Gly Asp Tyr Glu Glu Leu Met Leu Ala Leu Pro Ser
1               5                   10                  15

Gln Glu Asp Gly Leu Ala Asp Glu Ala Ala His Val Ala Thr Ala Thr
            20                  25                  30

Phe Arg Arg Cys Ser Lys Glu Ala Trp Arg Leu Pro Gly Thr Tyr Ile
        35                  40                  45

Val Val Leu Met Glu Glu Thr Gln Arg Leu Gln Ile Glu Gln Thr Ala
50                  55                  60

His Arg Leu Gln Thr Arg Ala Ala Arg Arg Gly Tyr Val Ile Lys Val
65                  70                  75                  80

Leu His Ile Phe Tyr Asp Leu Phe Pro Gly Phe Leu Val Lys Met Ser
                85                  90                  95

Ser Asp Leu Leu Gly Leu Ala Leu Lys Leu Pro His Val Glu Tyr Ile
            100                 105                 110

Glu Glu Asp Ser Phe Val Phe Ala Gln Ser Ile Pro Trp Asn Leu Glu
        115                 120                 125

Arg Ile Ile Pro Ala Trp His Gln Thr Glu Glu Asp Arg Ser Pro Asp
    130                 135                 140

Gly Ser Ser Gln Val Glu Val Tyr Leu Leu Asp Thr Ser Ile Gln Gly
145                 150                 155                 160
```

```
Ala His Arg Glu Ile Glu Gly Arg Val Thr Ile Thr Asp Phe Asn Ser
            165                 170                 175

Val Pro Glu Glu Asp Gly Thr Arg Phe His Arg Gln Ala Ser Lys Cys
            180                 185                 190

Asp Ser His Gly Thr His Leu Ala Gly Val Val Ser Gly Arg Asp Ala
            195                 200                 205

Gly Val Ala Lys Gly Thr Ser Leu His Ser Leu Arg Val Leu Asn Cys
210                 215                 220

Gln Gly Lys Gly Thr Val Ser Gly Thr Leu Ile Gly Leu Glu Phe Ile
225                 230                 235                 240

Arg Lys Ser Gln Leu Ile Gln Pro Ser Gly Pro Leu Val Val Leu Leu
            245                 250                 255

Pro Leu Ala Gly Gly Tyr Ser Arg Ile Leu Asn Ala Ala Cys Arg His
            260                 265                 270

Leu Ala Arg Thr Gly Val Val Leu Val Ala Ala Gly Asn Phe Arg
            275                 280                 285

Asp Asp Ala Cys Leu Tyr Ser Pro Ala Ser Ala Pro Glu Val Ile Thr
            290                 295                 300

Val Gly Ala Thr Asn Ala Gln Asp Gln Pro Val Thr Leu Gly Thr Leu
305                 310                 315                 320

Gly Thr Asn Phe Gly Arg Cys Val Asp Leu Phe Ala Pro Gly Lys Asp
            325                 330                 335

Ile Ile Gly Ala Ser Ser Asp Cys Ser Thr Cys Phe Met Ser Gln Ser
            340                 345                 350

Gly Thr Ser Gln Ala Ala Ala His Val Ala Gly Ile Val Ala Arg Met
            355                 360                 365

Leu Ser Arg Glu Pro Thr Leu Thr Leu Ala Glu Leu Arg Gln Arg Leu
370                 375                 380

Ile His Phe Ser Thr Lys Asp Val Ile Asn Met Ala Trp Phe Pro Glu
385                 390                 395                 400

Asp Gln Gln Val Leu Thr Pro Asn Leu Val Ala Thr Leu Pro Pro Ser
            405                 410                 415

Thr His Glu Thr Gly Gly Gln Leu Leu Cys Arg Thr Val Trp Ser Ala
            420                 425                 430

His Ser Gly Pro Thr Arg Thr Ala Thr Ala Thr Ala Arg Cys Ala Pro
            435                 440                 445

Glu Glu Glu Leu Leu Ser Cys Ser Ser Phe Ser Arg Ser Gly Arg Arg
            450                 455                 460

Arg Gly Asp Trp Ile Glu Ala Ile Gly Gly Gln Val Cys Lys Ala
465                 470                 475                 480

Leu Asn Ala Phe Gly Gly Glu Gly Val Tyr Ala Val Ala Arg Cys Cys
            485                 490                 495

Leu Val Pro Arg Ala Asn Cys Ser Ile His Asn Thr Pro Ala Ala Arg
            500                 505                 510

Ala Gly Leu Glu Thr His Val His Cys His Gln Lys Asp His Val Leu
            515                 520                 525

Thr Gly Cys Ser Phe His Trp Glu Val Glu Asp Leu Ser Val Arg Arg
            530                 535                 540

Gln Pro Ala Leu Arg Ser Arg Arg Gln Pro Gly Gln Cys Val Gly His
545                 550                 555                 560

Gln Ala Ala Ser Val Tyr Ala Ser Cys Cys His Ala Pro Gly Leu Glu
            565                 570                 575
```

```
Cys Lys Ile Lys Glu His Gly Ile Ser Gly Pro Ser Glu Gln Val Thr
                580                 585                 590

Val Ala Cys Glu Ala Gly Trp Thr Leu Thr Gly Cys Asn Val Leu Pro
            595                 600                 605

Gly Ala Ser Leu Thr Leu Gly Ala Tyr Ser Val Asp Asn Leu Cys Val
        610                 615                 620

Ala Arg Val His Asp Thr Ala Arg Ala Asp Arg Thr Ser Gly Glu Ala
625                 630                 635                 640

Thr Val Ala Ala Ala Ile Cys Cys Arg Ser Arg Pro Ser Ala Lys Ala
                645                 650                 655

Ser Trp Val Gln
            660

<210> SEQ ID NO 195
<211> LENGTH: 445
<212> TYPE: PRT
<213> ORGANISM: Homo Sapien

<400> SEQUENCE: 195

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285
```

```
Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
                435                 440                 445

<210> SEQ ID NO 196
<211> LENGTH: 220
<212> TYPE: PRT
<213> ORGANISM: Homo Sapien

<400> SEQUENCE: 196

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
                20                  25                  30

Ser Asn Asn Arg Asn Phe Leu Gly Trp Tyr Gln Gln Lys Pro Gly Gln
            35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
                130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
```

<210> SEQ ID NO 197
<211> LENGTH: 454
<212> TYPE: PRT
<213> ORGANISM: Homo Sapien

<400> SEQUENCE: 197

```
Glu Met Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Lys Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Ile Val Leu Met Val Tyr His Met Asp Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Glu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365
```

```
Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 198
<211> LENGTH: 219
<212> TYPE: PRT
<213> ORGANISM: Homo Sapien

<400> SEQUENCE: 198

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu His His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 199
<211> LENGTH: 116
<212> TYPE: PRT
<213> ORGANISM: Homo Sapien

<400> SEQUENCE: 199

Gln Val Gln Leu Gln Glu Ser Gly Pro Gly Leu Val Lys Pro Ser Gly
1               5                   10                  15
```

```
Thr Leu Ser Leu Thr Cys Ala Val Ser Gly Gly Ser Ile Ser Ser Ser
            20                  25                  30

Lys Trp Trp Ser Trp Val Arg Gln Pro Pro Gly Lys Gly Leu Glu Trp
        35                  40                  45

Ile Gly Glu Thr His Tyr Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Arg Ser Val Thr Ala Ala Asp Thr Ala Val Tyr Tyr Cys
                85                  90                  95

Ala Arg Val Gly Ala Thr Glu Asn Phe Trp Gly Gln Gly Thr Leu Val
            100                 105                 110

Thr Val Ser Ser
        115

<210> SEQ ID NO 200
<211> LENGTH: 348
<212> TYPE: DNA
<213> ORGANISM: Homo Sapien

<400> SEQUENCE: 200
caggtgcagc tgcaggagtc gggcccagga ctggtgaagc cttcgggac  cctgtccctc       60 acctgcgctg tctctggtgg ctccatcagc agtagtaaat ggtggagttg ggtccgccag      120
cccccaggga aggggctgga gtggattggg gaaacccatt atagtgggag caccaactac      180
aacccgtccc tcaagagtcg agtcaccata tcagtagaca gtccaagaa  ccagttctcc      240 ctgaagctga ggtctgtgac cgccgcggac acggccgttt attactgtgc gagagtgggt      300
gctactgaga acttctgggg ccagggaacc ctggtcaccg tctcctca                   348

<210> SEQ ID NO 201
<211> LENGTH: 25
<212> TYPE: PRT
<213> ORGANISM: Homo Sapien

<400> SEQUENCE: 201

Gln Val Gln Leu Gln Glu Ser Gly Pro Gly Leu Val Lys Pro Ser Gly
1               5                   10                  15

Thr Leu Ser Leu Thr Cys Ala Val Ser
            20                  25

<210> SEQ ID NO 202
<211> LENGTH: 75
<212> TYPE: DNA
<213> ORGANISM: Homo Sapien

<400> SEQUENCE: 202
caggtgcagc tgcaggagtc gggcccagga ctggtgaagc cttcgggac  cctgtccctc       60 acctgcgctg tctct                                                        75

<210> SEQ ID NO 203
<211> LENGTH: 9
<212> TYPE: PRT
<213> ORGANISM: Homo Sapien

<400> SEQUENCE: 203

Gly Gly Ser Ile Ser Ser Ser Lys Trp
1               5
```

```
<210> SEQ ID NO 204
<211> LENGTH: 27
<212> TYPE: DNA
<213> ORGANISM: Homo Sapien

<400> SEQUENCE: 204
ggtggctcca tcagcagtag taaatgg                                          27

<210> SEQ ID NO 205
<211> LENGTH: 17
<212> TYPE: PRT
<213> ORGANISM: Homo Sapien

<400> SEQUENCE: 205
```

Trp Ser Trp Val Arg Gln Pro Pro Gly Lys Gly Leu Glu Trp Ile Gly
1               5                   10                  15

Glu

```
<210> SEQ ID NO 206
<211> LENGTH: 51
<212> TYPE: DNA
<213> ORGANISM: Homo Sapien

<400> SEQUENCE: 206
tggagttggg tccgccagcc cccagggaag gggctggagt ggattgggga a               51

<210> SEQ ID NO 207
<211> LENGTH: 7
<212> TYPE: PRT
<213> ORGANISM: Homo Sapien

<400> SEQUENCE: 207
```

Thr His Tyr Ser Gly Ser Thr
1               5

```
<210> SEQ ID NO 208
<211> LENGTH: 21
<212> TYPE: DNA
<213> ORGANISM: Homo Sapien

<400> SEQUENCE: 208
acccattata gtgggagcac c                                                21

<210> SEQ ID NO 209
<211> LENGTH: 38
<212> TYPE: PRT
<213> ORGANISM: Homo Sapien

<400> SEQUENCE: 209
```

Asn Tyr Asn Pro Ser Leu Lys Ser Arg Val Thr Ile Ser Val Asp Lys
1               5                   10                  15

Ser Lys Asn Gln Phe Ser Leu Lys Leu Arg Ser Val Thr Ala Ala Asp
            20                  25                  30

Thr Ala Val Tyr Tyr Cys
        35

```
<210> SEQ ID NO 210
<211> LENGTH: 114
<212> TYPE: DNA
<213> ORGANISM: Homo Sapien

<400> SEQUENCE: 210
aactacaacc cgtccctcaa gagtcgagtc accatatcag tagacaagtc caagaaccag      60
```
ttctccctga agctgaggtc tgtgaccgcc gcggacacgg ccgtttatta ctgt      114

<210> SEQ ID NO 211
<211> LENGTH: 9
<212> TYPE: PRT
<213> ORGANISM: Homo Sapien

<400> SEQUENCE: 211

Ala Arg Val Gly Ala Thr Glu Asn Phe
1               5

<210> SEQ ID NO 212
<211> LENGTH: 27
<212> TYPE: DNA
<213> ORGANISM: Homo Sapien

<400> SEQUENCE: 212
gcgagagtgg gtgctactga aacttc                                    27

<210> SEQ ID NO 213
<211> LENGTH: 11
<212> TYPE: PRT
<213> ORGANISM: Homo Sapien

<400> SEQUENCE: 213

Trp Gly Gln Gly Thr Leu Val Thr Val Ser Ser
1               5                   10

<210> SEQ ID NO 214
<211> LENGTH: 34
<212> TYPE: DNA
<213> ORGANISM: Homo Sapien

<400> SEQUENCE: 214
tggggccagg gaaccctggt caccgtctcc tcag                           34

<210> SEQ ID NO 215
<211> LENGTH: 30
<212> TYPE: PRT
<213> ORGANISM: Homo Sapien

<400> SEQUENCE: 215

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser
            20                  25                  30

<210> SEQ ID NO 216
<211> LENGTH: 90
<212> TYPE: DNA
<213> ORGANISM: Homo Sapien

<400> SEQUENCE: 216
caggtgcagc tgcaggagtc gggcccagga ctggtgaagc cttcggggac cctgtccctc   60
acctgcgctg tctctggtgg ctccatcagc                                   90

<210> SEQ ID NO 217
<211> LENGTH: 6
<212> TYPE: PRT
<213> ORGANISM: Homo Sapien

<400> SEQUENCE: 217

Ser Ser Lys Trp Trp Ser
1               5

<210> SEQ ID NO 218
<211> LENGTH: 18
<212> TYPE: DNA
<213> ORGANISM: Homo Sapien

<400> SEQUENCE: 218
agtagtaaat ggtggagt                                                 18

<210> SEQ ID NO 219
<211> LENGTH: 14
<212> TYPE: PRT
<213> ORGANISM: Homo Sapien

<400> SEQUENCE: 219

Trp Val Arg Gln Pro Pro Gly Lys Gly Leu Glu Trp Ile Gly
1               5                   10

<210> SEQ ID NO 220
<211> LENGTH: 42
<212> TYPE: DNA
<213> ORGANISM: Homo Sapien

<400> SEQUENCE: 220
tgggtccgcc agccccccagg gaagggggctg gagtggattg gg                     42

<210> SEQ ID NO 221
<211> LENGTH: 16
<212> TYPE: PRT
<213> ORGANISM: Homo Sapien

<400> SEQUENCE: 221

Glu Thr His Tyr Ser Gly Ser Thr Asn Tyr Asn Pro Ser Leu Lys Ser
1               5                   10                  15

<210> SEQ ID NO 222
<211> LENGTH: 48
<212> TYPE: DNA
<213> ORGANISM: Homo Sapien

<400> SEQUENCE: 222
gaaacccatt atagtgggag caccaactac aacccgtccc tcaagagt                 48

<210> SEQ ID NO 223
<211> LENGTH: 32
<212> TYPE: PRT
<213> ORGANISM: Homo Sapien

<400> SEQUENCE: 223

Arg Val Thr Ile Ser Val Asp Lys Ser Lys Asn Gln Phe Ser Leu Lys
1               5                   10                  15
Leu Arg Ser Val Thr Ala Ala Asp Thr Ala Val Tyr Tyr Cys Ala Arg
                20                  25                  30

<210> SEQ ID NO 224
<211> LENGTH: 96
<212> TYPE: DNA
<213> ORGANISM: Homo Sapien

<400> SEQUENCE: 224
cgagtcacca tatcagtaga caagtccaag aaccagttct ccctgaagct gaggtctgtg   60
accgccgcgg acacggccgt ttattactgt gcgaga                                      96

<210> SEQ ID NO 225
<211> LENGTH: 7
<212> TYPE: PRT
<213> ORGANISM: Homo Sapien

<400> SEQUENCE: 225

Val Gly Ala Thr Glu Asn Phe
1               5

<210> SEQ ID NO 226
<211> LENGTH: 21
<212> TYPE: DNA
<213> ORGANISM: Homo Sapien

<400> SEQUENCE: 226
gtgggtgcta ctgagaactt c                                                     21

<210> SEQ ID NO 227
<211> LENGTH: 11
<212> TYPE: PRT
<213> ORGANISM: Homo Sapien

<400> SEQUENCE: 227

Trp Gly Gln Gly Thr Leu Val Thr Val Ser Ser
1               5                   10

<210> SEQ ID NO 228
<211> LENGTH: 34
<212> TYPE: DNA
<213> ORGANISM: Homo Sapien

<400> SEQUENCE: 228
tggggccagg gaaccctggt caccgtctcc tcag                                       34

<210> SEQ ID NO 229
<211> LENGTH: 107
<212> TYPE: PRT
<213> ORGANISM: Homo Sapien

<400> SEQUENCE: 229

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Phe Arg Tyr
                20                  25                  30

Leu Ala Trp Tyr Gln Gln Lys Pro Gly Gln Ala Pro Arg Leu Leu Ile
            35                  40                  45

Tyr Asp Ala Ser Thr Arg Ala Thr Asp Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 230
<211> LENGTH: 321
<212> TYPE: DNA
<213> ORGANISM: Homo Sapien

<400> SEQUENCE: 230

```
gaaattgtgt tgacacagtc tccagccacc ctgtctttgt ctccagggga aagagccacc    60
ctctcctgca gggccagtca gagtgttttc aggtacttag cctggtacca acagaaacct   120
ggccaggctc ccaggctcct catctatgat gcatccacca gggccactga catcccagcc   180
aggttcagtg gcagtgggtc tgggacagat ttcactctca ccatcagcag cctagagcct   240
gaagattttg cagtttatta ctgtcagcaa cgtagcaact ggcctccgac gttcggccaa   300
gggaccaagg tggaaatcaa a                                             321
```

<210> SEQ ID NO 231
<211> LENGTH: 26
<212> TYPE: PRT
<213> ORGANISM: Homo Sapien

<400> SEQUENCE: 231

```
Glu Ile Val Leu Thr Gln Ser Pro Ala Thr Leu Ser Leu Ser Pro Gly
1               5                  10                  15

Glu Arg Ala Thr Leu Ser Cys Arg Ala Ser
            20                  25
```

<210> SEQ ID NO 232
<211> LENGTH: 78
<212> TYPE: DNA
<213> ORGANISM: Homo Sapien

<400> SEQUENCE: 232

```
gaaattgtgt tgacacagtc tccagccacc ctgtctttgt ctccagggga aagagccacc    60
ctctcctgca gggccagt                                                 78
```

<210> SEQ ID NO 233
<211> LENGTH: 6
<212> TYPE: PRT
<213> ORGANISM: Homo Sapien

<400> SEQUENCE: 233

```
Gln Ser Val Phe Arg Tyr
1               5
```

<210> SEQ ID NO 234
<211> LENGTH: 18
<212> TYPE: DNA
<213> ORGANISM: Homo Sapien

<400> SEQUENCE: 234

```
cagagtgttt tcaggtac                                                 18
```

<210> SEQ ID NO 235
<211> LENGTH: 17
<212> TYPE: PRT
<213> ORGANISM: Homo Sapien

<400> SEQUENCE: 235

```
Leu Ala Trp Tyr Gln Gln Lys Pro Gly Gln Ala Pro Arg Leu Leu Ile
1               5                  10                  15

Tyr
```

<210> SEQ ID NO 236
<211> LENGTH: 51
<212> TYPE: DNA
<213> ORGANISM: Homo Sapien

<400> SEQUENCE: 236
ttagcctggt accaacagaa acctggccag gctcccaggc tcctcatcta t    51

<210> SEQ ID NO 237
<211> LENGTH: 3
<212> TYPE: PRT
<213> ORGANISM: Homo Sapien

<400> SEQUENCE: 237

Asp Ala Ser
1

<210> SEQ ID NO 238
<211> LENGTH: 9
<212> TYPE: DNA
<213> ORGANISM: Homo Sapien

<400> SEQUENCE: 238 gatgcatcc    9

<210> SEQ ID NO 239
<211> LENGTH: 36
<212> TYPE: PRT
<213> ORGANISM: Homo Sapien

<400> SEQUENCE: 239

Thr Arg Ala Thr Asp Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

Val Tyr Tyr Cys
        35

<210> SEQ ID NO 240
<211> LENGTH: 108
<212> TYPE: DNA
<213> ORGANISM: Homo Sapien

<400> SEQUENCE: 240
accagggcca ctgacatccc agccaggttc agtggcagtg ggtctgggac agatttcact    60
ctcaccatca gcagcctaga gcctgaagat tttgcagttt attactgt    108

<210> SEQ ID NO 241
<211> LENGTH: 9
<212> TYPE: PRT
<213> ORGANISM: Homo Sapien

<400> SEQUENCE: 241

Gln Gln Arg Ser Asn Trp Pro Pro Thr
1               5

<210> SEQ ID NO 242
<211> LENGTH: 27
<212> TYPE: DNA
<213> ORGANISM: Homo Sapien

<400> SEQUENCE: 242
cagcaacgta gcaactggcc tccgacg    27

<210> SEQ ID NO 243
<211> LENGTH: 10

```
<212> TYPE: PRT
<213> ORGANISM: Homo Sapien

<400> SEQUENCE: 243

Phe Gly Gln Gly Thr Lys Val Glu Ile Lys
1               5                   10

<210> SEQ ID NO 244
<211> LENGTH: 30
<212> TYPE: DNA
<213> ORGANISM: Homo Sapien

<400> SEQUENCE: 244
ttcggccaag ggaccaaggt ggaaatcaaa                                         30

<210> SEQ ID NO 245
<211> LENGTH: 23
<212> TYPE: PRT
<213> ORGANISM: Homo Sapien

<400> SEQUENCE: 245

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 246
<211> LENGTH: 69
<212> TYPE: DNA
<213> ORGANISM: Homo Sapien

<400> SEQUENCE: 246
gaaattgtgt tgacacagtc tccagccacc ctgtctttgt ctccagggga aagagccacc        60
ctctcctgc                                                                69

<210> SEQ ID NO 247
<211> LENGTH: 11
<212> TYPE: PRT
<213> ORGANISM: Homo Sapien

<400> SEQUENCE: 247

Arg Ala Ser Gln Ser Val Phe Arg Tyr Leu Ala
1               5                   10

<210> SEQ ID NO 248
<211> LENGTH: 33
<212> TYPE: DNA
<213> ORGANISM: Homo Sapien

<400> SEQUENCE: 248
agggccagtc agagtgtttt caggtactta gcc                                     33

<210> SEQ ID NO 249
<211> LENGTH: 15
<212> TYPE: PRT
<213> ORGANISM: Homo Sapien

<400> SEQUENCE: 249

Trp Tyr Gln Gln Lys Pro Gly Gln Ala Pro Arg Leu Leu Ile Tyr
1               5                   10                  15

<210> SEQ ID NO 250
<211> LENGTH: 45
```

```
<212> TYPE: DNA
<213> ORGANISM: Homo Sapien

<400> SEQUENCE: 250
tggtaccaac agaaacctgg ccaggctccc aggctcctca tctat              45

<210> SEQ ID NO 251
<211> LENGTH: 7
<212> TYPE: PRT
<213> ORGANISM: Homo Sapien

<400> SEQUENCE: 251

Asp Ala Ser Thr Arg Ala Thr
1               5

<210> SEQ ID NO 252
<211> LENGTH: 21
<212> TYPE: DNA
<213> ORGANISM: Homo Sapien

<400> SEQUENCE: 252
gatgcatcca ccagggccac t                                        21

<210> SEQ ID NO 253
<211> LENGTH: 32
<212> TYPE: PRT
<213> ORGANISM: Homo Sapien

<400> SEQUENCE: 253

Asp Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 254
<211> LENGTH: 96
<212> TYPE: DNA
<213> ORGANISM: Homo Sapien

<400> SEQUENCE: 254
gacatcccag ccaggttcag tggcagtggg tctgggacag atttcactct caccatcagc   60
agcctagagc ctgaagattt tgcagtttat tactgt                            96

<210> SEQ ID NO 255
<211> LENGTH: 9
<212> TYPE: PRT
<213> ORGANISM: Homo Sapien

<400> SEQUENCE: 255

Gln Gln Arg Ser Asn Trp Pro Pro Thr
1               5

<210> SEQ ID NO 256
<211> LENGTH: 27
<212> TYPE: DNA
<213> ORGANISM: Homo Sapien

<400> SEQUENCE: 256
cagcaacgta gcaactggcc tccgacg                                  27

<210> SEQ ID NO 257
<211> LENGTH: 10
<212> TYPE: PRT
```

<213> ORGANISM: Homo Sapien

<400> SEQUENCE: 257

Phe Gly Gln Gly Thr Lys Val Glu Ile Lys
1               5                   10

<210> SEQ ID NO 258
<211> LENGTH: 30
<212> TYPE: DNA
<213> ORGANISM: Homo Sapien

<400> SEQUENCE: 258
ttcggccaag ggaccaaggt ggaaatcaaa                              30

<210> SEQ ID NO 259
<211> LENGTH: 120
<212> TYPE: PRT
<213> ORGANISM: Homo Sapien

<400> SEQUENCE: 259

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly His Ile Phe Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Ser Glu Gly Gly Tyr Tyr Asp Ile Pro Asp Val Trp Gly Gln
            100                 105                 110

Gly Thr Thr Val Thr Val Ser Ser
        115                 120

<210> SEQ ID NO 260
<211> LENGTH: 360
<212> TYPE: DNA
<213> ORGANISM: Homo Sapien

<400> SEQUENCE: 260
caggtgcagc tgcaggagtc gggcccagga ctggtgaagc cttcacagac cctgtccctc     60
acctgcactg tctctggtgg ctccatcagc agtggtggtt actactggag ctggatccgc    120
cagcacccag gaagggcct ggagtggatt gggcacatct tttacagtgg gagcacctac    180
tacaacccgt ccctcaagag tcgagttacc atatcagttg acacgtctaa gaaccagttc    240
tccctgaagc tgaactctgt gactgccgcg gacacggccg tgtattactg tgcgagcgag    300
ggagggtatt acgatattcc ggacgtctgg ggccaaggga ccacggtcac cgtctcctca    360

<210> SEQ ID NO 261
<211> LENGTH: 25
<212> TYPE: PRT
<213> ORGANISM: Homo Sapien

<400> SEQUENCE: 261

Gln Val Gln Leu Gln Glu Ser Gly Pro Gly Leu Val Lys Pro Ser Gln
1               5                   10                  15

Thr Leu Ser Leu Thr Cys Thr Val Ser
           20                  25

<210> SEQ ID NO 262
<211> LENGTH: 75
<212> TYPE: DNA
<213> ORGANISM: Homo Sapien

<400> SEQUENCE: 262
caggtgcagc tgcaggagtc gggcccagga ctggtgaagc cttcacagac cctgtccctc    60
acctgcactg tctct                                                    75

<210> SEQ ID NO 263
<211> LENGTH: 10
<212> TYPE: PRT
<213> ORGANISM: Homo Sapien

<400> SEQUENCE: 263

Gly Gly Ser Ile Ser Ser Gly Gly Tyr Tyr
1               5                   10

<210> SEQ ID NO 264
<211> LENGTH: 30
<212> TYPE: DNA
<213> ORGANISM: Homo Sapien

<400> SEQUENCE: 264
ggtggctcca tcagcagtgg tggttactac                                    30

<210> SEQ ID NO 265
<211> LENGTH: 17
<212> TYPE: PRT
<213> ORGANISM: Homo Sapien

<400> SEQUENCE: 265

Trp Ser Trp Ile Arg Gln His Pro Gly Lys Gly Leu Glu Trp Ile Gly
1               5                   10                  15

His

<210> SEQ ID NO 266
<211> LENGTH: 51
<212> TYPE: DNA
<213> ORGANISM: Homo Sapien

<400> SEQUENCE: 266
tggagctgga tccgccagca cccagggaag ggcctggagt ggattgggca c            51

<210> SEQ ID NO 267
<211> LENGTH: 7
<212> TYPE: PRT
<213> ORGANISM: Homo Sapien

<400> SEQUENCE: 267

Ile Phe Tyr Ser Gly Ser Thr
1               5

<210> SEQ ID NO 268
<211> LENGTH: 21
<212> TYPE: DNA
<213> ORGANISM: Homo Sapien

<400> SEQUENCE: 268
atcttttaca gtgggagcac c    21

<210> SEQ ID NO 269
<211> LENGTH: 38
<212> TYPE: PRT
<213> ORGANISM: Homo Sapien

<400> SEQUENCE: 269

Tyr Tyr Asn Pro Ser Leu Lys Ser Arg Val Thr Ile Ser Val Asp Thr
1               5                   10                  15

Ser Lys Asn Gln Phe Ser Leu Lys Leu Asn Ser Val Thr Ala Ala Asp
            20                  25                  30

Thr Ala Val Tyr Tyr Cys
        35

<210> SEQ ID NO 270
<211> LENGTH: 114
<212> TYPE: DNA
<213> ORGANISM: Homo Sapien

<400> SEQUENCE: 270
tactacaacc cgtccctcaa gagtcgagtt accatatcag ttgacacgtc taagaaccag    60
ttctccctga agctgaactc tgtgactgcc gcggacacgg ccgtgtatta ctgt    114

<210> SEQ ID NO 271
<211> LENGTH: 12
<212> TYPE: PRT
<213> ORGANISM: Homo Sapien

<400> SEQUENCE: 271

Ala Ser Glu Gly Gly Tyr Tyr Asp Ile Pro Asp Val
1               5                   10

<210> SEQ ID NO 272
<211> LENGTH: 36
<212> TYPE: DNA
<213> ORGANISM: Homo Sapien

<400> SEQUENCE: 272
gcgagcgagg gagggtatta cgatattccg gacgtc    36

<210> SEQ ID NO 273
<211> LENGTH: 11
<212> TYPE: PRT
<213> ORGANISM: Homo Sapien

<400> SEQUENCE: 273

Trp Gly Gln Gly Thr Thr Val Thr Val Ser Ser
1               5                   10

<210> SEQ ID NO 274
<211> LENGTH: 33
<212> TYPE: DNA
<213> ORGANISM: Homo Sapien

<400> SEQUENCE: 274
tggggccaag ggaccacggt caccgtctcc tca    33

<210> SEQ ID NO 275
<211> LENGTH: 30
<212> TYPE: PRT
<213> ORGANISM: Homo Sapien

```
<400> SEQUENCE: 275

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser
            20                  25                  30

<210> SEQ ID NO 276
<211> LENGTH: 90
<212> TYPE: DNA
<213> ORGANISM: Homo Sapien

<400> SEQUENCE: 276
caggtgcagc tgcaggagtc gggcccagga ctggtgaagc cttcacagac cctgtccctc     60
acctgcactg tctctggtgg ctccatcagc                                     90

<210> SEQ ID NO 277
<211> LENGTH: 7
<212> TYPE: PRT
<213> ORGANISM: Homo Sapien

<400> SEQUENCE: 277

Ser Gly Gly Tyr Tyr Trp Ser
1               5

<210> SEQ ID NO 278
<211> LENGTH: 21
<212> TYPE: DNA
<213> ORGANISM: Homo Sapien

<400> SEQUENCE: 278
agtggtggtt actactggag c                                              21

<210> SEQ ID NO 279
<211> LENGTH: 14
<212> TYPE: PRT
<213> ORGANISM: Homo Sapien

<400> SEQUENCE: 279

Trp Ile Arg Gln His Pro Gly Lys Gly Leu Glu Trp Ile Gly
1               5                   10

<210> SEQ ID NO 280
<211> LENGTH: 42
<212> TYPE: DNA
<213> ORGANISM: Homo Sapien

<400> SEQUENCE: 280
tggatccgcc agcacccagg gaagggcctg gagtggattg gg                       42

<210> SEQ ID NO 281
<211> LENGTH: 16
<212> TYPE: PRT
<213> ORGANISM: Homo Sapien

<400> SEQUENCE: 281

His Ile Phe Tyr Ser Gly Ser Thr Tyr Tyr Asn Pro Ser Leu Lys Ser
1               5                   10                  15

<210> SEQ ID NO 282
<211> LENGTH: 48
<212> TYPE: DNA
<213> ORGANISM: Homo Sapien
```

```
<400> SEQUENCE: 282
cacatctttt acagtgggag cacctactac aacccgtccc tcaagagt         48

<210> SEQ ID NO 283
<211> LENGTH: 32
<212> TYPE: PRT
<213> ORGANISM: Homo Sapien

<400> SEQUENCE: 283

Arg Val Thr Ile Ser Val Asp Thr Ser Lys Asn Gln Phe Ser Leu Lys
1               5                   10                  15

Leu Asn Ser Val Thr Ala Ala Asp Thr Ala Val Tyr Tyr Cys Ala Ser
            20                  25                  30

<210> SEQ ID NO 284
<211> LENGTH: 96
<212> TYPE: DNA
<213> ORGANISM: Homo Sapien

<400> SEQUENCE: 284
cgagttacca tatcagttga cacgtctaag aaccagttct ccctgaagct gaactctgtg    60
actgccgcgg acacggccgt gtattactgt gcgagc                             96

<210> SEQ ID NO 285
<211> LENGTH: 10
<212> TYPE: PRT
<213> ORGANISM: Homo Sapien

<400> SEQUENCE: 285

Glu Gly Gly Tyr Tyr Asp Ile Pro Asp Val
1               5                   10

<210> SEQ ID NO 286
<211> LENGTH: 30
<212> TYPE: DNA
<213> ORGANISM: Homo Sapien

<400> SEQUENCE: 286
gagggagggt attacgatat tccggacgtc                                    30

<210> SEQ ID NO 287
<211> LENGTH: 11
<212> TYPE: PRT
<213> ORGANISM: Homo Sapien

<400> SEQUENCE: 287

Trp Gly Gln Gly Thr Thr Val Thr Val Ser Ser
1               5                   10

<210> SEQ ID NO 288
<211> LENGTH: 33
<212> TYPE: DNA
<213> ORGANISM: Homo Sapien

<400> SEQUENCE: 288
tggggccaag ggaccacggt caccgtctcc tca                                33

<210> SEQ ID NO 289
<211> LENGTH: 107
<212> TYPE: PRT
<213> ORGANISM: Homo Sapien

<400> SEQUENCE: 289
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
                20                  25                  30

Leu Ala Trp Tyr Gln Gln Lys Pro Gly Gln Ala Pro Arg Leu Leu Ile
            35                  40                  45

Ser Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                  80

Glu Asp Phe Ala Ile Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 290
<211> LENGTH: 321
<212> TYPE: DNA
<213> ORGANISM: Homo Sapien

<400> SEQUENCE: 290
gaaattgtgt tgacacagtc tccagccacc ctgtctttgt ctccagggga aagagccacc      60
ctctcctgca gggccagtca gagtgttagc aactacttag cctggtacca acagaaacct    120
ggccaggctc ccaggctcct catctctgat gcatccaaca gggccactgg catcccagcc    180
aggttcagtg gcagtgggtc tgggacagac ttcactctca ccatcagcag cctagagcct    240
gaagattttg caatttatta ctgtcagcag cgtagcaact ggccgctcac tttcggcgga    300
gggaccaagg tggagatcaa a                                              321

<210> SEQ ID NO 291
<211> LENGTH: 26
<212> TYPE: PRT
<213> ORGANISM: Homo Sapien

<400> SEQUENCE: 291

Glu Ile Val Leu Thr Gln Ser Pro Ala Thr Leu Ser Leu Ser Pro Gly
1               5                   10                  15

Glu Arg Ala Thr Leu Ser Cys Arg Ala Ser
                20                  25

<210> SEQ ID NO 292
<211> LENGTH: 78
<212> TYPE: DNA
<213> ORGANISM: Homo Sapien

<400> SEQUENCE: 292
gaaattgtgt tgacacagtc tccagccacc ctgtctttgt ctccagggga aagagccacc      60
ctctcctgca gggccagt                                                   78

<210> SEQ ID NO 293
<211> LENGTH: 6
<212> TYPE: PRT
<213> ORGANISM: Homo Sapien

<400> SEQUENCE: 293

Gln Ser Val Ser Asn Tyr
1               5

<210> SEQ ID NO 294
<211> LENGTH: 18
<212> TYPE: DNA
<213> ORGANISM: Homo Sapien

<400> SEQUENCE: 294
cagagtgtta gcaactac                                                    18

<210> SEQ ID NO 295
<211> LENGTH: 17
<212> TYPE: PRT
<213> ORGANISM: Homo Sapien

<400> SEQUENCE: 295

Leu Ala Trp Tyr Gln Gln Lys Pro Gly Gln Ala Pro Arg Leu Leu Ile
1               5                   10                  15

Ser

<210> SEQ ID NO 296
<211> LENGTH: 51
<212> TYPE: DNA
<213> ORGANISM: Homo Sapien

<400> SEQUENCE: 296
ttagcctggt accaacagaa acctggccag gctcccaggc tcctcatctc t              51

<210> SEQ ID NO 297
<211> LENGTH: 3
<212> TYPE: PRT
<213> ORGANISM: Homo Sapien

<400> SEQUENCE: 297

Asp Ala Ser
1

<210> SEQ ID NO 298
<211> LENGTH: 9
<212> TYPE: DNA
<213> ORGANISM: Homo Sapien

<400> SEQUENCE: 298 gatgcatcc                                                              9

<210> SEQ ID NO 299
<211> LENGTH: 36
<212> TYPE: PRT
<213> ORGANISM: Homo Sapien

<400> SEQUENCE: 299

Asn Arg Ala Thr Gly Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

Ile Tyr Tyr Cys
        35

<210> SEQ ID NO 300
<211> LENGTH: 108
<212> TYPE: DNA
<213> ORGANISM: Homo Sapien

<400> SEQUENCE: 300

```
aacagggcca ctggcatccc agccaggttc agtggcagtg ggtctgggac agacttcact    60
ctcaccatca gcagcctaga gcctgaagat tttgcaattt attactgt              108

<210> SEQ ID NO 301
<211> LENGTH: 9
<212> TYPE: PRT
<213> ORGANISM: Homo Sapien

<400> SEQUENCE: 301

Gln Gln Arg Ser Asn Trp Pro Leu Thr
1               5

<210> SEQ ID NO 302
<211> LENGTH: 27
<212> TYPE: DNA
<213> ORGANISM: Homo Sapien

<400> SEQUENCE: 302
cagcagcgta gcaactggcc gctcact                                      27

<210> SEQ ID NO 303
<211> LENGTH: 10
<212> TYPE: PRT
<213> ORGANISM: Homo Sapien

<400> SEQUENCE: 303

Phe Gly Gly Gly Thr Lys Val Glu Ile Lys
1               5                   10

<210> SEQ ID NO 304
<211> LENGTH: 30
<212> TYPE: DNA
<213> ORGANISM: Homo Sapien

<400> SEQUENCE: 304
ttcggcggag ggaccaaggt ggagatcaaa                                   30

<210> SEQ ID NO 305
<211> LENGTH: 23
<212> TYPE: PRT
<213> ORGANISM: Homo Sapien

<400> SEQUENCE: 305

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 306
<211> LENGTH: 69
<212> TYPE: DNA
<213> ORGANISM: Homo Sapien

<400> SEQUENCE: 306
gaaattgtgt tgacacagtc tccagccacc ctgtctttgt ctccagggga aagagccacc    60
ctctcctgc                                                          69

<210> SEQ ID NO 307
<211> LENGTH: 11
<212> TYPE: PRT
<213> ORGANISM: Homo Sapien

<400> SEQUENCE: 307
```

Arg Ala Ser Gln Ser Val Ser Asn Tyr Leu Ala
1               5                   10

<210> SEQ ID NO 308
<211> LENGTH: 33
<212> TYPE: DNA
<213> ORGANISM: Homo Sapien

<400> SEQUENCE: 308
agggccagtc agagtgttag caactactta gcc                                   33

<210> SEQ ID NO 309
<211> LENGTH: 15
<212> TYPE: PRT
<213> ORGANISM: Homo Sapien

<400> SEQUENCE: 309

Trp Tyr Gln Gln Lys Pro Gly Gln Ala Pro Arg Leu Leu Ile Ser
1               5                   10                  15

<210> SEQ ID NO 310
<211> LENGTH: 45
<212> TYPE: DNA
<213> ORGANISM: Homo Sapien

<400> SEQUENCE: 310
tggtaccaac agaaacctgg ccaggctccc aggctcctca tctct                     45

<210> SEQ ID NO 311
<211> LENGTH: 7
<212> TYPE: PRT
<213> ORGANISM: Homo Sapien

<400> SEQUENCE: 311

Asp Ala Ser Asn Arg Ala Thr
1               5

<210> SEQ ID NO 312
<211> LENGTH: 21
<212> TYPE: DNA
<213> ORGANISM: Homo Sapien

<400> SEQUENCE: 312
gatgcatcca acagggccac t                                               21

<210> SEQ ID NO 313
<211> LENGTH: 32
<212> TYPE: PRT
<213> ORGANISM: Homo Sapien

<400> SEQUENCE: 313

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Ile Tyr Tyr Cys
            20                  25                  30

<210> SEQ ID NO 314
<211> LENGTH: 96
<212> TYPE: DNA
<213> ORGANISM: Homo Sapien

<400> SEQUENCE: 314
ggcatcccag ccaggttcag tggcagtggg tctgggacag acttcactct caccatcagc     60
agcctagagc ctgaagattt tgcaatttat tactgt                96

<210> SEQ ID NO 315
<211> LENGTH: 9
<212> TYPE: PRT
<213> ORGANISM: Homo Sapien

<400> SEQUENCE: 315

Gln Gln Arg Ser Asn Trp Pro Leu Thr
1               5

<210> SEQ ID NO 316
<211> LENGTH: 27
<212> TYPE: DNA
<213> ORGANISM: Homo Sapien

<400> SEQUENCE: 316
cagcagcgta gcaactggcc gctcact                27

<210> SEQ ID NO 317
<211> LENGTH: 10
<212> TYPE: PRT
<213> ORGANISM: Homo Sapien

<400> SEQUENCE: 317

Phe Gly Gly Gly Thr Lys Val Glu Ile Lys
1               5                   10

<210> SEQ ID NO 318
<211> LENGTH: 30
<212> TYPE: DNA
<213> ORGANISM: Homo Sapien

<400> SEQUENCE: 318
ttcggcggag ggaccaaggt ggagatcaaa                30

<210> SEQ ID NO 319
<211> LENGTH: 120
<212> TYPE: PRT
<213> ORGANISM: Homo Sapien

<400> SEQUENCE: 319

Gln Val His Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Tyr Pro Gly Lys Gly Leu Glu Trp Ile
        35                  40                  45

Gly Tyr Ile Ser Tyr Ser Gly Ser Asn Tyr Asn Pro Ser Leu Lys
    50                  55                  60

Arg Arg Val Thr Ile Ser Arg Asp Thr Ser Lys Asn Gln Phe Ser Leu
65                  70                  75                  80

Gln Leu Thr Ser Val Ile Ala Ala Asp Thr Ala Val Tyr Tyr Cys Ala
            85                  90                  95

Arg Asn Leu Met Ile Arg Gly Ala Tyr Gly Met Asp Val Trp Gly Gln
            100                 105                 110

Gly Thr Thr Val Thr Val Ser Ser
        115                 120

<210> SEQ ID NO 320

```
<211> LENGTH: 360
<212> TYPE: DNA
<213> ORGANISM: Homo Sapien

<400> SEQUENCE: 320
caggtgcacc tgcaggagtc gggcccagga ctggtgaagc cttcggagac cctgtccctc      60
acgtgcactg tctctggtgg ctccatcagt agttactact ggagctggat ccggcagtac     120
ccaggaaagg gactggagtg gattggatat atctcttaca gtgggagcag caattataat     180
ccctccctca agaggcgagt caccatatca cgagacacgt ccaagaacca gttctccctg     240
cagctgacct ctgtaatcgc tgcggacacg gccgtttatt actgtgcgag aaatcttatg     300
attcggggag cctacggcat ggacgtctgg ggccaaggga ccacggtcac cgtctcctca     360

<210> SEQ ID NO 321
<211> LENGTH: 25
<212> TYPE: PRT
<213> ORGANISM: Homo Sapien

<400> SEQUENCE: 321

Gln Val His Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 322
<211> LENGTH: 75
<212> TYPE: DNA
<213> ORGANISM: Homo Sapien

<400> SEQUENCE: 322
caggtgcacc tgcaggagtc gggcccagga ctggtgaagc cttcggagac cctgtccctc      60
acgtgcactg tctct                                                       75

<210> SEQ ID NO 323
<211> LENGTH: 8
<212> TYPE: PRT
<213> ORGANISM: Homo Sapien

<400> SEQUENCE: 323

Gly Gly Ser Ile Ser Ser Tyr Tyr
1               5

<210> SEQ ID NO 324
<211> LENGTH: 24
<212> TYPE: DNA
<213> ORGANISM: Homo Sapien

<400> SEQUENCE: 324
ggtggctcca tcagtagtta ctac                                             24

<210> SEQ ID NO 325
<211> LENGTH: 17
<212> TYPE: PRT
<213> ORGANISM: Homo Sapien

<400> SEQUENCE: 325

Trp Ser Trp Ile Arg Gln Tyr Pro Gly Lys Gly Leu Glu Trp Ile Gly
1               5                   10                  15

Tyr
```

<210> SEQ ID NO 326
<211> LENGTH: 51
<212> TYPE: DNA
<213> ORGANISM: Homo Sapien

<400> SEQUENCE: 326
tggagctgga tccggcagta cccaggaaag ggactggagt ggattggata t         51

<210> SEQ ID NO 327
<211> LENGTH: 7
<212> TYPE: PRT
<213> ORGANISM: Homo Sapien

<400> SEQUENCE: 327

Ile Ser Tyr Ser Gly Ser Ser
1               5

<210> SEQ ID NO 328
<211> LENGTH: 21
<212> TYPE: DNA
<213> ORGANISM: Homo Sapien

<400> SEQUENCE: 328
atctcttaca gtgggagcag c                                           21

<210> SEQ ID NO 329
<211> LENGTH: 38
<212> TYPE: PRT
<213> ORGANISM: Homo Sapien

<400> SEQUENCE: 329

Asn Tyr Asn Pro Ser Leu Lys Arg Arg Val Thr Ile Ser Arg Asp Thr
1               5                   10                  15

Ser Lys Asn Gln Phe Ser Leu Gln Leu Thr Ser Val Ile Ala Ala Asp
            20                  25                  30

Thr Ala Val Tyr Tyr Cys
        35

<210> SEQ ID NO 330
<211> LENGTH: 114
<212> TYPE: DNA
<213> ORGANISM: Homo Sapien

<400> SEQUENCE: 330
aattataatc cctccctcaa gaggcgagtc accatatcac gagacacgtc caagaaccag   60
ttctccctgc agctgacctc tgtaatcgct gcggacacgg ccgttttatta ctgt       114

<210> SEQ ID NO 331
<211> LENGTH: 14
<212> TYPE: PRT
<213> ORGANISM: Homo Sapien

<400> SEQUENCE: 331

Ala Arg Asn Leu Met Ile Arg Gly Ala Tyr Gly Met Asp Val
1               5                   10

<210> SEQ ID NO 332
<211> LENGTH: 42
<212> TYPE: DNA
<213> ORGANISM: Homo Sapien

<400> SEQUENCE: 332
gcgagaaatc ttatgattcg gggagcctac ggcatggacg tc                    42

```
<210> SEQ ID NO 333
<211> LENGTH: 11
<212> TYPE: PRT
<213> ORGANISM: Homo Sapien

<400> SEQUENCE: 333

Trp Gly Gln Gly Thr Thr Val Thr Val Ser Ser
1               5                   10

<210> SEQ ID NO 334
<211> LENGTH: 33
<212> TYPE: DNA
<213> ORGANISM: Homo Sapien

<400> SEQUENCE: 334
tggggccaag ggaccacggt caccgtctcc tca                                    33

<210> SEQ ID NO 335
<211> LENGTH: 29
<212> TYPE: PRT
<213> ORGANISM: Homo Sapien

<400> SEQUENCE: 335

Gln Val His Leu Gln Glu Ser Gly Pro Gly Leu Val Lys Pro Ser Glu
1               5                   10                  15

Thr Leu Ser Leu Thr Cys Thr Val Ser Gly Gly Ser Ile
            20                  25

<210> SEQ ID NO 336
<211> LENGTH: 87
<212> TYPE: DNA
<213> ORGANISM: Homo Sapien

<400> SEQUENCE: 336
caggtgcacc tgcaggagtc gggcccagga ctggtgaagc cttcggagac cctgtccctc       60
acgtgcactg tctctggtgg ctccatc                                          87

<210> SEQ ID NO 337
<211> LENGTH: 6
<212> TYPE: PRT
<213> ORGANISM: Homo Sapien

<400> SEQUENCE: 337

Ser Ser Tyr Tyr Trp Ser
1               5

<210> SEQ ID NO 338
<211> LENGTH: 18
<212> TYPE: DNA
<213> ORGANISM: Homo Sapien

<400> SEQUENCE: 338
agtagttact actggagc                                                     18

<210> SEQ ID NO 339
<211> LENGTH: 14
<212> TYPE: PRT
<213> ORGANISM: Homo Sapien

<400> SEQUENCE: 339

Trp Ile Arg Gln Tyr Pro Gly Lys Gly Leu Glu Trp Ile Gly
1               5                   10
```

<210> SEQ ID NO 340
<211> LENGTH: 42
<212> TYPE: DNA
<213> ORGANISM: Homo Sapien

<400> SEQUENCE: 340
tggatccggc agtacccagg aaagggactg gagtggattg ga                42

<210> SEQ ID NO 341
<211> LENGTH: 16
<212> TYPE: PRT
<213> ORGANISM: Homo Sapien

<400> SEQUENCE: 341

Tyr Ile Ser Tyr Ser Gly Ser Ser Asn Tyr Asn Pro Ser Leu Lys Arg
1               5                   10                  15

<210> SEQ ID NO 342
<211> LENGTH: 48
<212> TYPE: DNA
<213> ORGANISM: Homo Sapien

<400> SEQUENCE: 342
tatatctctt acagtgggag cagcaattat aatccctccc tcaagagg           48

<210> SEQ ID NO 343
<211> LENGTH: 32
<212> TYPE: PRT
<213> ORGANISM: Homo Sapien

<400> SEQUENCE: 343

Arg Val Thr Ile Ser Arg Asp Thr Ser Lys Asn Gln Phe Ser Leu Gln
1               5                   10                  15

Leu Thr Ser Val Ile Ala Ala Asp Thr Ala Val Tyr Tyr Cys Ala Arg
                20                  25                  30

<210> SEQ ID NO 344
<211> LENGTH: 96
<212> TYPE: DNA
<213> ORGANISM: Homo Sapien

<400> SEQUENCE: 344
cgagtcacca tatcacgaga cacgtccaag aaccagttct ccctgcagct gacctctgta    60
atcgctgcgg acacggccgt ttattactgt gcgaga                             96

<210> SEQ ID NO 345
<211> LENGTH: 12
<212> TYPE: PRT
<213> ORGANISM: Homo Sapien

<400> SEQUENCE: 345

Asn Leu Met Ile Arg Gly Ala Tyr Gly Met Asp Val
1               5                   10

<210> SEQ ID NO 346
<211> LENGTH: 36
<212> TYPE: DNA
<213> ORGANISM: Homo Sapien

<400> SEQUENCE: 346
aatcttatga ttcggggagc ctacggcatg gacgtc                             36

<210> SEQ ID NO 347
<211> LENGTH: 11
<212> TYPE: PRT
<213> ORGANISM: Homo Sapien

<400> SEQUENCE: 347

Trp Gly Gln Gly Thr Thr Val Thr Val Ser Ser
1               5                   10

<210> SEQ ID NO 348
<211> LENGTH: 33
<212> TYPE: DNA
<213> ORGANISM: Homo Sapien

<400> SEQUENCE: 348
tggggccaag ggaccacggt caccgtctcc tca                                  33

<210> SEQ ID NO 349
<211> LENGTH: 112
<212> TYPE: PRT
<213> ORGANISM: Homo Sapien

<400> SEQUENCE: 349

Asp Thr Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Val Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Phe Thr Phe Gly Pro Gly Thr Lys Val Asp Ile Lys
            100                 105                 110

<210> SEQ ID NO 350
<211> LENGTH: 336
<212> TYPE: DNA
<213> ORGANISM: Homo Sapien

<400> SEQUENCE: 350
gatactgtga tgactcagtc tccactctcc ctgcccgtca cccctggaga gccggcctcc     60
atctcctgca ggtctagtca gagcctcctg catagtaatg gatacaatta tttggattgg    120
tacctgcaga aggcaggaca gtctccacaa ctcctgatct atttgggttc taatcgggcc    180
tccggggtcc ctgacaggtt cagtggcagt gtatcaggca cagatttcac actgaaaatc    240
agcagagtgg aggctgagga tgttgggatt tattactgca tgcaagctct acaaactcca    300
ttcactttcg gccctgggac caaagtggat atcaaa                              336

<210> SEQ ID NO 351
<211> LENGTH: 26
<212> TYPE: PRT
<213> ORGANISM: Homo Sapien

<400> SEQUENCE: 351

Asp Thr Val Met Thr Gln Ser Pro Leu Ser Leu Pro Val Thr Pro Gly

```
                1               5                  10                  15
Glu Pro Ala Ser Ile Ser Cys Arg Ser Ser
            20                  25
```

<210> SEQ ID NO 352
<211> LENGTH: 78
<212> TYPE: DNA
<213> ORGANISM: Homo Sapien

<400> SEQUENCE: 352
gatactgtga tgactcagtc tccactctcc ctgcccgtca cccctggaga gccggcctcc     60
atctcctgca ggtctagt                                                  78

<210> SEQ ID NO 353
<211> LENGTH: 11
<212> TYPE: PRT
<213> ORGANISM: Homo Sapien

<400> SEQUENCE: 353

```
Gln Ser Leu Leu His Ser Asn Gly Tyr Asn Tyr
1               5                   10
```

<210> SEQ ID NO 354
<211> LENGTH: 33
<212> TYPE: DNA
<213> ORGANISM: Homo Sapien

<400> SEQUENCE: 354
cagagcctcc tgcatagtaa tggatacaat tat                                 33

<210> SEQ ID NO 355
<211> LENGTH: 17
<212> TYPE: PRT
<213> ORGANISM: Homo Sapien

<400> SEQUENCE: 355

```
Leu Asp Trp Tyr Leu Gln Lys Ala Gly Gln Ser Pro Gln Leu Leu Ile
1               5                   10                  15
Tyr
```

<210> SEQ ID NO 356
<211> LENGTH: 51
<212> TYPE: DNA
<213> ORGANISM: Homo Sapien

<400> SEQUENCE: 356
ttggattggt acctgcagaa ggcaggacag tctccacaac tcctgatcta t              51

<210> SEQ ID NO 357
<211> LENGTH: 3
<212> TYPE: PRT
<213> ORGANISM: Homo Sapien

<400> SEQUENCE: 357

```
Leu Gly Ser
1
```

<210> SEQ ID NO 358
<211> LENGTH: 9
<212> TYPE: DNA
<213> ORGANISM: Homo Sapien

<400> SEQUENCE: 358

```
ttgggttct                                                          9
```

<210> SEQ ID NO 359
<211> LENGTH: 36
<212> TYPE: PRT
<213> ORGANISM: Homo Sapien

<400> SEQUENCE: 359

```
Asn Arg Ala Ser Gly Val Pro Asp Arg Phe Ser Gly Ser Val Ser Gly
1               5                   10                  15

Thr Asp Phe Thr Leu Lys Ile Ser Arg Val Glu Ala Glu Asp Val Gly
            20                  25                  30

Ile Tyr Tyr Cys
        35
```

<210> SEQ ID NO 360
<211> LENGTH: 108
<212> TYPE: DNA
<213> ORGANISM: Homo Sapien

<400> SEQUENCE: 360

```
aatcgggcct ccggggtccc tgacaggttc agtggcagtg tatcaggcac agatttcaca    60
ctgaaaatca gcagagtgga ggctgaggat gttgggattt attactgc                108
```

<210> SEQ ID NO 361
<211> LENGTH: 9
<212> TYPE: PRT
<213> ORGANISM: Homo Sapien

<400> SEQUENCE: 361

```
Met Gln Ala Leu Gln Thr Pro Phe Thr
1               5
```

<210> SEQ ID NO 362
<211> LENGTH: 27
<212> TYPE: DNA
<213> ORGANISM: Homo Sapien

<400> SEQUENCE: 362

```
atgcaagctc tacaaactcc attcact                                      27
```

<210> SEQ ID NO 363
<211> LENGTH: 10
<212> TYPE: PRT
<213> ORGANISM: Homo Sapien

<400> SEQUENCE: 363

```
Phe Gly Pro Gly Thr Lys Val Asp Ile Lys
1               5                   10
```

<210> SEQ ID NO 364
<211> LENGTH: 30
<212> TYPE: DNA
<213> ORGANISM: Homo Sapien

<400> SEQUENCE: 364

```
ttcggccctg ggaccaaagt ggatatcaaa                                   30
```

<210> SEQ ID NO 365
<211> LENGTH: 23
<212> TYPE: PRT
<213> ORGANISM: Homo Sapien

<400> SEQUENCE: 365

Asp Thr Val Met Thr Gln Ser Pro Leu Ser Leu Pro Val Thr Pro Gly
1               5                   10                  15

Glu Pro Ala Ser Ile Ser Cys
            20

<210> SEQ ID NO 366
<211> LENGTH: 69
<212> TYPE: DNA
<213> ORGANISM: Homo Sapien

<400> SEQUENCE: 366
gatactgtga tgactcagtc tccactctcc ctgcccgtca cccctggaga gccggcctcc    60
atctcctgc                                                           69

<210> SEQ ID NO 367
<211> LENGTH: 16
<212> TYPE: PRT
<213> ORGANISM: Homo Sapien

<400> SEQUENCE: 367

Arg Ser Ser Gln Ser Leu Leu His Ser Asn Gly Tyr Asn Tyr Leu Asp
1               5                   10                  15

<210> SEQ ID NO 368
<211> LENGTH: 48
<212> TYPE: DNA
<213> ORGANISM: Homo Sapien

<400> SEQUENCE: 368
aggtctagtc agagcctcct gcatagtaat ggatacaatt atttggat                48

<210> SEQ ID NO 369
<211> LENGTH: 15
<212> TYPE: PRT
<213> ORGANISM: Homo Sapien

<400> SEQUENCE: 369

Trp Tyr Leu Gln Lys Ala Gly Gln Ser Pro Gln Leu Leu Ile Tyr
1               5                   10                  15

<210> SEQ ID NO 370
<211> LENGTH: 45
<212> TYPE: DNA
<213> ORGANISM: Homo Sapien

<400> SEQUENCE: 370
tggtacctgc agaaggcagg acagtctcca caactcctga tctat                   45

<210> SEQ ID NO 371
<211> LENGTH: 7
<212> TYPE: PRT
<213> ORGANISM: Homo Sapien

<400> SEQUENCE: 371

Leu Gly Ser Asn Arg Ala Ser
1               5

<210> SEQ ID NO 372
<211> LENGTH: 21
<212> TYPE: DNA
<213> ORGANISM: Homo Sapien

<400> SEQUENCE: 372
ttgggttcta atcgggcctc c                                         21

<210> SEQ ID NO 373
<211> LENGTH: 32
<212> TYPE: PRT
<213> ORGANISM: Homo Sapien

<400> SEQUENCE: 373

Gly Val Pro Asp Arg Phe Ser Gly Ser Val Ser Gly Thr Asp Phe Thr
1               5                   10                  15

Leu Lys Ile Ser Arg Val Glu Ala Glu Asp Val Gly Ile Tyr Tyr Cys
            20                  25                  30

<210> SEQ ID NO 374
<211> LENGTH: 96
<212> TYPE: DNA
<213> ORGANISM: Homo Sapien

<400> SEQUENCE: 374
ggggtccctg acaggttcag tggcagtgta tcaggcacag atttcacact gaaaatcagc    60
agagtggagg ctgaggatgt tgggatttat tactgc                             96

<210> SEQ ID NO 375
<211> LENGTH: 9
<212> TYPE: PRT
<213> ORGANISM: Homo Sapien

<400> SEQUENCE: 375

Met Gln Ala Leu Gln Thr Pro Phe Thr
1               5

<210> SEQ ID NO 376
<211> LENGTH: 27
<212> TYPE: DNA
<213> ORGANISM: Homo Sapien

<400> SEQUENCE: 376
atgcaagctc tacaaactcc attcact                                    27

<210> SEQ ID NO 377
<211> LENGTH: 10
<212> TYPE: PRT
<213> ORGANISM: Homo Sapien

<400> SEQUENCE: 377

Phe Gly Pro Gly Thr Lys Val Asp Ile Lys
1               5                   10

<210> SEQ ID NO 378
<211> LENGTH: 30
<212> TYPE: DNA
<213> ORGANISM: Homo Sapien

<400> SEQUENCE: 378
ttcggccctg ggaccaaagt ggatatcaaa                                 30